(12) United States Patent
Prescott et al.

(10) Patent No.: US 7,202,033 B2
(45) Date of Patent: *Apr. 10, 2007

(54) IDENTIFICATION OF KINASE INHIBITORS

(75) Inventors: John C. Prescott, San Francisco, CA (US); Andrew Braisted, San Francisco, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 447 days.

This patent is subject to a terminal disclaimer.

(21) Appl. No.: 10/394,322

(22) Filed: Mar. 20, 2003

(65) Prior Publication Data

US 2003/0232391 A1    Dec. 18, 2003

Related U.S. Application Data

(60) Provisional application No. 60/366,892, filed on Mar. 21, 2002.

(51) Int. Cl.
  *C12Q 1/68*    (2006.01)
(52) U.S. Cl. ............................. 435/6; 435/4; 530/350
(58) Field of Classification Search .................... None
  See application file for complete search history.

(56) References Cited

U.S. PATENT DOCUMENTS

| 6,335,155 | B1 |  | 1/2002 | Wells et al. ................... 435/4 |
| 6,919,178 | B2 | * | 7/2005 | Erlanson et al. ............... 435/6 |
| 2001/0018511 | A1 | * | 8/2001 | Lane et al. ................. 536/24.5 |
| 2005/0059038 | A1 | * | 3/2005 | Adams et al. ................. 435/6 |

FOREIGN PATENT DOCUMENTS

| WO | WO 00/00823 | 1/2000 |
| WO | WO 02/42773 | 5/2002 |
| WO | WO 03/014072 | 2/2003 |
| WO | WO 03/014308 | 2/2003 |
| WO | WO 03/046200 | 6/2003 |

OTHER PUBLICATIONS

Erlanson et al., PNAS 97 (17):9367-9372 (2000).*
Schindler et al., Science 289:1938-1942 (2000).*
Tarricone et al., Molecular Cell 8:657-669 (2001).*
Sharma et al., The Journal of Biological Chemistry 274(14):9600-9606 (1999).*
Erlanson, Daniel A., et al., "Site-directed ligand discovery", PNAS, 97, (17), 2000, pp. 9367-9372.
Schindler, Thomas, et al., "Structural Mechanism for STI-571 Inhibition of Abelson Tyrosine Kinase", Science, 289, 2000, pp. 1938-1942.
Dudley, David T., et al., "A synthetic inhibitor of the mitogen-activated protein kinase cascade", Proc. Natl. Acad. Sci. USA, 92, 1995, pp. 7686-7689.
Sebolt-Leopold, Judith S., et al., "Blockade of the MAP kinase pathway suppresses growth of colon tumors in vivo", Nature Medicine, 5, (7), 1999, pp. 810-816.
Sebolt-Leopold, Judith, et al., "Development of anticancer drugs targeting the MAP kinase pathway", Onocogene, 19, 2000, pp. 6594-6599.
Pargellis, Christopher, et al., "Inhibition of p38 MAP kinase by utilizing a novel allosteric binding site", Nature Structural Biology, 9, (4), 2002, pp. 268-272.
Huse, Morgan, et al., "The Conformational Plasticity of Protein Kinases", Cell, 109, 2002, pp. 275-282.
Regan, John, et al., "Pyrazole Urea-Based Inhibitors of p38 MAP Kinase: From Lead Compound to Clinical Candidate", Journal of Medical Chemistry, 45, (14), 2002, pp. 2994-3008.
Taylor, Susan S., et al., "Protein kinase inhibition: natural and synthetic variations on a theme", Current Opinion in Chemical Biology, 1, 1997, pp. 219-226.
Johnson, Louise N., et al., "Structural Basis for Control by Phosphorylation", Chemical Reviews, 101, (8), 2001, pp. 2209-2242.
Dancey, Janet, et al., "Issues and Progress with Protein Kinase Inhibitors for Cancer Treatment", Nature Reviews-Drug Discovery, 2, 2003, pp. 296-313.
Cohen, Philip, "Protein kinases-the major drug targets of the twenty-first century?", Nature Reviews-Drug Discovery, 1, 2002, pp. 309-315.

* cited by examiner

*Primary Examiner*—Mark L. Shibuya
*Assistant Examiner*—Jeffrey S. Lundgren
(74) *Attorney, Agent, or Firm*—Heller Ehrman LLP

(57) ABSTRACT

The invention concerns the identification of protein kinase inhibitors that preferentially bind to the inactive conformation of a target protein kinase. The inhibitors are identified by locking the target protein kinase in an inactive conformation, and using a covalent tethering approach to identify inhibitors preferentially targeting the inactive conformation.

30 Claims, 2 Drawing Sheets

IDENTIFICATION OF KINASE INHIBITORS

CROSS-REFERENCE TO RELATED APPLICATION

This application claims the benefit of U.S. Provisional Patent Application No. 60/366,892, filed Mar. 21, 2002 which is incorporated herein by reference.

BACKGROUND OF THE INVENTION

Field of the Invention

The growth and differentiation of eukaryotic cells is regulated by a complex web of signal transduction pathways. Precise regulation of these pathways allows cells to respond to extracellular stimuli such as hormones, neurotransmitters, and stress as they proliferate and differentiate into specific tissues. Protein phosphorylation, a regulatory mechanism common to all eukaryotic cells, plays a central role in this signal taransduction web. First discovered as a regulatory mechanism nearly fifty years ago, protein phosphorylation is very likely the most important mechanism for regulation of signal transduction in mammalian cells. It is therefore not surprising that protein kinases, enzymes that catalyze the transfer of the y-phosphatase group of ATP to the oxygen atom of the hydroxyl group of serine, threonine or tyrosine residues in peptides and polypeptides, comprise one of the largest protein superfamilies. Indeed, with the complete sequencing of the human genome, it has been asserted that there are exactly 508 genes encoding human protein kinases, including 58 receptor tyrosine kinases and 32 nonreceptor tyrosine kinases.

Kinases and Cancer

Cancer consists of a variety of diseases characterized by abnormal cell growth. Cancer is caused by both internal and external factors that cause mutations in the genetic material of the cells. Cancer causing genetic mutations can be grouped into two categories, those that act in a positive manner to increase the rate of cell growth, and those that act in a negative manner by removing natural barriers to cell growth and differentiation. Mutated genes that increase the rate of cell growth and differentiation are called oncogenes, while those that remove natural barriers to growth are called tumor suppressor genes.

The first oncogene identified encoded the Src tyrosine kinase. Src is a key regulator of signal transduction in many different cell types. Present inside nearly all human cells in an inactive state, Src is poised to respond to extracellular signals from a variety of sources. Once triggered by a stimulus, Src is transformed into an active state in which it phosphorylates tyrosine residues on a number of effector proteins. While the tyrosine kinase activity of Src is tightly regulated in normal cells, mutations can occur which transform the enzyme into a constitutively active state. It was one such mutation, identified over 25 years ago, that gave Src the dubious honor of being known as the first oncogene. There are now about 30 tumor suppressor genes and over 100 oncogenes known, about 20% of which encode tyrosine kinases. The disregulation of such central regulators of cell growth and differentiation has disastrous consequences for the cell.

Kinase Inhibitors

Protein kinases play a crucial role not only in signal transduction but also in cellular proliferation, differentiation, and various regulatory mechanisms. The casual role that many protein kinases play in oncogenesis has made them exciting targets for the development of novel anti-cancer chemotherapies. The conserved and extremely well characterized nature of the ATP binding pocket has made it the most common, and most successful, target for kinase inhibition. Thus, libraries containing ATP (and purine) mimetics have been generated and screened against large panels of kinases in the hope of finding those rare pharmacophores that can outcompete ATP, thereby blocking kinase activity.

However, this approach has at least two major shortcomings. First, these inhibitors must compete directly with ATP for their binding site. ATP, which is used by thousands of cellular enzymes, is present in cells in very high concentration. Therefore, kinase inhibitors that act in a strictly ATP competitive manner must bind to their target kinase with extremely high affinity. Second, the high structural conservation surrounding the ATP binding pocket makes it difficult to design inhibitors that show specificity for one kinase over another. Given these two criticisms, it is perhaps not surprising that after twenty years of research there are only twelve small molecule tyrosine kinase inhibitors in clinical trials. All of these inhibitors compete directly with ATP for the ATP binding pocket, all bind this pocket extremely tightly, and all show varying degrees of specificity for their target kinase.

A possible exception is the small molecule kinase inhibitors, Gleevec™ (Novartis), a phenylamino-pyrimidine derivative, which binds the purine pocket of Abl tyrosine kinase. This compound shows unique properties that suggest that its mode of action is somewhat unusual. While this compound was approximately a thousand fold less potent than most kinase inhibitor clinical candidates when assayed in biochemical assays, it did not lose as much potency as most inhibitors did when tested in cells, suggesting that it is not competing directly with cellular ATP for binding to Abl. Co-crystallization studies have shown that Gleevec™ does indeed occupy the purine pocket of the Abl kinase, but it does so only when the kinase is in an inactive conformation, with the amino-terminal and carboxy-terminal lobes twisted such that the catalytic triad of lysine and two aspartic acids is not properly aligned to accept ATP or to catalyze the phosphate transfer reaction. Therefore, Gleevec™ makes use of the proven small molecule druggability of the purine pocket without directly competing against ATP, which binds to the inactive conformation with much lower affinity.

It would be desirable to develop protein kinase inhibitors that do not compete directly with ATP for binding to the active conformation of the ATP binding pocket of the target protein kinase. It would be further desirable to design fast, reliable, high-throughput screening assays for identifying such inhibitors. It would also be desirable to lock the ATP binding pocket of protein kinases in an inactive conformation in order to facilitate the design of such screening assays and the identification of protein kinase inhibitors with unique properties, such as increased specificity.

SUMMARY OF THE INVENTION

In one aspect, the invention concerns a method for identifying a ligand binding to an inactive conformation of a target protein kinase, comprising (a) contacting the inactive conformation of the target protein kinase, which contains or is modified to contain a reactive group at or near a binding site of interest, with one or more ligand candidates capable of covalently bonding to the reactive group thereby forming a kinase-ligand conjugate; and (b) detecting the formation of the kinase-ligand conjugate and identifying the ligand present in the kinase-ligand conjugate.

The kinase and the ligand candidate preferably form a disulfide bond to yield a kinase-ligand conjugate. In this embodiment, the kinase and the ligand candidate(s) can be contacted in the presence of a reducing agent, such as 2-mercaptoethanol or cysteamine.

The ligand candidates may be small molecules, and may be less than 1500 daltons, preferably less than 1000 daltons, more preferably less than 750 daltons, even more preferably less than 500 daltons, most preferably less than 250 daltons in size.

In another aspect, the invention concerns a method for identifying a ligand that binds to the inactive conformation of a target protein kinase, comprising
(a) obtaining the inactive conformation of the target protein kinase comprising an —SH group, masked —SH group, or activated —SH-group;
(b) combining the inactive conformation of the target protein kinase with one or more ligand candidates wherein said ligand candidates each comprises a disulfide bond;
(c) forming a kinase-ligand conjugate wherein at least one ligand candidate binds to the inactive conformation of the target protein kinase under disulfide exchange conditions, and
(d) detecting the formation of the kinase-ligand conjugate and identifying the ligand present in the conjugate.

In yet another aspect, the invention concerns a method for identifying ligands binding to an inactive conformation of a target protein kinase, comprising
(a) contacting the inactive conformation of the protein kinase having a first and a second binding site of interest and containing or modified to contain a nucleophile at or near the first site of interest with a plurality of ligand candidates, the candidates having a functional group reactive with the nucleophile, under conditions such that a reversible covalent bond is formed between the nucleophile and a candidate that has affinity for the first site of interest, to form a kinase-first ligand complex;
(b) identifying the first ligand from the complex of (a);
(c) designing a derivative of the first ligand identified in (a) to provide a small molecule extender (SME) having a first functional group reactive with the nucleophile on the kinase and a second functional group reactive with a second ligand having affinity for the binding second site of interest;
(d) contacting the SME with the kinase to form a kinase-SME complex, and
(e) contacting the kinase-SME complex with a plurality of second ligand candidates, the candidates having a functional group reactive with the SME in said kinase-SME complex, wherein a candidate that has affinity for the second binding site of interest on the kinase forms a reversible covalent bond with said kinase-SME complex, whereby a second ligand is identified.

In a still further aspect, the invention concerns a method for identifying ligands binding to an inactive conformation of a target protein kinase, comprising
(a) screening a library of ligand candidates with a kinase-ligand conjugate formed by the covalent bonding of the inactive conformation of a kinase comprising a first reactive functionality with a compound that comprises (1) a second reactive functionality and (2) a chemically reactive group, wherein the second reactive functionality of the compound reacts with the first reactive functionality of the inactive conformation of the target protein kinase to form a first covalent bond such that the kinase-ligand conjugate contains a free chemically reactive group, under conditions wherein at least one member of the library forms a second covalent bond with the kinase-ligand conjugate; and
(b) identifying a further ligand that binds covalently to the chemically reactive group of the kinase-ligand conjugate.

Figure 1:
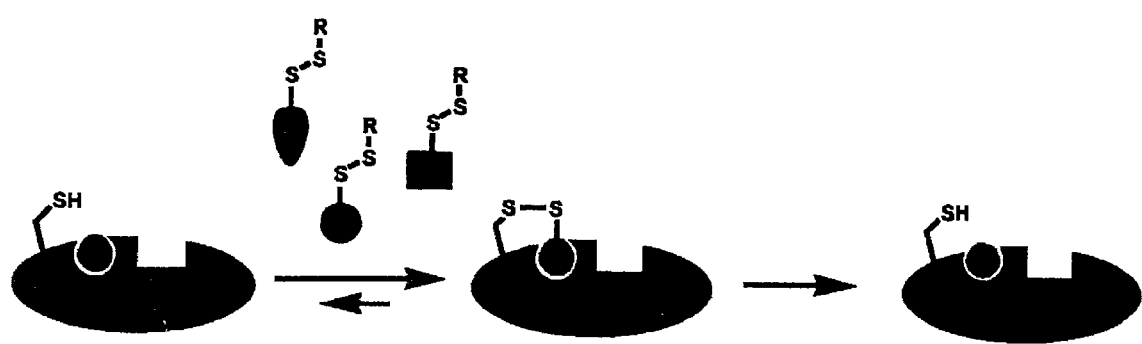
FIG. 1 is a schematic illustration of the basic tethering approach for identification of protein kinase inhibitor candidates.

Table 1 includes the type (Ser/Thr or Tyr), SwissProt an NCBI Accession numbers, length, and literature references, and SEQ ID NOs for the amino acid sequence of each protein kinase.

DETAILED DESCRIPTION OF THE PREFERRED EMBODIMENT

A. Definitions

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), and *Constituents of Signaling Pathways and their Chemistry*, New Science Press Ltd. 2002, provide one skilled in the art with a general guide to many of the terms used in the present application.

The term "protein kinase" is used to refer to an enzyme that catalyzes the transfer of the γ-phosphoryl group of ATP (ATP-$Mg^{2+}$ complex) to the oxygen atom of the hydroxyl group of serine, threonine or tyrosine residues in peptides and polypeptides (substrates).

The term "tyrosine kinase" is used to refer to an enzyme that catalyzes the transfer of the γ-phosphoryl group from an ATP-$Mg^{2+}$ complex to the oxygen atom of the hydroxyl group of tyrosine residues in another protein (substrate).

The term "serine-threonine kinase" is used to refer to an enzyme that catalyzes the transfer of the γ-phosphoryl group from an ATP-$Mg^{2+}$ complex to the oxygen atom of the hydroxyl group of serine/threonine residues in another protein (substrate).

The term "dual specificity kinase" is used to refer to kinases that have the ability to phosphorylate both tyrosine and serine/threonine residues of targeted protein substrates.

The term "phosphoryl donor" refers to an ATP-$Mg^{2+}$ complex, where the divalent $Mg^{2+}$ ion helps orient the nucleotide and shields the negative charges on its β- and γ phosphoryl groups, reducing electrostatic repulsion of attacking nucleophiles.

The term "phosphoacceptor" is used to refer to an atom with a free electron pair that serves as the nucleophile to attack ATP-$Mg^{2+}$ (e.g., the oxygen atom of the deprotonated hydroxyl groups of the side chains of Ser, Thr, or Tyr residues in a protein). For example, in the substrates of tyrosine kinases, the phosphoacceptor is the oxygen atom of the deprotonated hydroxyl group of the side chain of a tyrosine (Tyr) residue.

The term "allosteric" is used to refer to an effect that affects the activity of one part of an enzyme (such as an active site) by the binding of a molecule at a different site (regulatory site) at a different location on the enzyme.

"Allosteric binding sites" are contained in many enzymes and receptors. As a result of binding to allosteric binding sites, the interaction with the normal ligand may be either enhanced or reduced.

The term "activation loop" is used to a highly variable segment in protein kinases, situated between the DFG motif and the APE motif that contains the sites of activating phosphorylation in nearly all protein kinases.

The terms "catalytic loop" and "catalytic domain" are used interchangeably and refer to residues in conserved protein kinase motif VIb, which contains an invariant aspartic acid (Asp) residue that serves as the catalytic base in phosphotransfer and a nearly invariant arginine (Arg) residue, that makes electrostatic contact with phosphorylated residues in the activation loop, leading to the catalytically active state of the kinase.

The term "APE motif" is used to refer to the residues in conserved protein kinase motif VIII, which contains an invariant glutamic acid (Glu) residue that caps a small helix and an invariant proline (Pro) residue that terminates the same helix.

The term "DFG motif" is used to refer to the residues in conserved protein kinase motif VII, which contains an invariant aspartic acid (Asp) residue that helps mold the active site by forming hydrogen-bonds with the invariant lysine (Lys) in motif II and an invariant asparagine (Asn) residue in motif VIb, thus helping stabilize the conformation of the catalytic loop.

The term "inactive conformation," as used herein, refers to a catalytically inactive state of the protein. For example, a protein kinase is in an inactive conformation when the activation loop is not phosphorylated. A kinase is said to be locked in an inactive conformation when the kinase assumes the inactive conformation and does not phosphorylate its intended substrate.

An "inactivation site" on a protein kinase as used herein is any site on the kinase that, when occupied by a ligand, adversely affects the formation of the active conformation or otherwise impairs the kinase's ability to phosphorylate its intended substrate. Thus, without limitation, the site of interest may include amino acid residues participating in the phosphorylation of the activation loop, and/or in the presentation or transfer of the γ-phosphoryl group of ATP (ATP-$Mg^+$ complex) to the substrate of the protein kinase, and/or in any other interaction between the protein kinase and its substrate. By way of example, the site of interest on a protein kinase may include residues involved in catalytic function, such as residues within the catalytic loop (e.g. the ATP binding site including the catalytic triad), the substrate binding channel, any cofactor (e.g. Zn) binding site, residues involved in hydrogen bond donor/acceptor interactions, and residues involved in the "docking" of the substrate on its tyrosine kinase. The "inactivation site" may specifically include allosteric site(s) within the protein kinase.

A kinase inhibitor binds "preferentially" to an inactive conformation of a target kinase, if its binding affinity to the inactive conformation is at least two fold of its binding affinity to the active conformation.

The term "docking site", when used in connection with a substrate, refers to a sequence separate from the phosphoacceptor site in the substrate that binds with high affinity (typically about $K_d \leq 1$ μM) to the cognate protein kinase. Conversely, a "docking site" in a protein kinase is a surface separate from the active site that binds with high affinity to a substrate. As a result of docking, the effective local concentration of the substrate is increased, which in turn increases the efficacy and specificity of phosphorylation.

A "ligand" as defined herein is an entity which has an intrinsic binding affinity for the target. The ligand can be a molecule, or a portion of a molecule which binds the target. The ligands are typically small organic molecules which have an intrinsic binding affinity for the target molecule, but may also be other sequence-specific binding molecules, such as peptides (D-, L- or a mixture of D- and L-), peptidomimetics, complex carbohydrates or other oligomers of individual units or monomers which bind specifically to the target. The term also includes various derivatives and modifications that are introduced in order to enhance binding to the target. Ligands that inhibit a biological activity of a target molecule are called "inhibitors" of the target.

The term "inhibitor" is used in the broadest sense and includes any ligand that partially or fully blocks, inhibits or neutralizes a biological activity exhibited by a target protein kinase. In a similar manner, the term "agonist" is used in the broadest sense and includes any ligand that mimics a biological activity exhibited by a target protein kinase.

A "binding site of interest" on a target protein kinase as used herein is a site to which a specific ligand binds. Typically, the molecular interactions between the ligand and the binding site of interest on the target are non-covalent, and include hydrogen bonds, van der Waals interactions and electrostatic interactions. On target protein kinases, the binding site of interest broadly includes the amino acid residues involved in binding of the target to a molecule with which it forms a natural complex in vivo or in vitro.

"Small molecules" are usually less than about 10 kDa molecular weight, and include but are not limited to synthetic organic or inorganic compounds, peptides, (poly) nucleotides, (oligo)saccharides and the like. Small molecules specifically include small non-polymeric (i.e. not peptide or polypeptide) organic and inorganic molecules. Many pharmaceutical companies have extensive libraries of such molecules, which can be inconveniently screened by using the extended tethering approach of the present invention. Preferred small molecules have molecular weights of less than about 1000 Da, preferably about 750 Da, and most preferably about 500 Da.

The term "tether" as used herein refers to a structure which includes a moiety capable of forming a reversible covalent bond with a target kinase near or at a binding site of interest.

The phrase "Small Molecule Extender" (SME) as used herein refers to a small organic molecule having a molecular weight of from about 75 to about 1,500 daltons and having a first functional group reactive with a nucleophile or electrophile on a protein kinase target and a second functional group reactive with a ligand candidate or members of a library of ligand candidates. Preferably, the first functional group on one end of the SME is reactive with a nucleophile on a protein kinase (capable of forming an irreversible or reversible covalent bond with such nucleophile), and the reactive group at the other end of the SME is a free or protected thiol or a group that is a precursor of a free or protected thiol. In one embodiment, at least a portion of the small molecule extender is capable of forming a noncovalent bond with a first binding site of interest on the target protein kinase (i.e. has an inherent affinity for such first site of interest). Included within this definition are small organic (including non-polymeric) molecules containing metals such as Cd, Hg and Ag which may form a bond with the nucleophile e.g. SH of the target.

The phrase "reversible covalent bond" as used herein refers to a covalent bond which can be broken, preferably under conditions that do not denature the target. Examples include, without limitation, disulfides, Schiff-bases, thioesters, and the like.

The term "reactive group" with reference to a ligand is used to describe a chemical group or moiety providing a site at which a covalent bond with the ligand candidates (e.g. members of a library or small organic compounds) may be formed. Thus, the reactive group is chosen such that it is capable of forming a covalent bond with members of the library against which it is screened.

The phrases "modified to contain" and "modified to possess" are used interchangeably, and refer to making a mutant, variant or derivative of the target, or the reactive nucleophile or electrophile, including but not limited to chemical modifications. For example, in a protein one can substitute an amino acid residue having a side chain containing a nucleophile or electrophile for a wild-type residue. Another example is the conversion of the thiol group of a cysteine residue to an amine group.

The term "reactive nucleophile" as used herein refers to a nucleophile that is capable of forming a covalent bond with a compatible functional group on another molecule under conditions that do not denature or damage the target. The most relevant nucleophiles are thiols, alcohols, and amines. Similarly, the term "reactive electrophile" as used herein refers to an electrophile that is capable of forming a covalent bond with a compatible functional group on another molecule, preferably under conditions that do not denature or otherwise damage the target. The most relevant electrophiles are alkyl halides, imines, carbonyls, epoxides, aziridines, sulfonates, and hemiacetals.

A "first binding site of interest" on a target protein kinase, e.g. tyrosine kinase, refers to a site that can be contacted by at least a portion of the SME when it is covalently bound to the reactive nucleophile or electrophile. The first binding site of interest may, but does not have to possess the ability to form a bond with the SME.

The phrases "group reactive with the nucleophile," "nucleophile reactive group," "group reactive with an electrophile," and "electrophile reactive group," as used herein, refer to a functional group, e.g. on the SME, that can form a covalent bond with the nucleophile/electrophile on the target protein kinase under conditions that do not denature or otherwise damage the target.

The term "protected thiol" as used herein refers to a thiol that has been reacted with a group or molecule to form a covalent bond that renders it less reactive and which may be deprotected to regenerate a free thiol.

The phrase "adjusting the conditions" as used herein refers to subjecting a target protein kinase, such as a tyrosine kinase, to any individual, combination or series of reaction conditions or reagents necessary to cause a covalent bond to form between the ligand and the target, such as a nucleophile and the group reactive with the nucleophile on the SME, or to break a covalent bond already formed.

The term "covalent complex" as used herein refers to the combination of the SME and the target, e.g. target protein kinase which is both covalently bonded through the nucleophile/electrophile on the target with the group reactive with the nucleophile/electrophile on the SME, and non-covalently bonded through a portion of the small molecule extender and the first binding site of interest on the target.

The phrase "exchangeable disulfide linking group" as used herein refers to the library of molecules screened with the covalent complex displaying the thiol-containing small molecule extender, where each member of the library contains a disulfide group that can react with the thiol or protected thiol displayed on the covalent complex to form a new disulfide bond when the reaction conditions are adjusted to favor such thiol exchange.

The phase "highest affinity for the second binding site of interest" as used herein refers to the molecule having the greater thermodynamic stability toward the second site of interest on the target protein kinase that is preferentially selected from the library of disulfide-containing library members.

"Functional variants" of a molecule herein are variants having an activity in common with the reference molecule.

"Active" or "activity" means a qualitative biological and/or immunological property.

The term amino acid "alteration" includes amino acid substitutions, deletions, and/or insertions.

B. Detailed Description

In one aspect, the present invention provides a method for locking a protein kinase, such as a tyrosine kinase in an inactive conformation. In another aspect, the invention concerns the identification of inhibitors that preferentially bind to the inactive conformation of a target protein (e.g. tyrosine) kinase.

Protein Kinases

Protein kinases are enzymes that catalyze the transfer of the γ-phosphoryl group of ATP (ATP-$Mg^{2+}$ complex) to the oxygen atom of the hydroxyl group of serine, threonine or tyrosine residues in peptides and polypeptides (substrates). Protein kinases play a crucial role in signal transduction, cellular proliferation, differentiation, and various regulatory mechanisms. About 3% of the total coding sequences within the human genome encode protein kinases.

While there are many different subfamilies within the broad grouping of protein kinases, they all share a common feature; they all act as ATP phosphotransferases. It is, therefore, not surprising that protein kinases share a very high degree of structural similarity in the region where the ATP is bound, the ATP binding pocket. Structural analysis of many protein kinases shows that the catalytic domain, responsible for the phosphotransfer activity, is very highly conserved. This domain is comprised of two lobes that are connected by a flexible hinge region. The amino-terminal lobe is comprised of a single alpha helix and five beta sheets, while the carboxy-terminal lobe is comprised of a four alpha helix bundle and a flexible loop called the activation loop. The ATP binding pocket (also referred to as the purine binding pocket) is formed at the interface between these two lobes. There are several highly conserved residues, including an invariant catalytic triad consisting of a single lysine and two aspartic acids. The lysine of this catalytic triad is responsible for properly positioning the γ-phosphate of ATP with the hydroxyl group of the residue in the substrate to which it is transferred (phosphoacceptor residue), while the first aspartic acid acts as a general base catalyst in the phosphotransfer reaction. Strikingly, these three crucial residues span the two lobes of the catalytic domain. Furthermore, the two aspartic acid residues within the catalytic triad are separated from each other by a second flexible region called the activation loop. To allow the phosphotransfer reaction, the structure of a substrate must conform to the geometric constraints, surface electrostatics, and other features of the active site of the corresponding protein kinase. In turn, substrate binding can induce structural changes in a kinase that stimulate its catalytic activity. In particular, for enzyme—substrate interactions, residues within the activation loop and the catalytic loop need to be made available to make contacts with side chains in a substrate. Outside the conserved motifs crucial for catalytic activity (such as the ATP binding site), there are sequence differences in both loops that are critical for substrate recognition.

Structural States of Kinases and Allosteric Regulation of Kinase Activity

Proper regulation of protein kinase activity in a cell is critical, and kinases in a resting cell generally exist in an inactive conformation. In this inactive conformation, the catalytic triad may be oriented in a manner that will not catalyze phosphate transfer, the substrate binding cleft may be occluded by the flexible activation loop, or both. Relative to the active conformation, the amino- and carboxy-terminal lobes in the inactive conformation may-be opened up with resultant widening the active site cleft, twisted with resultant tortioning of the active site cleft, or both. Only when cells are confronted with specific stimuli do these kinases transition to a catalytically active conformation. Transition to the active conformation almost invariably involves phosphorylation of a residue in the activation loop, and subsequent formation of a salt bridge with a conserved arginine immediately adjacent to the catalytic aspartic acid. The resultant rearrangement of the activation loop, stabilized by this newly formed salt bridge, stabilizes a catalytically active conformation characterized by: proper amino- and carboxy-terminal domain orientation, proper orientation of the γ-phosphate of ATP to allow for phosphoryl transfer, opening of the substrate binding site, and a favorable electrostatic environment for the aspartic acid mediated base catalysis. While a common function dictates that the structure at the catalytic center is highly conserved among kinases in the active conformation, this is not the case with kinases in the inactive conformation. Indeed, kinases which have highly conserved active site architectures when in the active conformation may show considerable structural diversity in the same region when they are in the inactive conformation.

A list of representative protein kinases is provided in Table 1. This table includes the type (Ser/Thr or Tyr), SwissProt an NCBI Accession numbers, length, and literature references, and SEQ ID NOs for the amino acid sequence of each protein kinase. All references cited in Table 1 are hereby expressly incorporated by reference.

An important protein kinase target for drug development is EGFR1 (Ullrich et al, *Nature* 309:418–425 (1984)). EGFR1, a validated target for chemotherapeutics, is a cell surface receptor that contains an extracellular ligand binding domain and an intracellular tyrosine kinase domain. It is a key regulator of cell growth, survival, proliferation, and differentiation in epithelial cells. The binding of a number of ligands activates EGFR1, including EGF, TGF-α, amphiregulin, β-cellulin, and epiregulin. Ligand binding leads to receptor dimerization, autophosphorylation at a number of tyrosine residues including Tyr845 in the activation loop, and subsequent recruitment pf substrate proteins and stabilization of the active conformation of the kinase domain. EGFR1, in this activated state, phosphorylates a variety of downstream targets to propagate the extracellular stimulus of ligand binding to the eventual transcriptional upregulation of a variety of growth regulatory genes and resultant cell proliferation. In normal cells, EGFR1 regulates cell growth in a tightly controlled manner. However, overexpression of EGFR1 has been observed in a large number of tumor types, including breast, bladder, colon, lung, squamous cell head and neck, ovarian, and pancreatic cancers. A clear role for EGFR1 upregulation in the initiation and progression of a variety of cancers has lead to an intense search for therapeutics that inhibit signal transduction via EGFR1. In one embodiment, the invention is intended to cover dual specificity kinases and other protein kinases as is known in the art.

Another important family of protein kinases is the Src family. First of all, the Src family kinases, especially Lck, are well validated casual agents in a variety of cancers. Second, no current small molecule therapeutics effectively target Src kinases in humans. Finally, Src family kinases are the best structurally characterized of all tyrosine kinases.

A representative member of this family, Lck (Perlmutter et al., *J. Cell. Biochem.* 38:117–126 (1988)), is a cytosolic tyrosine kinase, which is expressed primarily in T-cells where it is centrally involved in transducing a signal from the T-cell receptor (TCR). Lck is found associated when the inner plasma membrane where it phosphorylates the CD3 and zeta chains of the TCR in response to antigenic stimulation, initiating a cascade of signal transduction events that eventually result in a clonal proliferation of the stimulated T-cell. Thus, Lck is well known as a therapeutic target for immunological disorders, such as graft versus host disease. However, Lck is also validated cancer therapeutic target. In humans, some neuroblastomas and non-Hodgkin's lymphomas show chromosomal abnormalities and translocations in the region of the Lck gene. In at least one case that has been molecularly characterized, the "derivative I chromosome" translocation focuses the transcriptional regulatory region of the beta T-cell receptor gene with the coding sequence of Lck, resulting in increased levels of Lck kinase in patients with T-cell acute lymphoblastic leukemia, much like the Philadelphia Chromosome translocation which upregulates Abl expression causing CML.

In addition to their value as therapeutic targets, Src family kinases are extremely well characterized structurally. Crystal coordinates are publicly available for three family members, hematopoietic cell kinase (Hck), Src, and Lck, covering both the active and the inactive conformational. Furthermore, Lck is known to express well in baculovirus and to crystallize readily.

Identification of Protein Kinase Inhibitors Preferentially Binding to the Inactive Conformation In an important aspect, the present invention provides methods for identifying protein kinase inhibitors that specifically target kinases in the inactive conformation. There are at least three principle reasons of screening for such inhibitors: (1) the majority of kinases in a cell exist in this conformation; (2) relative to the active conformation, kinases in the inactive conformation exhibit greater structural diversity; and (3) opening and tortioning of the active site region in this conformation often results in a decreased affinity for ATP, the primary intracellular competitor for small molecule kinase inhibitors.

Traditional high throughput screening techniques detect phosphoryl transfer to a substrate molecule by an activated kinase. As such, these assays primarily detect inhibitors that bind to the active conformation of kinases and make the identification of inhibitors targeting the inactive conformation very unlikely. In contrast, the present invention provides an efficient, high-throughput method to identify kinase inhibitors that bind preferentially to the inactive conformation of protein kinases. This method includes the step of locking the protein kinase in its inactive conformation, and using the powerful technique of covalent tethering to identify inhibitors specifically targeting the active kinase conformation.

a. Locking Kinases in an Inactive Conformation

In order to identify kinase inhibitors preferentially binding to the inactive conformation of the target kinase, according to the invention a target protein kinase is locked in a catalytically inactive conformation by introducing one or more amino acid alterations at an inactivating site such that the kinase cannot exert its kinase activity, in most cases because the alteration inhibits the phosphorylation of the activation loop. The alteration may target any site participating (directly or indirectly) in the formation of a catalytically active state of the kinase. For example, the alteration may take place at or near amino acid residues participating in the phosphorylation of the activation loop, and/or in the presentation or transfer of the γ-phosphoryl group of ATP to the substrate of the protein kinase, and/or in any other interaction between the protein kinase and its substrate. Alterations within or in the vicinity of the catalytic loop, e.g. the ATP binding site including the catalytic triad, the substrate binding channel, a cofactor binding site, if any, residues involved in hydrogen bond/acceptor interactions, and/or docking of the substrate on the tyrosine kinase are particularly preferred.

For purposes of shorthand designation of the protein kinase variants described herein, it is noted that numbers refer to the position of the altered amino acid residue along the amino acid sequences of respective wild-type protein kinases. Amino acid identification uses the single-letter alphabet of amino acids, as follows:

| Asp | D | Aspartic acid |
|---|---|---|
| Ile | I | Isoleucine |
| Thr | T | Threonine |
| Leu | L | Leucine |
| Ser | S | Serine |
| Tyr | Y | Tyrosine |
| Glu | E | Glutamic acid |
| Phe | F | Phenylalanine |
| Pro | P | Proline |
| His | H | Histidine |
| Gly | G | Glycine |
| Lys | K | Lysine |
| Ala | A | Alanine |
| Arg | R | Arginine |
| Cys | C | Cysteine |
| Trp | W | Tryptophan |
| Val | V | Valine |
| Gln | Q | Glutamine |
| Met | M | Methionine |
| Asn | N | Asparagine |

The designation for a substitution variant herein consists of a letter followed by a number followed by a letter. The first (leftmost) letter designates the amino acid in the wild-type protein kinase. In particular, variants of the protein kinases listed in Table 1 are designated with reference to the respective SEQ ID NOs listed in that table. The number refers to the amino acid position where the amino acid substitution is being made, and the second (right-hand) letter designates the amino acid that is used to replace the wild-type amino acid at that position. The designation for an insertion variant consists of the letter i followed by a number designating the position of the residue in wild-type protein kinase before which the insertion starts, followed by one or more capital letters indicating, inclusively, the insertion to be made. The designation for a deletion variant consists of the letter d followed by the number of the start position of the deletion to the number of the end position of the deletion, with the positions being based on the wild-type protein kinase. Multiple alterations are separated by a comma in the notation for ease of reading them.

In one embodiment, the kinase is locked in an inactive conformation by mutating one or more residues selected from the group consisting of the invariant aspartic acid in the catalytic loop; the arginine in the catalytic loop; the invariant aspartic acid in the DFG motif; and the invariant lysine in motif II. In preferred embodiments, one or more of these residues are substituted by an alanine residue.

Illustrative examples of kinase mutants where the invariant aspartic acid residue in the catalytic loop is mutated to X (wherein X denotes any amino acid residue other than aspartic acid) include:

D274X AKT1; D275X AKT2; D271X AKT3; D359X BLK; D521X BTK; D128X CDK1; D127X CDK2; D127X CDK3; D140X CDK4; D126X CDK5; D145X CDK6; D137X CDK7; D151X CDK8; D149X CDK9; D314X CSK; D837X EGFR1; D845X ERB2; D843X ERB4; D166X ERK1; D149X ERK2; D152X ERK3; D149X ERK4; D181X ERK5; D153X ERK6; D546X FAK1; D623X FGFR1; D626X FGFR2; D617X FGFR3; D612X FGFR4; D389X FYN; D381X HCK; D144X IKK-a; D145X IKK-b; D135X IKK-e; D991X JAK1; D976X JAK2; D949X JAK3; D151X JNK1; D151X JNK2; D189X JNK3; D363X Lck; D366X LYN; D150X MAPK; D515X NIK; D389X PAK1; D368X PAK2; D387X PAK3; D440X PAK4; D568X PAK5; D818X PDGFR-a; D826X PDGFR-b; D167X PIM1; D429X A-Raf; D575X B-Raf; D468X C-Raf; D388X SRC; D382X SRC2; D811X STK1; D494X SYK; D489X TEC; D333X TGFR1; D379X TGFR2; D979X TIE1; D964X TIE2; D1022X VEGFR1; D1028X VEGFR2; D1037X-VEGFR3; D386X YES; D461X ZAP-70.

Illustrative examples of kinase mutants where the arginine residue in the catalytic loop is mutated to X (wherein X denotes any amino acid residue other than arginine) include:

R273X AKT1; R274X AKT2; R270X AKT3; R358X BLK; R520X BTK; R127X CDK1; R126X CDK2; R126X CDK3; R139X CDK4; R125X CDK5; R144X CDK6; R136X CDK7; R150X CDK8; R148X CDK9; R313X CSK; R836X EGFR1; R844X ERB2; R842X ERB4; R165X ERK1; R148X ERK2; R151X ERK3; R148X ERK4; R180X ERK5; R152X ERK6; R545X FAK1; R622X FGFR1; R625X FGFR2; R616X FGFR3; R611X FGFR4; R388X FYN; R380X HCK; R143X IKK-a; R144X IKK-b; R134X IKK-e; R990X JAK1; R975X JAK2; R948X JAK3; R150X JNK1; R150X JNK2; R188X JNK3; R362X Lck; R365X LYN; R149X MAPK; R514X NIK; R388X PAK1; R367X PAK2; R386X PAK3; R439X PAK4; R567X PAK5; R817X PDGFR-a; R825X PDGFR-b; R166X PM1; R428X A-Raf; R574X B-Raf; R467X C-Raf; R387X SRC; R381X SRC2; R810X STK1; R493X SYK; R488X TEC; R322X TGFR1; R378X TGFR2; R978X TIE1; R963X TIE2; R1021 VEGFR1; R1027X VEGFR2; R1036X VEGFR3; R395X YES; R460X ZAP-70.

Illustrative examples of kinase mutants where the invariant aspartic acid in the DFG motif is mutated to X (wherein X denotes any amino acid residue other than aspartic acid) include:

D292X AKT1; D293X AKT2; D289X AKT3; D377X BLK; D539X BTK; D146X CDK1; D145X CDK2; D145X CDK3; D158X CDK4; D144X CDK5; D163X CDK6; D155X CDK7; D173X CDK8; D167X CDK9; D332X CSK; D855X EGFR1; D863X ERB2; D861X ERB4; D184X ERK1; D167X ERK2; D171X ERK3; D168X ERK4; D199X ERK5; D171X ERK6; D564X FAK1; D641X FGFR1; D644X FGFR2; D635X FGFR3; D630X FGFR4; D407X FYN; D399X HCK; D165X IKK-a; D166X IKK-b; D157X IKK-e; D1009X JAK1; D994X JAK2; D967X JAK3; D169X JNK1; D169X JNK2; D207X JNK3; D381X Lck; D384X LYN; D168X MAPK; D534X NIK; D407X PAK1; D386X PAK2; D405X PAK3; D458X PAK4; D586X PAK5; D836X PDGFR-a; D844X PDGFR-b;

D186X PIM1; D447X A-Raf; D593X B-Raf; D486X C-Raf; D406X SRC; D400X SRC2; D829X STK1; D512X SYK; D507X TEC; D351X TGFR1; D397X TGFR2; D997X TIE1; D982X TIE2; D1040X VEGFR1; D1046X VEGFR2; D1055X VEGFR3; D414X YES; D479X ZAP-70.

Illustrative examples of kinase mutants where the invariant lysine in motif II is mutated to X (wherein X denotes any amino acid residue other than lysine) include:

K179X AKT1; K181X AKT2; K177X AKT3; K268X BLK; K430X BTK; K33X CDK1; K33X CDK2; K33X CDK3; K35X CDK4; K33X CDK5; K43X CDK6; K41X CDK7; K52X CDK8; K48X CDK9; K222X CSK; K745X EGFR1; K753X ERB2; K751X ERB4; K71X ERK1; K54X ERK2; K49X ERK3; K49X ERK4; K83X ERK5; K56X ERK6; K454X FAK1; K514X FGFR1; K517X FGFR2; K508X FGFR3; K503X FGFR4; K298X FYN; K290X HCK; K44X IKK-a; K44X IKK-b; K38X IKK-e; K896X JAK1; K882X JAK2; K855X JAK3; K55X JNK1; K55X JNK2; K93X JNK3; K272X Lck; K274X LYN; K53X MAPK; K429X NIK; K299X PAK1; K228X PAK2; K297X PAK3; K350X PAK4; K478X PAK5; K627X PDGFR-a; K634X PDGFR-b; K67X PIM1; K336X A-Raf; K482X B-Raf; K375X C-Raf; L297X SRC; K291X SRC2; K644X STK1; K402X SYK; K398X TEC; K232X TGFR1; K277X TGFR2; K870X TIE1; K855X TIE2; K862X VEGFR1; K868X VEGFR2; K879X VEGFR3; K305X YES; K369 ZAP-70.

It will be appreciated that two or more of the foregoing or similar mutations can be combined to produce inactive kinase variants. Protein kinase variants comprising two or more of the above-listed mutations in any combination, including double, triple and quadruple mutants, are specifically within the scope herein.

Those skilled in the art are well aware of various recombinant, chemical, synthesis and/or other techniques that can be routinely employed to modify a protein kinase of interest such that it possesses a desired number of free thiol groups that are available for covalent binding to a ligand candidate comprising a free thiol group. Such techniques include, for example, site-directed mutagenesis of the nucleic acid sequence encoding the target protein kinase. Particularly preferred is site-directed mutagenesis using polymerase chain reaction (PCR) amplification (see, for example, U.S. Pat. No. 4,683,195 issued Jul. 28, 1987; and *Current Protocols In Molecular Biology*, Chapter 15 (Ausubel et al., ed., 1991). Other site-directed mutagenesis techniques are also well known in the art and are described, for example, in the following publications: Ausubel et al., supra, Chapter 8; *Molecular Cloning: A Laboratory Manual.*, 2$^{nd}$ edition (Sambrook et al., 1989); Zoller et al., *Methods Enzymol.* 100:468–500 (1983); Zoller & Smith, *DNA* 3:479–488 (1984); Zoller et al., *Nucl. Acids Res.*, 10:6487 (1987); Brake et al., *Proc. Natl. Acad. Sci. USA* 81:4642–4646 (1984); Botstein et al., *Science* 229:1193 (1985); Kunkel et al., *Methods Enzymol.* 154:367–82 (1987), Adelman et al., *DNA* 2:183 (1983); and Carter et al., *Nucl. Acids Res.*, 13:4331 (1986). Cassette mutagenesis (Wells et al., *Gene*, 34:315 [1985]), and restriction selection mutagenesis (Wells et al., *Philos. Trans. R. Soc. London SerA*, 317:415 [1986]) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

The nucleic acid encoding the desired kinase mutant is then inserted into a replicable expression vector for further cloning or expression. Expression and cloning vectors are well known in the art and contain a nucleic acid sequence that enables the vector to replicate in one or more selected host cells. The selection of an appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence. Suitable expression vectors, for use in combination with a variety of host cells, are well known in the art and are commercially available.

The protein kinase mutants can be produced in prokaryotic or eukaryotic host cells, including bacterial hosts, such as *E. coli*, eukaryotic microbes, such as filamentous fungi or yeast, and host cells derived from multicellular organisms. Examples of invertebrate cells include insect cells such as Drosophila S2 and Spodoptera Sf9, as well as plant cells, such as cell cultures of cotton, corn, potato, soybean, petunia, tomato, and tobacco. Numerous baculoviral strains and corresponding permissive insect host cells, e.g. cells from *Spodoptera frugiperda, Aedes aegypti, Aedes albopictus, Drosophila melanogaster*, and *Bombyx mori* have been identified. A variety of viral strains for transfection of insect host cells are publicly available, including for example variants of *Autographa California* NPV and *Bombyx mori* NPV strains. Further host cells include vertebrate cells. Examples of suitable mammalin host cell lines include, without limitation, human embryonic kidney cell line 293, Chinese hamster ovary (CHO) cells, etc.

Host cells are transformed with the expression or cloning vectors encoding the desired protein kinase mutants, and cultured in conventional nutrient media modified as appropriate for inducing promoters, selecting transformants, or amplifying the genes encoding the desired sequences.

b. Covalent Tethering

According to the present invention, the protein kinases locked in inactive conformation are used to screen for inhibitors preferentially binding to the inactive conformation by using a covalent tethering approach. This approach differs significantly from the conventional drug discovery route that is based on the synthesis of large organic compound libraries, and subsequent screening, usually for inhibitory activity against the target protein kinase. Following the covalent tethering approach to identify small molecule inhibitors of a target kinase, first smaller, drug-like fragments (monophores) are tested for binding activity to the desired kinase containing or modified to contain a tether, which are then used to synthesize conjugates of fragments that bind in non-overlapping sites to generate molecules that no longer require the tether for binding. The linking or merging of multiple fragments effectively results in the combination of individual binding energies, plus a favorable entropic term due to the high local concentration of the second fragment once the first fragment is bound, yielding dissociation constants at levels similar to a typical medicinal chemistry starting point. In quantitative terms, this means that two fragments, each having ~mM dissociation constants ($K_d$) can be combined to form a molecule having a ~μM $K_d$. This "screen then link" strategy is much more efficient than the traditional approach, allowing a much larger survey of chemical diversity space than is achievable by screening even the largest compound libraries.

In a preferred embodiment, molecules binding to the target protein kinase locked in an inactive conformation are identified using the tethering approach recently reported by Erlanson et al, *Proc. Nat. Acad. Sci. USA* 97:9367–9372 (2000). This strategy is suitable for rapid and reliable identification of small soluble drug fragments that bind with low affinity to a specifically targeted site on a protein or other macromolecule, using an intermediary disulfide "tether." According to a preferred embodiment of this approach, a library of disulfide-containing molecules is allowed to react with a cysteine-containing target protein under partially reducing conditions that promote rapid thiol exchange. If a molecule has even weak affinity for the target protein, the disulfide bond ("tether") linking the molecule to the target protein will be entropically stabilized. The disulfide-tethered fragments can then be identified by a variety of methods, including mass spectrometry (MS), and their affinity improved by traditional approaches upon removal of the disulfide tether. See also PCT Publication No. WO 00/00823, published on Jan. 6, 2000, the entire disclosure of which is hereby expressly incorporated by reference.

Briefly, according to this preferred embodiment of the basic covalent tethering approach, a disulfide bond is formed between the target protein kinase molecule locked in inactive configuration and a ligand candidate to yield a target protein-ligand conjugate, and the ligand present in the conjugate is identified. Optionally, the target protein is contacted with a ligand candidate (preferably a library of ligand candidates) in the presence of a reducing agent, such as 2-mercaptoethanol, or cysteamine. Most of the library members will have little or no intrinsic affinity for the target molecule, and thus by mass action the equilibrium will lie toward the unbound target molecule. However, if a library member does show intrinsic affinity for the target molecule, the equilibrium will shift toward the target molecule, having attached to it the library member with a disulfide tether.

The target contains, or is modified to contain, free or protected thiol groups, preferably not more than about 5 thiol groups, more preferably not more than about 2 thiol groups, more preferably not more than one free thiol group. The target protein kinase of interest may be initially obtained or selected such that it already possesses the desired number of thiol groups, or may be modified to possess the desired number of thiol groups.

In the simplified schematic shown in FIG. 1, a hypothetical target protein has two sites at which ligand candidates (candidate inhibitor fragments) may bind. If only one fragment out of 10,000 were to bind at each site, one would need to screen a collection of $10,000 \times 10,000 = 10^8$ linked fragments to find a good lead molecule. This is about 100-times moles compounds than are typically found in a small molecule library. Yet it is reasonable to expect that two such compounds would be found by screening the simplified library of about 10,000 fragments (monophores) against multiple cysteine mutant sites, following the tethering approach of the present invention. Furthermore, it would be expected that such fragments can be effectively linked, given the knowledge that their binding site lies in the vicinity of the cysteine tethering site.

As noted above, in certain embodiments the kinase of interest possesses at least one naturally occurring cysteine that is amenable to basic tethering. Illustrative examples of kinases that include naturally occurring cysteines that are amenable to basic tethering include: CDK5 (C53); ERK1 (C183); ERK2 (C166); ERK3 (C28); FGFR1 (C488); FGFR2 (C491); FGFR3 (C482); FGFR4 (C477); NIK (C533); PDGFR-a (C835); PDGFR-b (C843); SRC (C279); SRC2 (C273); STK1 (C828); TGFR2 (C396); VEGFR1 (C1039); VEGFR2 (C1045); VEGFR3 (C1054); YES (C287); ZAP-70 (C346).

In other embodiments, one or more amino acids are mutated into a cysteine. In general, cysteine mutants are made using the following guidelines.

Broadly, the "binding site of interest" on a particular target, such as a target protein kinase, is defined by the residues that are involved in binding of the target to a molecule with which it forms a natural complex in vivo or in vitro. If the target is a peptide, polypeptide, or protein, the site of interest is defined by the amino acid residues that participate in binding to (usually by non-covalent association) to a ligand of the target.

When the target biological molecule is an enzyme, the binding site of interest can include amino acids that make contact with, or lie within, about 4 angstroms of a bound substrate, inhibitor, activator, cofactor or allosteric modulator of the enzyme. For protein kinases, the binding site of interest includes the substrate-binding channel and the ATP binding site.

The target protein kinases either contain, or are modified to contain, a reactive residue at or near a binding site of interest. Preferably, the target tyrosine kinases contain or are modified to contain a thiol-containing amino acid residue at or near a binding site of interest. In this case, after a protein kinase is selected, the binding site of interest is calculated. Once the binding site of interest is known, a process of determining which amino acid residue within, or near, the binding site of interest to modify is undertaken. For example, one preferred modification results in substituting a cysteine residue for another amino acid residue located near the binding site of interest.

The choice of which residue within, or near, the binding site of interest to modify is determined based on the following selection criteria. First, a three dimensional description of the target protein kinase is obtained from one of several well-known sources. For example, the tertiary structure of many protein kinases has been determined through x-ray crystallography experiments. These x-ray structures are available from a wide variety of sources, such as the Protein Databank (PDB) which can be found on the Internet at www.rcsb.org Tertiary structures can also be found in the Protein Structure Database (PSdb) which is located at the Pittsburg Supercomputer Center at www.psc.com In addition, the tertiary structure of many proteins, and protein complexes, including protein kinases, has been determined through computer-based modeling approaches. Thus, models of protein three-dimensional conformations are now widely available.

Once the three dimensional structure of the target protein kinase is known, or modeled based on homology to a known structure, a measurement is made based on a structural model of the wild-type, or a variant form locked in an inactive configuration, from any atom of an amino acid within the site of interest across the surface of the protein for a distance of approximately 10 angstroms. Since the goal is to identify protein kinase inhibitors that preferentially bind to an inactive conformation of the target protein kinase, preferably the site(s) of interest is/are identified base upon a structural model of the protein kinase locked in an inactive conformation. The binding sites (pockets) presented by such inactive conformations are often significantly different from the binding sites (pockets) present on the wild-type structure. Tethered variants of the inactive protein kinases, which have been modified to contain the desired reactive groups (e.g. thiol groups, or thiol-containing residues) are based on the identification of one or more wild-type amino acid(s) on the surface of the target protein kinase that fall within that approximate 10-angstrom radius from the binding site of interest (which may have been first revealed as a result of the alteration resulting the stabilization of an inactive conformation). For the purposes of this measurement, any amino acid having at least one atom falling within the about 10 angstrom radius from any atom of an amino acid within the binding site of interest is a potential residue to be modified to a thiol containing residue.

Preferred residues for modification are those that are solvent-accessible. Solvent accessibility may be calculated from structural models using standard numeric (Lee, B. & Richards, F. M. *J. Mol. Biol* 55:379–400 (1971); Shrake, A. & Rupley, J. A. *J. Mol. Biol* 79:351–371 (1973)) or analytical (Connolly, M. L. *Science* 221:709–713 (1983); Richmond, T. J. *J. Mol. Biol.* 178:63–89 (1984)) methods. For example, a potential cysteine variant is considered solvent-accessible if the combined surface area of the carbon-beta (CB), or sulfur-gamma (SG) is greater than 21 $Å^2$ when calculated by the method of Lee and Richards (Lee, B. & Richards, F. M. *J. Mol. Biol* 55:379–400 (1971)). This value represents approximately 33% of the theoretical surface area accessible to a cysteine side-chain as described by Creamer et al. (Creamer, T. P. et al. *Biochemistry* 34:16245–16250 (1995)).

It is also preferred that the residue to be mutated to cysteine, or another thiol-containing amino acid residue for tethering purposes, not participate in hydrogen-bonding with backbone atoms or, that at most, it interacts with the backbone through only one hydrogen bond. Wild-type residues where the side-chain participates in multiple (>1) hydrogen bonds with other side-chains are also less preferred. Variants for which all standard rotamers (chi1 angle of −60°, 60°, or 180°) can introduce unfavorable steric contacts with the N, CA, C, O, or CB atoms of any other residue are also less preferred. Unfavorable contacts are defined as interatomic distances that are less than 80% of the sum of the van der Waals radii of the participating atoms.

Additionally, residues found on convex "ridge" regions adjacent to concave surfaces are more preferred while those within concave regions are less preferred cysteine residues to be modified. Convexity and concavity can be calculated based on surface vectors (Duncan, B. S. & Olson, A. J. *Biopolymers* 33:219–229 (1993)) or by determining the accessibility of water probes placed along the molecular surface (Nicholls, A. et al. *Proteins* 11:281–296 (1991); Brady, G. P., Jr. & Stouten, P. F. *J. Comput. Aided Mol. Des.* 14:383–401 (2000)). Residues possessing a backbone conformation that is nominally forbidden for L-amino acids (Ramachandran, G. N. et al. *J. Mol. Biol.* 7:95–99 (1963); Ramachandran, G. N. & Sasisekharahn, V. *Adv. Prot. Chem.* 23:283–437 (1968)) are less preferred targets for modification to a cysteine. Forbidden conformations commonly feature a positive value of the phi angle.

Other preferred variants are those which, when mutated to cysteine and linked via a disulfide bond to an alkyl tether, would possess a conformation that directs the atoms of that tether towards the binding site of interest. Two general procedures can be used to identify these preferred variants. In the first procedure, a search is made of unique structures (Hobohm, U. et al. *Protein Science* 1:409–417 (1992)) in the Protein Databank (Berman, H. M. et al. *Nucleic Acids Research* 28:235–242 (2000)) to identify structural fragments containing a disulfide-bonded cysteine at position j in which the backbone atoms of residues j−1, j, and j+1 of the fragment can be superimposed on the backbone atoms of residues i−1, i, and i+1 of the target molecule with an RMSD of less than 0.75 $Å^2$. If fragments are identified that place the CB atom of the residue disulfide-bonded to the cysteine at position j closer to any atom of the site of interest than the CB atom of residue i (when mutated to cysteine), position i is considered preferred. In an alternative procedure, the residue at position i is computationally "mutated" to a cysteine and capped with an S-Methyl group via a disulfide bond.

Further details of identifying binding site(s) of interest for tethering purposes on the protein kinase targets of the invention are provided in co-pending application Ser. No. 10/214,419, filed on Aug. 5, 2002, which claims priority from provisional patent application Ser. No. 60/310,725, filed on Aug. 7, 2001, the entire disclosures of both applications of which are hereby expressly incorporated by reference.

Illustrative examples of cysteine mutants of the kinases listed in Table 1 that are suitable for tethering include the following:

For the AKT1 kinase, the following cysteine mutants are illustrative examples of mutants that are used for tethering: L156C AKT1; K158C AKT1; T160C AKT1; F161C AKT1; K194C AKT1; E198C AKT1; M227C AKT1; E278C AKT1; T291C AKT1; K297C AKT1.

For the AKT2 kinase, the following cysteine mutants are illustrative examples of mutants that are used for tethering: K158C AKT2; K160C AKT2; T162C AKT2; F163C AKT2; H196C AKT2; E200C AKT2; M229C AKT2; E279C AKT2; T292C AKT2; K298C AKT2.

For the AKT3 kinase, the following cysteine mutants are illustrative examples of mutants that are used for tethering: L154C AKT3; K156C AKT3; T158C AKT3; F159C AKT3; H192C AKT3; E196C AKT3; M225C AKT3; E274C AKT3; T288C AKT3; K294C AKT3.

For the BLK kinase, the following cysteine mutants are illustrative examples of mutants that are used for tethering: L246C BLK; S248C BLK; Q151C BLK; F251C BLK; A279C BLK; E283C BLK; T311C BLK; A363C BLK; A376C BLK; R382C BLK.

For the BTK kinase, the following cysteine mutants are illustrative examples of mutants that re used for tethering: L408C BTK; T410C BTK; Q313C BTK; F413C BTK; E441C BTK; E445C BTK; T474C BTK; R525C BTK; S538C BTK; R544C BTK.

For the CDK1 kinase, the following cysteine mutants are illustrative examples of mutants that are used for tethering: I10C CDK1; E12C CDK1; T14C CDK1; Y15C CDK1; S53C CDK1; E57C CDK1; F80C CDK1; Q432C CDK1; A145C CDK1; R151C CDK1.

For the CDK2 kinase, the following cysteine mutants are illustrative examples of mutants that are used for tethering: I10C CDK2; E12C CDK2; T14C CDK2; Y15C CDK2; S53C CDK2; E57C CDK2; F80C CDK2; Q431C CDK2; A144C CDK2; R150C CDK2.

For the CDK3 kinase, the following cysteine mutants are illustrative examples of mutants that are used for tethering: I10C CDK3; E12C CDK3; T14C CDK3; Y15C CDK3; S53C CDK3; E57C CDK3; F80C CDK3; Q431C CDK3; A144C CDK3; R150C CDK3.

For the CDK4 kinase, the following cysteine mutants are illustrative examples of mutants that are used for tethering: I12C CDK4; V14C CDK4; A16C CDK4; Y17C CDK4; R55C CDK4; L59C CDK4; F93C CDK4; E153C CDK4; A157C CDK4; R163C CDK4.

For the CDK5 kinase, the following cysteine mutants are illustrative examples of mutants that are used for tethering: I10C CDK5; E12C CDK5; T14C CDK5; Y15C CDK5; E57C CDK5; F80C CDK5; Q430C CDK5; A143C CDK5; R149C CDK5.

For the CDK6 kinase, the following cysteine mutants are illustrative examples of mutants that are used for tethering: I19C CDK6; E21C CDK6; A23C CDK6; Y24C CDK6; A63C CDK6; H$_{67}$C CDK6; F98C CDK6; Q449C CDK6; A162C CDK6; R168C CDK6.

For the CDK7 kinase, the following cysteine mutants are illustrative examples of mutants that are used for tethering: L18C CDK7; E20C CDK7; Q22C CDK7; F23C CDK7; R61C CDK7; L65C CDK7; F91C CDK7; N141C CDK7; A154C CDK7; K161C CDK7.

For the CDK8 kinase, the following cysteine mutants are illustrative examples of mutants that are used for tethering: V27C CDK8; R29C CDK8; T31C CDK8; Y32C CDK8; R65C CDK8; L69C CDK8; F97C CDK8; A155C CDK8; A172C CDK8; H178C CDK8.

For the CDK9 kinase, the following cysteine mutants are illustrative examples of mutants that are used for tethering: I25C CDK9; Q27C CDK9; T29C CDK9; F30C CDK9; R65C CDK9; I69C CDK9; F103C CDK9; A153C CDK9; A166C CDK9; R172C CDK9.

For the CSK kinase, the following cysteine mutants are illustrative examples of mutants that are used for tethering: I201C CSK; K203C CSK; E205C CSK; F206C CSK; A232C CSK; E236C CSK; T266C CSK; R318C CSK; S331C CSK; K337C CSK.

For the EGFR1 kinase, the following cysteine mutants are illustrative examples of mutants that are used for tethering: L718C EGFR1; S720C EGFR1; A722C EGFR1; F723C EGFR1; E758C EGFR1; E762C EGFR1; T790C EGFR1; R841C EGFR1; T854C EGFR1; K860C EGFR1.

For the ERB2 (also referred to as ErbB2) kinase, the following cysteine mutants are illustrative examples of mutants that are used for tethering: L726C ERB2; S728C ERB2; A730C ERB2; F731 C ERB2; E766C ERB2; E770C ERB2; T798C ERB2R849C ERB2; T862C ERB2; R868C ERB2.

For the ERB4 (also referred to as ErbB4) kinase, the following cysteine mutants are illustrative examples of mutants that are used for tethering: L724C ERB4; S726C ERB4; A728C ERB4; F729C ERB4; E764C ERB4; E768C ERB4; T796C ERB4; R847C ERB4; T860C ERB4; R864C ERB4.

For the ERK1 kinase, the following cysteine mutants are illustrative examples of mutants that are used for tethering: I48C ERK1; E50C ERK1; A52C ERK1; Y53C ERK1; R84C ERK1; E88C ERK1; Q122C ERK1; S170C ERK1; R189C ERK1.

For the ERK2 kinase, the following cysteine mutants are illustrative examples of mutants that are used for tethering: I31C ERK2; E33C ERK2; A35C ERK2; Y36C ERK2; R67C ERK2; E71C ERK2; Q105C ERK2; S153C ERK2; R172C ERK2.

For the ERK3 kinase, the following cysteine mutants are illustrative examples of mutants that are used for tethering: L26C ERK3; G30C ERK3; N31C ERK3; H$_{61}$C ERK3; E65C ERK3; Q108C ERK3; A156C ERK3; G170C ERK3; R176C ERK3.

For the ERK4 kinase, the following cysteine mutants are illustrative examples of mutants that are used for tethering: L26C ERK4; F28C ERK4; V30C ERK4; N31C ERK4; H$_{61}$C ERK4; E65C ERK4; Q105C ERK4; A153C ERK4; G167C ERK4; R173C ERK4.

For the ERK5 kinase, the following cysteine mutants are illustrative examples of mutants that are used for tethering: I60C ERK5; N62C ERK5; A64C ERK5; Y65C ERK5; R97C ERK5; E101C ERK5; L136C ERK5; S185C ERK5; G198C ERK5; R204C ERK5.

For the ERK6 kinase, the following cysteine mutants are illustrative examples of mutants that are used for tethering: V33C ERK6; S35C ERK6; A37C ERK6; Y38C ERK6; R70C ERK6; E74C ERK6; M109C ERK6; G157C ERK6; L170C ERK6; R176C ERK6.

For the FAK1 kinase, the following cysteine mutants are illustrative examples of mutants that are used for tethering: I428C FAK1; E430C FAK2; Q333C FAK1; F433C FAK1; K467C FAK1; E471C FAK1; M499C FAK1; R550C FAK1; G563C FAK1; R569C FAK1.

For the FGFR1 kinase, the following cysteine mutants are illustrative examples of mutants that are used for tethering: L484C FGFR1; E486C FGFR1; F489C FGFR1; L528C FGFR1; M532C FGFR1; V561C FGFR1; R627C FGFR1; A640C FGFR1; R646C FGFR1.

For the FGFR2 kinase, the following cysteine mutants are illustrative examples of mutants that are used for tethering: L487C FGFR2; E489C FGFR2; F492C FGFR2; L531C FGFR2; M535C FGFR2; V564C FGFR2; R630C FGFR2; A643C FGFR2; R649C FGFR2.

For the FGFR3 kinase, the following cysteine mutants are illustrative examples of mutants that are used for tethering: L478C FGFR3; E480C FGFR3; F483C FGFR3; L522C FGFR3; M526C FGFR3; V555C FGFR3; R621C FGFR3; A634C FGFR3; R640C FGFR3.

For the FGFR4 kinase, the following cysteine mutants are illustrative examples of mutants that are used for tethering: L473C FGFR4; E475C FGFR4; F478C FGFR4; L517C FGFR4; M521C FGFR4; V550C FGFR4; R616C FGFR4; A629C FGFR4; R635C FGFR4.

For the FYN kinase, the following cysteine mutants are illustrative examples of mutants that are used for tethering: L276C FYN; N278C FYN; Q 181C FYN; F281C FYN; S309C FYN; E313C FYN; T341C FYN; A393C FYN; A406C FYN; R412C FYN.

For the HCK kinase, the following cysteine mutants are illustrative examples of mutants that are used for tethering: L268C HCK; A270C HCK; Q173C HCK; F273C HCK; A301C HCK; E305C HCK; T333C HCK; A385C HCK; A398C HCK; R404C HCK.

For the IKK-a kinase, the following cysteine mutants are illustrative examples of mutants that are used for tethering: L21C IKK-a; T23C IKK-a; G25C IKK-a; F26C IKK-a; R57C IKK-a; E61C IKK-a; M95C IKK-a; E148C IKK-a; I164C IKK-a; K170C IKK-a.

For the IKK-b kinase, the following cysteine mutants are illustrative examples of mutants that are used for tethering: L21C IKK-b; T23C IKK-b; G25C IKK-b; F26C IKK-b; R57 C IKK-b; E61C IKK-b; M96C IKK-b; E149C IKK-b; I165C IKK-b; K171C IKK-b.

For the IKK-e kinase, the following cysteine mutants are illustrative examples of mutants that are used for tethering: L15C IKK-e; Q17C IKK-e; A19C IKK-e; T20C IKK-e; V51C IKK-e; E55C IKK-e; M86C IKK-e; G139C IKK-e; T156C IKK-e; R163C IKK-e. MAPK; Y35C MAPK; R67C MAPK; E71C MAPK; T106C MAPK; S154C MAPK; L167C MAPK; R173C MAPK.

For the NIK kinase, the following cysteine mutants are illustrative examples of mutants that are used for tethering: L406C NIK; R408C NIK; S410C NIK; F411C NIK; F436C NIK; E439C NIK; M469C NIK; D519C NIK; V540C NIK.

For the PAK1 kinase, the following cysteine mutants are illustrative examples of mutants that are used for tethering: I276C PAK1; Q179C PAK1; A280C PAK1; S281C PAK1; N314C PAK1; V318C PAK1; M344C PAK1; D393C PAK1; T406C PAK1; A412C PAK1.

For the PAK2 kinase, the following cysteine mutants are illustrative examples of mutants that are used for tethering: I255C PAK2; Q158C PAK2; A259C PAK2; S260C PAK2; N293C PAK2; V297C PAK2; M323C PAK2; D372C PAK2; T385C PAK2; A391C PAK2.

For the PAK3 kinase, the following cysteine mutants are illustrative examples of mutants that are used for tethering:

I274C PAK3; Q177C PAK3; A278C PAK3; S279C PAK3; N312C PAK3; V316C PAK3; M342C PAK3; D391C PAK3; T404C PAK3; A410C PAK3.

For the PAK4 kinase, the following cysteine mutants are illustrative examples of mutants that are used for tethering: I327C PAK4; E329C PAK4; S331 C PAK4; R332C PAK4; N365C PAK4;I369C PAK4; M395C PAK4; D444C PAK4; S457C PAK4; A463C PAK4.

For the PAK5 kinase, the following cysteine mutants are illustrative examples of mutants that are used for tethering: I455C PAK5; E457C PAK5; S459C PAK5; T460C PAK5; N492C PAK5; I496C PAK5; M523C PAK5; D572C PAK5; D585C PAK5; A591C PAK5.

For the PDGFR-a kinase, the following cysteine mutants are illustrative examples of mutants that are used for tethering: L599C PDGFR-a; S601C PDGFR-a; A603C PDGFR-a; F604C PDGFR-a; L641C PDGFR-a; L645C PDGFR-a; T674C PDGR-a; R822C PDGFR-a; R841C PDGFR-a.

For the PDGFR-b kinase, the following cysteine mutants are illustrative examples of mutants that are used for tethering: L606C PDGFR-b; S608C PDGFR-b; A700C PDGFR-b; F701C PDGFR-b; L648C PDGFR-b; L652C PDGFR-b; T681C PDGFR-b; R830C PDGFR-b; R849C PDGFR-b.

For the PIM1 kinase, the following cysteine mutants are illustrative examples of mutants that are used for tethering: L44C PIM1; S46C PIM1; G48C PIM1; F49C PIM1; M87C PIM1; L91C PIM1; E121C PIM1; E171C PIM1; E171C PIM1; I85C PIM1; A192C PIM1.

For the A-Raf kinase, the following cysteine mutants are illustrative examples of mutants that are used for tethering: I316C A-Raf; T318C A-Raf; S320C A-Raf; F321 C A-Raf; A350C A-Raf; E354C A-Raf; T382C A-Raf; N433C A-Raf; G446C A-Raf; T452C A-Raf.

For the B-Raf kinase, the following cysteine mutants are illustrative examples of mutants that are used for tethering: I462C B-Raf; S464C B-Raf; S466C B-Raf; F467C B-Raf; A496C B-Raf; E500C B-Raf; T528C B-Raf; N579C B-Raf; G592C B-Raf; T598C B-Raf.

For the C-Raf kinase, the following cysteine mutants are illustrative examples of mutants that are used for tethering: I355C C-Raf; S357C C-Raf; S359C C-Raf; F-360C C-Raf; A89C C-Raf; E393C C-Raf; T421C C-Raf; N472C C-Raf; G485C C-Raf; T491C C-Raf.

For the SRC kinase, the following cysteine mutants are illustrative examples of mutants that are used for tethering: L275C SRC; Q 178C SRC; F280C SRC; A308C SRC; E402C SRC; T340C SRC; A392C SRC; A405C SRC; R411C SRC.

For the SRC2 kinase, the following cysteine mutants are illustrative examples of mutants that are used for tethering: L269C SRC2; T271C SRC2; F274C SRC2; A302C SRC2; E306C SRC2; T334C SRC2; A386C SRC2; A399C SRC2; R405C SRC2.

For the STK1 kinase, the following cysteine mutants are illustrative examples of mutants that are used for tethering: L616C STK1; S618C STK1; A620C STK1; F6P1; C STK1; L658C STK1; L662C STK1; F691C STK1; R815C STK, R834STK1.

For the SYK kinase, the following cysteine mutants are illustrative examples of mutants that are used for tethering: L377C SYK; S379C SYK; N381C SYK; F382C SYK; E416C SYK; E420C SYK; M448C SYK; R498C SYK; S511C SYK; K 518C SYK.

For the TBC kinase, the following cysteine mutants are illustrative examples of mutants that are used for tethering: L376C TEC; S378C TEC; L380C TEC; F381C TEC; D409C TEC; E413C TEC; T442C TEC; R493C TEC; S506C TEC; R513C TEC.

For the TGFR1 kinase, the following cysteine mutants are illustrative examples of mutants that are used for tethering: I211C TGFR1; K213C TGFR1; R215C TGFR1; F216C TGFR1; F243C TGFR1; E247C TGFR1; S280C TGFR1; K337C TGFR1; A350C TGFR1; V357C TGFR1.

For the TGFR2 kinase, the following cysteine mutants are illustrative examples of mutants that are used for tethering: V250C TGFR2; K252C TGFR2; R254C TGFR2; F255C TGFR2; K288C TGFR2; D292C TGFR2; T325C TGFR2; S383C TGFR2; L403C TGFR2.

For the TIE1 kinase, the following cysteine mutants are illustrative examples of mutants that are used for tethering: I845C TIE1; E847C TIE1; N849C TIE1; F850C TIE1; F884C TIE1; L888C TIE1; I917C TIE1; R983C TIE1; A996C TIE 1; R1002C TIE1.

For the TIE2 kinase, the following cysteine mutants are illustrative examples of mutants that are used for tethering: I830C TIE2; E832C TIE2; N834C TIE2; F835C TIE2; F869C TIE2; L873C TIE2; I902C TIE2; R968C TIE2; A981C TIE2; R987C TIE2.

For the VEGFR1 kinase, the following cysteine mutants are illustrative examples of mutants that are used for tethering: L834C VEGFR1; R836C VEGFR1; A838C VEGFR1; F839C VEGFR1; L876C VEGFR1; L880C VEGFR1; V910C VEGFR1; R1026C VEGFR1; R1045C VEGFR1.

For the VEGFR2 kinase, the following cysteine mutants are illustrative examples of mutants that are used for tethering: L840C VEGFR2; R842C VEGFR2; A844C VEGFR2; F845C VEGFR2; L882C VEGFR2; L886C VEGFR2; V916C VEGFR2; R1032C VEGFR2; R1051C VEGFR2.

For the VEGFR3 kinase, the following cysteine mutants are illustrative examples of mutants that are used for tethering: L851C VEGFR3; Y853C VEGFR3; A855C VEGFR3; F856C VEGFR3; L893C VEGFR3; L987C VEGFR3; V927C VEGFR3; R1041C VEGFR3; R1060C VEGFR3.

For the YES kinase, the following cysteine mutants are illustrative examples of mutants that are used for tethering: L283C YES; Q286C YES; C287C YES; F288C YES; A316C YES; E320C YES; T348C YES; A400C YES; A413C YES; R419C YES.

For the ZAP-70 kinase, the following cysteine mutants are illustrative examples of mutants that are used for tethering: L344C ZAP-70; N348C ZAP-70; F349C ZAP-70; E382C ZAP-70; E386C ZAP-70; .M414C ZAP-70; R465C ZAP-70; S478C ZAP-70; and K485C ZAP-70.

Although this approach is typically exemplified with reference to a protein kinase target having a thiol functionality to screen a disulfide-containing library, other chemistries are also available and can be readily used to achieve tethering. Since such chemistries are similar to those used in the extended tethering approach discussed below, they will be reviewed in greater detail in the following section.

c. Extended Tethering

This approach is based on the design of a Small Molecule Extender (SME) that is tethered, via a reversible or irreversible covalent bond, to a protein kinase target locked in an inactive configuration at or near a first binding site of interest, and has a chemically reactive group reactive with small organic molecules to be screened for affinity to a second binding site of interest on the protein kinase target.

According to a particular embodiment, the SME forms a "static" or irreversible covalent bond through the nucleophile or electrophile, preferably nucleophile, on the protein kinase target, thereby forming an irreversible protein kinase-SME complex. Optionally the SME also forms a non-covalent bond with a first binding site of interest on the protein kinase. Additionally the SME contains a second functional group capable of forming a reversible bond with a member of a library of small organic molecules, each molecule having a functional group capable of forming a reversible bond with the second functional group of the SME. The protein kinase target —SME complex and library are subjected to conditions wherein the library member

A285C LYN; E289C LYN; T318C LYN; A370C LYN; A383C LYN; D389C LYN.

For the MAPK kinase, the following cysteine mutants are illustrative examples of mutants that are used for tethering: V30C MAPK; S32C MAPK; A34C Derivatizing such kinases with a SME to produce a static kinase-SME complex and its reaction with a library member is illustrated below.

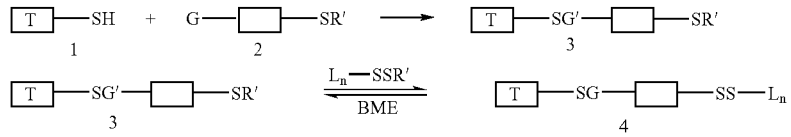

having affinity, preferably the highest affinity, for the second binding site of interest on the protein kinase target forms a reversible bond with the kinase-SME complex.

For static extended tethering, the preferred nucleophiles on the target protein kinase suitable for forming an irreversible kinase-SME complex include —SH, —OH, —NH$_2$ and —COOH usually arising from side chains of cys, ser or thr, lys and asp or glu respectively. Protein kinases may be modified (e.g. mutants or derivatives) to contain these nucleophiles or may contain them naturally. For example, BLK, BTK, EGFR1, ERB2, ERB4, ERK1, ERK2, FGFR1, FGFR2, FGFR3, FGFR4, etc. are examples of suitable protein kinases containing naturally occurring cysteine thiol nucleophiles.

For the JAK1 kinase, the following cysteine mutants are illustrative examples of mutants that are used for tethering: L870C JAK1; E872C JAK1; H874C JAK1; F875C JAK1; D909C JAK1; E913C JAK1; M944C JAK1; R995C JAK1; G1008JAK1; K1014C JAKI.

For the JAK2 kinase, the following cysteine mutants are illustrative examples of mutants that are used for tethering: L855C JAK2; L857C JAK2; N859C JAK2; F860C JAK2; D894C JAK2; E898C JAK2; M929C JAK2; R980C JAK2; G993C JAK2; K999C JAK2.

For the JAK3 kinase, the following cysteine mutants are illustrative examples of mutants that are used for tethering: L828C JAK3; K830C JAK3; N832C JAK3; F833C JAK3; D867C JAK3; E871C JAK3; M902C JAK3; R953C JAK3; A966C JAK3; K972C JAK3.

For the JNK1 kinase, the following cysteine mutants are illustrative examples of mutants that are used for tethering: I32C JNK1; S34C JNK1; A36C JNK1; Q37C JNK1; R69C JNK1; E73C JNK1; M108C JNK1; S155C JNK1; L168C JNK1; R174C JNK1.

For the JNK2 kinase, the following cysteine mutants are illustrative examples of mutants that are used for tethering: I32C JNK2; S34C JNK2; A36C JNK2; Q37C JNK2; R69C JNK2; E73C JNK2; M108C JNK2; S155C JNK2; L168C JNK2; R174C JNK2.

For the JNK3 kinase, the following cysteine mutants are illustrative examples of mutants that are used for tethering: I70C JNK3; S72C JNK3; A74C JNK3; Q75C JNK3; R107C JNK3; E111C JNK3; M146C JNK3; S193C JNK3; L206C JNK3; R212C JNK3.

For the Lck kinase, the following cysteine mutants are illustrative examples of mutants that are used for tethering: L250C Lck; A252C Lck; Q155C Lck; F255C Lck; A283C Lck; E287C Lck; T315C Lck; A367C Lek; A380C Lck; R386C Lck.

For the LYN kinase, the following cysteine mutants are illustrative examples of mutants that are used for tethering: L252C LYN; A254C LYN; Q157C LYN; F257C LYN;

Here, the nucleophile on the kinase is the sulfur of a thiol, usually a cysteine, which is reacted with 2, a SME containing a substituent G capable of forming an irreversible (under conditions that do not denature the target) covalent bond and a free thiol protected thiol or derivatized thiol SR'. Preferably G is a group capable of undergoing SN2-like attack by the thiol or forming a Michael-type adduct with the thiol to produce the irreversible reaction product 3 of that attack having a new covalent linkage —SG'—. The following are representative examples of G groups capable of undergoing SN2-like or Michael-type addition.

1) α-halo acids: F, Cl and Br substituted α to a COOH, PO$_3$H$_2$ or P(OR)O$_2$H acid that is part of the SME can form a thioether with the thiol of the target kinase. Illustrative examples of generic a-halo acids are shown below.

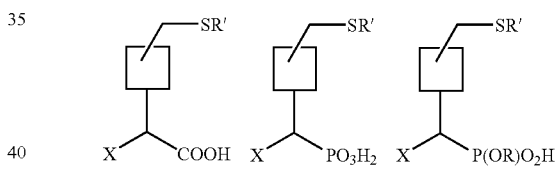

where X is the halogen, R is C1–C20 unsubstituted aliphatic, C1–C20 substituted aliphatic, unsubstituted aryl or substituted aryl, and R' is H, SCH$_3$, S(CH$_2$)$_n$A, where A is OH, COOH, SO$_3$H, CONH$_2$ or NH$_2$ and n is 1 to 5, preferably n is 2 to 4.

2) Fluorophosph(on)ates: These can be Sarin-like compounds which react readily with both SH and OH nucleophiles. Illustrative examples of general fluorophosph(on)ates are shown below.

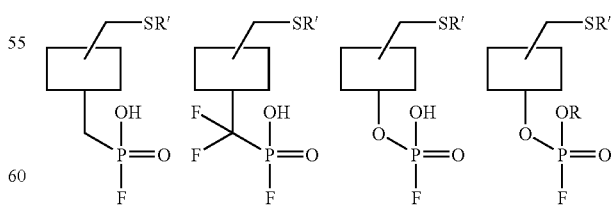

where R and R' are as defined above.

3) Epoxides, aziridines and thiiranes: SME's containing these reactive functional groups are capable of undergoing SN2 ring opening reactions with —SH, —OH and —COOH nucleophiles. Preferred examples of the latter are aspartyl proteases like β-secretase (BASE). Preferred generic examples of epoxides, aziridines and thiiranes are shown below.

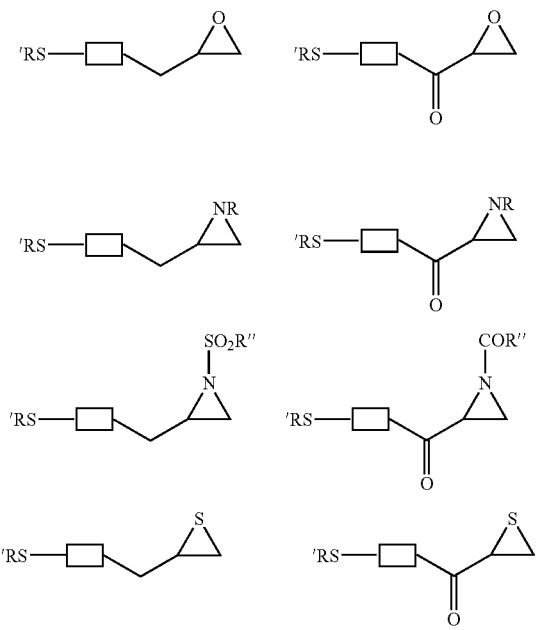

Here, R' is as defined above, R is usually H or lower alkyl and R'' is lower alkyl, lower alkoxy, OH, NH₂ or SR'. In the case of thiiranes the group SR' is optionally present because upon nucleophilic attack and ring opening a free thiol is produced which may be used in the subsequent extended tethering reaction.

4) Halo-methyl ketones/amides: These compounds have the form —(C=O)—CH₂-X. Where X may be a large number of good leaving groups like halogens, N₂, O—R (where R may be substituted or unsubstituted heteroaryl, aryl, alkyl, —(P=O)Ar₂, —N—O—(C=O) aryl/alkyl, —(C=O) aryl/alkyl/alkylaryl and the like), S-Aryl, S-heteroaryl and vinyl sulfones.

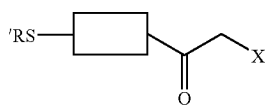

Fluromethylketones are simple examples of this class of activated ketones which result in the formation of a thioether when reacted with a thiol containing protein. Other well known examples include acyloxymethyl ketones like benzoyloxymethyl ketone, aminomethyl ketones like phenylmethylaminomethyl ketone and sulfonylaminomethyl ketones. These and other types of suitable compounds are reviewed in J. Med. Chem. 43(18) p 3351–71, Sep. 7, 2000.

5) Electrophilic aromatic systems: Examples of these include 7-halo-2,1,3-benzoxadiazoles and ortho/para nitro substituted halobenzenes.

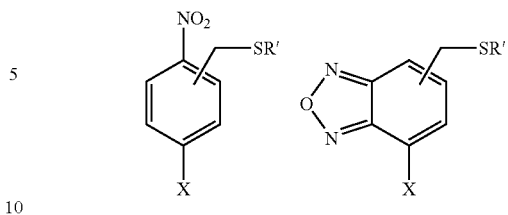

Compounds of this type form arylalkylthioethers with protein kinases containing a thiol.

6) Other suitable SN2 like reactions suitable for formation of static covalent bonds with protein kinase nucleophiles include formation of a Schiff base between an aldehyde and the amine group of lysine of enzymes like DNA repair proteins followed by reduction with for example NaCNBH₄.

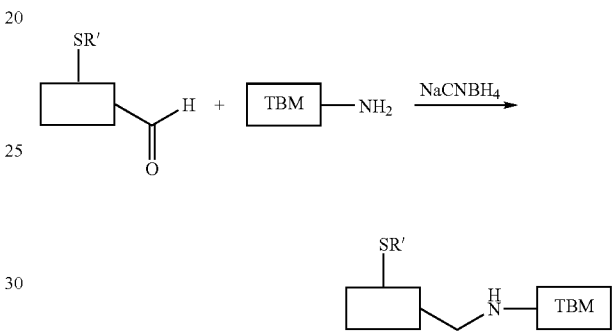

7) Michael-type additions: Compounds of the form —RC=CR-Q, or —C≡C-Q where Q is C(=O)H, C(=O)R (including quinines), COOR, C(=O)NH₂, C(=O)NHR, CN, NO₂, SOR, SO₂R, where each R is independently substituted or unsubstituted alkyl, aryl, hydrogen, halogen or another Q can form Michael adducts with SR (where R is H, glutathione or S-lower alkyl substituted with NH₂ or OH), OH and NH₂ on the target protein kinase.

8) Boronic acids: These compounds can be used where the reactive nucleophile on the target kinase is a hydroxyl. For example serine, theonine, or tyrosine on a target kinase can be labeled to form kinase-SME complexes for use in the present invention. The formation of such a kinase-SME complex is shown below.

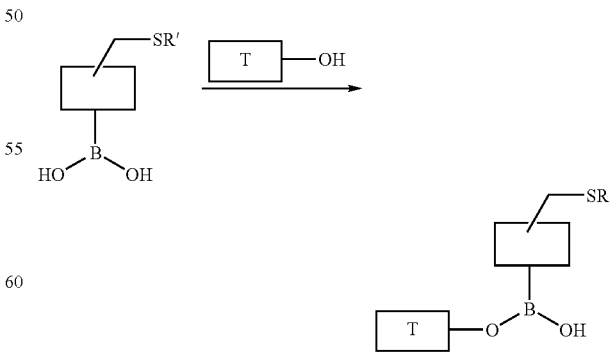

where R' is as defined above.

In each of the foregoing cases a "static" or irreversible covalent bond is formed through the nucleophile on the target kinase producing an irreversible kinase-SME complex containing a thiol or protected thiol. These complexes are then exposed to a library of thiol or disulfide containing organic compounds in the presence of a reducing agent (e.g. mercaptoethanol) for selection of a small molecule ligand capable of binding a second binding site on the target protein kinase (T).

kinase-SME complex and the second library are subjected to conditions wherein the library member having the highest affinity for a second binding site of interest on the target protein kinase forms a reversible bond with the target protein kinase—SME complex. Preferably the covalent bonds are disulfides, which may be reversible in the presence of a reducing agent (e.g. BME).

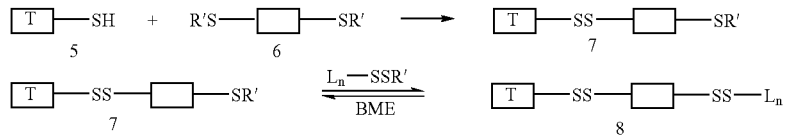

In certain embodiments, the kinase of interest possesses a cysteine that is amenable to static or dynamic extended tethering. These include: BLK (C318); BTK (C481); EGFR1 (C797); ERB2 (C805); ERB4 (C803); JAK3 (C909); TEC (C449).

Illustrative examples of cysteine mutants for extended tethering include: E234C AKT1; E236C ALT2; E232C AKT3; D86C CDK1; D86C CDK2; D86C CDK3; D99C CDK4; D86C CDK5; D104C CDK6; D97C CDK7; D103C CDK8; D108C CDK9; S273C CSK; D128C ERK1; D111C ERK2; D114C ERK3; D111C ERK4; D142C ERK5; D 15C ERK6; E506C FAK1; N568C FGFR1; N571C FGFR2; N562C FGFR3; N557C FGFR4; D348C FYN; S340C HCK; D102C IKK-a; D103C IKK-b; S93C IKK-e; S951C JAK1; S936C JAK2; N114C JNK1; N114C JNK2; N152C JNK3; S322C LCK; S325C LYN; D112C MAPK; S476C NIK; S351C PAK1; S330C PAK2; S349C PAK3; A402C PAK4; A530C PAK5; D861C PDGFR-a; D688C PDGFR-b; D128C PIM1; S389C A-Raf; S535C B-Raf; S428C C-Raf; S347C SRC; S341C SRC2; D698C STK1; P455C SYK; S287C TGFR1; N332C TGFR2; N924C TIE1; N909C TIE2; N917C VEGFR1; N923C VEGFR2; N934C VEGFR3; S355C YES; P421C ZAP-70.

As noted above, in this static approach, the SME may, but does not have to, include a portion that has binding affinity (i.e. is capable of bonding to) a first site of interest on the target kinase. Even if the SME does not include such portion, it must be of appropriate length and flexibility to ensure that the ligand candidates have free access to the second site of interest on the target.

Figure 2:
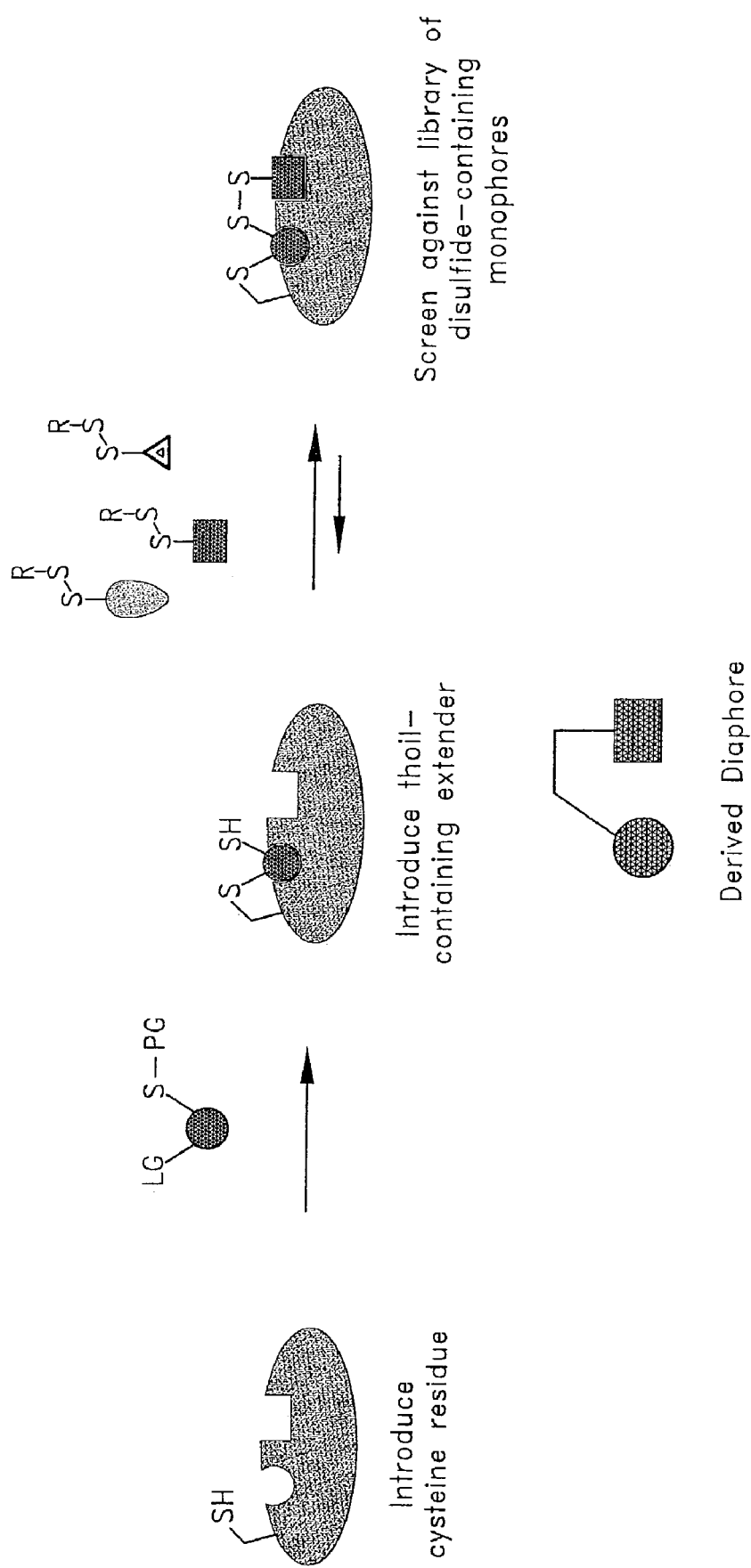
FIG. 2 is a schematic illustration of the static extended tethering approach for identification of protein kinase inhibitor candidates.

In another embodiment, the SME is a double reversible covalent bond SME ("double disulfide" extender), that is, this SME is bifunctional and contains two functional groups (usually disulfide) capable of forming reversible covalent bonds. This SME forms a "dynamic" or first reversible covalent bond through a first functional group on the SME with the nucleophile on the target protein kinase locked in an inactive conformation, thereby forming a reversible kinase-SME complex. Optionally the SME also forms a noncovalent bond with a first binding site of interest on the protein kinase target (the portion of the SME that forms a non-covalent bond with the kinase target is referred to herein as SME'). Additionally the SME contains or is modified to contain a second functional group capable of forming a second reversible bond with a library member of a second library of small organic molecules, each molecule having a functional group capable of forming a reversible bond with the first or second functional group of the SME. The protein The dynamic extended tethering process is illustrated in FIG. 2 where a target protein kinase containing or modified to contain a thiol or protected thiol is incubated with a first library of small organic molecules containing a thiol or protected thiol (a disulfide-containing monophore) under conditions, such as with a reducing agent, wherein at least one member of the library forms a disulfide bond linking the selected library member with the kinase. Optionally this process is repeated with a library of kinases differing from one another by the location of the thiol or protected thiol, i.e. different cysteine mutants of the same protein kinase. Preferably each member of the small molecule library differs in molecular weight from each of the other library members. Preferably the small molecule library contains from 1–100 members, more preferable from 5–15 and most preferably about 10 members. Optionally the selected small molecule library member (selected monophore) also forms a noncovalent bond with a first site of interest on the target protein kinase. The selected monophore, or a derivative thereof, is then modified to contain a second thiol or protected thiol thereby forming a "double disulfide" extender. This synthetic double disulfide extender is then incubated with the target kinase in the presence of a second library of small organic molecules containing a thiol or protected thiol (the library may be the same or different from the first library) under conditions, such as with a reducing agent like mercaptoethanol (β-mercaptoethanol or BME), wherein at least one member of the second library forms a disulfide bond linking the selected library member with the target kinase through the double disulfide extender as shown in 8 above. Optionally thereafter a diaphore is synthesized based on the two selected library members (monophores).

Two basic strategies exist for synthesizing a "double disulfide" extender. In the first, synthesis of the dynamic extender proceeds generically, that is by modification of the monophore linker without any modification of the portion of the monophore that forms a non-covalent bond with the kinase. By way of illustration, the extender usually arises from the screening of a disulfide monophore library. A typical monophore selected from the library or pool will contain a linker of 2 or 3 methylene units between the disulfide that links the monophore to the kinase cysteine and the portion of the monophore that binds non-covalently to the first site of interest on the kinase. This monophore linker can be derivatized as shown below to produce a double disulfide extender in which the "R" or variable group of the monophore remains invariant and becomes the portion of the extender (SME') that binds non-covalently with the first binding site of interest on the kinase.

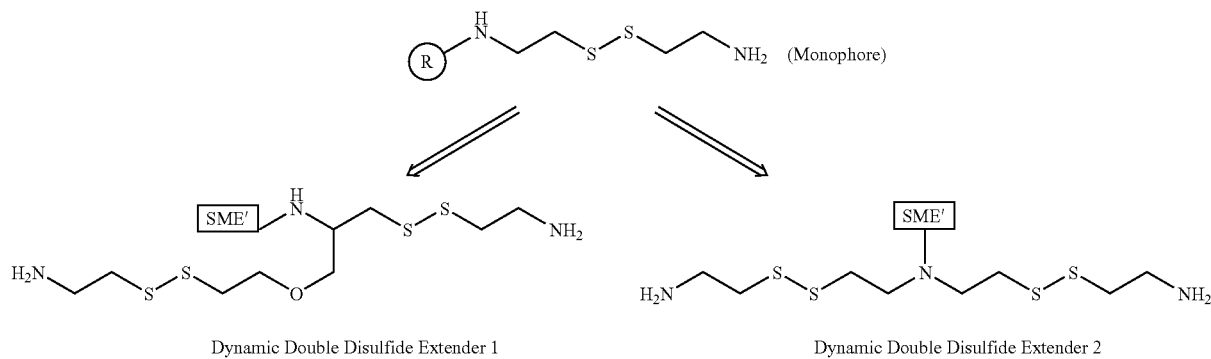

Here the monophore is derivatized either at the methylene nearest the cysteamine nitrogen to produce dynamic double disulfide extender 1 or at the cysteamine nitrogen itself to produce the symmetrical dynamic double disulfide extender 2.

Alternatively, when the monophore is a 3-mercaptopropionic acid derivative the alpha carbon can be derivatized to produce a generic dynamic double disulfide extender of the form shown in 3 below.

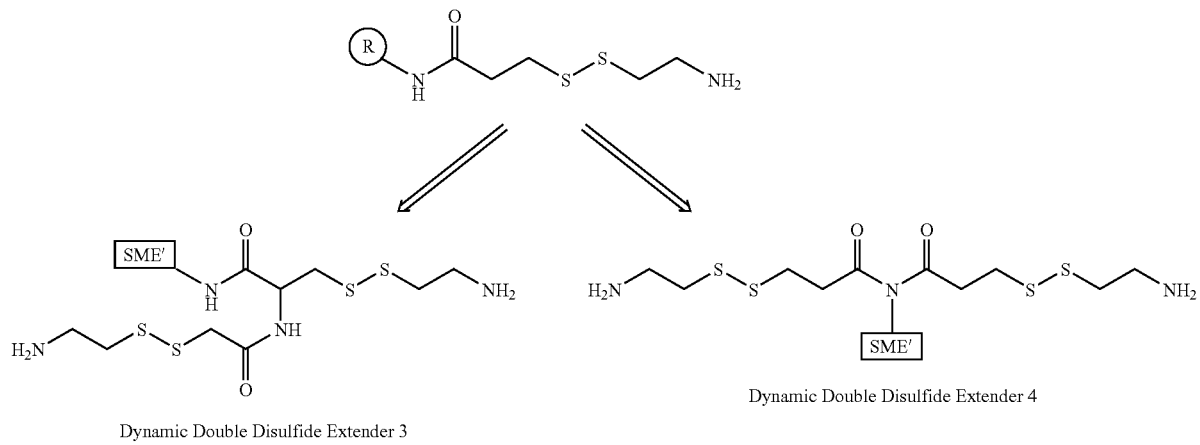

Optionally the amide nitrogen may be derivatized with an acyl or sulfonyl to produce an extender of the form shown in 4 above.

A second strategy involves derivatizing the portion of the monophore that binds non-covalently to the first site of interest on the target kinase. The derivatization is preferably carried out at a site that minimally alters the binding of the monophore to the first site of interest. An illustrative example of such derivatization is shown below for a hypothetical monophore that binds to a target kinase.

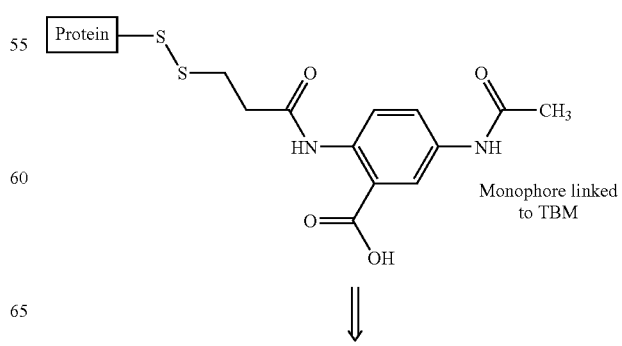

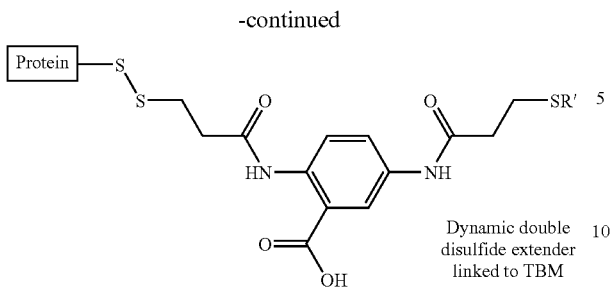

Dynamic double disulfide extender linked to TBM

Here the dynamic tether is shown bound to the kinase thiol forming the kinase-SME complex, where R' is the cysteamine radical. This complex can then be contacted with a disulfide monophore or library of disulfide monophores to obtain a linked compound having a higher affinity for the kinase than either the SME or selected monophore alone.

A second example of a SME designed form an exemplary disulfide monophore that binds to the protein kinase is shown below. This dynamic SME can be contacted with the target kinase in the presence of one or more disulfide monophores to form a covalent kinase-SME-monophore complex where the SME has an affinity for the first site of interest and the monophore has an affinity for the second site of interest on the kinase.

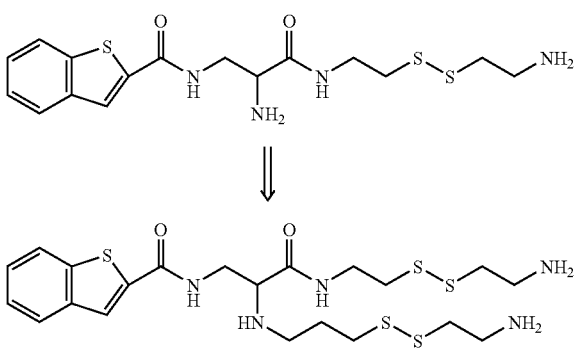

Detection and identification of the structure of the kinase-SME-monophore complex can be carried out by mass spectrometry or inhibition in a functional assay (e.g. ELISA, enzyme assay etc.).

Suitable SME's for kinases include:

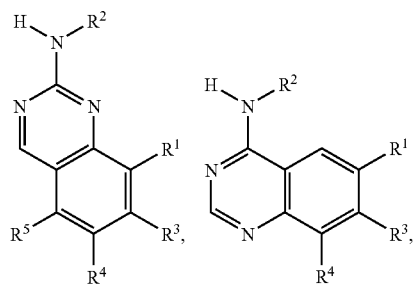

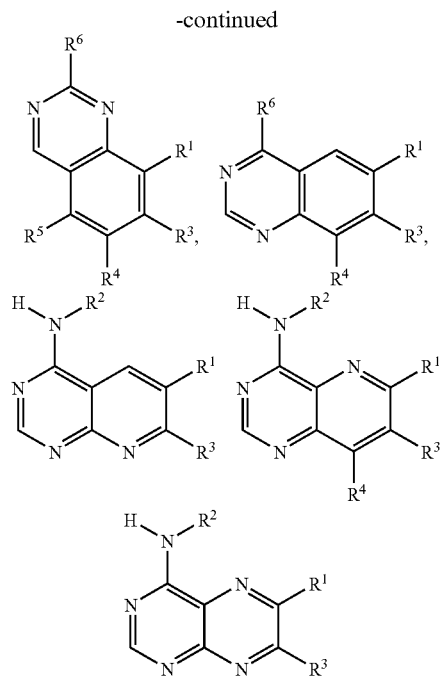

where R1, R2, R3, R4, R5, and R6 are each independently selected from the group consisting of hydrogen, C1–C5 alkyl, C1–C5 alkylamine, and aryl provided that at least one R group on the SME is a Michael acceptor and another R group is selected from $-(CH_2)_n-SR'$; $-C(=O)-(CH_2)_n-SR'$, $-O-(CH_2)_n-SR'$; $-(CH_2)_n-SR'$; and a thiol protecting group. In one embodiment, $R^1$ is a Michael acceptor selected from the group consisting of

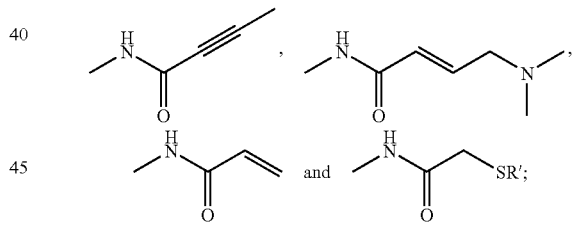

and R2, R3, R4, R5, and R6 are each independently selected from the group consisting of hydrogen, C1–C5 alkyl; C1–C5 alkylamine; aryl; $-(CH_2)_n-SR'$; $-C(=O)-(CH_2)_n-SR'$; $-O-(CH_2)_n-SR'$; $-(CH_2)_n-SR'$; and a thiol protecting group provided that one of R2, R3, R4, R5, and R6 is selected from $-(CH_2)_n-SR'$; $-C(=O)-(CH_2)_n-SR'$; $-O-(CH_2)_n-SR'$; $-(CH_2)_n-SR'$; and a thiol protecting group. In another embodiment, R3 is a Michael acceptor selected from the group consisting of

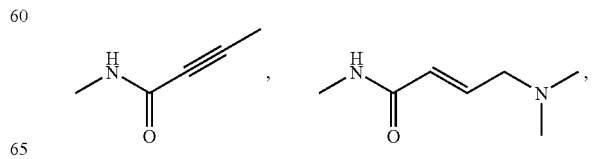

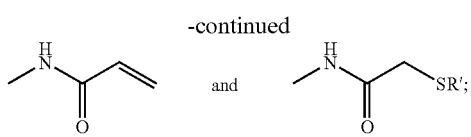

and R1, R2, R4, R5, and R6 are each independently selected from the group consisting of hydrogen, C1–C5 alkyl; C1–C5 alkylamine; aryl; —(CH$_2$)$_n$—SR'; —C(=O)—(CH$_2$)$_n$ (CH$_2$)$_n$ —SR'; —(CH$_2$)$_n$—SR'; and a thiol protecting group provided that one of R1, R2, R4, R5, and R6 is selected from —(CH$_2$)$_n$—SR'; —C(=O)—(CH$_2$)$_n$—SR'; —O—(CH$_2$)$_n$—SR'; —(CH$_2$)$_n$—SR'; and a thiol protecting group. In all formulas, R' is hydrogen, disulfide, or a thiol protecting group, and n is 1 to 5, preferably n is 2 to 4.

The dynamic extenders are used to select a second fragment by covalent tethering as described above. When bound to the target and titrated against B-mercaptoethanol, a BME50 value (the concentration of β-mercaptoethanol that, at equilibrium, is capable of displacing 50% of the bound compound from the target) is determined. When using the dynamic extender, it is preferred to measure the BME50 for the dynamic extender and to screen for a second fragment by covalent tethering at a total thiol concentration (BMR+ library thiols) at or below the BME50 of the dynamic extender. For example, if the dynamic extender has a BME50 of 2.5 mM, the total thiol concentration in the second fragment screening step should be 2.5 mM or less and more preferably about 2 fold or less, e.g. about 1 mM or less. Alternatively, the dynamic extender may be converted to a static extender removing the second fragment screening total thiol concentration issue. When converting a dynamic extender to a static extender, it is important to maintain the same atom count so that non-covalent binding of the static extender to the target will not be distorted. For similar reasons, it is important to minimize introduction of other bulky atoms or groups.

Other chemistries available for forming a reversible or irreversible covalent bond between reactive groups on a protein kinase and a target or ligand, respectively, or between two ligands, are well known in the art, and are described in basic textbooks, such as, e.g. March, *Advanced Organic Chemistry*, John Wiley & Sons, New York, 4$^{th}$ edition, 1992. Reductive aminations between aldehydes and ketones and amines are described, for example, in March et al., supra, at pp. 898–900; alternative methods for preparing amines at page 1276; reactions between aldehydes and ketones and hydrazide derivatives to give hydrazones and hydrazone derivatives such as semicarbazones at pp. 904–906; amide bond formation at p. 1275; formation of ureas at p. 1299; formation of thiocarbamates at p. 892; formation of carbamates at p. 1280; formation of sulfonamides at p. 1296; formation of thioethers at p. 1297; formation of disulfides at p. 1284; formation of ethers at p. 1285; formation of esters at p. 1281; additions to epoxides at p. 368; additions to aziridines at p. 368; formation of acetals and ketals at p. 1269; formation of carbonates at p. 392; formation of enamines at p. 1264; metathesis of alkenes at pp. 1146–1148 (see also Grubbs et al., *Acc. Chem. Res.* 28:446–453 [1995]); transition metal-catalyzed couplings of aryl halides and sulfonates with alkanes and acetylenes, e.g. Heck reactions, at pp. 717–178; the reaction of aryl halides and sulfonates with organometallic reagents, such as organoboron, reagents, at p. 662 (see also Miyaura et al., *Chem. Rev.* 95:2457 [1995]); organotin, and organozinc reagents, formation of oxazolidines (Ede et al., *Tetrahedron Letts.* 28:7119–7122 [1997]); formation of thiazolidines (Patek et al., *Tetrahedron Letts.* 36:2227–2230 [1995]); amines linked through amidine groups by coupling amines through imidoesters (Davies et al., *Canadian J. Biochem.*c50:416–422 [1972]), and the like. In particular, disulfide-containing small molecule libraries may be made from commercially available carboxylic acids and protected cysteamine (e.g. mono-BOC-cysteamine) by adapting the method of Parlow et al., *Mol. Diversity* 1:266–269 (1995), and can be screened for binding to polypeptides that contain, or have been modified to contain, reactive cysteines. All of the references cited in this section are hereby expressly incorporated by reference.

While it is usually preferred that the attachment of the SME does not denature the target, the kinase-SME complex may also be formed under denaturing conditions, followed by refolding the complex by methods known in the art. Moreover, the SME and the covalent bond should not substantially alter the three-dimensional structure of the target protein kinase, so that the ligands will recognize and bind to a binding site of interest on the target with useful site specificity. Finally, the SME should be substantially unreactive with other sites on the target under the reaction and assay conditions.

d. Detection and Identification of Ligands Bound to a Target

The ligands bound to a target can be readily detected and identified by mass spectroscopy (MS). MS detects molecules based on mass-to-charge ratio (m/z) and thus can resolve molecules based on their sizes (reviewed in Yates, *Trends Genet.* 16: 5–8 [2000]). A mass spectrometer first converts molecules into gas-phase ions, then individual ions are separated on the basis of m/z ratios and are finally detected. A mass analyzer, which is an integral part of a mass spectrometer, uses a physical property (e.g. electric or magnetic fields, or time-of-flight [TOF]) to separate ions of a particular m/z value that then strikes the ion detector. Mass spectrometers are capable of generating data quickly and thus have a great potential for high-throughput analysis. MS offers a very versatile tool that can be used for drug discovery. Mass spectroscopy may be employed either alone or in combination with other means for detection or identifying the organic compound ligand bound to the target. Techniques employing mass spectroscopy are well known in the art and have been employed for a variety of applications (see, e.g., Fitzgerald and Siuzdak, *Chemistry & Biology* 3: 707–715 [1996]; Chu et al., *J. Am. Chem. Soc.* 118: 7827–7835 [1996]; Siudzak, *Proc. Natl. Acad. Sci. USA* 91: 11290–11297 [1994]; Burlingame et al., *Anal. Chem.* 68: 599R–651R [1996]; Wu et al., *Chemistry & Biology* 4: 653–657 [1997]; and Loo et al., *Am. Reports Med. Chem.* 31: 319–325 [1996]).

However, the scope of the instant invention is not limited to the use of MS. In fact, any other suitable technique for the detection of the adduct formed between the protein kinase target molecule and the library member can be used. For example, one may employ various chromatographic techniques such as liquid chromatography, thin layer chromatography and likes for separation of the components of the reaction mixture so as to enhance the ability to identify the covalently bound organic molecule. Such chromatographic techniques may be employed in combination with mass spectroscopy or separate from mass spectroscopy. One may optionally couple a labeled probe (fluorescently, radioactively, or otherwise) to the liberated organic compound so as to facilitate its identification using any of the above techniques. In yet another embodiment, the formation of the new bonds liberates a labeled probe, which can then be monitored. Other techniques that may find use for identifying the organic compound bound to the target molecule include, for example, nuclear magnetic resonance (NMR), capillary electrophoresis, X-ray crystallography, and the like, all of which will be well known to those skilled in the art.

Validation of Kinase Inhibitor Activity

The molecules, e.g. small molecule ligands, identified by the initial binding assays, including direct or extended tethering, using the inactive conformation of the target protein kinase as target, need to be validated as tyrosine kinase inhibitors assays in physiologically relevant activity assays. In view of the physiological importance of protein kinases, numerous high-throughput screening assays for measuring kinase activity have been developed. A common theme to these assays the measurement of kinase activity (typically through measuring phosphorylation of the substrate of the kinase of interest) in the presence and absence of the candidate kinase inhibitor, typically in competition in ATP or another known kinase inhibitor. These assays can use the entire substrate, or any part of it retaining the kinase recognition sequence.

Some assays use the detection of radioactively labeled (e.g. $^{32}P$ or $^{33}P$) phosphate incorporated into the substrate to quantify kinase activity. In other assays, quantification of the tyrosine kinase activity is based on the use of phospho-specific antibodies. In the latter case, typically a fluorescent label is attached to the antibody or the substrate, or both, a HRP or AP enzyme is conjugated to the antibody and the antibody is detected with a calorimetric readout, e.g. time-resolved fluorescence (TRF), fluorescence resonance energy transfer (FRET), or fluorescence polarization (FP). For example, the HitHunter™ assay (Discover$_x$) for identifying serine-threonine kinase inhibitors measures substrate phosphorylation in a competitive immunoassay format, using an anti-phospho-peptide antibody and chemiluminescent or fluorescent readout. An antibody-free fluorescence polarization-based protein kinase assay is available, for example, from Chromagen (San Diego, Calif.). Protein tyrosine kinase assay systems are also available, for example, from Invitrogen (Pan Vera FP Assay Kit).

After initial identification and preliminary characterization, the candidate kinase inhibitors may be evaluated in cell-based and animal model assays in order to further confirm their ability to function as inhibitors of the target protein kinase. Cell-based assays can use any cell functionally expressing the protein kinase of interest and its substrate, either endogenously, and/or as a result of introducing the respective coding sequences by techniques of recombinant DNA technology. Readouts of the cell-based assays are similar to those used in assays using purified proteins.

Selectivity of protein kinase inhibitors can be tested, for example, by assaying a candidate inhibitor against a panel of protein kinases in any of the known assay formats, such as those discussed above.

Further details of the invention are illustrated in the following non-limiting examples.

EXAMPLE 1

Construction and Characterization of EGFR1 and Lck Variants

Two key mutations are introduced into the kinase domains of EGFR1 and Lck, respectively. The first mutation introduces a cysteine residue into the floor of the purine-binding pocket of Lck, adjacent to the position occupied by the 2'—OH of ATP, and analogous to Cys797 (Cys773 when numbered from the first residue remaining after cleavage of the signal sequence) of the EGFR1. The second mutation substitutes the conserved lysine of the catalytic triad with an arginine. While this is a conservative mutation, it is sufficient to prevent catalysis, thus preventing autophosphorylation of the kinase domain, and thereby locking the kinase domain in the inactive conformation.

Cloning and Mutagenesis

The Lck kinase domain (Lck-KD) comprising residues 30–495 was cloned from Jurkat cells, using standard RT-PCR techniques. The EGFR1kinase domain (EGFR1-KD) comprising residues 698–970 are similarly cloned from A431 cells. In short, RNA is isolated from cells using Tri-reagent (Sigma) and mRNA purified using Oligotex oligo dT resin (Promega). First strand cDNA is synthesized using poly(A)RNA, reverse transcriptase, and a gene specific primer, and cDNA is amplified using a pair of internal primers flanking the region to be amplified. Amplified cDNAs are subcloned in frame with and downstream of the 6 HIS epitope tag sequence into the plasmid pFastBac HTA (Gibco-BRL). Point mutations (K745R in EGFR1; S322C and K272R in Lck) are then introduced using long range PCR and a pair of complementary primers spanning the mutated region. Recombinant plasmids bearing the desired mutations are generated in E. coli through overlap recombination. All mutant alleles are verified by sequencing.

Virus Construction, Expression and Purification of Kinase Domains

Recombinant baculovirus is generated using standard overlap recombination techniques, using the Gibco-BRL Bac-to-Bac baculovirus expression system according to manufacturer's directions. In short, plasmids are transfected into DH1Bac cells, and colonies containing recombinant bacmids identified by their growth on selective media. Recombinant bacmid DNA, isolated form these selected cells, is transfected into Sf9 insect cells, and shed recombinant virions are further amplified in Sf9 cells as necessary. Recombinant kinase domains are expressed in High Five insect cells following infection with the corresponding baculovirus strains. Recombinant protein expression is monitored by Western analysis of cell lysates using either anti 5×HIS antibodies, protein specific antibodies (anti-EGFR1 or anti-Lck), or phosphor-specific antibodies (anti-EGFR1 pY872 or anti-LCK pY393) which are commercially available form Qiagen, Biosource International, or Upstate Biotechnology. Whole cell extracts are prepared from High Five insect cells expressing the various recombinant kinase domains by sonication in M-PER non-ionic detergent lysis buffer (Pierce). Extracts will be dialyzed overnight against Ni-NTA loading buffer (Qiagen) to remove EDTA, purified on Ni-NTA (Qiagen) and eluted with imidazole according to manufacturer's suggestions.

Characterization of Enzymatically Active Kinase Domains

Enzymatic properties of EGFR1-KD, Lck-KD, and Lck-KD S322C are characterized using one or more of three standard essay formats. In the first format, $\gamma^{33}P$-labeled ATP is incubated with enzyme and kemptide (KKKGP-WLEEEEEAYGWLDF; SEQ ID NO: 70), a non-specific tyrosine kinase substrate. Positively charged reaction products are isolated by binding to phosphocellulose membrane and quantitated using a phosphorimager (Amersham Pharmacia Biotech). In the second format, ATP is incubated with enzyme and a biotinylated oligo $E_4Y$ copolymer substrate (Sigma). Reaction products are captured on an avidin-coated 96-well plate and quantitated using a horseradish peroxidase conjugated anti-pY antibody (Pierce) using standard ELISA techniques. In the third format, ATP is incubated with kinase and substrate and ADP production is monitored in a coupled reaction with pyruvate kinase and lactate dehydrogenase. Each of these three formats offers advantages. The first one is exceptionally straightforward to quantitate. The second format is amenable to relatively high-throughput format. The third format is amenable to kinetic analyses. Using these assay formats, the functionality of the kinase domain constructs is validated, ruling out any detrimental effects due to the. S322C mutation in Lck-KD, and screening hits are characterized.

Development of Kinase Specific Tethering Extenders

There are two primary objectives in developing a set of kinase-specific tether extenders. The first is to develop a minimalized set of extenders that can be used to irreversibly label a variety of kinases, with little specificity for one kinase over another. The second is to "activate" a subset of these extenders by appending thiol groups onto the core scaffold. Once these two objectives have been accomplished, these generic extenders can be used to label the purine pocket of a variety of kinases with a thiol-activated scaffold and to screen a library of thiol-activated small molecules that bind preferentially to either the active or the inactive conformation of the kinase. Once identified, these molecules consisting of an extender coupled to a diversity element, can be characterized and optimized using standard medicinal chemistry methods.

Quinazolines, broad specificity kinase inhibitors, are known to bind to the purine pocket of a myriad of protein kinases and are possibly the most commonly used of all the kinase inhibitor structural motifs. Furthermore, 6-arylamido quinazoline-based inhibitors are known to irreversibly label the EGFR1 kinase through reactivity with a cysteine residue (Cys773) located on the floor of the purine-binding pocket. Surprisingly, 7-acrylamido quinazolines also irreversibly modify the EGFR1 kinase, indicating that despite the high affinity of these compounds for the purine pocket, they do have limited mobility within their binding site. Thus, similarly modified quinazolines are ideal compounds to adapt into extenders that bind covalently but with loose specificity to the purine-binding pocket of an appropriately engineered protein kinase.

Accordingly, a set of eight 4-phenylamino quinazolines containing Michael acceptors in the 6 and 7 positions, are synthesized. These structures are shown below.

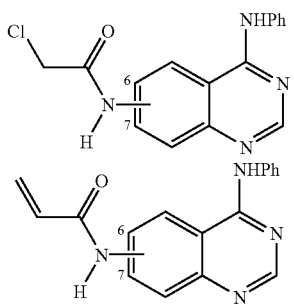

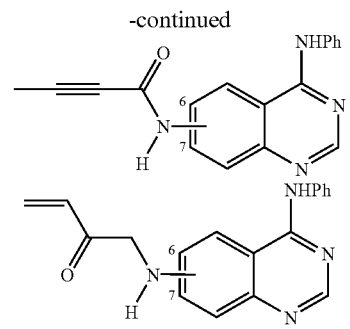

These compounds are designed to bind in the purine pocket of protein kinases, with little specificity for any particular kinase. Synthesis and purification of these compounds is relatively straightforward. Taken together, this panel accommodates possible slight variations in the position of the residue analogous to C773 of EGFR1 by varying the position, special orientation, and reactivity of the Michael acceptor.

Characterization of Enzymatically Inactive Kinase Domains:

To validate the functional and structural integrity of the constructs constrained in the enzymatically inactive conformation (EGFR1-KD, K745R and Lck-Kd, S322C, K272R), their ability to bind quinazoline-based inhibitors are tested using one or more of the following standard assay formats. In the first two formats, the Micahel-acceptor derivatized compounds are first labeled with $^{35}$S by reaction with $^{35}$S Cysteine (Amersham). Alternatively, Michael acceptor derivatized compound can be first labeled with $^{14}$C labeled 2-mercaptoethanol. Binding to the kinase domain is then quantitated either through filter binding assays or through scintillation proximity assays (SPA) in which the 6×His tagged kinase domain is immobilized to an anti-HIS IgG coated SPA bead. In the third format, the acrylamide derivatized compounds are covalently conjugated to a BIACORE CM5 sensor chip which has itself been derivatized with cysteamine according to the company's recommended procedure. Protein binding is then quantitated using surface plasmon resonance with the BIACORE 3000 equipment. Filter binding assays and SPA assays offer quick determinations of binding affinity and specificity, and are amenable to high throughput format. Additionally, SPA assays are solution-based assays, which may make competition assays, designed to show specificity to the binding reaction and to measure its affinity, easier to interpret. Surface plasmon resonance, in addition to being a radioactivity free assay, allows for detailed characterization of binding kinetics in addition to binding affinity.

EXAMPLE 2

Screening of Small Molecule Library with Kinase Domain Locked in Inactive Conformation This example illustrates the use of kinase domains locked in the inactive conformation and containing a tethering extender to screen a library of sulfhydryl-containing fragments in a small molecule library. The binding conditions, such as final concentration of protein, reductant, and extender, are determined empirically. Modification of the protein with various extenders is assessed and quantitated by mass spectrometry (MS). Since both Lck and EGFR1 contain surface exposed cysteine residues, modification of EGFR1 C773 and Lck S322C is verified by competing with either ADP or other inhibitors that are known to bind EGFR1 and Lck in the purine pocket. If necessary, solvent accessible cysteine residues other than EGFR1 C773 and Lck S322C are replaced with serine.

Design of Extenders

The exact extenders used depend on which of the 4-phenylamino quinazolines discussed in Example 1 bind most efficiently to EGRR1-KD, K745R and Lck-KD, S322C, K272R. Thiols are appended to the 5, 6, 7, or 8 position of the best quinazolines, separated by a 1-, 2-, or 3-atom spacer. Based on the crystal structure of Lck and the structure model of EGFR1, these extenders are expected to access the substrate binding region, activation loop, and ribosome pocket, all of which undergo significant structural rearrangements during the transition from the inactive to the active conformation. The binding conditions for these thiol-containing extenders are empirically determined, and the site of modification verified as described for the non-thiol-containing versions. A set of nine tether extender candidates for EGFR1 is shown below.

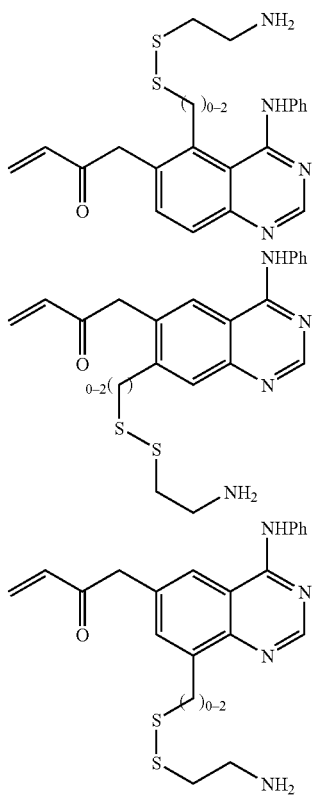

Library of Sulfhydryl-Containing Fragments

The assembly of a collection of drug-like fragments or "monophores" that display a masked sulfhydryl group is a critical component of the tethering screening approach. The sulfhydryl must be installed such that the fragment can participate in a disulfide exchange reaction with the cysteine residue on an enzyme or receptor, such as a protein kinase, target. The monophores fragments should also be broadly representative of recognized and unique drug-like pharmacophores and fragments thereof. At a minimum, candidate fragments need to satisfy two primary criteria. First, they must contain a functional group that will permit the installation of a disulfide linker. Suitable functional groups include a free amine, carboxylate, sulfonyl chloride, isocyanate, aldehyde, ketone, etc. Second, they should be chosen such that the combination of two such entities results in a product with drug-like physical properties, including molecular weight (approximately 500 Da or less) and hydrophobicity (cLog P between −1 and 5).

An assortment of different linkers are used to prepare tethering fragments, and two representative linkers are shown below. The amino linker can be used to react with building blocks bearing eletrophilic functionality (carboxylates, sulfonylchlorides, isocyanates, etc.) while the carboxylate linker can be used to react with nucleophiles (e.g., amines). These tethering groups are retained as disulfide-containing compounds in the library.

The monophores library can be derived from commercially available compounds that satisfy the above criteria. However, many motifs common in biologically active compounds are rare or absent in commercial sources of chemicals. Therefore, the fragment collection is preferably supplemented by synthesizing monophores fragments that help fill these gaps. A typical library can contain 10,000 or more compounds.

The fragment library is then screened against the thiol-extender modified EGFR1 and Lck catalytic domains. The tethering experiments are performed in the presence of BME (beta-mercaptoethanol) to facilitate the competitive interchange of disulfides based on the thermodynamics of affinity. The redox potential in the experimental solutions is set to a level that stringently screens for compounds that utilize binding energy from hydrophobic and polar interactions between the monophores and clefts in the surrounding enzyme surface, rather than the disulfide bond alone.

Identification and Characterization of Hits

The initial screening conditions for kinase-extender covalent complexes are determined empirically. Pools containing compounds that covalently modify the extender are identified by mass spectrometry (MS) analysis. From the deconvoluted MS profile, the molecular weight of the bound compound can be precisely calculated, and thus its identity in the pool determined. The discrete compound is then tested alone to determine if it can covalently modify the kinase-extender complex. Each screen is likely to identiy multiple hits. Hits are prioritized according to their relative binding affinities and according to their relative preference for the inactive enzyme conformation. Relative enzyme binding affinities, expressed as a $BME_{50}$, are then determined using a BME titration curve to determine the concentration that allows 50% modification while using a constant concentration of compound. From this one can easily rank the compounds, based upon their binding affinities. Relative preference for the inactive conformation is determined by re-screening lead compounds against the extender-modified active constructs, EGFR1-KD and Lck-Kd S322C.

Upon compilation of the confirmed monophores hits, additional valuable information can be gained from analyzing the structure-activity relationship (SAR) between hit compounds and their relatives in the monophores library. For example, if several hit molecules for a particular tyrosine kinase-extender pair fall into a closely related family, one may then go back to the monophores library and find structurally similar compounds that were not selected in the initial screen. These relatives are re-screened as discrete compounds to verify their activity (or inactivity), followed by rank ordering of the entire family in terms of affinity for both the active and inactive enzyme conformations. From this dataset, one can identify features critical to activity, and potential sites of modification the alteration of which is expected to improve affinity.

In parallel with the SAR studies, the tethered compounds are co-crystallized with the Lck kinase domain. This entails complete modification of the protein-extender complex by the compound of interest followed by crystal growth. Alternatively, extender-compound diaphores lacking the Michael acceptor are synthesized and either soaked into crystals of Lck-KD or co-crystallized with Lck-KD. X-ray data are collected and programmed by using commercially available equipments and softwares.

The examples described above are set forth solely to assist in the understanding of the invention, and are not intended to limit the scope of the invention in any way.

One skilled in the art will readily appreciate that the present invention is well adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention, which is limited only by the following claims.

TABLE 1

| Kinase | Ser/Thr or Tyr | SwissProt | NCBI | Length | | References | SEQ ID NO. |
|---|---|---|---|---|---|---|---|
| AKT1 | Ser/Thr | P31749 | M63167 | 480 | AUTHORS | JONES, P. F., JAKUBOWICZ, T., PITOSSI, F. J., MAURER, F. AND HEMMINGS, B. A. | 1 |
| | | | | | TITLE | MOLECULAR CLONING AND IDENTIFICATION OF A SERINE/THREONINE PROTEIN KINASE OF THE SECOND-MESSENGER SUBFAMILY | |
| | | | | | JOURNAL | PROC. NATL. ACAD. SCI. U.S.A. 88, 4171–4175 (1991) | |
| AKT2 | Ser/Thr | P31751 | M77198 | 481 | AUTHORS | JONES, P. F., JAKUBOWICZ, T. AND HEMMINGS, B. A. | 2 |
| | | | | | TITLE | MOLECULAR CLONING OF A SECOND FORM OF RAC PROTEIN KINASE | |
| | | | | | JOURNAL | CELL REGUL. 2 (12), 1001–1009 (1991) | |
| AKT3 | Ser/Thr | Q9Y243 | AF124141 | 479 | AUTHORS | BRODBECK, D., CRON, P. AND HEMMINGS, B. A. | 3 |
| | | | | | TITLE | A HUMAN PROTEIN KINASE BGAMMA WITH REGULATORY PHOSPHORYLATION SITES IN THE ACTIVATION LOOP AND IN THE C-TERMINAL HYDROPHOBIC DOMAIN | |
| | | | | | JOURNAL | J. BIOL. CHEM. 274 (14), 9133–9136 (1999) | |
| BLK | Tyr | P51451 | Z33998 | 504 | AUTHORS | ISLAM, K. B., RABBANI, H., LARSSON, C., SANDERS, R. AND SMITH, C. I. | 4 |
| | | | | | TITLE | MOLECULAR CLONING, CHARACTERIZATION, AND CHROMOSOMAL LOCALIZATION OF A HUMAN LYMPHOID TYROSINE KINASE RELATED TO MURINE BLK | |
| | | | | | JOURNAL | J. IMMUNOL. 154 (3), 1265–1272 (1995) | |
| BTK | Tyr | Q06187 | X58957 | 659 | AUTHORS | VETRIE, D., VORECHOVSKY, I., SIDERAS, P., HOLLAND, J., DAVIES, A., FLINTER, F., HAMMARSTROM, L., KINNON, C., LEVINSKY, R., BOBROW, M., SMITH, C. I. E. AND BENTLEY, D. R. | 5 |
| | | | | | TITLE | THE GENE INVOLVED IN X-LINKED AGAMMAGLOBULINAEMIA IS A MEMBER OF THE SRC FAMILY OF PROTEIN-TYROSINE KINASES | |
| | | | | | JOURNAL | NATURE 361 (6409), 226–233 (1993) | |
| CDK1 | Ser/Thr | P06493 | X05360 | 297 | AUTHORS | LEE, M. G. AND NURSE, P. | 6 |
| | | | | | TITLE | COMPLEMENTATION USED TO CLONE A HUMAN HOMOLOGUE OF THE FISSION YEAST CELL CYCLE | |

TABLE 1-continued

| Kinase | Ser/Thr or Tyr | SwissProt | NCBI | Length | | References | SEQ ID NO. |
|---|---|---|---|---|---|---|---|
| CDK2 | Ser/Thr | P24941 | X61622 | 298 | JOURNAL<br>AUTHORS<br>TITLE<br><br>JOURNAL | CONTROL GENE CDC2<br>NATURE 327 (6117), 31–35 (1987)<br>Elledge, S. J. and Spottswood, M. R.<br>A new human p34 protein kinase, CDK2,<br>identified by complementation of a cdc28<br>mutation in Saccharomyces cerevisiae, is<br>a homolog of Xenopus Eg1<br>EMBO J. 10 (9), 2653–2659 (1991) | 7 |
| CDK3 | Ser/Thr | Q00526 | X66357 | 305 | REFERENCE<br>AUTHORS<br>TITLE<br>JOURNAL<br><br><br><br>REFERENCE<br>AUTHORS<br><br><br>TITLE<br><br>JOURNAL | 1 (BASES 1 TO 1161)<br>MEYERSON, M. L.<br>DIRECT SUBMISSION<br>SUBMITTED (12-May-1992) M. L. MEYERSON,<br>MASSACHUSETTS GENERAL HOSPITAL, CANCER<br>CENTER, BLDG 149, 13TH STREET, CHARLESTON<br>MA 02129, USA<br>2 (BASES 1 TO 1161)<br>MEYERSON, M., ENDERS, G. H., WU, C. L., SU, L. K.,<br>GORKA, C., NELSON, C., HARLOW, E.<br>AND TSAI, L. H.<br>A FAMILY OF HUMAN CDC2-RELATED PROTEIN<br>KINASES<br>EMBO J. 11 (8), 2909–2917 (1992) | 8 |
| CDK4 | Ser/Thr | P11802 | M14505 | 303 | AUTHORS<br>TITLE<br><br><br>JOURNAL<br><br>MEDLINE<br>COMMENT | HANKS, S. K.<br>HOMOLOGY PROBING: IDENTIFICATION OF CDNA<br>CLONES ENCODING MEMBERS OF THE PROTEIN-<br>SERINE KINASE FAMILY<br>PROC. NATL. ACAD. SCI. U.S.A. 84, 388–392<br>(1987)<br>87092414<br>ON FEB 24, 1994 THIS SEQUENCE VERSION<br>REPLACED GI: 190661.<br>REFERENCE HANKS, S. K. (1987) REFERS TO<br>BASES 489–791 DRAFT ENTR AND CLEAN COPY<br>SEQUENCED FOR [1] KINDLY provided by<br>S. K. Hanks, FEB 18, 1987. | 9 |
| CDK5 | Ser/Thr | Q00535 | X66365 | 292 | AUTHORS<br>TITLE<br>JOURNAL<br><br><br><br>REMARK<br>REFERENCE<br>AUTHORS<br><br><br>TITLE<br><br>JOURNAL | MEYERSON, M. L.<br>DIRECT SUBMISSION<br>SUBMITTED (12-May-1992) M. L. MEYERSON,<br>MASSACHUSETTS GENERAL HOSPITAL, CANCER<br>CENTER, BLDG 149, 13TH STREET, CHARLESTON<br>MA 02129, USA<br>SEQUENCE REVISED BY [3]<br>2 (BASES 1 TO 983)<br>MEYERSON, M., ENDERS, G. H., WU, C. L., SU, L. K.,<br>GORKA, C., NELSON, C., HARLOW, E.<br>AND TSAI, L. H.<br>A FAMILY OF HUMAN CDC2-RELATED PROTEIN<br>KINASES<br>EMBO J. 11 (8), 2909–2917 (1992) | 10 |
| CDK6 | Ser/Thr | Q00534 | X66365 | 326 | REFERENCE<br>AUTHORS<br>TITLE<br>JOURNAL<br><br><br><br>REFERENCE<br>AUTHORS<br><br><br>TITLE<br><br>JOURNAL | 1 (BASES 1 TO 1249)<br>MEYERSON, M. L.<br>DIRECT SUBMISSION<br>SUBMITTED (12-May-1992) M. L. MEYERSON,<br>MASSACHUSETTS GENERAL HOSPITAL, CANCER<br>CENTER, BLDG 149, 13TH STREET, CHARLESTON<br>MA 02129, USA<br>2 (BASES 1 TO 1249)<br>MEYERSON, M., ENDERS, G. H., WU, C. L., SU, L. K.,<br>GORKA, C., NELSON, C., HARLOW, E.<br>AND TSAI, L. H.<br>A FAMILY OF HUMAN CDC2-RELATED PROTEIN<br>KINASES<br>EMBO J. 11 (8), 2909–2917 (1992) | 11 |
| CDK7 | Ser/Thr | P50613 | X79193 | 346 | REFERENCE<br>AUTHORS<br><br>TITLE<br><br><br><br>JOURNAL | 1 (BASES 1 TO 1304)<br>TASSAN, J. P., SCHULTZ, S. J., BARTEK, J. AND<br>NIGG, E. A.<br>CELL CYCLE ANALYSIS OF THE ACTIVITY,<br>SUBCELLULAR LOCALIZATION, AND SUBUNIT<br>COMPOSITION OF HUMAN CAK (CDK-ACTIVATING<br>KINASE)<br>J. CELL BIOL. 127 (2), 467–478 (1994) | 12 |
| CDK8 | Ser/Thr | P49336 | X85753 | 464 | AUTHORS<br><br>TITLE | TASSAN, J. P., JAQUENOUD, M., LEOPOLD, P.,<br>SCHULTZ, S. J. AND NIGG, E. A.<br>IDENTIFICATION OF HUMAN CYCLIN-DEPENDENT<br>KINASE 8, A PUTATIVE PROTEIN KINASE<br>PARTNER FOR CYCLIN C | 13 |

TABLE 1-continued

| Kinase | Ser/Thr or Tyr | SwissProt | NCBI | Length | | References | SEQ ID NO. |
|---|---|---|---|---|---|---|---|
| | | | | | JOURNAL | PROC. NATL. ACAD. SCI. U.S.A. 92 (19), 8871–8875 (1995) | |
| CDK9 | Ser/Thr | P50750 | L25676 | 372 | AUTHORS | GRANA, X., DE LUCA, A., SANG, N., FU, Y., CLAUDIO, P. P., ROSENBLATT, J., MORGAN, D. O. AND GIORDANO, A. | 14 |
| | | | | | TITLE | PITALRE, A NUCLEAR CDC2-RELATED PROTEIN KINASE THAT PHOSPHORYLATES THE RETINOBLASTOMA PROTEIN IN VITRO | |
| | | | | | JOURNAL | PROC. NATL. ACAD. SCI. U.S.A. 91, 3834–3838 (1994) | |
| CSK | Tyr | P41240 | X74765 | 450 | AUTHORS | BRAUNINGER, A., KARN, T., STREBHARDT, K. AND RUBSAMEN-WAIGMANN, H. | 15 |
| | | | | | TITLE | CHARACTERIZATION OF THE HUMAN CSK LOCUS | |
| | | | | | JOURNAL | ONCOGENE 8 (5), 1365–1369 (1993) | |
| EGFR1 | Tyr | P00533 | X00588 | 1210 | AUTHORS | ULLRICH, A., COUSSENS, L., HAYFLICK, J. S., DULL, T. J., GRAY, A., TAM, A. W., LEE, J., YARDEN, Y., LIBERMANN, T. A., SCHLESSINGER, J., DOWNWARD, J., MAYES, E. L., WHITTLE, N., WATERFIELD, M. D. AND SEEBURG, P. H. | 16 |
| | | | | | TITLE | HUMAN EPIDERMAL GROWTH FACTOR RECEPTOR CDNA SEQUENCE AND ABERRANT EXPRESSION OF THE AMPLIFIED GENE IN A431 EPIDERMOID CARCINOMA CELLS | |
| | | | | | JOURNAL | NATURE 309 (5967), 418–425 (1984) | |
| ERB2 | Tyr | P04626 | M11767 | 1255 | AUTHORS | SEMBA, K., KAMATA, N., TOYOSHIMA, K. AND YAMAMOTO, T. | 17 |
| | | | | | TITLE | A V-ERBB-RELATED PROTOONCOGENE, C-ERBB-2, IS DISTINCT FROM THE C-ERBB-1/EPIDERMAL GROWTH FACTOR-RECEPTOR GENE AND IS AMPLIFIED IN A HUMAN SALIVARY GLAND ADENOCARCINOMA | |
| | | | | | JOURNAL | PROC. NATL. ACAD. SCI. U.S.A. 82, 6497–6501 (1985) | |
| ERB4 | Tyr | Q15303 | L07868 | 1308 | AUTHORS | PLOWMAN, G. D., CULOUSCOU, J. M., WHITNEY, G. S., GREEN, J. M., CARLTON, G. W., FOY, L., NEUBAUER, M. G. AND SHOYAB, M. | 18 |
| | | | | | TITLE | LIGAND-SPECIFIC ACTIVATION OF HER4/P180ERBB4, A FOURTH MEMBER OF THE EPIDERMAL GROWTH FACTOR RECEPTOR FAMILY | |
| | | | | | JOURNAL | PROC. NATL. ACAD. SCI. U.S.A. 90 (5), 1746–1750 (1993) | |
| ERK1 | Ser/Thr | P27361 | X60188 | 379 | AUTHORS | PELECH, S. L. | 19 |
| | | | | | TITLE | DIRECT SUBMISSION | |
| | | | | | JOURNAL | SUBMITTED (JUN-23-1991) S. L. PELECH, BIOMEDICAL RES CENTRE, 2222 HEALTH SCIENCE HALL, UNIV OF BRITISH COLUMBIA, VANCOUVER B C V6T 1Z3, CANADA | |
| | | | | | REFERENCE | 2 (BASES 1 TO 1866) | |
| | | | | | AUTHORS | CHAREST, D. L., MORDRET, G., HARDER, K. W., JIRIK, F. AND PELECH, S. L. | |
| | | | | | TITLE | MOLECULAR CLONING, EXPRESSION, AND CHARACTERIZATION OF THE HUMAN MITOGEN-ACTIVATED PROTEIN KINASE P44ERK1 | |
| | | | | | JOURNAL | MOL. CELL. BIOL. 13 (8), 4679–4690 (1993) | |
| ERK2 | Ser/Thr | P28482 | M84489 | 360 | AUTHORS | OWAKI, H., MAKAR, R., BOULTON, T. G., COBB, M. H. AND GEPPERT, T. D. | 20 |
| | | | | | TITLE | EXTRACELLULAR SIGNAL-REGULATED KINASES IN T CELLS: CHARACTERIZATION OF HUMAN ERK1 AND ERK2 CDNAS | |
| | | | | | JOURNAL | BIOCHEM. BIOPHYS. RES. COMMUN. 182 (3), 1416–1422 (1992) | |
| ERK3 | Ser/Thr | Q16659 | X80692 | 721 | AUTHORS | ZHU, A. X., ZHAO, Y., MOLLER, D. E. AND FLIER, J. S. | 21 |
| | | | | | TITLE | CLONING AND CHARACTERIZATION OF P97MAPK, A NOVEL HUMAN HOMOLOG OF RAT ERK-3 | |
| | | | | | JOURNAL | MOL. CELL. BIOL. 14 (12), 8202–8211 (1994) | |
| ERK4 | Ser/Thr | P31152 X59727 S38873 | | 557 | REFERENCE | 1 (BASES 1 TO 2354) | 22 |
| | | | | | AUTHORS | GONZALEZ, F. A., RADEN, D. L., RIGBY, M. R. AND DAVIS, R. J. | |
| | | | | | TITLE | HETEROGENEOUS EXPRESSION OF FOUR MAP KINASE ISOFORMS IN HUMAN TISSUES | |
| | | | | | JOURNAL | FEBS LETT. 304 (2–3), 170–178 (1992) MEDLINE 92316223 | |
| | | | | | REFERENCE | 2 (BASES 1 TO 4219) | |

TABLE 1-continued

| Kinase | Ser/Thr or Tyr | SwissProt | NCBI | Length | References | | SEQ ID NO. |
|---|---|---|---|---|---|---|---|
| | | | | | AUTHORS | GONZALEZ, F. A. | |
| | | | | | TITLE | DIRECT SUBMISSION | |
| | | | | | JOURNAL | SUBMITTED (27-JAN-1992) FERNANDO A GONZALEZ, BIOCHEMISTRY AND MOLECULAR BIOLOGY, UNIVERSITY OF MASSACHUSETTS MEDICAL SCHOOL, 373 PLANTATION ST., WORCESTER, MA, 01605, USA | |
| ERK5 | Ser/Thr | Q13164 | U25278 | 815 | AUTHORS | ZHOU, G., BAO, Z. Q. AND DIXON, J. E. | 23 |
| | | | | | TITLE | COMPONENTS OF A NEW HUMAN PROTEIN KINASE SIGNAL TRANSDUCTION PATHWAY | |
| | | | | | JOURNAL | J. BIOL. CHEM. 270 (21), 12665–12669 (1995) | |
| ERK6 | Ser/Thr | P53778 | X79483 | 367 | AUTHORS | LECHNER, C., ZAHALKA, M. A., GIOT, J. F., MOLLER, N. P. AND ULLRICH, A. | 24 |
| | | | | | TITLE | ERK6, A MITOGEN-ACTIVATED PROTEIN KINASE INVOLVED IN C2C12 MYOBLAST DIFFERENTIATION | |
| | | | | | JOURNAL | PROC. NATL. ACAD. SCI. U.S.A. 93 (9), 4355–4359 (1996) | |
| FAK1 | Tyr | Q05397 | L13616 | 1052 | AUTHORS | WHITNEY, G. S., CHAN, P. Y., BLAKE, J., COSAND, W. L., NEUBAUER, M. G., ARUFFO, A. AND KANNER, S. B. | 25 |
| | | | | | TITLE | HUMAN T AND B LYMPHOCYTES EXPRESS A STRUCTURALLY CONSERVED FOCAL ADHESION KINASE, PP125FAK | |
| | | | | | JOURNAL | DNA CELL BIOL. 12 (9), 823–830 (1993) | |
| FGFR1 | Tyr | P11362 | X51803 | 822 | AUTHORS | ISACCHI, A. | 26 |
| | | | | | TITLE | DIRECT SUBMISSION | |
| | | | | | JOURNAL | SUBMITTED (FEB-06-1990) ISACCHI A., FARMITALIA CARLO ERBA, VIALEBEZZI 24, 20146 MILANO, ITALY | |
| | | | | | REFERENCE | 2 (BASES 1 TO 2733) | |
| | | | | | AUTHORS | ISACCHI, A., BERGONZONI, L. AND SARMIENTOS, P. | |
| | | | | | TITLE | COMPLETE SEQUENCE OF A HUMAN RECEPTOR FOR ACIDIC AND BASIC FIBROBLAST GROWTH FACTORS | |
| | | | | | JOURNAL | NUCLEIC ACIDS RES. 18 (7), 1906 (1990) | |
| FGFR2 | Tyr | P21802 | M55614 M37715 | 821 | AUTHORS | HOUSSAINT, E., BLANQUET, P. R., CHAMPION-ARNAUD, P., GESNEL, M. C., TORRIGLIA, A., COURTOIS, Y. AND BREATHNACH, R. | 27 |
| | | | | | TITLE | RELATED FIBROBLAST GROWTH FACTOR RECEPTOR GENES EXIST IN THE HUMAN GENOME | |
| | | | | | JOURNAL | PROC. NATL. ACAD. SCI. U.S.A. 87 (20), 8180–8184 (1990) | |
| FGFR3 | Tyr | P22607 | M58051 | 806 | AUTHORS | KEEGAN, K., JOHNSON, D. E., WILLIAMS, L. T. AND HAYMAN, M. J. | 28 |
| | | | | | TITLE | ISOLATION OF AN ADDITIONAL MEMBER OF THE FIBROBLAST GROWTH FACTOR RECEPTOR FAMILY, FGFR-3 | |
| | | | | | JOURNAL | PROC. NATL. ACAD. SCI. U.S.A. 88 (4), 1095–1099 (1991) | |
| FGFR4 | Tyr | P22455 | X57205 | 802 | AUTHORS | PARTANEN, J. M. | 29 |
| | | | | | TITLE | DIRECT SUBMISSION | |
| | | | | | JOURNAL | SUBMITTED (14-JAN-1991) J. M. PARTANEN, UNIVERSITY OF HELSINKI, DEPARTEMENTS OF VIROLOGY & PATHOLOGY, CANCER BIOLOGY LABORATORY, HAARTMANINKATU 3, 00290 HELSINKI 29, FINLAND | |
| | | | | | REFERENCE | 2 (BASES 1 TO 2915) | |
| | | | | | AUTHORS | PARTANEN, J., MAKELA, T. P., EEROLA, E., KORHONEN, J., HIRVONEN, H., CLAESSONWELSH, L. AND ALITALO, K. | |
| | | | | | TITLE | FGFR-4, A NOVEL ACIDIC FIBROBLAST GROWTH FACTOR RECEPTOR WITH A DISTINCT EXPRESSION PATTERN | |
| | | | | | JOURNAL | EMBO J. 10 (6), 1347–1354 (1991) | |
| FYN | Tyr | P06241 | M14333 | 536 | AUTHORS | SEMBA, K., NISHIZAWA, M., MIYAJIMA, N., YOSHIDA, M. C., SUKEGAWA, J., YAMANASHI, Y., SASAKI, M., YAMAMOTO, T. AND TOYOSHIMA, K. | 30 |
| | | | | | TITLE | YES-RELATED PROTOONCOGENE, SYN, BELONGS TO THE PROTEIN-TYROSINE KINASE FAMILY | |
| | | | | | JOURNAL | PROC. NATL. ACAD. SCI. U.S.A. 83, 5459–5463 (1986) | |

TABLE 1-continued

| Kinase | Ser/Thr or Tyr | SwissProt | NCBI | Length | | References | SEQ ID NO. |
|---|---|---|---|---|---|---|---|
| HCK | Tyr | P08631 | M16591 | 526 | AUTHORS | QUINTRELL, N., LEBO, R., VARMUS, H., BISHOP, J. M., PETTENATI, M. J., LE BEAU, M. M., DIAZ, M. O. AND ROWLEY, J. D. | 31 |
| | | | | | TITLE | IDENTIFICATION OF A HUMAN GENE (HCK) THAT ENCODES A PROTEIN-TYROSINE KINASE AND IS EXPRESSED IN HEMOPOIETIC CELLS | |
| | | | | | JOURNAL | MOL. CELL. BIOL. 7 (6), 2267–2275 (1987) | |
| IKK-a | Ser/Thr | O15111 | AF012890 | 745 | AUTHORS | REGNIER, C. H., SONG, H. Y., GAO, X., GOEDDEL, D. V., CAO, Z. AND ROTHE, M. | 32 |
| | | | | | TITLE | IDENTIFICATION AND CHARACTERIZATION OF AN IKAPPAB KINASE | |
| | | | | | JOURNAL | CELL 90 (2), 373–383 (1997) | |
| IKK-b | Ser/Thr | O14920 | AF029684 | 756 | AUTHORS | Woronicz, J. D., Gao, X., Cac, Z., Rothe, M. and Goeddel, D. V. | 33 |
| | | | | | TITLE | IkappaB kinase-beta: NF-kappaB activation and complex formation with IkappaB kinase-alpha and NIK | |
| | | | | | JOURNAL | Science 278 (5339), 866–869 (1997) | |
| IKK-e | Ser/Thr | Q14164 | D63485 | 716 | AUTHORS | NAGASE, T., SEKI, N., TANAKA, A., ISHIKAWA, K. AND NOMURA, N. | 34 |
| | | | | | TITLE | PREDICTION OF THE CODING SEQUENCES OF UNIDENTIFIED HUMAN GENES. IV. THE CODING SEQUENCES OF 40 NEW GENES (KIAA0121–KIAA0160) DEDUCED BY ANALYSIS OF CDNA CLONES FROM HUMAN CELL LINE KG-1 | |
| | | | | | JOURNAL | DNA RES. 2 (4), 167–174 (1995) | |
| JAK1 | Tyr | P23458 | M64174 M35203 | 1142 | AUTHORS | WILKS, A. F., HARPUR, A. G., KURBAN, R. R., RALPH, S. J., ZUERCHER, G. AND ZIEMIECKI, A. | 35 |
| | | | | | TITLE | TWO NOVEL PROTEIN-TYROSINE KINASES, EACH WITH A SECOND PHOSPHOTRANSFERASE-RELATED CATALYTIC DOMAIN, DEFINE A NEW CLASS OF PROTEIN KINASE | |
| | | | | | JOURNAL | MOL. CELL. BIOL. 11, 2057–2065 (1991) | |
| JAK2 | Tyr | O60674 | AF058925 | 1132 | AUTHORS | SALTZMAN, A., STONE, M., FRANKS, C., SEARFOSS, G., MUNRO, R., JAYE, M. AND IVASHCHENKO, Y. | 36 |
| | | | | | TITLE | CLONING AND CHARACTERIZATION OF HUMAN JAK-2 KINASE: HIGH MRNA EXPRESSION IN IMMUNE CELLS AND MUSCLE TISSUE | |
| | | | | | JOURNAL | BIOCHEM. BIOPHYS. RES. COMMUN. 246 (3), 627–633 (1998) | |
| JAK3 | Tyr | P52333 | U09607 | 1124 | AUTHORS | KAWAMURA, M., MCVICAR, D. W., JOHNSTON, J. A., BLAKE, T. B., CHEN, Y., LAL, B. K., LLOYD, A. R., KELVIN, D. J., STAPLES, J. E., ORTALDO, J. R. AND O'SHEA, J. | 37 |
| | | | | | TITLE | MOLECULAR CLONING OF L-JAK, A JANUS FAMILY PROTEIN-TYROSINE KINASE EXPRESSED IN NATURAL KILLER CELLS AND ACTIVATED LEUKOCYTES | |
| | | | | | JOURNAL | PROC. NATL. ACAD. SCI. U.S.A. 91, 6374–6378 (1994) | |
| JNK1 | Ser/Thr | P45983 | L26318 | 427 | AUTHORS | DERIJARD, B., HIBI, M., WU, I.-H., BARRETT, T., SU, B., DENG, T., KARIN, M. AND DAVIS, R. J. | 38 |
| | | | | | TITLE | JNK1: A PROTEIN KINASE STIMULATED BY UV LIGHT AND HA-RAS THAT BINDS AND PHOSPHORYLATES THE C-JUN ACTIVATION DOMAIN | |
| | | | | | JOURNAL | CELL 76, 1025–1037 (1994) | |
| JNK2 | Ser/Thr | P45984 | L31951 | 424 | AUTHORS | SLUSS, H. K., BARRETT, T., DERIJARD, B. AND DAVIS, R. J. | 39 |
| | | | | | TITLE | SIGNAL TRANSDUCTION BY TUMOR NECROSIS FACTOR MEDIATED BY JNK PROTEIN KINASES | |
| | | | | | JOURNAL | MOL. CELL. BIOL. 14, 8376–8384 (1994) | |
| JNK3 | Ser/Thr | P53779 | U07620 | 464 | AUTHORS | MOHIT, A. A., MARTIN, J. H. AND MILLER, C. A. | 40 |
| | | | | | TITLE | P493F12 KINASE: A NOVEL MAP KINASE EXPRESSED IN A SUBSET OF NEURONS IN THE HUMAN NERVOUS SYSTEM | |
| | | | | | JOURNAL | NEURON 14 (1), 67–78 (1995) | |
| LCK | Tyr | P06239 | X13529 | 508 | AUTHORS | PERLMUTTER, R. M., MARTH, J. D., LEWIS, D. B., PEET, R., ZIEGLER, S. F. AND WILSON, C. B. | 41 |
| | | | | | TITLE | STRUCTURE AND EXPRESSION OF LCK TRANSCRIPTS IN HUMAN LYMPHOID CELLS | |
| | | | | | JOURNAL | J. CELL. BIOCHEM. 38 (2), 117–126 (1988) | |

TABLE 1-continued

| Kinase | Ser/Thr or Tyr | SwissProt | NCBI | Length | | References | SEQ ID NO. |
|---|---|---|---|---|---|---|---|
| LYN | Tyr | P07948 | M16038 | 511 | AUTHORS | YAMANASHI, Y., FUKUSHIGE, S., SEMBA, K., SUKEGAWA, J., MIYAJIMA, N., MATSUBARA, K., YAMAMOTO, T. AND TOYOSHIMA, K. | 42 |
| | | | | | ITLE | THE YES-RELATED CELLULAR GENE LYN ENCODES A POSSIBLE TYROSINE KINASE SIMILAR TO P56LCK | |
| | | | | | JOURNAL | MOL. CELL. BIOL. 7 (1), 237–243 (1987) | |
| MAPK | Ser/Thr | Q16539 | L35263 | 360 | AUTHORS | LEE, J. C., LAYDON, J. T., MCDONNELL, P. C., GALLAGHER, T. F., KUMAR, S., GREEN, D. W., MCNULTY, D., BLUMENTHAL, M. J., HEYS, R. J., LANDVATTER, S. W., STRICKLER, J. E., MCLAUGHLIN, M. M., SIEMENS, I., FISHER, S. H., LIVI, G. P., WHITE, J. R., ADAMS, J. L. AND YOUNG, P. R. | 43 |
| | | | | | TITLE | IDENTIFICATION AND CHARACTERIZATION OF A NOVEL PROTEIN KINASE INVOLVED IN THE REGULATION OF INFLAMMATORY CYTOKINE BIOSYNTHESIS | |
| | | | | | JOURNAL | NATURE 372, 739–746 (1994) | |
| NIK | Ser/Thr | Q99558 | Y10256 | 947 | AUTHORS | MALININ, N. L., BOLDIN, M. P., KOVALENKO, A. V. AND WALLACH, D. | 44 |
| | | | | | TITLE | MAP3K-RELATED KINASE INVOLVED IN NF-KAPPAB INDUCTION BY TNF, CD95 AND IL-1 | |
| | | | | | JOURNAL | NATURE 385 (6616), 540–544 (1997) | |
| PAK1 | Ser/Thr | P50527 | U22371 | 545 | AUTHORS | OTTILIE, S., MILLER, P. J., JOHNSON, D. I., CREASY, C. L., SELLS, M. A., BAGRODIA, S., FORSBURG, S. L. AND CHERNOFF, J. | 45 |
| | | | | | TITLE | FISSION YEAST PAK1+ ENCODES A PROTEIN KINASE THAT INTERACTS WITH CDC42P AND IS INVOLVED IN THE CONTROL OF CELL POLARITY AND MATING | |
| | | | | | JOURNAL | EMBO J. 14 (23), 5908–5919 (1995) | |
| PAK2 | Ser/Thr | Q13177 | U24153 | 524 | AUTHORS | SELLS, M., KNAUSE, U. J., BAGRODIA, S., AMBROSE, D., BOKOCH, G. M. AND CHERNOFF, J. | 46 |
| | | | | | TITLE | HUMAN P21-ACTIVATED PROTEIN KINASES REGULATE ACTIN ORGANIZATION IN MAMMALIAN CELLS | |
| | | | | | JOURNAL | UNPUBLISHED | |
| | | | | | REFERENCE | 2 (BASES 1 TO 2019) | |
| | | | | | AUTHORS | CHERNOFF, J. | |
| | | | | | TITLE | DIRECT SUBMISSION | |
| | | | | | JOURNAL | SUBMITTED (05-APR-1995) JONATHAN CHERNOFF, FOX CHASE CANCER CENTER, 7701 BURHOLME AVE, PHILADELPHIA, PA 19111, USA | |
| PAK3 | Ser/Thr | O75914 | AF068864 | 544 | AUTHORS | ALLEN, K. M., GLEESON, J. G., BAGRODIA, S., PARTINGTON, M. W., MACMILLAN, J. C., CERIONE, R. A., MULLEY, J. C. AND WALSH, C. A. | 47 |
| | | | | | TITLE | PAK3 MUTATION IN NONSYNDROMIC X-LINKED MENTAL RETARDATION | |
| | | | | | JOURNAL | NAT. GENET. 20 (1), 25–30 (1998) | |
| PAK4 | Ser/Thr | O96013 | AJ011855 | 591 | AUTHORS | ABO, A., QU, J., CAMMARANO, M. S., DAN, C., FRITSCH, A., BAUD, V., BELISLE, B. AND MINDEN, A. | 48 |
| | | | | | TITLE | PAK4, A NOVEL EFFECTOR FOR CDC42HS, IS IMPLICATED IN THE REORGANIZATION OF THE ACTIN CYTOSKELETON AND IN THE FORMATION OF FILOPODIA | |
| | | | | | JOURNAL | EMBO J. 17 (22), 6527–6540 (1998) | |
| PAK5 | Ser/Thr | Q9P286 | AB040812 | 719 | AUTHORS | WATANABE, N. M., DAN, I., SUZUKI-YAMASHITA, K., KIMURA, W. K., NAKASHIMA, T. M., KAJIKAWA, E., FUKAGAYA, Y. AND KUSUMI, A. | 49 |
| | | | | | TITLE | PAK5, A NOVEL GROUP II PAK FAMILY KINASE THAT IS PREDOMINANTLY EXPRESSED IN BRAIN | |
| | | | | | JOURNAL | UNPUBLISHED | |
| | | | | | REFERENCE | 2 (BASES 1 TO 4612) | |
| | | | | | AUTHORS | KIMURA, W. K., WATANABE, N. M., DAN, I. AND KUSUMI, A. | |
| | | | | | TITLE | DIRECT SUBMISSION | |
| | | | | | JOURNAL | SUBMITTED (29-MAR-2000) IPPEITA DAN, NAGOYA UNIVERSITY, DEPT. OF BIOLOGICAL SCIENCE; CHIKUSA-KU, FURO-CHO, NAGOYA, AICHI 464–8602, JAPAN (E-MAIL: DANG@BIO.NAGOYA-U.AC.JP, | |

TABLE 1-continued

| Kinase | Ser/Thr or Tyr | SwissProt | NCBI | Length | References | | SEQ ID NO. |
|---|---|---|---|---|---|---|---|
| | | | | | | URL: http://www.supra.bio.nagoya-U.AC.JP/DNA/, TEL: 81-52-789-2497, FAX: 81-52-789-2968) | |
| PDGFR-a | Tyr | P16234 | M21574 | 1089 | AUTHORS | MATSUI, T., HEIDARAN, M., MIKI, T., POPESCU, N., LA ROCHELLE, W., KRAUS, M., PIERCE, J. AND AARONSON, S. | 50 |
| | | | | | TITLE | ISOLATION OF A NOVEL RECEPTOR CDNA ESTABLISHES THE EXISTENCE OF TWO PDGF RECEPTOR GENES | |
| | | | | | JOURNAL | SCIENCE 243 (4892), 800–804 (1989) | |
| PDGFR-b | Tyr | P09619 | J03278 | 1106 | AUTHORS | GRONWALD, R. G., GRANT, F. J., HALDEMAN, B. A., HART, C. E., O'HARA, P. J., HAGEN, F. S., ROSS, R., BOWEN-POPE, D. F. AND MURRAY, M. J. | 51 |
| | | | | | TITLE | CLONING AND EXPRESSION OF A CDNA CODING FOR THE HUMAN PLATELET-DERIVED GROWTH FACTOR RECEPTOR: EVIDENCE FOR MORE THAN ONE RECEPTOR CLASS | |
| | | | | | JOURNAL | PROC. NATL. ACAD. SCI. U.S.A. 85 (10), 3435–3439 (1988) | |
| PIM1 | Ser/Thr | P11309 | M27903 | 313 | AUTHORS | REEVES, R., SPIES, G. A., KIEFER, M., BARR, P. J. AND POWER, M. | 52 |
| | | | | | TITLE | PRIMARY STRUCTURE OF THE PUTATIVE HUMAN ONCOGENE, PIM-1 | |
| | | | | | JOURNAL | GENE 90 (2), 303–307 (1990) | |
| A-Raf | Ser/Thr | P10398 | X04790 | 606 | AUTHORS | BECK, T. W., HULEIHEL, M., GUNNELL, M., BONNER, T. I. AND RAPP, U. R. | 53 |
| | | | | | TITLE | THE COMPLETE CODING SEQUENCE OF THE HUMAN A-RAF-1 ONCOGENE AND TRANSFORMING ACTIVITY OF A HUMAN A-RAF CARRYING RETROVIRUS | |
| | | | | | JOURNAL | NUCLEIC ACIDS RES. 15 (2), 595–609 (1987) | |
| B-Raf | Ser/Thr | P15056 | M95712 M95720 X54072 | 765 | REFERENCE JOURNAL | 1 (sites) AUTHORS Sithanandam, G. Unpublished (1990) | 54 |
| | | | | | REFERENCE AUTHORS | 2 (BASES 285 TO 2510) SITHANANDAM, G., KOLCH, W., DUH, F. M. AND RAPP, U. R. | |
| | | | | | TITLE | COMPLETE CODING SEQUENCE OF A HUMAN B-RAF CDNA AND DETECTION OF B-RAF POTEIN KINASE WITH ISOZYME SPECIFIC ANTIBODIES | |
| | | | | | JOURNAL | ONCOGENE 5, 1775–1780 (1990) | |
| | | | | | REFERENCE AUTHORS | 3 (sites) Stephens, R. M., Sithanandam, G., Copeland, T., Kaplan, D. R., Rapp, U. R. and Morrison, D. K. | |
| | | | | | TITLE | 95 kDa b-Raf serine/threonine kinase: idendification of the protein and its major autophosphorylation site | |
| | | | | | JOURNAL | Unpublished (1992) | |
| C-Raf | Ser/Thr | P04049 | X03484 | 648 | AUTHORS | BONNER, T. I., OPPERMANN, H., SEEBURG, P., KERBY, S. B., GUNNELL, M. A., YOUNG, A. C. AND RAPP, U. R. | 55 |
| | | | | | TITLE | THE COMPLETE CODING SEQUENCE OF THE HUMAN RAF ONCOGENE AND THE CORRESPONDING STRUCTURE OF THE C-RAF-1 GENE | |
| | | | | | JOURNAL | NUCLEIC ACIDS RES. 14 (2), 1009–1015 (1986) | |
| SRC | Tyr | P12931 | AL133293 | 535 | AUTHORS TITLE JOURNAL | WALLIS, J. DIRECT SUBMISSION SUBMITTED (06-MAR-2001) SANGER CENTRE, HINXTON, CAMBRIDGESHIRE, CB10 1SA, UK. E-MAIL ENQUIRIES: HUMQUERY@SANGER.AC.UK CLONE REQUESTS: CLONEREQUEST@SANGER.AC.UK | 56 |
| | | | | | COMMENT | ON AUG 2, 2000 THIS SEQUENCE VERSION REPLACED GI: 8919193. DURING SEQUENCE ASSEMBLY DATA IS COMPARED. FROM OVERLAPPING CLONES. WHERE DIFFERENCES ARE FOUND THESE ARE ANNOTATED AS VARIATIONS TOGETHER WITH A NOTE OF THE OVERLAPPING CLONE NAME. NOTE THAT THE VARIATION ANNOTATION MAY NOT BE FOUND IN THE SEQUENCE SUBMISSION CORRESPONDING TO THE OVERLAPPING CLONE, AS WE SUBMIT SEQUENCES WITH ONLY A SMALL OVERLAP AS DESCRIBED ABOVE. THE FOLLOWING | |

TABLE 1-continued

| Kinase | Ser/Thr or Tyr | SwissProt | NCBI | Length | | References | SEQ ID NO. |
|---|---|---|---|---|---|---|---|
| | | | | | | ABBREVIATIONS ARE USED TO ASSOCIATE PRIMARY ACCESSION NUMBERS GIVEN IN THE FEATURE TABLE WITH THEIR SOURCE DATABASES: EM:, EMBL; SW:, SWISSPROT; TR:, TREMBL; WP:, WORMPEP; INFORMATION ON THE WORMPEP DATABASE CAN BE FOUND AT HTTP://WWW.SANGER.AC.UK/ PROJECTS/C_ELEGANS/ WORMPEP THIS SEQUENCE WAS GENERATED FROM PART OF BACTERIAL CLONE CONTIGS OF HUMAN CHROMOSOME 20, CONSTRUCTED BY THE SANGER CENTRE CHROMOSOME 20 MAPPING GROUP.FURTHER INFORMATION CAN BE FOUND AT HTTP://WWW.SANGER.AC.UK/HGP/CHR20 IMPORTANT: THIS SEQUENCE IS NOT THE ENTIRE INSERT OF CLONE RP5-823N20 IT MAY BE SHORTER BECAUSE WE SEQUENCE OVERLAPPING SECTIONS ONLY ONCE, EXCEPT FOR A 100 BASE OVERLAP. THE TRUE LEFT END OF CLONE RP5-823N20 IS AT 1 IN THIS SEQUENCE. THE TRUE LEFT END OF CLONE RP4-592G19 IS AT 68563 IN THIS SEQUENCE. THIS SEQUENCE WAS FINISHED AS FOLLOWS UNLESS OTHERWISE NOTED: ALL REGIONS WERE EITHER DOUBLE-STRANDED OR SEQUENCED WITH AN ALTERNATE CHEMISTRY OR COVERED BY HIGH QUALITY DATA (I.E., PHRED QUALITY >= 30); AN ATTEMPT WAS MADE TO RESOLVE ALL SEQUENCING PROBLEMS, SUCH AS COMPRESSIONS AND REPEATS; ALL REGIONS WERE COVERED BY AT LEAST ONE PLASMID SUBCLONE OR MORE THAN ONE M13 SUBCLONE; AND THE ASSEMBLY WAS CONFIRMED BY RESTRICTION DIGEST. RP5-823N20 IS FROM THE LIBRARY RPCI-5 CONSTRUCTED BY THE GROUP OF PIETER DE JONG. FOR FURTHER DETAILS SEE HTTP://WWW.CHORI.ORG/BACPAC/HOME.HTM VECTOR: PCYPAC2. | |
| SRC2 (c-FGR) | Tyr | P09769 | M19722 J03429 | 529 | AUTHORS | KATAMINE, S., NOTARIO, V., RAO, C.D., MIKI, T., CHEAH, M. S., TRONICK, S. R. AND ROBBINS, K. C. | 57 |
| | | | | | TITLE | PRIMARY STRUCTURE OF THE HUMAN FGR PROTO-ONCOGENE PRODUCT P55C-FGR | |
| | | | | | JOURNAL | MOL. CELL. BIOL. 8 (1), 259–266 (1988) | |
| STK1 (FLT3) | Tyr | P36888 | U02687 | 993 | AUTHORS | SMALL, D., LEVENSTEIN, M., KIM, E., CAROW, C., AMIN S,. ROCKWELL, P., WITTE, L., BURROW, C., RATAJCZAK, M. Z., GEWIRTZ, A. M. AND CIVIN, C. I. | 58 |
| | | | | | TITLE | STK-1, THE HUMAN HOMOLOG OF FLK-2/FLT-3, IS SELECTIVELY EXPRESSED IN CD34+ HUMAN BONE MARROW CELLS AND IS INVOLVED IN THE PROLIFERATION OF EARLY PROGENITOR/STEM CELLS | |
| | | | | | JOURNAL | PROC. NATL. ACAD. SCI. U.S.A. 91, 459–463 (1994) | |
| SYK | Tyr | P43405 | Z29630 | 635 | AUTHORS | YAGI, S., SUZUKI, K., HASEGAWA, A., OKUMURA, K. AND RA, C. | 59 |
| | | | | | TITLE | CLONING OF THE CDNA FOR THE DELETED SYK KINASE HOMOLOGOUS TO ZAP-70 FROM HUMAN BASOPHILIC LEUKEMIA CELL LINE (KU812) | |
| | | | | | JOURNAL | BIOCHEM. BIOPHYS. RES. COMMUN. 200 (1), 28–34 (1994) | |
| TEC | Tyr | P42680 | D29767 | 631 | AUTHORS | MANO, H. | 60 |
| | | | | | TITLE | DIRECT SUBMISSION | |
| | | | | | JOURNAL | SUBMITTED (01-APR-1994) HIROYUKI MANO, JICHI MEDICAL SCHOOL, DEPARTMENT OF MOLECULAR BIOLOGY; 3311–1 YAKUSHIJI, MINAMIKAWACHI-MACHI, KAWACHI-GUN, TOCHIGI 329-04, JAPAN (E-MAIL: HMANO@JICHI.AC.JP, TEL: 0285-44-2111 (EX.3482), (FAX: 0285-44-8675) | |
| | | | | | REFERENCE | 2 (BASES 1 TO 3650) | |
| | | | | | AUTHORS | SATO, K., MANO, H., ARIYAMA, T., INAZAWA, J., YAZAKI, Y. AND HIRAI, H. | |
| | | | | | TITLE | MOLECULAR CLONING AND ANALYSIS OF THE | |

TABLE 1-continued

| Kinase | Ser/Thr or Tyr | SwissProt | NCBI | Length | | References | SEQ ID NO. |
|---|---|---|---|---|---|---|---|
| TFGR1 | Ser/Thr | P36897 | L11695 | 503 | JOURNAL<br>AUTHORS<br><br>TITLE | HUMAN TEC PROTEIN-TYROSINE KINASE<br>LEUKEMIA 8 (10), 1663–1672 (1994)<br>FRANZEN, P., TEN DIJKE, P., ICHIJO, H.,<br>YAMASHITA, H., SCHULZ, P., HELDIN, C.H. AND<br>MIYAZONO, K.<br>CLONING OF A TGF BETA TYPE I RECEPTOR<br>THAT FORMS A HETEROMERIC COMPLEX WITH THE<br>TGF BETA TYPE II RECEPTOR | 61 |
| TGFR2 | Ser/Thr | P37173 | M85079 | 567 | JOURNAL<br>AUTHORS<br><br>TITLE | CELL 75 (4), 681–692 (1993)<br>LIN, H. Y., WANG, X. F., NG-EATON, E.,<br>WEINBERG, R. A. AND LODISH, H. F.<br>EXPRESSION CLONING OF THE TGF-BETA TYPE<br>II RECEPTOR, A FUNCTIONAL TRANSMEMBRANE<br>SERINE/THREONINE KINASE [PUBLISHED<br>ERRATUM APPEARS IN CELL 1992 SEP<br>18;70 (6): FOLLOWING 1068] | 62 |
| TIE1 | Tyr | P35590 | X60957<br>S89716 | 1138 | JOURNAL<br>AUTHORS<br>TITLE<br>JOURNAL<br><br><br><br><br>REMARK<br>REFERENCE<br>AUTHORS<br><br><br>TITLE | CELL 68 (4), 775–785 (1992)<br>PARTANEN, J. M.<br>DIRECT SUBMISSION<br>SUBMITTED (18-JUL-1991) J. M. PARTANEN,<br>UNIVERSITY OF HELSINKI, CANCER BIOLOGY<br>LABORATORY, DEPT OF PATHOLOGY AND<br>VIROLOGY, HAARTMANINKATU 3, 00290<br>HELSINKI, FINLAND<br>REVISED BY [3]<br>2 (BASES 1 TO 3845)<br>PARTANEN, J., ARMSTRONG, E., MAKELA, T. P.,<br>KORHONEN, J., SANDBERG, M.,<br>RENKONEN, R., KNUUTILA, S., HUEBNER, K.<br>AND ALITALO, K.<br>A NOVEL ENDOTHELIAL CELL SURFACE RECEPTOR<br>TYROSINE KINASE WITH EXTRACELLULAR<br>EPIDERMAL GROWTH FACTOR HOMOLOGY DOMAINS | 63 |
| TIE2 | Tyr | Q02763 | L06139 | 1124 | JOURNAL<br>AUTHORS<br><br>TITLE | MOL. CELL. BIOL. 12 (4), 1698–1707 (1992)<br>ZIEGLER, S. F., BIRD, T. A., SCHNERINGER, J. A.,<br>SCHOOLEY, K. A. AND BAUM, P. R.<br>MOLECULAR CLONING AND CHARACTERIZATION OF<br>A NOVEL RECEPTOR PROTEIN TYROSINE KINASE<br>FROM HUMAN PLACENTA | 64 |
| VEGFR1 | Tyr | P53767 | D28498 | 1333 | JOURNAL<br>AUTHORS<br>TITLE<br>JOURNAL<br><br><br><br><br>REFERENCE<br>AUTHORS<br>JOURNAL<br>REFERENCE<br>AUTHORS<br><br><br>TITLE | ONCOGENE 8 (3), 663–670 (1993)<br>SHIBUYA, M.<br>DIRECT SUBMISSION<br>SUBMITTED (06-FEB-1994) MASABUMI SHIBUYA,<br>INSTITUTE OF MEDICAL SCIENCE, UNIVERSITY<br>OF TOKYO, DEPARTMENT OF INTERNAL<br>MEDICINE; 4-6-1 SHIROKANEDAI, MINATO-KU,<br>TOKYO 108, JAPAN (TEL: 03-5449-5550,<br>FAX: 03-5449-5425)<br>2 (BASES 1 TO 4734)<br>SHIBUYA, M.<br>UNPUBLISHED<br>3 (SITES)<br>YAMANE, A., SEETHARAM, L., YAMAGUCHI, S.,<br>GOTOH, N., TAKAHASHI, T., NEUFELD, G. AND<br>SHIBUYA, M.<br>A NEW COMMUNICATION SYSTEM BETWEEN<br>HEPATOCYTES AND SINUSOIDAL ENDOTHELIAL<br>CELLS IN LIVER THROUGH VASCULAR<br>ENDOTHELIAL GROWTH FACTOR AND FLT<br>TYROSINE KINASE RECEPTOR FAMILY (FLT-1<br>AND KDR/FLK-1) | 65 |
| VEGFR2 | Tyr | P35968 | AF035121 | 1356 | JOURNAL<br>AUTHORS<br>TITLE | ONCOGENE 9 (9), 2683–2690 (1994)<br>YIN, L. Y., WU, Y. AND PATTERSON, C.<br>FULL LENGTH HUMAN KDR/FLK-1 SEQUENCE | 66 |

What is claimed is:

1. A method for identifying ligands binding to an inactive conformation of a target protein kinase, comprising
   (a) contacting the inactive conformation of said protein kinase having a first and a second binding site of interest and containing or modified to contain a nucleophile at or near the first site of interest with a plurality of ligand candidates, said candidates having a functional group reactive with the nucleophile, under conditions such that a reversible covalent bond is formed between the nucleophile and a candidate that has affinity for the first site of interest, to form a kinase-first ligand complex;
   (b) identifying the first ligand from the complex of (a);
   (c) designing a derivative of the first ligand identified in (a) to provide a small molecule extender (SME) having a first functional group reactive with the nucleophile on the kinase and a second functional group reactive with a second ligand having affinity for the second binding site of interest;
   (d) contacting the SME with the kinase to form a kinase-SME complex, and
   (e) contacting the kinase-SME complex with a plurality of second ligand candidates, said candidates having a functional group reactive with the SME in said kinase-SME complex, wherein a candidate that has affinity for said second binding site of interest on said kinase forms a reversible covalent bond with said kinase-SME complex, whereby a second ligand is identified.

2. The method of claim 1 wherein said nucleophile is selected from the group consisting of —SH, —OH, —NH₂ and —COOH groups.

3. The method of claim 2 wherein said nucleophile is provided by a side chain of an amino acid residue selected from the group consisting of cysteine, serine, threonine, lysine, asparagine, and glutamine.

4. The method of claim 3 wherein said nucleophile is an —SH group provided by the side chain of a cysteine residue.

5. The method of claim 4 wherein said kinase contains said cysteine residue without further modification.

6. The method of claim 5 wherein said cysteine residue is selected from the group consisting of C53 of CDK5; C183 of ERK1; C166 of ERK2; C28 of ERK3; C488 of FGFR1; C491 of FGFR2; C482 of FGFR3; C477 of FGFR4; C533 of NIK; C835 of PDGFR-a; C-843 of PDGFR-b; C279 of SRC; C273 of SRC2; C828 of STK1; C39 of TGFR2; C1039 of VEGFR1; C1045 of VEGFR2; C1054 of VEGFR3; C287 of YES; and C346 of ZAP-70.

7. The method of claim 4 wherein said kinase is modified to contain said cysteine residue.

8. The method of claim 7 wherein said cysteine residue is introduced into said target protein kinase to result in a variant selected from the group consisting of E234C AKT1; E236C ALT2; E232C AKT3; D86C CDK1; D86C CDK2; D86C CDK3; D99C CDK4; D86C CDK5; D104C CDK6;

D97C CDK7; D103C CDK8; D108C CDK9; S273C CSK; D128C ERK1; D111C ERK2; D114C ERK3; D111C ERK4; D142C ERK5; D115C ERK6; E506C FAK1; N568C FGFR1; N571C FGFR2; N562C FGFR3; N557C FGFR4; D348C FYN; S340C HCK; D102C IKK-a; D103C IKK-b; S93C IKK-e; S951C JAK1; S936C JAK2; N114C JNK1; N114C JNK2; N152C JNK3; S322C LCK; S325C LYN; D112C MAPK; S476C NIK; S351C PAK1; S330C PAK2; S349C PAK3; A402C PAK4; A530C PAK5; D861C PDGFR-a; D688C PDGFR-b; D128C PIM1; S389C A-Raf; S535C B-Raf; S428C C-Raf; S347C SRC; S341C SRC2; D698C STK1; P455C SYK; S287C TGFR1; N332C TGFR2; N924C TIE1; N909C TIE2; N917C VEGFR1; N923C VEGFR2; N934C VEGFR3; S355C YES; and P421C ZAP-70.

9. The method of claim 4 wherein said SME comprises a group capable of undergoing SN2-like attack or forming a Michael-type adduct with the —SH group of said cysteine residue.

10. The method of claim 9 wherein said group is selected from the group consisting of α-halo acids, fluorophoph(on)ates, epoxides, aziridines, thiiranes, halo-methyl ketones, and halo-methyl amides.

11. The method of claim 4 wherein said second functional group is an —SH group.

12. The method of claim 1 wherein wherein said ligand candidates are members of a small molecule library of less than 1500 daltons, less than 1000 daltons, less than 750 daltons, less than 500 daltons, or less than 250 daltons in size.

13. The method of claim 12 wherein each member of said library differs in molecular weight from each other member of said library.

14. The method of claim 13 wherein said library contains 1 to 100 members.

15. The method of claim 1 wherein said small molecule extender is selected from the group consisting of

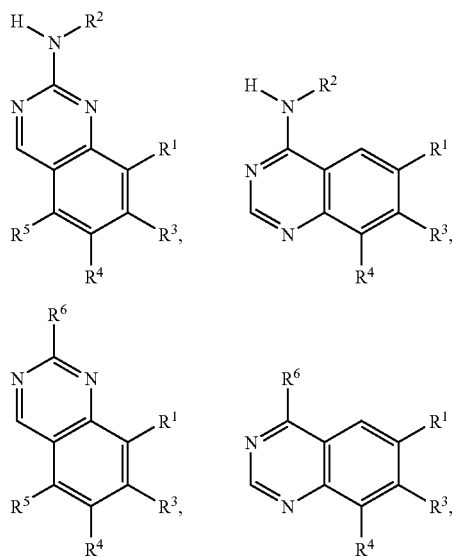

-continued

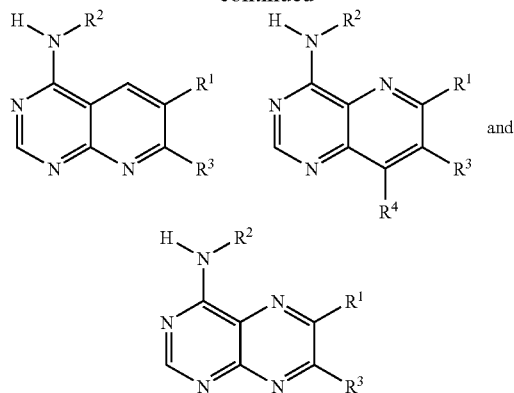

where R1, R2, R3, R4, R5, and R6 are each independently selected from the group consisting of hydrogen, C1–C5 alkyl, C1–C5 alkylamine, and aryl provided that at least one R group on the SME is a Michael acceptor and another R group is selected from —(CH$_2$)$_n$—SR'; —C(=O)—(CH$_2$)$_n$—SR'; —O—(CH$_2$)$_n$—SR'; —(CH$_2$)$_n$—SR'; a thiol protecting group, wherein R' is hydrogen, a disulfide, or a thiol protecting group, and n is 1 to 5.

16. The method of claim 15 wherein R$^1$ is a Michael acceptor selected from the group consisting of

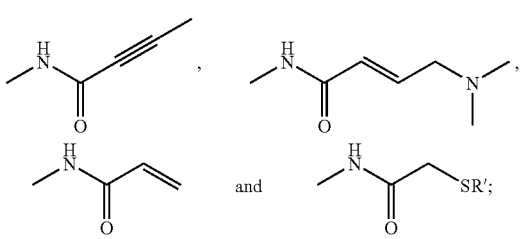

and R2, R3, R4, R5, and R6 are each independently selected from the group consisting of hydrogen, C1–C5 alkyl, C1–C5 alkylamine, aryl; —(CH$_2$)$_n$—SR'; —C(=O)—(CH$_2$)$_n$—SR'; —(CH$_2$)$_n$—SR'; —(CH$_2$)$_n$—SR'; and a thiol protecting group provided that one of R2, R3, R4, R5, and R6 is selected from —(CH$_2$)$_n$—SR'; —C(=O)—(CH$_2$)$_n$—SR'; —O—(CH$_2$)$_n$—SR'; and a thiol protecting group, wherein R' is hydrogen, a disulfide, or a thiol protecting group, and n is 1 to 5.

17. The method of claim 15, wherein R3 is a Michael acceptor selected from the group consisting of

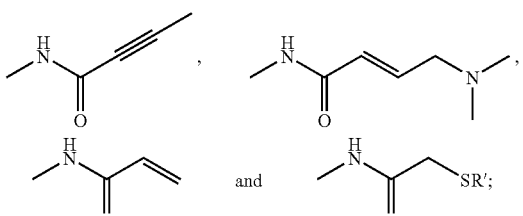

and R1, R2, R4, R5, and R6 are each independently selected from the group consisting of hydrogen, C1–C5 alkyl, C1–C5 alkylamine, aryl; —(CH$_2$)$_n$—SR'; —C(=O)—(CH$_2$)$_n$—

SR'; —O—(CH₂)ₙ—SR'; —(CH₂)—SR'; and a thiol protecting group provided that one of R1, R2, R4, R5, and R6 is selected from —(CH₂)ₙ—SR'; —C(=O)—(CH₂)ₙ—SR'; —O—(CH₂)ₙ—SR'; —(CH₂)ₙ—SR'; and a thiol protecting group, wherein R' is hydrogen, a disulfide, or a thiol protecting group, and n is 1 to 5.

18. A method for identifying ligands binding to an inactive conformation of a target protein kinase, comprising
  (a) screening a library of ligand candidates with a kinase-ligand conjugate formed by the covalent bonding of the inactive conformation of a kinase comprising a first reactive functionality with a compound that comprises (1) a second reactive functionality and (2) a chemically reactive group, wherein the second reactive functionality of the compound reacts with the first reactive functionality of the inactive conformation of said target protein kinase to form a first covalent bond such that the kinase-ligand conjugate contains a free chemically reactive group, under conditions wherein at least one member of the library forms a second covalent bond with the kinase-ligand conjugate; and
  (b) identifying a further ligand that binds covalently to the chemically reactive group of the kinase-ligand conjugate.

19. The method of claim 18 wherein the first reactive functionality of the kinase comprises a nucleophile that is selected from the group consisting of —SH, —OH, —NH₂ and —COOH groups.

20. The method of claim 19 wherein said nucleophile is provided by a side chain of an amino acid residue selected from the group consisting of cysteine, serine, threonine, lysine, asparagine, and glutamine.

21. The method of claim 18 wherein said nucleophile is an —SH group provided by the side chain of a cysteine residue.

22. The method of claim 21 wherein said cysteine residue is selected from the group consisting of C53 of CDK5; C183 of ERK1; C166 of ERK2; C28 of ERK3; C488 of FGFR1; C491 of FGFR2; C482 of FGFR3; C477 of FGFR4; C533 of NIK; C835 of PDGFR-a; C-843 of PDGFR-b; C279 of SRC; C273 of SRC2; C828 of STK1; C39 of TGFR2; C1039 of VEGFR1; C1045 of VEGFR2; C1054 of VEGFR3; C287 of YES; and C346 of ZAP-70.

23. The method of claim 21 wherein said kinase is modified to contain said cysteine residue.

24. The method of claim 23 wherein said cysteine residue is introduced into said target protein kinase to result in a variant selected from the group consisting of E234C AKT1; E236C ALT2; E232C AKT3; D86C CDK1; D86C CDK2; D86C CDK3; D99C CDK4; D86C CDK5; D104C CDK6; D97C CDK7; D103C CDK8; D108C CDK9; S273C CSK; D128C ERK1; D111C ERK2; D114C ERK3; D111C ERK4; D142C ERK5; D115C ERK6; E506C FAK1; N568C FGFR1; N571C FGFR2; N562C FGFR3; N557C FGFR4; D348C FYN; S340C HCK; D102C IKK-a; D103C IKK-b; S93C IKK-e; S951C JAK1; S936C JAK2; N114C JNK1; N114C JNK2; N152C JNK3; S322C LCK; S325C LYN; D112C MAPK; S476C NIK; S351C PAK1; S330C PAK2; S349C PAK3; A402C PAK4; A530C PAK5; D861C PDGFR-a; D688C PDGFR-b; D128C PIM1; S389C A-Raf; S535C B-Raf; S428C C-Raf; S347C SRC; S341C SRC2; D698C STK1; P455C SYK; S287C TGFR1; N332C TGFR2; N924C TIE1; N909C TIE2; N917C VEGFR1; N923C VEGFR2; N934C VEGFR3; S355C YES; and P421C ZAP-70.

25. The method of claim 21 wherein said kinase-ligand conjugate is formed from the ligand comprising a group capable of undergoing SN2-like attack or forming a Michael-type adduct with the —SH group of said cysteine residue.

26. The method of claim 25 wherein said group capable of undergoing SN2-like attack is selected from the group consisting of α-halo acids, fluorophosph(on)ates, epoxides, aziridines, thiiranes, halo-methyl ketones, and halo-methyl amides.

27. The method of claim 21 wherein said free chemically reactive group is an —SH group.

28. The method of claim 18 wherein wherein said ligand candidates are members of a small molecule library of less than 1500 daltons, less than 1000 daltons, less than 750 daltons, less than 500 daltons, or less than 250 daltons in size.

29. The method of claim 28 wherein each member of said library differs in molecular weight from each other member of said library.

30. The method of claim 29 wherein said library contains 1 to 100 members.

* * * * *

SEQUENCE LISTING

<160> NUMBER OF SEQ ID NOS: 70

<210> SEQ ID NO 1

```
<211> LENGTH: 480
<212> TYPE: PRT
<213> ORGANISM: Homo sapiens

<400> SEQUENCE: 1

Met Ser Asp Val Ala Ile Val Lys Glu Gly Trp Leu His Lys Arg Gly
  1               5                  10                  15

Glu Tyr Ile Lys Thr Trp Arg Pro Arg Tyr Phe Leu Leu Lys Asn Asp
             20                  25                  30

Gly Thr Phe Ile Gly Tyr Lys Glu Arg Pro Gln Asp Val Asp Gln Arg
         35                  40                  45

Glu Ala Pro Leu Asn Asn Phe Ser Val Ala Gln Cys Gln Leu Met Lys
     50                  55                  60

Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                 85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
```

```
                385                 390                 395                 400
Glu Ile Met Gln His Arg Phe Phe Ala Gly Ile Val Trp Gln His Val
                    405                 410                 415

Tyr Glu Lys Lys Leu Ser Pro Pro Phe Lys Pro Gln Val Thr Ser Glu
                420                 425                 430

Thr Asp Thr Arg Tyr Phe Asp Glu Glu Phe Thr Ala Gln Met Ile Thr
                435                 440                 445

Ile Thr Pro Pro Asp Gln Asp Asp Ser Met Glu Cys Val Asp Ser Glu
            450                 455                 460

Arg Arg Pro His Phe Pro Gln Phe Ser Tyr Ser Ala Ser Ser Thr Ala
465                 470                 475                 480

<210> SEQ ID NO 2
<211> LENGTH: 481
<212> TYPE: PRT
<213> ORGANISM: Homo sapiens

<400> SEQUENCE: 2

Met Asn Glu Val Ser Val Ile Lys Glu Gly Trp Leu His Lys Arg Gly
1               5                   10                  15

Glu Tyr Ile Lys Thr Trp Arg Pro Arg Tyr Phe Leu Leu Lys Ser Asp
                20                  25                  30

Gly Ser Phe Ile Gly Tyr Lys Glu Arg Pro Glu Ala Pro Asp Gln Thr
            35                  40                  45

Leu Pro Pro Leu Asn Asn Phe Ser Val Ala Glu Cys Gln Leu Met Lys
    50                  55                  60

Thr Glu Arg Pro Arg Pro Asn Thr Phe Val Ile Arg Cys Leu Gln Trp
65                  70                  75                  80

Thr Thr Val Ile Glu Arg Thr Phe His Val Asp Ser Pro Asp Glu Arg
                85                  90                  95

Glu Glu Trp Met Arg Ala Ile Gln Met Val Ala Asn Ser Leu Lys Gln
                100                 105                 110

Arg Ala Pro Gly Glu Asp Pro Met Asp Tyr Lys Cys Gly Ser Pro Ser
            115                 120                 125

Asp Ser Ser Thr Thr Glu Glu Met Glu Val Ala Val Ser Lys Ala Arg
    130                 135                 140

Ala Lys Val Thr Met Asn Asp Phe Asp Tyr Leu Lys Leu Leu Gly Lys
145                 150                 155                 160

Gly Thr Phe Gly Lys Val Ile Leu Val Arg Glu Lys Ala Thr Gly Arg
                165                 170                 175

Tyr Tyr Ala Met Lys Ile Leu Arg Lys Glu Val Ile Ile Ala Lys Asp
                180                 185                 190

Glu Val Ala His Thr Val Thr Glu Ser Arg Val Leu Gln Asn Thr Arg
            195                 200                 205

His Pro Phe Leu Thr Ala Leu Lys Tyr Ala Phe Gln Thr His Asp Arg
    210                 215                 220

Leu Cys Phe Val Met Glu Tyr Ala Asn Gly Gly Glu Leu Phe Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
                260                 265                 270

Tyr Arg Asp Ile Lys Leu Glu Asn Leu Met Leu Asp Lys Asp Gly His
            275                 280                 285
```

```
Ile Lys Ile Thr Asp Phe Gly Leu Cys Lys Glu Gly Ile Ser Asp Gly
290                 295                 300

Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
            340                 345                 350

Gln Asp His Glu Arg Leu Phe Glu Leu Ile Leu Met Glu Glu Ile Arg
        355                 360                 365

Phe Pro Arg Thr Leu Ser Pro Glu Ala Lys Ser Leu Leu Ala Gly Leu
    370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
                420                 425                 430

Glu Val Asp Thr Arg Tyr Phe Asp Asp Glu Phe Thr Ala Gln Ser Ile
                435                 440                 445

Thr Ile Thr Pro Pro Asp Arg Tyr Asp Ser Leu Gly Leu Leu Glu Leu
450                 455                 460

Asp Gln Arg Thr His Phe Pro Gln Phe Ser Tyr Ser Ala Ser Ile Arg
465                 470                 475                 480

Glu

<210> SEQ ID NO 3
<211> LENGTH: 479
<212> TYPE: PRT
<213> ORGANISM: Homo sapiens

<400> SEQUENCE: 3

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
                20                  25                  30

Gly Ser Phe Ile Gly Tyr Lys Glu Lys Pro Gln Asp Val Asp Leu Pro
            35                  40                  45

Tyr Pro Leu Asn Asn Phe Ser Val Ala Lys Cys Gln Leu Met Lys Thr
        50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
                100                 105                 110

Glu Glu Glu Arg Met Asn Cys Ser Pro Thr Ser Gln Ile Asp Asn Ile
            115                 120                 125

Gly Glu Glu Glu Met Asp Ala Ser Thr Thr His His Lys Arg Lys Thr
        130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175
```

-continued

```
Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
    210                 215                 220

Met Glu Tyr Val Asn Gly Gly Glu Leu Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
    290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
    370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
        435                 440                 445

Pro Glu Lys Tyr Asp Glu Asp Gly Met Asp Cys Met Asp Asn Glu Arg
    450                 455                 460

Arg Pro His Phe Pro Gln Phe Ser Tyr Ser Ala Ser Gly Arg Glu
465                 470                 475

<210> SEQ ID NO 4
<211> LENGTH: 504
<212> TYPE: PRT
<213> ORGANISM: Homo sapiens

<400> SEQUENCE: 4

Gly Leu Val Ser Ser Lys Lys Pro Asp Lys Glu Lys Pro Ile Lys Glu
  1               5                  10                  15

Lys Asp Lys Gly Gln Trp Ser Pro Leu Lys Val Ser Ala Gln Asp Lys
                20                  25                  30

Asp Ala Pro Pro Leu Pro Pro Leu Val Val Phe Asn His Leu Thr Pro
            35                  40                  45

Pro Pro Pro Asp Glu His Leu Asp Glu Asp Lys His Phe Val Val Ala
        50                  55                  60

Leu Tyr Asp Tyr Thr Ala Met Asn Asp Arg Asp Leu Gln Met Leu Lys
65                  70                  75                  80
```

```
Gly Glu Lys Leu Gln Val Leu Lys Gly Thr Gly Asp Trp Trp Leu Ala
                85                  90                  95

Arg Ser Leu Val Thr Gly Arg Glu Gly Tyr Val Pro Ser Asn Phe Val
            100                 105                 110

Ala Arg Val Glu Ser Leu Glu Met Glu Arg Trp Phe Phe Arg Ser Gln
        115                 120                 125

Gly Arg Lys Glu Ala Glu Arg Gln Leu Leu Ala Pro Ile Asn Lys Ala
    130                 135                 140

Gly Ser Phe Leu Ile Arg Glu Ser Glu Thr Asn Lys Gly Ala Phe Ser
145                 150                 155                 160

Leu Ser Val Lys Asp Val Thr Thr Gln Gly Glu Leu Ile Lys His Tyr
                165                 170                 175

Lys Ile Arg Cys Leu Asp Glu Gly Gly Tyr Tyr Ile Ser Pro Arg Ile
            180                 185                 190

Thr Phe Pro Ser Leu Gln Ala Leu Val Gln His Tyr Ser Lys Lys Gly
        195                 200                 205

Asp Gly Leu Cys Gln Arg Leu Thr Leu Pro Cys Val Arg Pro Ala Pro
    210                 215                 220

Gln Asn Pro Trp Ala Gln Asp Glu Trp Glu Ile Pro Arg Gln Ser Leu
225                 230                 235                 240

Arg Leu Val Arg Lys Leu Gly Ser Gly Gln Phe Gly Glu Val Trp Met
                245                 250                 255

Gly Tyr Tyr Lys Asn Asn Met Lys Val Ala Ile Lys Thr Leu Lys Glu
            260                 265                 270

Gly Thr Met Ser Pro Glu Ala Phe Leu Gly Glu Ala Asn Met Met Lys
        275                 280                 285

Ala Leu Gln His Glu Arg Leu Val Arg Leu Tyr Ala Val Val Thr Lys
    290                 295                 300

Glu Pro Ile Tyr Ile Val Thr Glu Tyr Met Ala Arg Gly Cys Leu Leu
305                 310                 315                 320

Asp Phe Leu Lys Thr Asp Glu Gly Ser Arg Leu Ser Leu Pro Arg Leu
                325                 330                 335

Ile Asp Met Ser Ala Gln Ile Ala Glu Gly Met Ala Tyr Ile Glu Arg
            340                 345                 350

Met Asn Ser Ile His Arg Asp Leu Arg Ala Ala Asn Ile Leu Val Ser
        355                 360                 365

Glu Ala Leu Cys Cys Lys Ile Ala Asp Phe Gly Leu Ala Arg Ile Ile
    370                 375                 380

Asp Ser Glu Tyr Thr Ala Gln Glu Gly Ala Lys Phe Pro Ile Lys Trp
385                 390                 395                 400

Thr Ala Pro Glu Ala Ile His Phe Gly Val Phe Thr Ile Lys Ala Asp
                405                 410                 415

Val Trp Ser Phe Gly Val Leu Leu Met Glu Val Val Thr Tyr Gly Arg
            420                 425                 430

Val Pro Tyr Pro Gly Met Ser Asn Pro Glu Val Ile Arg Asn Leu Glu
        435                 440                 445

Arg Gly Tyr Arg Met Pro Arg Pro Asp Thr Cys Pro Pro Glu Leu Tyr
    450                 455                 460

Arg Gly Val Ile Ala Glu Cys Trp Arg Ser Arg Pro Glu Glu Arg Pro
465                 470                 475                 480

Thr Phe Glu Phe Leu Gln Ser Val Leu Glu Asp Phe Tyr Thr Ala Thr
                485                 490                 495
```

-continued

Glu Arg Gln Tyr Glu Leu Gln Pro
              500

<210> SEQ ID NO 5
<211> LENGTH: 659
<212> TYPE: PRT
<213> ORGANISM: Homo sapiens

<400> SEQUENCE: 5

Met Ala Ala Val Ile Leu Glu Ser Ile Phe Leu Lys Arg Ser Gln Gln
 1               5                  10                  15

Lys Lys Lys Thr Ser Pro Leu Asn Phe Lys Arg Leu Phe Leu Leu
             20                  25                  30

Thr Val His Lys Leu Ser Tyr Tyr Glu Tyr Asp Phe Glu Arg Gly Arg
             35                  40                  45

Arg Gly Ser Lys Lys Gly Ser Ile Asp Val Glu Lys Ile Thr Cys Val
 50                  55                  60

Glu Thr Val Val Pro Glu Lys Asn Pro Pro Glu Arg Gln Ile Pro
 65                  70                  75                  80

Arg Arg Gly Glu Glu Ser Ser Glu Met Glu Gln Ile Ser Ile Ile Glu
                 85                  90                  95

Arg Phe Pro Tyr Pro Phe Gln Val Val Tyr Asp Glu Gly Pro Leu Tyr
                100                 105                 110

Val Phe Ser Pro Thr Glu Glu Leu Arg Lys Arg Trp Ile His Gln Leu
            115                 120                 125

Lys Asn Val Ile Arg Tyr Asn Ser Asp Leu Val Gln Lys Tyr His Pro
130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Pro Leu Pro Pro Thr Pro
            180                 185                 190

Glu Glu Asp Gln Ile Leu Lys Lys Pro Leu Pro Pro Glu Pro Ala Ala
            195                 200                 205

Ala Pro Val Ser Thr Ser Glu Leu Lys Lys Val Val Ala Leu Tyr Asp
210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
            260                 265                 270

Glu Asp Ser Ile Glu Met Tyr Glu Trp Tyr Ser Lys His Met Thr Arg
        275                 280                 285

Ser Gln Ala Glu Gln Leu Leu Lys Gln Glu Gly Lys Glu Gly Gly Phe
    290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
            340                 345                 350

Ser Thr Ile Pro Glu Leu Ile Asn Tyr His Gln His Asn Ser Ala Gly
        355                 360                 365

```
Leu Ile Ser Arg Leu Lys Tyr Pro Val Ser Gln Gln Asn Lys Asn Ala
    370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
            420                 425                 430

Lys Glu Gly Ser Met Ser Glu Asp Glu Phe Ile Glu Glu Ala Lys Val
        435                 440                 445

Met Met Asn Leu Ser His Glu Lys Leu Val Gln Leu Tyr Gly Val Cys
450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
            500                 505                 510

Glu Ser Lys Gln Phe Leu His Arg Asp Leu Ala Ala Arg Asn Cys Leu
        515                 520                 525

Val Asn Asp Gln Gly Val Val Lys Val Ser Asp Phe Gly Leu Ser Arg
530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
                565                 570                 575

Lys Ser Asp Ile Trp Ala Phe Gly Val Leu Met Trp Glu Ile Tyr Ser
            580                 585                 590

Leu Gly Lys Met Pro Tyr Glu Arg Phe Thr Asn Ser Glu Thr Ala Glu
        595                 600                 605

His Ile Ala Gln Gly Leu Arg Leu Tyr Arg Pro His Leu Ala Ser Glu
610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
                645                 650                 655

Glu Glu Ser

<210> SEQ ID NO 6
<211> LENGTH: 297
<212> TYPE: PRT
<213> ORGANISM: Homo sapiens

<400> SEQUENCE: 6

Met Glu Asp Tyr Thr Lys Ile Glu Lys Ile Gly Glu Gly Thr Tyr Gly
1               5                   10                  15

Val Val Tyr Lys Gly Arg His Lys Thr Thr Gly Gln Val Val Ala Met
            20                  25                  30

Lys Lys Ile Arg Leu Glu Ser Glu Glu Glu Gly Val Pro Ser Thr Ala
        35                  40                  45

Ile Arg Glu Ile Ser Leu Leu Lys Glu Leu Arg His Pro Asn Ile Val
    50                  55                  60

Ser Leu Gln Asp Val Leu Met Gln Asp Ser Arg Leu Tyr Leu Ile Phe
65                  70                  75                  80
```

```
Glu Phe Leu Ser Met Asp Leu Lys Lys Tyr Leu Asp Ser Ile Pro Pro
                85                  90                  95

Gly Gln Tyr Met Asp Ser Ser Leu Val Lys Ser Tyr Leu Tyr Gln Ile
            100                 105                 110

Leu Gln Gly Ile Val Phe Cys His Ser Arg Arg Val Leu His Arg Asp
        115                 120                 125

Leu Lys Pro Gln Asn Leu Leu Ile Asp Asp Lys Gly Thr Ile Lys Leu
    130                 135                 140

Ala Asp Phe Gly Leu Ala Arg Ala Phe Gly Ile Pro Ile Arg Val Tyr
145                 150                 155                 160

Thr His Glu Val Val Thr Leu Trp Tyr Arg Ser Pro Glu Val Leu Leu
                165                 170                 175

Gly Ser Ala Arg Tyr Ser Thr Pro Val Asp Ile Trp Ser Ile Gly Thr
            180                 185                 190

Ile Phe Ala Glu Leu Ala Thr Lys Lys Pro Leu Phe His Gly Asp Ser
        195                 200                 205

Glu Ile Asp Gln Leu Phe Arg Ile Phe Arg Ala Leu Gly Thr Pro Asn
    210                 215                 220

Asn Glu Val Trp Pro Glu Val Glu Ser Leu Gln Asp Tyr Lys Asn Thr
225                 230                 235                 240

Phe Pro Lys Trp Lys Pro Gly Ser Leu Ala Ser His Val Lys Asn Leu
                245                 250                 255

Asp Glu Asn Gly Leu Asp Leu Leu Ser Lys Met Leu Ile Tyr Asp Pro
            260                 265                 270

Ala Lys Arg Ile Ser Gly Lys Met Ala Leu Asn His Pro Tyr Phe Asn
        275                 280                 285

Asp Leu Asp Asn Gln Ile Lys Lys Met
    290                 295

<210> SEQ ID NO 7
<211> LENGTH: 298
<212> TYPE: PRT
<213> ORGANISM: Homo sapiens

<400> SEQUENCE: 7

Met Glu Asn Phe Gln Lys Val Glu Lys Ile Gly Glu Gly Thr Tyr Gly
1               5                   10                  15

Val Val Tyr Lys Ala Arg Asn Lys Leu Thr Gly Glu Val Val Ala Leu
            20                  25                  30

Lys Lys Ile Arg Leu Asp Thr Glu Thr Glu Gly Val Pro Ser Thr Ala
        35                  40                  45

Ile Arg Glu Ile Ser Leu Leu Lys Glu Leu Asn His Pro Asn Ile Val
    50                  55                  60

Lys Leu Leu Asp Val Ile His Thr Glu Asn Lys Leu Tyr Leu Val Phe
65                  70                  75                  80

Glu Phe Leu His Gln Asp Leu Lys Lys Phe Met Asp Ala Ser Ala Leu
                85                  90                  95

Thr Gly Ile Pro Leu Pro Leu Ile Lys Ser Tyr Leu Phe Gln Leu Leu
            100                 105                 110

Gln Gly Leu Ala Phe Cys His Ser His Arg Val Leu His Arg Asp Leu
        115                 120                 125

Lys Pro Gln Asn Leu Leu Ile Asn Thr Glu Gly Ala Ile Lys Leu Ala
    130                 135                 140

Asp Phe Gly Leu Ala Arg Ala Phe Gly Val Pro Val Arg Thr Tyr Thr
```

```
                145                 150                 155                 160
His Glu Val Val Thr Leu Trp Tyr Arg Ala Pro Glu Ile Leu Leu Gly
                    165                 170                 175

Cys Lys Tyr Tyr Ser Thr Ala Val Asp Ile Trp Ser Leu Gly Cys Ile
                    180                 185                 190

Phe Ala Glu Met Val Thr Arg Arg Ala Leu Phe Pro Gly Asp Ser Glu
                    195                 200                 205

Ile Asp Gln Leu Phe Arg Ile Phe Arg Thr Leu Gly Thr Pro Asp Glu
                    210                 215                 220

Val Val Trp Pro Gly Val Thr Ser Met Pro Asp Tyr Lys Pro Ser Phe
225                 230                 235                 240

Pro Lys Trp Ala Arg Gln Asp Phe Ser Lys Val Val Pro Pro Leu Asp
                    245                 250                 255

Glu Asp Gly Arg Ser Leu Leu Ser Gln Met Leu His Tyr Asp Pro Asn
                    260                 265                 270

Lys Arg Ile Ser Ala Lys Ala Ala Leu Ala His Pro Phe Phe Gln Asp
                    275                 280                 285

Val Thr Lys Pro Val Pro His Leu Arg Leu
                    290                 295

<210> SEQ ID NO 8
<211> LENGTH: 305
<212> TYPE: PRT
<213> ORGANISM: Homo sapiens

<400> SEQUENCE: 8

Met Asp Met Phe Gln Lys Val Glu Lys Ile Gly Glu Gly Thr Tyr Gly
1               5                   10                  15

Val Val Tyr Lys Ala Lys Asn Arg Glu Thr Gly Gln Leu Val Ala Leu
                    20                  25                  30

Lys Lys Ile Arg Leu Asp Leu Glu Met Glu Gly Val Pro Ser Thr Ala
                    35                  40                  45

Ile Arg Glu Ile Ser Leu Leu Lys Glu Leu Lys His Pro Asn Ile Val
                    50                  55                  60

Arg Leu Leu Asp Val Val His Asn Glu Arg Lys Leu Tyr Leu Val Phe
65                  70                  75                  80

Glu Phe Leu Ser Gln Asp Leu Lys Lys Tyr Met Asp Ser Thr Pro Gly
                    85                  90                  95

Ser Glu Leu Pro Leu His Leu Ile Lys Ser Tyr Leu Phe Gln Leu Leu
                    100                 105                 110

Gln Gly Val Ser Phe Cys His Ser His Arg Val Ile His Arg Asp Leu
                    115                 120                 125

Lys Pro Gln Asn Leu Leu Ile Asn Glu Leu Gly Ala Ile Lys Leu Ala
                    130                 135                 140

Asp Phe Gly Leu Ala Arg Ala Phe Gly Val Pro Leu Arg Thr Tyr Thr
145                 150                 155                 160

His Glu Val Val Thr Leu Trp Tyr Arg Ala Pro Glu Ile Leu Leu Gly
                    165                 170                 175

Ser Lys Phe Tyr Thr Thr Ala Val Asp Ile Trp Ser Ile Gly Cys Ile
                    180                 185                 190

Phe Ala Glu Met Val Thr Arg Lys Ala Leu Phe Pro Gly Asp Ser Glu
                    195                 200                 205

Ile Asp Gln Leu Phe Arg Ile Phe Arg Met Leu Gly Thr Pro Ser Glu
                    210                 215                 220
```

```
Asp Thr Trp Pro Gly Val Thr Gln Leu Pro Asp Tyr Lys Gly Ser Phe
225                 230                 235                 240

Pro Lys Trp Thr Arg Lys Gly Leu Glu Glu Ile Val Pro Asn Leu Glu
            245                 250                 255

Pro Glu Gly Arg Asp Leu Leu Met Gln Leu Leu Gln Tyr Asp Pro Ser
        260                 265                 270

Gln Arg Ile Thr Ala Lys Thr Ala Leu Ala His Pro Tyr Phe Ser Ser
    275                 280                 285

Pro Glu Pro Ser Pro Ala Ala Arg Gln Tyr Val Leu Gln Arg Phe Arg
    290                 295                 300

His
305

<210> SEQ ID NO 9
<211> LENGTH: 303
<212> TYPE: PRT
<213> ORGANISM: Homo sapiens

<400> SEQUENCE: 9

Met Ala Thr Ser Arg Tyr Glu Pro Val Ala Glu Ile Gly Val Gly Ala
1               5                   10                  15

Tyr Gly Thr Val Tyr Lys Ala Arg Asp Pro His Ser Gly His Phe Val
            20                  25                  30

Ala Leu Lys Ser Val Arg Val Pro Asn Gly Gly Gly Gly Gly Gly Gly
        35                  40                  45

Leu Pro Ile Ser Thr Val Arg Glu Val Ala Leu Leu Arg Arg Leu Glu
50                  55                  60

Ala Phe Glu His Pro Asn Val Val Arg Leu Met Asp Val Cys Ala Thr
65                  70                  75                  80

Ser Arg Thr Asp Arg Glu Ile Lys Val Thr Leu Val Phe Glu His Val
                85                  90                  95

Asp Gln Asp Leu Arg Thr Tyr Leu Asp Lys Ala Pro Pro Pro Gly Leu
            100                 105                 110

Pro Ala Glu Thr Ile Lys Asp Leu Met Arg Gln Phe Leu Arg Gly Leu
        115                 120                 125

Asp Phe Leu His Ala Asn Cys Ile Val His Arg Asp Leu Lys Pro Glu
    130                 135                 140

Asn Ile Leu Val Thr Ser Gly Gly Thr Val Lys Leu Ala Asp Phe Gly
145                 150                 155                 160

Leu Ala Arg Ile Tyr Ser Tyr Gln Met Ala Leu Thr Pro Val Val Val
                165                 170                 175

Thr Leu Trp Tyr Arg Ala Pro Glu Val Leu Leu Gln Ser Thr Tyr Ala
            180                 185                 190

Thr Pro Val Asp Met Trp Ser Val Gly Cys Ile Phe Ala Glu Met Phe
        195                 200                 205

Arg Arg Lys Pro Leu Phe Cys Gly Asn Ser Glu Ala Asp Gln Leu Gly
    210                 215                 220

Lys Ile Phe Asp Leu Ile Gly Leu Pro Pro Glu Asp Asp Trp Pro Arg
225                 230                 235                 240

Asp Val Ser Leu Pro Arg Gly Ala Phe Pro Pro Arg Gly Pro Arg Pro
                245                 250                 255

Val Gln Ser Val Val Pro Glu Met Glu Glu Ser Gly Ala Gln Leu Leu
            260                 265                 270

Leu Glu Met Leu Thr Phe Asn Pro His Lys Arg Ile Ser Ala Phe Arg
        275                 280                 285
```

```
Ala Leu Gln His Ser Tyr Leu His Lys Asp Glu Gly Asn Pro Glu
    290                 295                 300
```

<210> SEQ ID NO 10
<211> LENGTH: 292
<212> TYPE: PRT
<213> ORGANISM: Homo sapiens

<400> SEQUENCE: 10

```
Met Gln Lys Tyr Glu Lys Leu Glu Lys Ile Gly Glu Gly Thr Tyr Gly
  1               5                  10                  15

Thr Val Phe Lys Ala Lys Asn Arg Glu Thr His Glu Ile Val Ala Leu
             20                  25                  30

Lys Arg Val Arg Leu Asp Asp Asp Asp Glu Gly Val Pro Ser Ser Ala
         35                  40                  45

Leu Arg Glu Ile Cys Leu Leu Lys Glu Leu Lys His Lys Asn Ile Val
     50                  55                  60

Arg Leu His Asp Val Leu His Ser Asp Lys Lys Leu Thr Leu Val Phe
 65                  70                  75                  80

Glu Phe Cys Asp Gln Asp Leu Lys Lys Tyr Phe Asp Ser Cys Asn Gly
                 85                  90                  95

Asp Leu Asp Pro Glu Ile Val Lys Ser Phe Leu Phe Gln Leu Leu Lys
            100                 105                 110

Gly Leu Gly Phe Cys His Ser Arg Asn Val Leu His Arg Asp Leu Lys
        115                 120                 125

Pro Gln Asn Leu Leu Ile Asn Arg Asn Gly Glu Leu Lys Leu Ala Asp
    130                 135                 140

Phe Gly Leu Ala Arg Ala Phe Gly Ile Pro Val Arg Cys Tyr Ser Ala
145                 150                 155                 160

Glu Val Val Thr Leu Trp Tyr Arg Pro Pro Asp Val Leu Phe Gly Ala
                165                 170                 175

Lys Leu Tyr Ser Thr Ser Ile Asp Met Trp Ser Ala Gly Cys Ile Phe
            180                 185                 190

Ala Glu Leu Ala Asn Ala Gly Arg Pro Leu Phe Pro Gly Asn Asp Val
        195                 200                 205

Asp Asp Gln Leu Lys Arg Ile Phe Arg Leu Leu Gly Thr Pro Thr Glu
    210                 215                 220

Glu Gln Trp Pro Ser Met Thr Lys Leu Pro Asp Tyr Lys Pro Tyr Pro
225                 230                 235                 240

Met Tyr Pro Ala Thr Thr Ser Leu Val Asn Val Val Pro Lys Leu Asn
                245                 250                 255

Ala Thr Gly Arg Asp Leu Leu Gln Asn Leu Leu Lys Cys Asn Pro Val
            260                 265                 270

Gln Arg Ile Ser Ala Glu Glu Ala Leu Gln His Pro Tyr Phe Ser Asp
        275                 280                 285

Phe Cys Pro Pro
    290
```

<210> SEQ ID NO 11
<211> LENGTH: 326
<212> TYPE: PRT
<213> ORGANISM: Homo sapiens

<400> SEQUENCE: 11

```
Met Glu Lys Asp Gly Leu Cys Arg Ala Asp Gln Gln Tyr Glu Cys Val
  1               5                  10                  15
```

```
Ala Glu Ile Gly Glu Gly Ala Tyr Gly Lys Val Phe Lys Ala Arg Asp
            20                  25                  30

Leu Lys Asn Gly Gly Arg Phe Val Ala Leu Lys Arg Val Arg Val Gln
            35                  40                  45

Thr Gly Glu Glu Gly Met Pro Leu Ser Thr Ile Arg Glu Val Ala Val
            50                  55                  60

Leu Arg His Leu Glu Thr Phe Glu His Pro Asn Val Val Arg Leu Phe
65                      70                  75                  80

Asp Val Cys Thr Val Ser Arg Thr Asp Arg Glu Thr Lys Leu Thr Leu
                85                  90                  95

Val Phe Glu His Val Asp Gln Asp Leu Thr Thr Tyr Leu Asp Lys Val
            100                 105                 110

Pro Glu Pro Gly Val Pro Thr Glu Thr Ile Lys Asp Met Met Phe Gln
            115                 120                 125

Leu Leu Arg Gly Leu Asp Phe Leu His Ser His Arg Val Val His Arg
            130                 135                 140

Asp Leu Lys Pro Gln Asn Ile Leu Val Thr Ser Ser Gly Gln Ile Lys
145                 150                 155                 160

Leu Ala Asp Phe Gly Leu Ala Arg Ile Tyr Ser Phe Gln Met Ala Leu
                165                 170                 175

Thr Ser Val Val Val Thr Leu Trp Tyr Arg Ala Pro Glu Val Leu Leu
            180                 185                 190

Gln Ser Ser Tyr Ala Thr Pro Val Asp Leu Trp Ser Val Gly Cys Ile
            195                 200                 205

Phe Ala Glu Met Phe Arg Arg Lys Pro Leu Phe Arg Gly Ser Ser Asp
            210                 215                 220

Val Asp Gln Leu Gly Lys Ile Leu Asp Val Ile Gly Leu Pro Gly Glu
225                 230                 235                 240

Glu Asp Trp Pro Arg Asp Val Ala Leu Pro Arg Gln Ala Phe His Ser
                245                 250                 255

Lys Ser Ala Gln Pro Ile Glu Lys Phe Val Thr Asp Ile Asp Glu Leu
            260                 265                 270

Gly Lys Asp Leu Leu Leu Lys Cys Leu Thr Phe Asn Pro Ala Lys Arg
            275                 280                 285

Ile Ser Ala Tyr Ser Ala Leu Ser His Pro Tyr Phe Gln Asp Leu Glu
            290                 295                 300

Arg Cys Lys Glu Asn Leu Asp Ser His Leu Pro Pro Ser Gln Asn Thr
305                 310                 315                 320

Ser Glu Leu Asn Thr Ala
                325

<210> SEQ ID NO 12
<211> LENGTH: 346
<212> TYPE: PRT
<213> ORGANISM: Homo sapiens

<400> SEQUENCE: 12

Met Ala Leu Asp Val Lys Ser Arg Ala Lys Arg Tyr Glu Lys Leu Asp
1               5                   10                  15

Phe Leu Gly Glu Gly Gln Phe Ala Thr Val Tyr Lys Ala Arg Asp Lys
            20                  25                  30

Asn Thr Asn Gln Ile Val Ala Ile Lys Lys Ile Lys Leu Gly His Arg
            35                  40                  45

Ser Glu Ala Lys Asp Gly Ile Asn Arg Thr Ala Leu Arg Glu Ile Lys
```

-continued

```
            50                  55                  60
Leu Leu Gln Glu Leu Ser His Pro Asn Ile Ile Gly Leu Leu Asp Ala
 65                  70                  75                  80

Phe Gly His Lys Ser Asn Ile Ser Leu Val Phe Asp Phe Met Glu Thr
                 85                  90                  95

Asp Leu Glu Val Ile Ile Lys Asp Asn Ser Leu Val Leu Thr Pro Ser
                100                 105                 110

His Ile Lys Ala Tyr Met Leu Met Thr Leu Gln Gly Leu Glu Tyr Leu
                115                 120                 125

His Gln His Trp Ile Leu His Arg Asp Leu Lys Pro Asn Asn Leu Leu
130                 135                 140

Leu Asp Glu Asn Gly Val Leu Lys Leu Ala Asp Phe Gly Leu Ala Lys
145                 150                 155                 160

Ser Phe Gly Ser Pro Asn Arg Ala Tyr Thr His Gln Val Val Thr Arg
                165                 170                 175

Trp Tyr Arg Ala Pro Glu Leu Leu Phe Gly Ala Arg Met Tyr Gly Val
                180                 185                 190

Gly Val Asp Met Trp Ala Val Gly Cys Ile Leu Ala Glu Leu Leu Leu
                195                 200                 205

Arg Val Pro Phe Leu Pro Gly Asp Ser Asp Leu Asp Gln Leu Thr Arg
210                 215                 220

Ile Phe Glu Thr Leu Gly Thr Pro Thr Glu Glu Gln Trp Pro Asp Met
225                 230                 235                 240

Cys Ser Leu Pro Asp Tyr Val Thr Phe Lys Ser Phe Pro Gly Ile Pro
                245                 250                 255

Leu His His Ile Phe Ser Ala Ala Gly Asp Asp Leu Leu Asp Leu Ile
                260                 265                 270

Gln Gly Leu Phe Leu Phe Asn Pro Cys Ala Arg Ile Thr Ala Thr Gln
                275                 280                 285

Ala Leu Lys Met Lys Tyr Phe Ser Asn Arg Pro Gly Pro Thr Pro Gly
                290                 295                 300

Cys Gln Leu Pro Arg Pro Asn Cys Pro Val Glu Thr Leu Lys Glu Gln
305                 310                 315                 320

Ser Asn Pro Ala Leu Ala Ile Lys Arg Lys Arg Thr Glu Ala Leu Glu
                325                 330                 335

Gln Gly Gly Leu Pro Lys Lys Leu Ile Phe
                340                 345
```

<210> SEQ ID NO 13
<211> LENGTH: 464
<212> TYPE: PRT
<213> ORGANISM: Homo sapiens

<400> SEQUENCE: 13

```
Met Asp Tyr Asp Phe Lys Val Lys Leu Ser Ser Glu Arg Glu Arg Val
 1                   5                  10                  15

Glu Asp Leu Phe Glu Tyr Glu Gly Cys Lys Val Gly Arg Gly Thr Tyr
                 20                  25                  30

Gly His Val Tyr Lys Ala Lys Arg Lys Asp Gly Lys Asp Asp Lys Asp
                 35                  40                  45

Tyr Ala Leu Lys Gln Ile Glu Gly Thr Gly Ile Ser Met Ser Ala Cys
     50                  55                  60

Arg Glu Ile Ala Leu Leu Arg Glu Leu Lys His Pro Asn Val Ile Ser
 65                  70                  75                  80
```

```
Leu Gln Lys Val Phe Leu Ser His Ala Asp Arg Lys Val Trp Leu Leu
                85                  90                  95

Phe Asp Tyr Ala Glu His Asp Leu Trp His Ile Ile Lys Phe His Arg
            100                 105                 110

Ala Ser Lys Ala Asn Lys Lys Pro Val Gln Leu Pro Arg Gly Met Val
            115                 120                 125

Lys Ser Leu Leu Tyr Gln Ile Leu Asp Gly Ile His Tyr Leu His Ala
        130                 135                 140

Asn Trp Val Leu His Arg Asp Leu Lys Pro Ala Asn Ile Leu Val Met
145                 150                 155                 160

Gly Glu Gly Pro Glu Arg Gly Arg Val Lys Ile Ala Asp Met Gly Phe
                165                 170                 175

Ala Arg Leu Phe Asn Ser Pro Leu Lys Pro Leu Ala Asp Leu Asp Pro
            180                 185                 190

Val Val Val Thr Phe Trp Tyr Arg Ala Pro Glu Leu Leu Leu Gly Ala
            195                 200                 205

Arg His Tyr Thr Lys Ala Ile Asp Ile Trp Ala Ile Gly Cys Ile Phe
        210                 215                 220

Ala Glu Leu Leu Thr Ser Glu Pro Ile Phe His Cys Arg Gln Glu Asp
225                 230                 235                 240

Ile Lys Thr Ser Asn Pro Tyr His His Asp Gln Leu Asp Arg Ile Phe
                245                 250                 255

Asn Val Met Gly Phe Pro Ala Asp Lys Asp Trp Glu Asp Ile Lys Lys
            260                 265                 270

Met Pro Glu His Ser Thr Leu Met Lys Asp Phe Arg Arg Asn Thr Tyr
        275                 280                 285

Thr Asn Cys Ser Leu Ile Lys Tyr Met Glu Lys His Lys Val Lys Pro
290                 295                 300

Asp Ser Lys Ala Phe His Leu Leu Gln Lys Leu Leu Thr Met Asp Pro
305                 310                 315                 320

Ile Lys Arg Ile Thr Ser Glu Gln Ala Met Gln Asp Pro Tyr Phe Leu
                325                 330                 335

Glu Asp Pro Leu Pro Thr Ser Asp Val Phe Ala Gly Cys Gln Ile Pro
            340                 345                 350

Tyr Pro Lys Arg Glu Phe Leu Thr Glu Glu Pro Asp Asp Lys Gly
        355                 360                 365

Asp Lys Lys Asn Gln Gln Gln Gln Gly Asn Asn His Thr Asn Gly
370                 375                 380

Thr Gly His Pro Gly Asn Gln Asp Ser Ser His Thr Gln Gly Pro Pro
385                 390                 395                 400

Leu Lys Lys Val Arg Val Val Pro Pro Thr Thr Thr Ser Gly Gly Leu
                405                 410                 415

Ile Met Thr Ser Asp Tyr Gln Arg Ser Asn Pro His Ala Ala Tyr Pro
            420                 425                 430

Asn Pro Gly Pro Ser Thr Ser Gln Pro Gln Ser Ser Met Gly Tyr Ser
        435                 440                 445

Ala Thr Ser Gln Gln Pro Pro Gln Tyr Ser His Gln Thr His Arg Tyr
450                 455                 460

<210> SEQ ID NO 14
<211> LENGTH: 372
<212> TYPE: PRT
<213> ORGANISM: Homo sapiens

<400> SEQUENCE: 14
```

```
Met Ala Lys Gln Tyr Asp Ser Val Glu Cys Pro Phe Cys Asp Glu Val
  1               5                  10                  15

Ser Lys Tyr Glu Lys Leu Ala Lys Ile Gly Gln Gly Thr Phe Gly Glu
             20                  25                  30

Val Phe Lys Ala Arg His Arg Lys Thr Gly Gln Lys Val Ala Leu Lys
         35                  40                  45

Lys Val Leu Met Glu Asn Glu Lys Glu Gly Phe Pro Ile Thr Ala Leu
 50                  55                  60

Arg Glu Ile Lys Ile Leu Gln Leu Leu Lys His Glu Asn Val Val Asn
 65                  70                  75                  80

Leu Ile Glu Ile Cys Arg Thr Lys Ala Ser Pro Tyr Asn Arg Cys Lys
                 85                  90                  95

Gly Ser Ile Tyr Leu Val Phe Asp Phe Cys Glu His Asp Leu Ala Gly
             100                 105                 110

Leu Leu Ser Asn Val Leu Val Lys Phe Thr Leu Ser Glu Ile Lys Arg
             115                 120                 125

Val Met Gln Met Leu Leu Asn Gly Leu Tyr Tyr Ile His Arg Asn Lys
130                 135                 140

Ile Leu His Arg Asp Met Lys Ala Ala Asn Val Leu Ile Thr Arg Asp
145                 150                 155                 160

Gly Val Leu Lys Leu Ala Asp Phe Gly Leu Ala Arg Ala Phe Ser Leu
                165                 170                 175

Ala Lys Asn Ser Gln Pro Asn Arg Tyr Thr Asn Arg Val Val Thr Leu
             180                 185                 190

Trp Tyr Arg Pro Pro Glu Leu Leu Gly Glu Arg Asp Tyr Gly Pro
             195                 200                 205

Pro Ile Asp Leu Trp Gly Ala Gly Cys Ile Met Ala Glu Met Trp Thr
        210                 215                 220

Arg Ser Pro Ile Met Gln Gly Asn Thr Glu Gln His Gln Leu Ala Leu
225                 230                 235                 240

Ile Ser Gln Leu Cys Gly Ser Ile Thr Pro Glu Val Trp Pro Asn Val
                245                 250                 255

Asp Asn Tyr Glu Leu Tyr Glu Lys Leu Glu Leu Val Lys Gly Gln Lys
             260                 265                 270

Arg Lys Val Lys Asp Arg Leu Lys Ala Tyr Val Arg Asp Pro Tyr Ala
         275                 280                 285

Leu Asp Leu Ile Asp Lys Leu Leu Val Leu Asp Pro Ala Gln Arg Ile
         290                 295                 300

Asp Ser Asp Asp Ala Leu Asn His Asp Phe Phe Trp Ser Asp Pro Met
305                 310                 315                 320

Pro Ser Asp Leu Lys Gly Met Leu Ser Thr His Leu Thr Ser Met Phe
                325                 330                 335

Glu Tyr Leu Ala Pro Pro Arg Arg Lys Gly Ser Gln Ile Thr Gln Gln
             340                 345                 350

Ser Thr Asn Gln Ser Arg Asn Pro Ala Thr Thr Asn Gln Thr Glu Phe
             355                 360                 365

Glu Arg Val Phe
370

<210> SEQ ID NO 15
<211> LENGTH: 450
<212> TYPE: PRT
<213> ORGANISM: Homo sapiens
```

<400> SEQUENCE: 15

```
Met Ser Ala Ile Gln Ala Ala Trp Pro Ser Gly Thr Glu Cys Ile Ala
  1               5                  10                  15

Lys Tyr Asn Phe His Gly Thr Ala Glu Gln Asp Leu Pro Phe Cys Lys
             20                  25                  30

Gly Asp Val Leu Thr Ile Val Ala Val Thr Lys Asp Pro Asn Trp Tyr
             35                  40                  45

Lys Ala Lys Asn Lys Val Gly Arg Glu Gly Ile Ile Pro Ala Asn Tyr
 50                  55                  60

Val Gln Lys Arg Glu Gly Val Lys Ala Gly Thr Lys Leu Ser Leu Met
 65                  70                  75                  80

Pro Trp Phe His Gly Lys Ile Thr Arg Glu Gln Ala Glu Arg Leu Leu
             85                  90                  95

Tyr Pro Pro Glu Thr Gly Leu Phe Leu Val Arg Glu Ser Thr Asn Tyr
            100                 105                 110

Pro Gly Asp Tyr Thr Leu Cys Val Ser Cys Asp Gly Lys Val Glu His
            115                 120                 125

Tyr Arg Ile Met Tyr His Ala Ser Lys Leu Ser Ile Asp Glu Glu Val
        130                 135                 140

Tyr Phe Glu Asn Leu Met Gln Leu Val Glu His Tyr Thr Ser Asp Ala
145                 150                 155                 160

Asp Gly Leu Cys Thr Arg Leu Ile Lys Pro Lys Val Met Glu Gly Thr
            165                 170                 175

Val Ala Ala Gln Asp Glu Phe Tyr Arg Ser Gly Trp Ala Leu Asn Met
            180                 185                 190

Lys Glu Leu Lys Leu Leu Gln Thr Ile Gly Lys Gly Glu Phe Gly Asp
        195                 200                 205

Val Met Leu Gly Asp Tyr Arg Gly Asn Lys Val Ala Val Lys Cys Ile
210                 215                 220

Lys Asn Asp Ala Thr Ala Gln Ala Phe Leu Ala Glu Ala Ser Val Met
225                 230                 235                 240

Thr Gln Leu Arg His Ser Asn Leu Val Gln Leu Leu Gly Val Ile Val
            245                 250                 255

Glu Glu Lys Gly Gly Leu Tyr Ile Val Thr Glu Tyr Met Ala Lys Gly
        260                 265                 270

Ser Leu Val Asp Tyr Leu Arg Ser Arg Gly Arg Ser Val Leu Gly Gly
        275                 280                 285

Asp Cys Leu Leu Lys Phe Ser Leu Asp Val Cys Glu Ala Met Glu Tyr
        290                 295                 300

Leu Glu Gly Asn Asn Phe Val His Arg Asp Leu Ala Ala Arg Asn Val
305                 310                 315                 320

Leu Val Ser Glu Asp Asn Val Ala Lys Val Ser Asp Phe Gly Leu Thr
            325                 330                 335

Lys Glu Ala Ser Ser Thr Gln Asp Thr Gly Lys Leu Pro Val Lys Trp
            340                 345                 350

Thr Ala Pro Glu Ala Leu Arg Glu Lys Lys Phe Ser Thr Lys Ser Asp
        355                 360                 365

Val Trp Ser Phe Gly Ile Leu Leu Trp Glu Ile Tyr Ser Phe Gly Arg
370                 375                 380

Val Pro Tyr Pro Arg Ile Pro Leu Lys Asp Val Pro Arg Val Glu
385                 390                 395                 400

Lys Gly Tyr Lys Met Asp Ala Pro Asp Gly Cys Pro Pro Ala Val Tyr
            405                 410                 415
```

```
Glu Val Met Lys Asn Cys Trp His Leu Asp Ala Ala Met Arg Pro Ser
                420                 425                 430

Phe Leu Gln Leu Arg Glu Gln Leu Glu His Ile Lys Thr His Glu Leu
            435                 440                 445

His Leu
    450

<210> SEQ ID NO 16
<211> LENGTH: 1210
<212> TYPE: PRT
<213> ORGANISM: Homo sapiens

<400> SEQUENCE: 16

Met Arg Pro Ser Gly Thr Ala Gly Ala Ala Leu Leu Ala Leu Leu Ala
  1               5                  10                  15

Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
```

-continued

```
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
        370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
            405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
            485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
        530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
            565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
            645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
            725                 730                 735
Lys Val Lys Ile Pro Val Ala Ile Lys Glu Leu Arg Glu Ala Thr Ser
            740                 745                 750
```

```
Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
        1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
            1140                1145                1150

Ser Pro Ala His Trp Ala Gln Lys Gly Ser His Gln Ile Ser Leu Asp
        1155                1160                1165
```

Asn Pro Asp Tyr Gln Gln Asp Phe Phe Pro Lys Glu Ala Lys Pro Asn
    1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
                1205                1210

<210> SEQ ID NO 17
<211> LENGTH: 1255
<212> TYPE: PRT
<213> ORGANISM: Homo sapiens

<400> SEQUENCE: 17

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

```
Pro Cys Ala Arg Val Cys Tyr Gly Leu Gly Met Glu His Leu Arg Glu
        340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
                450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
                530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
                610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
                675                 680                 685

Arg Leu Leu Gln Glu Thr Glu Leu Val Glu Pro Leu Thr Pro Ser Gly
                690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750
```

-continued

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
        770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr Leu
    1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
        1155                1160                1165

Arg Pro Lys Thr Leu Ser Pro Gly Lys Asn Gly Val Val Lys Asp Val

-continued

```
            1170                1175                1180
Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
                1205                1210                1215

Phe Asp Asn Leu Tyr Tyr Trp Asp Gln Asp Pro Pro Glu Arg Gly Ala
                1220                1225                1230

Pro Ser Thr Phe Lys Gly Thr Pro Thr Ala Glu Asn Pro Glu Tyr
            1235                1240                1245

Leu Gly Leu Asp Val Pro Val
        1250                1255

<210> SEQ ID NO 18
<211> LENGTH: 1308
<212> TYPE: PRT
<213> ORGANISM: Homo sapiens

<400> SEQUENCE: 18

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
                20                  25                  30

Glu Asn Lys Leu Ser Ser Leu Ser Asp Leu Glu Gln Gln Tyr Arg Ala
            35                  40                  45

Leu Arg Lys Tyr Tyr Glu Asn Cys Glu Val Val Met Gly Asn Leu Glu
        50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
            260                 265                 270

Phe Gln Leu Glu His Asn Phe Asn Ala Lys Tyr Thr Tyr Gly Ala Phe
        275                 280                 285
```

```
Cys Val Lys Lys Cys Pro His Asn Phe Val Val Asp Ser Ser Cys
    290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
            340                 345                 350

Ile Asp Lys Phe Ile Asn Cys Thr Lys Ile Asn Gly Asn Leu Ile Phe
        355                 360                 365

Leu Val Thr Gly Ile His Gly Asp Pro Tyr Asn Ala Ile Glu Ala Ile
    370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
            420                 425                 430

Ser Leu Leu Ile Leu Lys Gln Gln Gly Ile Thr Ser Leu Gln Phe Gln
        435                 440                 445

Ser Leu Lys Glu Ile Ser Ala Gly Asn Ile Tyr Ile Thr Asp Asn Ser
450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
            500                 505                 510

Trp Gly Pro Gly Pro Asp Gln Cys Leu Ser Cys Arg Arg Phe Ser Arg
        515                 520                 525

Gly Arg Ile Cys Ile Glu Ser Cys Asn Leu Tyr Asp Gly Glu Phe Arg
    530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
                565                 570                 575

Cys Thr Lys Cys Ser His Phe Lys Asp Gly Pro Asn Cys Val Glu Lys
            580                 585                 590

Cys Pro Asp Gly Leu Gln Gly Ala Asn Ser Phe Ile Phe Lys Tyr Ala
        595                 600                 605

Asp Pro Asp Arg Glu Cys His Pro Cys His Pro Asn Cys Thr Gln Gly
    610                 615                 620

Cys Asn Gly Pro Thr Ser His Asp Cys Ile Tyr Tyr Pro Trp Thr Gly
625                 630                 635                 640

His Ser Thr Leu Pro Gln His Ala Arg Thr Pro Leu Ile Ala Ala Gly
                645                 650                 655

Val Ile Gly Gly Leu Phe Ile Leu Val Ile Val Gly Leu Thr Phe Ala
            660                 665                 670

Val Tyr Val Arg Arg Lys Ser Ile Lys Lys Arg Ala Leu Arg Arg
        675                 680                 685

Phe Leu Glu Thr Glu Leu Val Glu Pro Leu Thr Pro Ser Gly Thr Ala
    690                 695                 700

Pro Asn Gln Ala Gln Leu Arg Ile Leu Lys Glu Thr Glu Leu Lys Arg
```

```
            705                 710                 715                 720
        Val Lys Val Leu Gly Ser Gly Ala Phe Gly Thr Val Tyr Lys Gly Ile
                        725                 730                 735

Trp Val Pro Glu Gly Glu Thr Val Lys Ile Pro Val Ala Ile Lys Ile
                        740                 745                 750

Leu Asn Glu Thr Thr Gly Pro Lys Ala Asn Val Glu Phe Met Asp Glu
                        755                 760                 765

Ala Leu Ile Met Ala Ser Met Asp His Pro His Leu Val Arg Leu Leu
                        770                 775                 780

Gly Val Cys Leu Ser Pro Thr Ile Gln Leu Val Thr Gln Leu Met Pro
        785                 790                 795                 800

His Gly Cys Leu Leu Glu Tyr Val His Glu His Lys Asp Asn Ile Gly
                            805                 810                 815

Ser Gln Leu Leu Leu Asn Trp Cys Val Gln Ile Ala Lys Gly Met Met
                        820                 825                 830

Tyr Leu Glu Glu Arg Arg Leu Val His Arg Asp Leu Ala Ala Arg Asn
                        835                 840                 845

Val Leu Val Lys Ser Pro Asn His Val Lys Ile Thr Asp Phe Gly Leu
        850                 855                 860

Ala Arg Leu Leu Glu Gly Asp Glu Lys Glu Tyr Asn Ala Asp Gly Gly
        865                 870                 875                 880

Lys Met Pro Ile Lys Trp Met Ala Leu Glu Cys Ile His Tyr Arg Lys
                        885                 890                 895

Phe Thr His Gln Ser Asp Val Trp Ser Tyr Gly Val Thr Ile Trp Glu
                        900                 905                 910

Leu Met Thr Phe Gly Gly Lys Pro Tyr Asp Gly Ile Pro Thr Arg Glu
                        915                 920                 925

Ile Pro Asp Leu Leu Glu Lys Gly Glu Arg Leu Pro Gln Pro Pro Ile
                        930                 935                 940

Cys Thr Ile Asp Val Tyr Met Val Met Val Lys Cys Trp Met Ile Asp
        945                 950                 955                 960

Ala Asp Ser Arg Pro Lys Phe Lys Glu Leu Ala Ala Glu Phe Ser Arg
                        965                 970                 975

Met Ala Arg Asp Pro Gln Arg Tyr Leu Val Ile Gln Gly Asp Asp Arg
                        980                 985                 990

Met Lys Leu Pro Ser Pro Asn Asp Ser Lys Phe Phe Gln Asn Leu Leu
                        995                 1000                1005

Asp Glu Glu Asp Leu Glu Asp Met Met Asp Ala Glu Glu Tyr Leu Val
                        1010                1015                1020

Pro Gln Ala Phe Asn Ile Pro Pro Pro Ile Tyr Thr Ser Arg Ala Arg
        1025                1030                1035                1040

Ile Asp Ser Asn Arg Ser Glu Ile Gly His Ser Pro Pro Ala Tyr
                        1045                1050                1055

Thr Pro Met Ser Gly Asn Gln Phe Val Tyr Arg Asp Gly Gly Phe Ala
                        1060                1065                1070

Ala Glu Gln Gly Val Ser Val Pro Tyr Arg Ala Pro Thr Ser Thr Ile
                        1075                1080                1085

Pro Glu Ala Pro Val Ala Gln Gly Ala Thr Ala Glu Ile Phe Asp Asp
                        1090                1095                1100

Ser Cys Cys Asn Gly Thr Leu Arg Lys Pro Val Ala Pro His Val Gln
        1105                1110                1115                1120

Glu Asp Ser Ser Thr Gln Arg Tyr Ser Ala Asp Pro Thr Val Phe Ala
                        1125                1130                1135
```

-continued

```
Pro Glu Arg Ser Pro Arg Gly Glu Leu Asp Glu Gly Tyr Met Thr
            1140                1145                1150
Pro Met Arg Asp Lys Pro Lys Gln Glu Tyr Leu Asn Pro Val Glu Glu
        1155                1160                1165
Asn Pro Phe Val Ser Arg Arg Lys Asn Gly Asp Leu Gln Ala Leu Asp
    1170                1175                1180
Asn Pro Glu Tyr His Asn Ala Ser Asn Gly Pro Pro Lys Ala Glu Asp
1185                1190                1195                1200
Glu Tyr Val Asn Glu Pro Leu Tyr Leu Asn Thr Phe Ala Asn Thr Leu
            1205                1210                1215
Gly Lys Ala Glu Tyr Leu Lys Asn Asn Ile Leu Ser Met Pro Glu Lys
        1220                1225                1230
Ala Lys Lys Ala Phe Asp Asn Pro Asp Tyr Trp Asn His Ser Leu Pro
    1235                1240                1245
Pro Arg Ser Thr Leu Gln His Pro Asp Tyr Leu Gln Glu Tyr Ser Thr
1250                1255                1260
Lys Tyr Phe Tyr Lys Gln Asn Gly Arg Ile Arg Pro Ile Val Ala Glu
1265                1270                1275                1280
Asn Pro Glu Tyr Leu Ser Glu Phe Ser Leu Lys Pro Gly Thr Val Leu
            1285                1290                1295
Pro Pro Pro Pro Tyr Arg His Arg Asn Thr Val Val
        1300                1305
```

<210> SEQ ID NO 19
<211> LENGTH: 379
<212> TYPE: PRT
<213> ORGANISM: Homo sapiens

<400> SEQUENCE: 19

```
Met Ala Ala Ala Ala Gln Gly Gly Gly Gly Glu Pro Arg Arg
 1               5                  10                  15
Thr Glu Gly Val Gly Pro Gly Val Pro Gly Glu Val Glu Met Val Lys
            20                  25                  30
Gly Gln Pro Phe Asp Val Gly Pro Arg Tyr Thr Gln Leu Gln Tyr Ile
        35                  40                  45
Gly Glu Gly Ala Tyr Gly Met Val Ser Ser Ala Tyr Asp His Val Arg
    50                  55                  60
Lys Thr Arg Val Ala Ile Lys Lys Ile Ser Pro Phe Glu His Gln Thr
65                  70                  75                  80
Tyr Cys Gln Arg Thr Leu Arg Glu Ile Gln Ile Leu Leu Arg Phe Arg
                85                  90                  95
His Glu Asn Val Ile Gly Ile Arg Asp Ile Leu Arg Ala Ser Thr Leu
            100                 105                 110
Glu Ala Met Arg Asp Val Tyr Ile Val Gln Asp Leu Met Glu Thr Asp
        115                 120                 125
Leu Tyr Lys Leu Leu Lys Ser Gln Gln Leu Ser Asn Asp His Ile Cys
    130                 135                 140
Tyr Phe Leu Tyr Gln Ile Leu Arg Gly Leu Lys Tyr Ile His Ser Ala
145                 150                 155                 160
Asn Val Leu His Arg Asp Leu Lys Pro Ser Asn Leu Leu Ile Asn Thr
                165                 170                 175
Thr Cys Asp Leu Lys Ile Cys Asp Phe Gly Leu Ala Arg Ile Ala Asp
            180                 185                 190
Pro Glu His Asp His Thr Gly Phe Leu Thr Glu Tyr Val Ala Thr Arg
```

```
                195                 200                 205
Trp Tyr Arg Ala Pro Glu Ile Met Leu Asn Ser Lys Gly Tyr Thr Lys
    210                 215                 220

Ser Ile Asp Ile Trp Ser Val Gly Cys Ile Leu Ala Glu Met Leu Ser
225                 230                 235                 240

Asn Arg Pro Ile Phe Pro Gly Lys His Tyr Leu Asp Gln Leu Asn His
                245                 250                 255

Ile Leu Gly Ile Leu Gly Ser Pro Ser Gln Glu Asp Leu Asn Cys Ile
            260                 265                 270

Ile Asn Met Lys Ala Arg Asn Tyr Leu Gln Ser Leu Pro Ser Lys Thr
        275                 280                 285

Lys Val Ala Trp Ala Lys Leu Phe Pro Lys Ser Asp Ser Lys Ala Leu
    290                 295                 300

Asp Leu Leu Asp Arg Met Leu Thr Phe Asn Pro Asn Lys Arg Ile Thr
305                 310                 315                 320

Val Glu Glu Ala Leu Ala His Pro Tyr Leu Glu Gln Tyr Tyr Asp Pro
                325                 330                 335

Thr Asp Glu Pro Val Ala Glu Glu Pro Phe Thr Phe Ala Met Glu Leu
            340                 345                 350

Asp Asp Leu Pro Lys Glu Arg Leu Lys Glu Leu Ile Phe Gln Glu Thr
        355                 360                 365

Ala Arg Phe Gln Pro Gly Val Leu Glu Ala Pro
    370                 375

<210> SEQ ID NO 20
<211> LENGTH: 360
<212> TYPE: PRT
<213> ORGANISM: Homo sapiens

<400> SEQUENCE: 20

Met Ala Ala Ala Ala Ala Gly Ala Gly Pro Glu Met Val Arg Gly
  1               5                  10                  15

Gln Val Phe Asp Val Gly Pro Arg Tyr Thr Asn Leu Ser Tyr Ile Gly
                 20                  25                  30

Glu Gly Ala Tyr Gly Met Val Cys Ser Ala Tyr Asp Asn Val Asn Lys
             35                  40                  45

Val Arg Val Ala Ile Lys Lys Ile Ser Pro Phe Glu His Gln Thr Tyr
         50                  55                  60

Cys Gln Arg Thr Leu Arg Glu Ile Lys Ile Leu Leu Arg Phe Arg His
 65                  70                  75                  80

Glu Asn Ile Ile Gly Ile Asn Asp Ile Ile Arg Ala Pro Thr Ile Glu
                 85                  90                  95

Gln Met Lys Asp Val Tyr Ile Val Gln Asp Leu Met Glu Thr Asp Leu
            100                 105                 110

Tyr Lys Leu Leu Lys Thr Gln His Leu Ser Asn Asp His Ile Cys Tyr
        115                 120                 125

Phe Leu Tyr Gln Ile Leu Arg Gly Leu Lys Tyr Ile His Ser Ala Asn
    130                 135                 140

Val Leu His Arg Asp Leu Lys Pro Ser Asn Leu Leu Leu Asn Thr Thr
145                 150                 155                 160

Cys Asp Leu Lys Ile Cys Asp Phe Gly Leu Ala Arg Val Ala Asp Pro
                165                 170                 175

Asp His Asp His Thr Gly Phe Leu Thr Glu Tyr Val Ala Thr Arg Trp
            180                 185                 190
```

Tyr Arg Ala Pro Glu Ile Met Leu Asn Ser Lys Gly Tyr Thr Lys Ser
    195                 200                 205

Ile Asp Ile Trp Ser Val Gly Cys Ile Leu Ala Glu Met Leu Ser Asn
210                 215                 220

Arg Pro Ile Phe Pro Gly Lys His Tyr Leu Asp Gln Leu Asn His Ile
225                 230                 235                 240

Leu Gly Ile Leu Gly Ser Pro Ser Gln Glu Asp Leu Asn Cys Ile Ile
                245                 250                 255

Asn Leu Lys Ala Arg Asn Tyr Leu Leu Ser Leu Pro His Lys Asn Lys
            260                 265                 270

Val Pro Trp Asn Arg Leu Phe Pro Asn Ala Asp Ser Lys Ala Leu Asp
        275                 280                 285

Leu Leu Asp Lys Met Leu Thr Phe Asn Pro His Lys Arg Ile Glu Val
    290                 295                 300

Glu Gln Ala Leu Ala His Pro Tyr Leu Glu Gln Tyr Tyr Asp Pro Ser
305                 310                 315                 320

Asp Glu Pro Ile Ala Glu Ala Pro Phe Lys Phe Asp Met Glu Leu Asp
                325                 330                 335

Asp Leu Pro Lys Glu Lys Leu Lys Glu Leu Ile Phe Glu Glu Thr Ala
            340                 345                 350

Arg Phe Gln Pro Gly Tyr Arg Ser
    355                 360

<210> SEQ ID NO 21
<211> LENGTH: 721
<212> TYPE: PRT
<213> ORGANISM: Homo sapiens

<400> SEQUENCE: 21

Met Ala Glu Lys Phe Glu Ser Leu Met Asn Ile His Gly Phe Asp Leu
1               5                   10                  15

Gly Ser Arg Tyr Met Asp Leu Lys Pro Leu Gly Cys Gly Gly Asn Gly
            20                  25                  30

Leu Val Phe Ser Ala Val Asp Asn Asp Cys Asp Lys Arg Val Ala Ile
        35                  40                  45

Lys Lys Ile Val Leu Thr Asp Pro Gln Ser Val Lys His Ala Leu Arg
    50                  55                  60

Glu Ile Lys Ile Ile Arg Arg Leu Asp His Asp Asn Ile Val Lys Val
65                  70                  75                  80

Phe Glu Ile Leu Gly Pro Ser Gly Ser Gln Leu Thr Asp Asp Val Gly
                85                  90                  95

Ser Leu Thr Glu Leu Asn Ser Val Tyr Ile Val Gln Glu Tyr Met Glu
                100                 105                 110

Thr Asp Leu Ala Asn Val Leu Glu Gln Gly Pro Leu Leu Glu Glu His
            115                 120                 125

Ala Arg Leu Phe Met Tyr Gln Leu Leu Arg Gly Leu Lys Tyr Ile His
        130                 135                 140

Ser Ala Asn Val Leu His Arg Asp Leu Lys Pro Ala Asn Leu Phe Ile
145                 150                 155                 160

Asn Thr Glu Asp Leu Val Leu Lys Ile Gly Asp Phe Gly Leu Ala Arg
                165                 170                 175

Ile Met Asp Pro His Tyr Ser His Lys Gly His Leu Ser Glu Gly Leu
            180                 185                 190

Val Thr Lys Trp Tyr Arg Ser Pro Arg Leu Leu Leu Ser Pro Asn Asn
    195                 200                 205

```
Tyr Thr Lys Ala Ile Asp Met Trp Ala Ala Gly Cys Ile Phe Ala Glu
            210                 215                 220

Met Leu Thr Gly Lys Thr Leu Phe Ala Gly Ala His Glu Leu Glu Gln
225                 230                 235                 240

Met Gln Leu Ile Leu Glu Ser Ile Pro Val Val His Glu Glu Asp Arg
                245                 250                 255

Gln Glu Leu Leu Ser Val Ile Pro Val Tyr Ile Arg Asn Asp Met Thr
                260                 265                 270

Glu Pro His Lys Pro Leu Thr Gln Leu Leu Pro Gly Ile Ser Arg Glu
            275                 280                 285

Ala Leu Asp Phe Leu Glu Gln Ile Leu Thr Phe Ser Pro Met Asp Arg
290                 295                 300

Leu Thr Ala Glu Glu Ala Leu Ser His Pro Tyr Met Ser Ile Tyr Ser
305                 310                 315                 320

Phe Pro Met Asp Glu Pro Ile Ser Ser His Pro Phe His Ile Glu Asp
                325                 330                 335

Glu Val Asp Asp Ile Leu Leu Met Asp Glu Thr His Ser His Ile Tyr
            340                 345                 350

Asn Trp Glu Arg Tyr His Asp Cys Gln Phe Ser Glu His Asp Trp Pro
            355                 360                 365

Val His Asn Asn Phe Asp Ile Asp Glu Val Gln Leu Asp Pro Arg Ala
370                 375                 380

Leu Ser Asp Val Thr Asp Glu Glu Val Gln Val Asp Pro Arg Lys
385                 390                 395                 400

Tyr Leu Asp Gly Asp Arg Glu Lys Tyr Leu Glu Asp Pro Ala Phe Asp
                405                 410                 415

Thr Asn Tyr Ser Thr Glu Pro Cys Trp Gln Tyr Ser Asp His His Glu
            420                 425                 430

Asn Lys Tyr Cys Asp Leu Glu Cys Ser His Thr Cys Asn Tyr Lys Thr
            435                 440                 445

Arg Ser Ser Ser Tyr Leu Asp Asn Leu Val Trp Arg Glu Ser Glu Val
450                 455                 460

Asn His Tyr Tyr Glu Pro Lys Leu Ile Ile Asp Leu Ser Asn Trp Lys
465                 470                 475                 480

Glu Gln Ser Lys Glu Lys Ser Asp Lys Gly Lys Ser Lys Cys Glu
                485                 490                 495

Arg Asn Gly Leu Val Lys Ala Gln Ile Ala Leu Glu Glu Ala Ser Gln
            500                 505                 510

Gln Leu Ala Gly Lys Glu Arg Glu Lys Asn Gln Gly Phe Asp Phe Asp
            515                 520                 525

Ser Phe Ile Ala Gly Thr Ile Gln Leu Ser Ser Gln His Glu Pro Thr
530                 535                 540

Asp Val Val Asp Lys Leu Asn Asp Leu Asn Ser Ser Val Ser Gln Leu
545                 550                 555                 560

Glu Leu Lys Ser Leu Ile Ser Lys Ser Val Ser Gln Glu Lys Gln Glu
                565                 570                 575

Lys Gly Met Ala Asn Leu Ala Gln Leu Glu Ala Leu Tyr Gln Ser Ser
            580                 585                 590

Trp Asp Ser Gln Phe Val Ser Gly Gly Glu Asp Cys Phe Phe Ile Asn
            595                 600                 605

Gln Phe Cys Glu Val Arg Lys Asp Glu Gln Val Glu Lys Glu Asn Thr
610                 615                 620
```

```
Tyr Thr Ser Tyr Leu Asp Lys Phe Phe Ser Arg Lys Glu Asp Thr Glu
625                 630                 635                 640

Met Leu Glu Thr Glu Pro Val Glu Asp Gly Lys Leu Gly Glu Arg Gly
                645                 650                 655

His Glu Glu Gly Phe Leu Asn Asn Ser Gly Glu Phe Leu Phe Asn Lys
            660                 665                 670

Gln Leu Glu Ser Ile Gly Ile Pro Gln Phe His Ser Pro Val Gly Ser
        675                 680                 685

Pro Leu Lys Ser Ile Gln Ala Thr Leu Thr Pro Ser Ala Met Lys Ser
    690                 695                 700

Ser Pro Gln Ile Pro His Gln Thr Tyr Ser Ser Ile Leu Lys His Leu
705                 710                 715                 720

Asn

<210> SEQ ID NO 22
<211> LENGTH: 557
<212> TYPE: PRT
<213> ORGANISM: Homo sapiens

<400> SEQUENCE: 22

Met Ala Glu Lys Gly Asp Cys Ile Ala Ser Val Tyr Gly Tyr Asp Leu
1               5                   10                  15

Gly Gly Arg Phe Val Asp Phe Gln Pro Leu Gly Phe Gly Val Asn Gly
            20                  25                  30

Leu Val Leu Ser Ala Val Asp Ser Arg Ala Cys Arg Lys Val Ala Val
        35                  40                  45

Lys Lys Ile Ala Leu Ser Asp Ala Arg Ser Met Lys His Ala Leu Arg
    50                  55                  60

Glu Ile Lys Ile Ile Arg Arg Leu Asp His Asp Asn Ile Val Lys Val
65                  70                  75                  80

Tyr Glu Val Leu Gly Pro Lys Gly Thr Asp Leu Gln Gly Glu Leu Phe
                85                  90                  95

Lys Phe Ser Val Ala Tyr Ile Val Gln Glu Tyr Met Glu Thr Asp Leu
            100                 105                 110

Ala Arg Leu Leu Glu Gln Gly Thr Leu Ala Glu Glu His Ala Lys Leu
        115                 120                 125

Phe Met Tyr Gln Leu Leu Arg Gly Leu Lys Tyr Ile His Ser Ala Asn
    130                 135                 140

Val Leu His Arg Asp Leu Lys Pro Ala Asn Ile Phe Ile Ser Thr Glu
145                 150                 155                 160

Asp Leu Val Leu Lys Ile Gly Asp Phe Gly Leu Ala Arg Ile Val Asp
                165                 170                 175

Gln His Tyr Ser His Lys Gly Tyr Leu Ser Glu Gly Leu Val Thr Lys
            180                 185                 190

Trp Tyr Arg Ser Pro Arg Leu Leu Leu Ser Pro Asn Asn Tyr Thr Lys
        195                 200                 205

Ala Ile Asp Met Trp Ala Ala Gly Cys Ile Leu Ala Glu Met Leu Thr
    210                 215                 220

Gly Arg Met Leu Phe Ala Gly Ala His Glu Leu Glu Gln Met Gln Leu
225                 230                 235                 240

Ile Leu Glu Thr Ile Pro Val Ile Arg Glu Glu Asp Lys Asp Glu Leu
                245                 250                 255

Leu Arg Val Met Pro Ser Phe Val Ser Ser Thr Trp Glu Val Lys Arg
            260                 265                 270
```

```
Pro Leu Arg Lys Leu Leu Pro Glu Val Asn Ser Glu Ala Ile Asp Phe
        275                 280                 285

Leu Glu Lys Ile Leu Thr Phe Asn Pro Met Asp Arg Leu Thr Ala Glu
    290                 295                 300

Met Gly Leu Gln His Pro Tyr Met Ser Pro Tyr Ser Cys Pro Glu Asp
305                 310                 315                 320

Glu Pro Thr Ser Gln His Pro Phe Arg Ile Glu Asp Glu Ile Asp Asp
                325                 330                 335

Ile Val Leu Met Ala Ala Asn Gln Ser Gln Leu Ser Asn Trp Asp Thr
            340                 345                 350

Cys Ser Ser Arg Tyr Pro Val Ser Leu Ser Ser Asp Leu Glu Trp Arg
        355                 360                 365

Pro Asp Arg Cys Gln Asp Ala Ser Glu Val Gln Arg Asp Pro Arg Gly
    370                 375                 380

Phe Gly Ala Leu Ala Glu Asp Val Gln Val Asp Pro Arg Lys Asp Ser
385                 390                 395                 400

His Ser Ser Glu Arg Phe Leu Glu Gln Ser His Ser Ser Met Glu
                405                 410                 415

Arg Ala Phe Glu Ala Asp Tyr Gly Arg Ser Cys Asp Tyr Lys Val Gly
            420                 425                 430

Ser Pro Ser Tyr Leu Asp Lys Leu Leu Trp Arg Asp Asn Lys Pro His
        435                 440                 445

His Tyr Ser Glu Pro Lys Leu Ile Leu Asp Leu Ser His Trp Lys Gln
    450                 455                 460

Ala Ala Gly Ala Pro Thr Ala Thr Gly Leu Ala Asp Thr Gly Ala
465                 470                 475                 480

Arg Glu Asp Glu Pro Ala Ser Leu Phe Leu Glu Ile Ala Gln Trp Val
                485                 490                 495

Lys Ser Thr Gln Gly Ala Gln Ser Thr Pro Ala Arg Pro Pro Thr Thr
            500                 505                 510

Pro Ser Ala Ala Cys Leu Pro Arg Pro Pro Pro Gly Pro Gly Gly
        515                 520                 525

Arg Arg Arg Gln Pro Pro Val Arg Pro Gly Arg Val His Leu Pro Arg
    530                 535                 540

Pro Glu Ala Leu His Gln Ala Arg Gly Pro Ala Gly Gln
545                 550                 555

<210> SEQ ID NO 23
<211> LENGTH: 815
<212> TYPE: PRT
<213> ORGANISM: Homo sapiens

<400> SEQUENCE: 23

Met Ala Glu Pro Leu Lys Glu Glu Asp Gly Glu Asp Gly Ser Ala Glu
1               5                   10                  15

Pro Pro Ala Arg Glu Gly Arg Thr Arg Pro His Arg Cys Leu Cys Ser
            20                  25                  30

Ala Lys Asn Leu Ala Leu Leu Lys Ala Arg Ser Phe Asp Val Thr Phe
        35                  40                  45

Asp Val Gly Asp Glu Tyr Glu Ile Ile Glu Thr Ile Gly Asn Gly Ala
    50                  55                  60

Tyr Gly Val Val Ser Ser Ala Arg Arg Arg Leu Thr Gly Gln Gln Val
65                  70                  75                  80

Ala Ile Lys Lys Ile Pro Asn Ala Phe Asp Val Val Thr Asn Ala Lys
                85                  90                  95
```

```
Arg Thr Leu Arg Glu Leu Lys Ile Leu Lys His Phe Lys His Asp Asn
            100                 105                 110
Ile Ile Ala Ile Lys Asp Ile Leu Arg Pro Thr Val Pro Tyr Gly Glu
        115                 120                 125
Phe Lys Ser Val Tyr Val Leu Asp Leu Met Glu Ser Asp Leu His
    130                 135                 140
Gln Ile Ile His Ser Ser Gln Pro Leu Thr Leu Glu His Val Arg Tyr
145                 150                 155                 160
Phe Leu Tyr Gln Leu Leu Arg Gly Leu Lys Tyr Met His Ser Ala Gln
            165                 170                 175
Val Ile His Arg Asp Leu Lys Pro Ser Asn Leu Leu Val Asn Glu Asn
        180                 185                 190
Cys Glu Leu Lys Ile Gly Asp Phe Gly Met Ala Arg Gly Leu Cys Thr
            195                 200                 205
Ser Pro Ala Glu His Gln Tyr Phe Met Thr Glu Tyr Val Ala Thr Arg
    210                 215                 220
Trp Tyr Arg Ala Pro Glu Leu Met Leu Ser Leu His Glu Tyr Thr Gln
225                 230                 235                 240
Ala Ile Asp Leu Trp Ser Val Gly Cys Ile Phe Gly Glu Met Leu Ala
            245                 250                 255
Arg Arg Gln Leu Phe Pro Gly Lys Asn Tyr Val His Gln Leu Gln Leu
        260                 265                 270
Ile Met Met Val Leu Gly Thr Pro Ser Pro Ala Val Ile Gln Ala Val
            275                 280                 285
Gly Ala Glu Arg Val Arg Ala Tyr Ile Gln Ser Leu Pro Pro Arg Gln
    290                 295                 300
Pro Val Pro Trp Glu Thr Val Tyr Pro Gly Ala Asp Arg Gln Ala Leu
305                 310                 315                 320
Ser Leu Leu Gly Arg Met Leu Arg Phe Glu Pro Ser Ala Arg Ile Ser
            325                 330                 335
Ala Ala Ala Ala Leu Arg His Pro Phe Leu Ala Lys Tyr His Asp Pro
            340                 345                 350
Asp Asp Glu Pro Asp Cys Ala Pro Pro Phe Asp Phe Ala Phe Asp Arg
    355                 360                 365
Glu Ala Leu Thr Arg Glu Arg Ile Lys Glu Ala Ile Val Ala Glu Ile
    370                 375                 380
Glu Asp Phe His Ala Arg Arg Glu Gly Ile Arg Gln Gln Ile Arg Phe
385                 390                 395                 400
Gln Pro Ser Leu Gln Pro Val Ala Ser Glu Pro Gly Cys Pro Asp Val
            405                 410                 415
Glu Met Pro Ser Pro Trp Ala Pro Ser Gly Asp Cys Ala Met Glu Ser
            420                 425                 430
Pro Pro Pro Ala Pro Pro Cys Pro Gly Pro Ala Pro Asp Thr Ile
    435                 440                 445
Asp Leu Thr Leu Gln Pro Pro Pro Val Ser Glu Pro Ala Pro Pro
    450                 455                 460
Lys Lys Asp Gly Ala Ile Ser Asp Asn Thr Lys Ala Ala Leu Lys Ala
465                 470                 475                 480
Ala Leu Leu Lys Ser Leu Arg Ser Arg Leu Arg Asp Gly Pro Ser Ala
            485                 490                 495
Pro Leu Glu Ala Pro Glu Pro Arg Lys Pro Val Thr Ala Gln Glu Arg
    500                 505                 510
```

```
Gln Arg Glu Arg Glu Lys Arg Arg Arg Gln Glu Arg Ala Lys
            515                 520                 525
Glu Arg Glu Lys Arg Arg Gln Glu Arg Glu Arg Lys Glu Arg Gly Ala
530                 535                 540
Gly Ala Ser Gly Gly Pro Ser Thr Asp Pro Leu Ala Gly Leu Val Leu
545                 550                 555                 560
Ser Asp Asn Asp Arg Ser Leu Leu Glu Arg Trp Thr Arg Met Ala Arg
                565                 570                 575
Pro Ala Ala Pro Ala Leu Thr Ser Val Pro Ala Pro Ala Pro Ala Pro
                580                 585                 590
Thr Pro Thr Pro Thr Pro Val Gln Pro Thr Ser Pro Pro Gly Pro
            595                 600                 605
Leu Ala Gln Pro Thr Gly Pro Gln Pro Gln Ser Ala Gly Ser Thr Ser
            610                 615                 620
Gly Pro Val Pro Gln Pro Ala Cys Pro Pro Gly Pro Ala Pro His
625                 630                 635                 640
Pro Thr Gly Pro Pro Gly Pro Ile Pro Val Pro Ala Pro Gln Ile
                645                 650                 655
Ala Thr Ser Thr Ser Leu Leu Ala Ala Gln Ser Leu Val Pro Pro
                660                 665                 670
Gly Leu Pro Gly Ser Ser Thr Pro Gly Val Leu Pro Tyr Phe Pro Pro
            675                 680                 685
Gly Leu Pro Pro Asp Ala Gly Gly Ala Pro Gln Ser Ser Met Ser
            690                 695                 700
Glu Ser Pro Asp Val Asn Leu Val Thr Gln Gln Leu Ser Lys Ser Gln
705                 710                 715                 720
Val Glu Asp Pro Leu Pro Pro Val Phe Ser Gly Thr Pro Lys Gly Ser
                725                 730                 735
Gly Ala Gly Tyr Gly Val Gly Phe Asp Leu Glu Glu Phe Leu Asn Gln
            740                 745                 750
Ser Phe Asp Met Gly Val Ala Asp Gly Pro Gln Asp Gly Gln Ala Asp
            755                 760                 765
Ser Ala Ser Leu Ser Ala Ser Leu Leu Ala Asp Trp Leu Glu Gly His
            770                 775                 780
Gly Met Asn Pro Ala Asp Ile Glu Ser Leu Gln Arg Glu Ile Gln Met
785                 790                 795                 800
Asp Ser Pro Met Leu Leu Ala Asp Leu Pro Asp Leu Gln Asp Pro
                805                 810                 815

<210> SEQ ID NO 24
<211> LENGTH: 367
<212> TYPE: PRT
<213> ORGANISM: Homo sapiens

<400> SEQUENCE: 24

Met Ser Ser Pro Pro Ala Arg Ser Gly Phe Tyr Arg Gln Glu Val
 1               5                  10                  15
Thr Lys Thr Ala Trp Glu Val Arg Ala Val Tyr Arg Asp Leu Gln Pro
            20                  25                  30
Val Gly Ser Gly Ala Tyr Gly Ala Val Cys Ser Ala Val Asp Gly Arg
            35                  40                  45
Thr Gly Ala Lys Val Ala Ile Lys Lys Leu Tyr Arg Pro Phe Gln Ser
        50                  55                  60
Glu Leu Phe Ala Lys Arg Ala Tyr Arg Glu Leu Arg Leu Leu Lys His
65                  70                  75                  80
```

```
Met Arg His Glu Asn Val Ile Gly Leu Leu Asp Val Phe Thr Pro Asp
                85                  90                  95

Glu Thr Leu Asp Asp Phe Thr Asp Phe Tyr Leu Val Met Pro Phe Met
            100                 105                 110

Gly Thr Asp Leu Gly Lys Leu Met Lys His Glu Lys Leu Gly Glu Asp
            115                 120                 125

Arg Ile Gln Phe Leu Val Tyr Gln Met Leu Lys Gly Leu Arg Tyr Ile
            130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
            180                 185                 190

Ala Pro Glu Val Ile Leu Asn Trp Met Arg Tyr Thr Gln Thr Val Asp
            195                 200                 205

Ile Trp Ser Val Gly Cys Ile Met Ala Glu Met Ile Thr Gly Lys Thr
210                 215                 220

Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Glu Lys Lys Asp
            260                 265                 270

Phe Ala Ser Ile Leu Thr Asn Ala Ser Pro Leu Ala Val Asn Leu Leu
            275                 280                 285

Glu Lys Met Leu Val Leu Asp Ala Glu Gln Arg Val Thr Ala Gly Glu
            290                 295                 300

Ala Leu Ala His Pro Tyr Phe Glu Ser Leu His Asp Thr Glu Asp Glu
305                 310                 315                 320

Pro Gln Val Gln Lys Tyr Asp Asp Ser Phe Asp Asp Val Asp Arg Thr
                325                 330                 335

Leu Asp Glu Trp Lys Arg Val Thr Tyr Lys Glu Val Leu Ser Phe Lys
            340                 345                 350

Pro Pro Arg Gln Leu Gly Ala Arg Val Ser Lys Glu Thr Pro Leu
            355                 360                 365

<210> SEQ ID NO 25
<211> LENGTH: 1052
<212> TYPE: PRT
<213> ORGANISM: Homo sapiens

<400> SEQUENCE: 25

Met Ala Ala Ala Tyr Leu Asp Pro Asn Leu Asn His Thr Pro Asn Ser
1               5                   10                  15

Ser Thr Lys Thr His Leu Gly Thr Gly Met Glu Arg Ser Pro Gly Ala
            20                  25                  30

Met Glu Arg Val Leu Lys Val Phe His Tyr Phe Glu Ser Asn Ser Glu
        35                  40                  45

Pro Thr Thr Trp Ala Ser Ile Ile Arg His Gly Asp Ala Thr Asp Val
    50                  55                  60

Arg Gly Ile Ile Gln Lys Ile Val Asp Ser His Lys Val Lys His Val
65                  70                  75                  80

Ala Cys Tyr Gly Phe Arg Leu Ser His Leu Arg Ser Glu Glu Val His
```

-continued

```
                    85                  90                  95
Trp Leu His Val Asp Met Gly Val Ser Val Arg Glu Lys Tyr Glu
                100                 105                 110
Leu Ala His Pro Pro Glu Glu Trp Lys Tyr Glu Leu Arg Ile Arg Tyr
                115                 120                 125
Leu Pro Lys Gly Phe Leu Asn Gln Phe Thr Glu Asp Lys Pro Thr Leu
130                 135                 140
Asn Phe Phe Tyr Gln Gln Val Lys Ser Asp Tyr Met Leu Glu Ile Ala
145                 150                 155                 160
Asp Gln Val Asp Gln Glu Ile Ala Leu Lys Leu Gly Cys Leu Glu Ile
                165                 170                 175
Arg Arg Ser Tyr Trp Glu Met Arg Gly Asn Ala Leu Glu Lys Lys Ser
                180                 185                 190
Asn Tyr Glu Val Leu Glu Lys Asp Val Gly Leu Lys Arg Phe Phe Pro
                195                 200                 205
Lys Ser Leu Leu Asp Ser Val Lys Ala Lys Thr Leu Arg Lys Leu Ile
                210                 215                 220
Gln Gln Thr Phe Arg Gln Phe Ala Asn Leu Asn Arg Glu Glu Ser Ile
225                 230                 235                 240
Leu Lys Phe Phe Glu Ile Leu Ser Pro Val Tyr Arg Phe Asp Lys Glu
                245                 250                 255
Cys Phe Lys Cys Ala Leu Gly Ser Ser Trp Ile Ile Ser Val Glu Leu
                260                 265                 270
Ala Ile Gly Pro Glu Glu Gly Ile Ser Tyr Leu Thr Asp Lys Gly Cys
                275                 280                 285
Asn Pro Thr His Leu Ala Asp Phe Thr Gln Val Gln Thr Ile Gln Tyr
                290                 295                 300
Ser Asn Ser Glu Asp Lys Asp Arg Lys Gly Met Leu Gln Leu Lys Ile
305                 310                 315                 320
Ala Gly Ala Pro Glu Pro Leu Thr Val Thr Ala Pro Ser Leu Thr Ile
                325                 330                 335
Ala Glu Asn Met Ala Asp Leu Ile Asp Gly Tyr Cys Arg Leu Val Asn
                340                 345                 350
Gly Thr Ser Gln Ser Phe Ile Ile Arg Pro Gln Lys Glu Gly Glu Arg
                355                 360                 365
Ala Leu Pro Ser Ile Pro Lys Leu Ala Asn Ser Glu Lys Gln Gly Met
                370                 375                 380
Arg Thr His Ala Val Ser Val Ser Glu Thr Asp Tyr Ala Glu Ile
385                 390                 395                 400
Ile Asp Glu Glu Asp Thr Tyr Thr Met Pro Ser Thr Arg Asp Tyr Glu
                405                 410                 415
Ile Gln Arg Glu Arg Ile Glu Leu Gly Arg Cys Ile Gly Glu Gly Gln
                420                 425                 430
Phe Gly Asp Val His Gln Gly Ile Tyr Met Ser Pro Glu Asn Pro Ala
                435                 440                 445
Leu Ala Val Ala Ile Lys Thr Cys Lys Asn Cys Thr Ser Asp Ser Val
450                 455                 460
Arg Glu Lys Phe Leu Gln Glu Ala Leu Thr Met Arg Gln Phe Asp His
465                 470                 475                 480
Pro His Ile Val Lys Leu Ile Gly Val Ile Thr Glu Asn Pro Val Trp
                485                 490                 495
Ile Ile Met Glu Leu Cys Thr Leu Gly Glu Leu Arg Ser Phe Leu Gln
                500                 505                 510
```

```
Val Arg Lys Tyr Ser Leu Asp Leu Ala Ser Leu Ile Leu Tyr Ala Tyr
        515                 520                 525

Gln Leu Ser Thr Ala Leu Ala Tyr Leu Glu Ser Lys Arg Phe Val His
    530                 535                 540

Arg Asp Ile Ala Ala Arg Asn Val Leu Val Ser Ser Asn Asp Cys Val
545                 550                 555                 560

Lys Leu Gly Asp Phe Gly Leu Ser Arg Tyr Met Glu Asp Ser Thr Tyr
                565                 570                 575

Tyr Lys Ala Ser Lys Gly Lys Leu Pro Ile Lys Trp Met Ala Pro Glu
            580                 585                 590

Ser Ile Asn Phe Arg Arg Phe Thr Ser Ala Ser Asp Val Trp Met Phe
        595                 600                 605

Gly Val Cys Met Trp Glu Ile Leu Met His Gly Val Lys Pro Phe Gln
    610                 615                 620

Gly Val Lys Asn Asn Asp Val Ile Gly Arg Ile Glu Asn Gly Glu Arg
625                 630                 635                 640

Leu Pro Met Pro Pro Asn Cys Pro Pro Thr Leu Tyr Ser Leu Met Thr
                645                 650                 655

Lys Cys Trp Ala Tyr Asp Pro Ser Arg Arg Pro Arg Phe Thr Glu Leu
            660                 665                 670

Lys Ala Gln Leu Ser Thr Ile Leu Glu Glu Lys Ala Gln Gln Glu
        675                 680                 685

Glu Arg Met Arg Met Glu Ser Arg Arg Gln Ala Thr Val Ser Trp Asp
    690                 695                 700

Ser Gly Gly Ser Asp Glu Ala Pro Pro Lys Pro Ser Arg Pro Gly Tyr
705                 710                 715                 720

Pro Ser Pro Arg Ser Ser Glu Gly Phe Tyr Pro Ser Pro Gln His Met
                725                 730                 735

Val Gln Thr Asn His Tyr Gln Val Ser Gly Tyr Pro Gly Ser His Gly
            740                 745                 750

Ile Thr Ala Met Ala Gly Ser Ile Tyr Pro Gly Gln Ala Ser Leu Leu
        755                 760                 765

Asp Gln Thr Asp Ser Trp Asn His Arg Pro Gln Glu Ile Ala Met Trp
    770                 775                 780

Gln Pro Asn Val Glu Asp Ser Thr Val Leu Asp Leu Arg Gly Ile Gly
785                 790                 795                 800

Gln Val Leu Pro Thr His Leu Met Glu Glu Arg Leu Ile Arg Gln Gln
                805                 810                 815

Gln Glu Met Glu Glu Asp Gln Arg Trp Leu Glu Lys Glu Arg Phe
            820                 825                 830

Leu Lys Pro Asp Val Arg Leu Ser Arg Gly Ser Ile Asp Arg Glu Asp
    835                 840                 845

Gly Ser Leu Gln Gly Pro Ile Gly Asn Gln His Ile Tyr Gln Pro Val
850                 855                 860

Gly Lys Pro Asp Pro Ala Ala Pro Pro Lys Lys Pro Pro Arg Pro Gly
865                 870                 875                 880

Ala Pro Gly His Leu Gly Ser Leu Ala Ser Leu Ser Ser Pro Ala Asp
                885                 890                 895

Ser Tyr Asn Glu Gly Val Lys Leu Gln Pro Gln Glu Ile Ser Pro Pro
            900                 905                 910

Pro Thr Ala Asn Leu Asp Arg Ser Asn Asp Lys Val Tyr Glu Asn Val
        915                 920                 925
```

-continued

```
Thr Gly Leu Val Lys Ala Val Ile Glu Met Ser Ser Lys Ile Gln Pro
    930                 935                 940

Ala Pro Pro Glu Glu Tyr Val Pro Met Val Lys Glu Val Gly Leu Ala
945                 950                 955                 960

Leu Arg Thr Leu Leu Ala Thr Val Asp Glu Thr Ile Pro Leu Leu Pro
                965                 970                 975

Ala Ser Thr His Arg Glu Ile Glu Met Ala Gln Lys Leu Leu Asn Ser
            980                 985                 990

Asp Leu Gly Glu Leu Ile Asn Lys Met Lys Leu Ala Gln Gln Tyr Val
            995                1000                1005

Met Thr Ser Leu Gln Gln Glu Tyr Lys Lys Gln Met Leu Thr Ala Ala
        1010                1015                1020

His Ala Leu Ala Val Asp Ala Lys Asn Leu Leu Asp Val Ile Asp Gln
1025                1030                1035                1040

Ala Arg Leu Lys Met Leu Gly Gln Thr Arg Pro His
                1045                1050
```

<210> SEQ ID NO 26
<211> LENGTH: 822
<212> TYPE: PRT
<213> ORGANISM: Homo sapiens

<400> SEQUENCE: 26

```
Met Trp Ser Trp Lys Cys Leu Leu Phe Trp Ala Val Leu Val Thr Ala
1               5                  10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255
```

```
Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
            275                 280                 285

Trp Leu Lys His Ile Glu Val Asn Gly Ser Lys Ile Gly Pro Asp Asn
            290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
            325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Arg Pro Ala Val
            355                 360                 365

Met Thr Ser Pro Leu Tyr Leu Glu Ile Ile Ile Tyr Cys Thr Gly Ala
            370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
            405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
            435                 440                 445

Leu Ser Ser Ser Gly Thr Pro Met Leu Ala Gly Val Ser Glu Tyr Glu
            450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
            485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
            530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
            565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
            610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
            645                 650                 655

Thr Thr Asn Gly Arg Leu Pro Val Lys Trp Met Ala Pro Glu Ala Leu
            660                 665                 670
```

```
Phe Asp Arg Ile Tyr Thr His Gln Ser Asp Val Trp Ser Phe Gly Val
        675                 680                 685

Leu Leu Trp Glu Ile Phe Thr Leu Gly Gly Ser Pro Tyr Pro Gly Val
        690                 695                 700

Pro Val Glu Glu Leu Phe Lys Leu Leu Lys Gly His Arg Met Asp
705                 710                 715                 720

Lys Pro Ser Asn Cys Thr Asn Glu Leu Tyr Met Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
            755                 760                 765

Leu Ser Met Pro Leu Asp Gln Tyr Ser Pro Ser Phe Pro Asp Thr Arg
        770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
                805                 810                 815

Gly Gly Leu Lys Arg Arg
            820

<210> SEQ ID NO 27
<211> LENGTH: 821
<212> TYPE: PRT
<213> ORGANISM: Homo sapiens

<400> SEQUENCE: 27

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220
```

```
Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
            245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
            355                 360                 365

Ile Thr Ala Ser Pro Asp Tyr Leu Glu Ile Ala Ile Tyr Cys Ile Gly
370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
            405                 410                 415

Lys Leu Thr Lys Arg Ile Pro Leu Arg Arg Gln Val Thr Val Ser Ala
            420                 425                 430

Glu Ser Ser Ser Ser Met Asn Ser Asn Thr Pro Leu Val Arg Ile Thr
            435                 440                 445

Thr Arg Leu Ser Ser Thr Ala Asp Thr Pro Met Leu Ala Gly Val Ser
    450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
            500                 505                 510

Thr Val Ala Val Lys Met Leu Lys Asp Asp Ala Thr Glu Lys Asp Leu
    515                 520                 525

Ser Asp Leu Val Ser Glu Met Glu Met Met Lys Met Ile Gly Lys His
530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
            595                 600                 605

Gln Leu Ala Arg Gly Met Glu Tyr Leu Ala Ser Gln Lys Cys Ile His
            610                 615                 620

Arg Asp Leu Ala Ala Arg Asn Val Leu Val Thr Glu Asn Asn Val Met
625                 630                 635                 640
```

```
Lys Ile Ala Asp Phe Gly Leu Ala Arg Asp Ile Asn Asn Ile Asp Tyr
            645                 650                 655

Tyr Lys Lys Thr Thr Asn Gly Arg Leu Pro Val Lys Trp Met Ala Pro
                660                 665                 670

Glu Ala Leu Phe Asp Arg Val Tyr Thr His Gln Ser Asp Val Trp Ser
            675                 680                 685

Phe Gly Val Leu Met Trp Glu Ile Phe Thr Leu Gly Gly Ser Pro Tyr
        690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
                820

<210> SEQ ID NO 28
<211> LENGTH: 806
<212> TYPE: PRT
<213> ORGANISM: Homo sapiens

<400> SEQUENCE: 28

Met Gly Ala Pro Ala Cys Ala Leu Ala Leu Cys Val Ala Val Ala Ile
  1               5                  10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 155                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190
```

-continued

```
Arg Glu Phe Arg Gly Glu His Arg Ile Gly Gly Ile Lys Leu Arg His
            195                 200                 205
Gln Gln Trp Ser Leu Val Met Glu Ser Val Val Pro Ser Asp Arg Gly
        210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
            260                 265                 270
Phe His Cys Lys Val Tyr Ser Asp Ala Gln Pro His Ile Gln Trp Leu
        275                 280                 285
Lys His Val Glu Val Asn Gly Ser Lys Val Gly Pro Asp Gly Thr Pro
        290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
            340                 345                 350
Trp Leu Val Val Leu Pro Ala Glu Glu Glu Leu Val Glu Ala Asp Glu
        355                 360                 365
Ala Gly Ser Val Tyr Ala Gly Ile Leu Ser Tyr Gly Val Gly Phe Phe
    370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
        435                 440                 445
Pro Thr Leu Ala Asn Val Ser Glu Leu Glu Leu Pro Ala Asp Pro Lys
    450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
        515                 520                 525
Met Lys Met Ile Gly Lys His Lys Asn Ile Ile Asn Leu Leu Gly Ala
        530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
            580                 585                 590
Asp Leu Val Ser Cys Ala Tyr Gln Val Ala Arg Gly Met Glu Tyr Leu
        595                 600                 605
```

-continued

```
Ala Ser Gln Lys Cys Ile His Arg Asp Leu Ala Ala Arg Asn Val Leu
    610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
            660                 665                 670
His Gln Ser Asp Val Trp Ser Phe Gly Val Leu Leu Trp Glu Ile Phe
        675                 680                 685
Thr Leu Gly Gly Ser Pro Tyr Pro Gly Ile Pro Val Glu Glu Leu Phe
    690                 695                 700
Lys Leu Leu Lys Glu Gly His Arg Met Asp Lys Pro Ala Asn Cys Thr
705                 710                 715                 720
His Asp Leu Tyr Met Ile Met Arg Glu Cys Trp His Ala Ala Pro Ser
                725                 730                 735
Gln Arg Pro Thr Phe Lys Gln Leu Val Glu Asp Leu Asp Arg Val Leu
            740                 745                 750
Thr Val Thr Ser Thr Asp Glu Tyr Leu Asp Leu Ser Ala Pro Phe Glu
        755                 760                 765
Gln Tyr Ser Pro Gly Gly Gln Asp Thr Pro Ser Ser Ser Ser Ser Gly
    770                 775                 780
Asp Asp Ser Val Phe Ala His Asp Leu Leu Pro Pro Ala Pro Pro Ser
785                 790                 795                 800
Ser Gly Gly Ser Arg Thr
                805

<210> SEQ ID NO 29
<211> LENGTH: 802
<212> TYPE: PRT
<213> ORGANISM: Homo sapiens

<400> SEQUENCE: 29

Met Arg Leu Leu Leu Ala Leu Leu Gly Val Leu Leu Ser Val Pro Gly
1               5                   10                  15
Pro Pro Val Leu Ser Leu Glu Ala Ser Glu Glu Val Glu Leu Glu Pro
            20                  25                  30
Cys Leu Ala Pro Ser Leu Glu Gln Gln Glu Gln Glu Leu Thr Val Ala
        35                  40                  45
Leu Gly Gln Pro Val Arg Leu Cys Cys Gly Arg Ala Glu Arg Gly Gly
    50                  55                  60
His Trp Tyr Lys Glu Gly Ser Arg Leu Ala Pro Ala Gly Arg Val Arg
65                  70                  75                  80
Gly Trp Arg Gly Arg Leu Glu Ile Ala Ser Phe Leu Pro Glu Asp Ala
                85                  90                  95
Gly Arg Tyr Leu Cys Leu Ala Arg Gly Ser Met Ile Val Leu Gln Asn
            100                 105                 110
Leu Thr Leu Ile Thr Gly Asp Ser Leu Thr Ser Ser Asn Asp Asp Glu
        115                 120                 125
Asp Pro Lys Ser His Arg Asp Pro Ser Asn Arg His Ser Tyr Pro Gln
    130                 135                 140
Gln Ala Pro Tyr Trp Thr His Pro Gln Arg Met Glu Lys Lys Leu His
145                 150                 155                 160
Ala Val Pro Ala Gly Asn Thr Val Lys Phe Arg Cys Pro Ala Ala Gly
                165                 170                 175
```

```
Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
            260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
            340                 345                 350

Glu Glu Asp Pro Thr Trp Thr Ala Ala Pro Glu Ala Arg Tyr Thr
        355                 360                 365

Asp Ile Ile Leu Tyr Ala Ser Gly Ser Leu Ala Leu Ala Val Leu Leu
    370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Gly Lys Ser Ser Ser Ser Leu
            420                 425                 430

Val Arg Gly Val Arg Leu Ser Ser Ser Gly Pro Ala Leu Leu Ala Gly
        435                 440                 445

Leu Val Ser Leu Asp Leu Pro Leu Asp Pro Leu Trp Glu Phe Pro Arg
    450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
            500                 505                 510

Asp Leu Ala Asp Leu Val Ser Glu Met Glu Val Met Lys Leu Ile Gly
        515                 520                 525

Arg His Lys Asn Ile Ile Asn Leu Leu Gly Val Cys Thr Gln Glu Gly
    530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
            580                 585                 590
```

```
Ala Tyr Gln Val Ala Arg Gly Met Gln Tyr Leu Glu Ser Arg Lys Cys
            595                 600                 605

Ile His Arg Asp Leu Ala Ala Arg Asn Val Leu Val Thr Glu Asp Asn
        610                 615                 620

Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
        755                 760                 765

Gly Asp Ala Ser Ser Thr Cys Ser Ser Ser Asp Ser Val Phe Ser His
770                 775                 780

Asp Pro Leu Pro Leu Gly Ser Ser Ser Phe Pro Phe Gly Ser Gly Val
785                 790                 795                 800

Gln Thr

<210> SEQ ID NO 30
<211> LENGTH: 536
<212> TYPE: PRT
<213> ORGANISM: Homo sapiens

<400> SEQUENCE: 30

Gly Cys Val Gln Cys Lys Asp Lys Glu Ala Thr Lys Leu Thr Glu Glu
1               5                   10                  15

Arg Asp Gly Ser Leu Asn Gln Ser Ser Gly Tyr Arg Tyr Gly Thr Asp
            20                  25                  30

Pro Thr Pro Gln His Tyr Pro Ser Phe Gly Val Thr Ser Ile Pro Asn
        35                  40                  45

Tyr Asn Asn Phe His Ala Ala Gly Gly Gln Gly Leu Thr Val Phe Gly
50                  55                  60

Gly Val Asn Ser Ser Ser His Thr Gly Thr Leu Arg Thr Arg Gly Gly
65                  70                  75                  80

Thr Gly Val Thr Leu Phe Val Ala Leu Tyr Asp Tyr Glu Ala Arg Thr
                85                  90                  95

Glu Asp Asp Leu Ser Phe His Lys Gly Glu Lys Phe Gln Ile Leu Asn
            100                 105                 110

Ser Ser Glu Gly Asp Trp Trp Glu Ala Arg Ser Leu Thr Thr Gly Glu
        115                 120                 125

Thr Gly Tyr Ile Pro Ser Asn Tyr Val Ala Pro Val Asp Ser Ile Gln
130                 135                 140

Ala Glu Glu Trp Tyr Phe Gly Lys Leu Gly Arg Lys Asp Ala Glu Arg
145                 150                 155                 160
```

```
Gln Leu Leu Ser Phe Gly Asn Pro Arg Gly Thr Phe Leu Ile Arg Glu
                165                 170                 175

Ser Glu Thr Thr Lys Gly Ala Tyr Ser Leu Ser Ile Arg Asp Trp Asp
            180                 185                 190

Asp Met Lys Gly Asp His Val Lys His Tyr Lys Ile Arg Lys Leu Asp
        195                 200                 205

Asn Gly Gly Tyr Tyr Ile Thr Thr Arg Ala Gln Phe Glu Thr Leu Gln
    210                 215                 220

Gln Leu Val Gln His Tyr Ser Glu Arg Ala Ala Gly Leu Cys Cys Arg
225                 230                 235                 240

Leu Val Val Pro Cys His Lys Gly Met Pro Arg Leu Thr Asp Leu Ser
                245                 250                 255

Val Lys Thr Lys Asp Val Trp Glu Ile Pro Arg Glu Ser Leu Gln Leu
            260                 265                 270

Ile Lys Arg Leu Gly Asn Gly Gln Phe Gly Glu Val Trp Met Gly Thr
        275                 280                 285

Trp Asn Gly Asn Thr Lys Val Ala Ile Lys Thr Leu Lys Pro Gly Thr
    290                 295                 300

Met Ser Pro Glu Ser Phe Leu Glu Glu Ala Gln Ile Met Lys Lys Leu
305                 310                 315                 320

Lys His Asp Lys Leu Val Gln Leu Tyr Ala Val Val Ser Glu Glu Pro
                325                 330                 335

Ile Tyr Ile Val Thr Glu Tyr Met Asn Lys Gly Ser Leu Leu Asp Phe
            340                 345                 350

Leu Lys Asp Gly Glu Gly Arg Ala Leu Lys Leu Pro Asn Leu Val Asp
        355                 360                 365

Met Ala Ala Gln Val Ala Ala Gly Met Ala Tyr Ile Glu Arg Met Asn
    370                 375                 380

Tyr Ile His Arg Asp Leu Arg Ser Ala Asn Ile Leu Val Gly Asn Gly
385                 390                 395                 400

Leu Ile Cys Lys Ile Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
        435                 440                 445

Trp Ser Phe Gly Ile Leu Leu Thr Glu Leu Val Thr Lys Gly Arg Val
    450                 455                 460

Pro Tyr Pro Gly Met Asn Asn Arg Glu Val Leu Glu Gln Val Glu Arg
465                 470                 475                 480

Gly Tyr Arg Met Pro Cys Pro Gln Asp Cys Pro Ile Ser Leu His Glu
                485                 490                 495

Leu Met Ile His Cys Trp Lys Lys Asp Pro Glu Glu Arg Pro Thr Phe
            500                 505                 510

Glu Tyr Leu Gln Ser Phe Leu Glu Asp Tyr Phe Thr Ala Thr Glu Pro
        515                 520                 525

Gln Tyr Gln Pro Gly Glu Asn Leu
    530                 535

<210> SEQ ID NO 31
<211> LENGTH: 526
<212> TYPE: PRT
<213> ORGANISM: Homo sapiens

<400> SEQUENCE: 31
```

```
Met Gly Gly Arg Ser Ser Cys Glu Asp Pro Gly Cys Pro Arg Asp Glu
  1               5                  10                  15
Glu Arg Ala Pro Arg Met Gly Ser Met Lys Ser Lys Phe Leu Gln Val
             20                  25                  30
Gly Gly Asn Thr Phe Ser Lys Thr Glu Thr Ser Ala Ser Pro His Cys
             35                  40                  45
Pro Val Tyr Val Pro Asp Pro Thr Ser Thr Ile Lys Pro Gly Pro Asn
         50                  55                  60
Ser His Asn Ser Asn Thr Pro Gly Ile Arg Glu Ala Gly Ser Glu Asp
 65              70                  75                  80
Ile Ile Val Val Ala Leu Tyr Asp Tyr Glu Ala Ile His His Glu Asp
                 85                  90                  95
Leu Ser Phe Gln Lys Gly Asp Gln Met Val Val Leu Glu Glu Ser Gly
            100                 105                 110
Glu Trp Trp Lys Ala Arg Ser Leu Ala Thr Arg Lys Glu Gly Tyr Ile
            115                 120                 125
Pro Ser Asn Tyr Val Ala Arg Val Asp Ser Leu Glu Thr Glu Glu Trp
        130                 135                 140
Phe Phe Lys Gly Ile Ser Arg Lys Asp Ala Glu Arg Gln Leu Leu Ala
145                 150                 155                 160
Pro Gly Asn Met Leu Gly Ser Phe Met Ile Arg Asp Ser Glu Thr Thr
                165                 170                 175
Lys Gly Ser Tyr Ser Leu Ser Val Arg Asp Tyr Asp Pro Arg Gln Gly
            180                 185                 190
Asp Thr Val Lys His Tyr Lys Ile Arg Thr Leu Asp Asn Gly Gly Phe
            195                 200                 205
Tyr Ile Ser Pro Arg Ser Thr Phe Ser Thr Leu Gln Glu Leu Val Asp
        210                 215                 220
His Tyr Lys Lys Gly Asn Asp Gly Leu Cys Gln Lys Leu Ser Val Pro
225                 230                 235                 240
Cys Met Ser Ser Lys Pro Gln Lys Pro Trp Glu Lys Asp Ala Trp Glu
                245                 250                 255
Ile Pro Arg Glu Ser Leu Lys Leu Glu Lys Lys Leu Gly Ala Gly Gln
            260                 265                 270
Phe Gly Glu Val Trp Met Ala Thr Tyr Asn Lys His Thr Lys Val Ala
            275                 280                 285
Val Lys Thr Met Lys Pro Gly Ser Met Ser Val Glu Ala Phe Leu Ala
        290                 295                 300
Glu Ala Asn Val Met Lys Thr Leu Gln His Asp Lys Leu Val Lys Leu
305                 310                 315                 320
His Ala Val Val Thr Lys Glu Pro Ile Tyr Ile Ile Thr Glu Phe Met
                325                 330                 335
Ala Lys Gly Ser Leu Leu Asp Phe Leu Lys Ser Asp Glu Gly Ser Lys
            340                 345                 350
Gln Pro Leu Pro Lys Leu Ile Asp Phe Ser Ala Gln Ile Ala Glu Gly
            355                 360                 365
Met Ala Phe Ile Glu Gln Arg Asn Tyr Ile His Arg Asp Leu Arg Ala
        370                 375                 380
Ala Asn Ile Leu Val Ser Ala Ser Leu Val Cys Lys Ile Ala Asp Phe
385                 390                 395                 400
Gly Leu Ala Arg Val Ile Glu Asp Asn Glu Tyr Thr Ala Arg Glu Gly
                405                 410                 415
```

```
Ala Lys Phe Pro Ile Lys Trp Thr Ala Pro Glu Ala Ile Asn Phe Gly
            420                 425                 430

Ser Phe Thr Ile Lys Ser Asp Val Trp Ser Phe Gly Ile Leu Leu Met
            435                 440                 445

Glu Ile Val Thr Tyr Gly Arg Ile Pro Tyr Pro Gly Met Ser Asn Pro
            450                 455                 460

Glu Val Ile Arg Ala Leu Glu Arg Gly Tyr Arg Met Pro Arg Pro Glu
465                 470                 475                 480

Asn Cys Pro Glu Glu Leu Tyr Asn Ile Met Met Arg Cys Trp Lys Asn
                485                 490                 495

Arg Pro Glu Glu Arg Pro Thr Phe Glu Tyr Ile Gln Ser Val Leu Asp
            500                 505                 510

Asp Phe Tyr Thr Ala Thr Glu Ser Gln Tyr Gln Gln Pro
            515                 520                 525

<210> SEQ ID NO 32
<211> LENGTH: 745
<212> TYPE: PRT
<213> ORGANISM: Homo sapiens

<400> SEQUENCE: 32

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
            20                  25                  30

Gln His Arg Glu Leu Asp Leu Lys Ile Ala Ile Lys Ser Cys Arg Leu
        35                  40                  45

Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
            260                 265                 270
```

-continued

```
Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
        290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
            355                 360                 365

Ser Gln Cys Val Leu Asp Gly Val Arg Gly Cys Asp Ser Tyr Met Val
        370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
            515                 520                 525

Tyr Leu Glu Asp Gln Ile Met Ser Leu His Ala Glu Ile Met Glu Leu
        530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
        610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
            660                 665                 670

Gly Ala Val Thr Pro Gln Thr Ser Ala Trp Leu Pro Pro Thr Ser Ala
        675                 680                 685
```

-continued

```
Glu His Asp His Ser Leu Ser Cys Val Val Thr Pro Gln Asp Gly Glu
    690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
                725                 730                 735

Asn Leu Asp Trp Ser Trp Leu Thr Glu
            740                 745

<210> SEQ ID NO 33
<211> LENGTH: 756
<212> TYPE: PRT
<213> ORGANISM: Homo sapiens

<400> SEQUENCE: 33

Met Ser Trp Ser Pro Ser Leu Thr Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Thr Tyr Gly Pro Asn Gly Cys Phe Lys Ala Leu Asp
    290                 295                 300

Asp Ile Leu Asn Leu Lys Leu Val His Ile Leu Asn Met Val Thr Gly
305                 310                 315                 320
```

-continued

```
Thr Ile His Thr Tyr Pro Val Thr Glu Asp Glu Ser Leu Gln Ser Leu
            325                 330                 335

Lys Ala Arg Ile Gln Gln Asp Thr Gly Ile Pro Glu Glu Asp Gln Glu
            340                 345                 350

Leu Leu Gln Glu Ala Gly Leu Ala Leu Ile Pro Asp Lys Pro Ala Thr
            355                 360                 365

Gln Cys Ile Ser Asp Gly Lys Leu Asn Glu Gly His Thr Leu Asp Met
    370                 375                 380

Asp Leu Val Phe Leu Phe Asp Asn Ser Lys Ile Thr Tyr Glu Thr Gln
385                 390                 395                 400

Ile Ser Pro Arg Pro Gln Pro Glu Ser Val Ser Cys Ile Leu Gln Glu
                405                 410                 415

Pro Lys Arg Asn Leu Ala Phe Phe Gln Leu Arg Lys Val Trp Gly Gln
                420                 425                 430

Val Trp His Ser Ile Gln Thr Leu Lys Glu Asp Cys Asn Arg Leu Gln
            435                 440                 445

Gln Gly Gln Arg Ala Ala Met Met Asn Leu Leu Arg Asn Asn Ser Cys
    450                 455                 460

Leu Ser Lys Met Lys Asn Ser Met Ala Ser Met Ser Gln Gln Leu Lys
465                 470                 475                 480

Ala Lys Leu Asp Phe Phe Lys Thr Ser Ile Gln Ile Asp Leu Glu Lys
                485                 490                 495

Tyr Ser Glu Gln Thr Glu Phe Gly Ile Thr Ser Asp Lys Leu Leu Leu
                500                 505                 510

Ala Trp Arg Glu Met Glu Gln Ala Val Glu Leu Cys Gly Arg Glu Asn
            515                 520                 525

Glu Val Lys Leu Leu Val Glu Arg Met Met Ala Leu Gln Thr Asp Ile
            530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
                580                 585                 590

Leu Leu Leu Gln Ala Ile Gln Ser Phe Glu Lys Lys Val Arg Val Ile
            595                 600                 605

Tyr Thr Gln Leu Ser Lys Thr Val Val Cys Lys Gln Lys Ala Leu Glu
            610                 615                 620

Leu Leu Pro Lys Val Glu Glu Val Val Ser Leu Met Asn Glu Asp Glu
625                 630                 635                 640

Lys Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Ala Ser Arg Leu Ser Gln Pro Gly Gln Leu Met
            675                 680                 685

Ser Gln Pro Ser Thr Ala Ser Asn Ser Leu Pro Glu Pro Ala Lys Lys
    690                 695                 700

Ser Glu Glu Leu Val Ala Glu Ala His Asn Leu Cys Thr Leu Leu Glu
705                 710                 715                 720

Asn Ala Ile Gln Asp Thr Val Arg Glu Gln Asp Gln Ser Phe Thr Ala
                725                 730                 735
```

```
Leu Asp Trp Ser Trp Leu Gln Thr Glu Glu Glu His Ser Cys Leu
            740                 745                 750
Glu Gln Ala Ser
        755

<210> SEQ ID NO 34
<211> LENGTH: 716
<212> TYPE: PRT
<213> ORGANISM: Homo sapiens

<400> SEQUENCE: 34

Met Gln Ser Thr Ala Asn Tyr Leu Trp His Thr Asp Asp Leu Leu Gly
  1               5                  10                  15
Gln Gly Ala Thr Ala Ser Val Tyr Lys Ala Arg Asn Lys Lys Ser Gly
             20                  25                  30
Glu Leu Val Ala Val Lys Val Phe Asn Thr Thr Ser Tyr Leu Arg Pro
         35                  40                  45
Arg Glu Val Gln Val Arg Glu Phe Glu Val Leu Arg Lys Leu Asn His
     50                  55                  60
Gln Asn Ile Val Lys Leu Phe Ala Val Glu Glu Thr Gly Gly Ser Arg
 65                  70                  75                  80
Gln Lys Val Leu Val Met Glu Tyr Cys Ser Ser Gly Ser Leu Leu Ser
                 85                  90                  95
Val Leu Glu Ser Pro Glu Asn Ala Phe Gly Leu Pro Glu Asp Glu Phe
            100                 105                 110
Leu Val Val Leu Arg Cys Val Val Ala Gly Met Asn His Leu Arg Glu
        115                 120                 125
Asn Gly Ile Val His Arg Asp Ile Lys Pro Gly Asn Ile Met Arg Leu
    130                 135                 140
Val Gly Glu Glu Gly Gln Ser Ile Tyr Lys Leu Thr Asp Phe Gly Ala
145                 150                 155                 160
Ala Arg Glu Leu Asp Asp Asp Glu Lys Phe Val Ser Val Tyr Gly Thr
                165                 170                 175
Glu Glu Tyr Leu His Pro Asp Met Tyr Glu Arg Ala Val Leu Arg Lys
            180                 185                 190
Pro Gln Gln Lys Ala Phe Gly Val Thr Val Asp Leu Trp Ser Ile Gly
        195                 200                 205
Val Thr Leu Tyr His Ala Ala Thr Gly Ser Leu Pro Phe Ile Pro Phe
    210                 215                 220
Gly Gly Pro Arg Arg Asn Lys Glu Ile Met Tyr Arg Ile Thr Thr Glu
225                 230                 235                 240
Lys Pro Ala Gly Ala Ile Ala Gly Ala Gln Arg Arg Glu Asn Gly Pro
                245                 250                 255
Leu Glu Trp Ser Tyr Thr Leu Pro Ile Thr Cys Gln Leu Ser Leu Gly
            260                 265                 270
Leu Gln Ser Gln Leu Val Pro Ile Leu Ala Asn Ile Leu Glu Val Glu
        275                 280                 285
Gln Ala Lys Cys Trp Gly Phe Asp Gln Phe Phe Ala Glu Thr Ser Asp
    290                 295                 300
Ile Leu Gln Arg Val Val Val His Val Phe Ser Leu Ser Gln Ala Val
305                 310                 315                 320
Leu His His Ile Tyr Ile His Ala His Asn Thr Ile Ala Ile Phe Gln
                325                 330                 335
Glu Ala Val His Lys Gln Thr Ser Val Ala Pro Arg His Gln Glu Tyr
            340                 345                 350
```

```
Leu Phe Glu Gly His Leu Cys Val Leu Glu Pro Ser Val Ala Gln
            355                 360                 365

His Ile Ala His Thr Ala Ser Ser Pro Leu Thr Leu Phe Ser Thr
        370                 375                 380

Ala Ile Pro Lys Gly Leu Ala Phe Arg Asp Pro Ala Leu Asp Val Pro
385                 390                 395                 400

Lys Phe Val Pro Lys Val Asp Leu Gln Ala Asp Tyr Asn Thr Ala Lys
                405                 410                 415

Gly Val Leu Gly Ala Gly Tyr Gln Ala Leu Arg Leu Ala Arg Ala Leu
            420                 425                 430

Leu Asp Gly Gln Glu Leu Met Phe Arg Gly Leu His Trp Val Met Glu
            435                 440                 445

Val Leu Gln Ala Thr Cys Arg Arg Thr Leu Glu Val Ala Arg Thr Ser
    450                 455                 460

Leu Leu Tyr Leu Ser Ser Leu Gly Thr Glu Arg Phe Ser Ser Val
465                 470                 475                 480

Ala Gly Thr Pro Glu Ile Gln Glu Leu Lys Ala Ala Ala Glu Leu Arg
            485                 490                 495

Ser Arg Leu Arg Thr Leu Ala Glu Val Leu Ser Arg Cys Ser Gln Asn
            500                 505                 510

Ile Thr Glu Thr Gln Ser Leu Ser Ser Leu Asn Arg Glu Leu Val
            515                 520                 525

Lys Ser Arg Asp Gln Val His Glu Asp Arg Ser Ile Gln Gln Ile Gln
530                 535                 540

Cys Cys Leu Asp Lys Met Asn Phe Ile Tyr Lys Gln Phe Lys Lys Ser
545                 550                 555                 560

Arg Met Arg Pro Gly Leu Gly Tyr Asn Glu Glu Gln Ile His Lys Leu
                565                 570                 575

Asp Lys Val Asn Phe Ser His Leu Ala Lys Arg Leu Leu Gln Val Phe
                580                 585                 590

Gln Glu Glu Cys Val Gln Lys Tyr Gln Ala Ser Leu Val Thr His Gly
            595                 600                 605

Lys Arg Met Arg Val Val His Glu Thr Arg Asn His Leu Arg Leu Val
    610                 615                 620

Gly Cys Ser Val Ala Ala Cys Asn Thr Glu Ala Gln Gly Val Gln Glu
625                 630                 635                 640

Ser Leu Ser Lys Leu Leu Glu Glu Leu Ser His Gln Leu Leu Gln Asp
                645                 650                 655

Arg Ala Lys Gly Ala Gln Ala Ser Pro Pro Ile Ala Pro Tyr Pro
            660                 665                 670

Ser Pro Thr Arg Lys Asp Leu Leu His Met Gln Glu Leu Cys Glu
    675                 680                 685

Gly Met Lys Leu Leu Ala Ser Asp Leu Leu Asp Asn Asn Arg Ile Ile
            690                 695                 700

Glu Arg Leu Asn Arg Val Pro Ala Pro Pro Asp Val
705                 710                 715

<210> SEQ ID NO 35
<211> LENGTH: 1142
<212> TYPE: PRT
<213> ORGANISM: Homo sapiens

<400> SEQUENCE: 35

Met Ala Phe Cys Ala Lys Met Arg Ser Ser Lys Lys Thr Glu Val Asn
```

```
                1               5              10              15
Leu Glu Ala Pro Glu Pro Gly Val Glu Val Ile Phe Tyr Leu Ser Asp
                   20              25              30

Arg Glu Pro Leu Arg Leu Gly Ser Gly Glu Tyr Thr Ala Glu Glu Leu
                   35              40              45

Cys Ile Arg Ala Ala Gln Ala Cys Arg Ile Ser Pro Leu Cys His Asn
                   50              55              60

Leu Phe Ala Leu Tyr Asp Glu Asn Thr Lys Leu Trp Tyr Ala Pro Asn
 65                 70              75              80

Arg Thr Ile Thr Val Asp Asp Lys Met Ser Leu Arg Leu His Tyr Arg
                   85              90              95

Met Arg Phe Tyr Phe Thr Asn Trp His Gly Thr Asn Asp Asn Glu Gln
                  100             105             110

Ser Val Trp Arg His Ser Pro Lys Lys Gln Lys Asn Gly Tyr Glu Lys
                  115             120             125

Lys Lys Ile Pro Asp Ala Thr Pro Leu Leu Asp Ala Ser Ser Leu Glu
                  130             135             140

Tyr Leu Phe Ala Gln Gly Gln Tyr Asp Leu Val Lys Cys Leu Ala Pro
145                150             155             160

Ile Arg Asp Pro Lys Thr Glu Gln Asp Gly His Asp Ile Glu Asn Glu
                  165             170             175

Cys Leu Gly Met Ala Val Leu Ala Ile Ser His Tyr Ala Met Met Lys
                  180             185             190

Lys Met Gln Leu Pro Glu Leu Pro Lys Asp Ile Ser Tyr Lys Arg Tyr
                  195             200             205

Ile Pro Glu Thr Leu Asn Lys Ser Ile Arg Gln Arg Asn Leu Leu Thr
                  210             215             220

Arg Met Arg Ile Asn Asn Val Phe Lys Asp Phe Leu Lys Glu Phe Asn
225                230             235             240

Asn Lys Thr Ile Cys Asp Ser Ser Val Ser Thr His Asp Leu Lys Val
                  245             250             255

Lys Tyr Leu Ala Thr Leu Glu Thr Leu Thr Lys His Tyr Gly Ala Glu
                  260             265             270

Ile Phe Glu Thr Ser Met Leu Leu Ile Ser Ser Glu Asn Glu Met Asn
                  275             280             285

Trp Phe His Ser Asn Asp Gly Gly Asn Val Leu Tyr Tyr Glu Val Met
                  290             295             300

Val Thr Gly Asn Leu Gly Ile Gln Trp Arg His Lys Pro Asn Val Val
305                310             315             320

Ser Val Glu Lys Glu Lys Asn Lys Leu Lys Arg Lys Lys Leu Glu Asn
                  325             330             335

Lys Asp Lys Lys Asp Glu Glu Lys Asn Lys Ile Arg Glu Glu Trp Asn
                  340             345             350

Asn Phe Ser Phe Phe Pro Glu Ile Thr His Ile Val Ile Lys Glu Ser
                  355             360             365

Val Val Ser Ile Asn Lys Gln Asp Asn Lys Met Glu Leu Lys Leu
                  370             375             380

Ser Ser His Glu Glu Ala Leu Ser Phe Val Ser Leu Val Asp Gly Tyr
385                390             395             400

Phe Arg Leu Thr Ala Asp Ala His His Tyr Leu Cys Thr Asp Val Ala
                  405             410             415

Pro Pro Leu Ile Val His Asn Ile Gln Asn Gly Cys His Gly Pro Ile
                  420             425             430
```

```
Cys Thr Glu Tyr Ala Ile Asn Lys Leu Arg Gln Glu Gly Ser Glu Glu
            435                 440                 445

Gly Met Tyr Val Leu Arg Trp Ser Cys Thr Asp Phe Asp Asn Ile Leu
        450                 455                 460

Met Thr Val Thr Cys Phe Glu Lys Ser Glu Gln Val Gln Gly Ala Gln
465                 470                 475                 480

Lys Gln Phe Lys Asn Phe Gln Ile Glu Val Gln Lys Gly Arg Tyr Ser
                485                 490                 495

Leu His Gly Ser Asp Arg Ser Phe Pro Ser Leu Gly Asp Leu Met Ser
            500                 505                 510

His Leu Lys Lys Gln Ile Leu Arg Thr Asp Asn Ile Ser Phe Met Leu
        515                 520                 525

Lys Arg Cys Cys Gln Pro Lys Pro Arg Glu Ile Ser Asn Leu Leu Val
    530                 535                 540

Ala Thr Lys Lys Ala Gln Glu Trp Gln Pro Val Tyr Pro Met Ser Gln
545                 550                 555                 560

Leu Ser Phe Asp Arg Ile Leu Lys Lys Asp Leu Val Gln Gly Glu His
                565                 570                 575

Leu Gly Arg Gly Thr Arg Thr His Ile Tyr Ser Gly Thr Leu Met Asp
            580                 585                 590

Tyr Lys Asp Asp Glu Gly Thr Ser Glu Glu Lys Ile Lys Val Ile
        595                 600                 605

Leu Lys Val Leu Asp Pro Ser His Arg Asp Ile Ser Leu Ala Phe Phe
    610                 615                 620

Glu Ala Ala Ser Met Met Arg Gln Val Ser His Lys His Ile Val Tyr
625                 630                 635                 640

Leu Tyr Gly Val Cys Val Arg Asp Val Glu Asn Ile Met Val Glu Glu
                645                 650                 655

Phe Val Glu Gly Gly Pro Leu Asp Leu Phe Met His Arg Lys Ser Asp
            660                 665                 670

Val Leu Thr Thr Pro Trp Lys Phe Lys Val Ala Lys Gln Leu Ala Ser
        675                 680                 685

Ala Leu Ser Tyr Leu Glu Asp Lys Asp Leu Val His Gly Asn Val Cys
    690                 695                 700

Thr Lys Asn Leu Leu Leu Ala Arg Glu Gly Ile Asp Ser Glu Cys Gly
705                 710                 715                 720

Pro Phe Ile Lys Leu Ser Asp Pro Gly Ile Pro Ile Thr Val Leu Ser
                725                 730                 735

Arg Gln Glu Cys Ile Glu Arg Ile Pro Trp Ile Ala Pro Glu Cys Val
            740                 745                 750

Glu Asp Ser Lys Asn Leu Ser Val Ala Ala Asp Lys Trp Ser Phe Gly
        755                 760                 765

Thr Thr Leu Trp Glu Ile Cys Tyr Asn Gly Glu Ile Pro Leu Lys Asp
    770                 775                 780

Lys Thr Leu Ile Glu Lys Glu Arg Phe Tyr Glu Ser Arg Cys Arg Pro
785                 790                 795                 800

Val Thr Pro Ser Cys Lys Glu Leu Ala Asp Leu Met Thr Arg Cys Met
                805                 810                 815

Asn Tyr Asp Pro Asn Gln Arg Pro Phe Phe Arg Ala Ile Met Arg Asp
            820                 825                 830

Ile Asn Lys Leu Glu Glu Gln Asn Pro Asp Ile Val Ser Arg Lys Lys
        835                 840                 845
```

-continued

```
Asn Gln Pro Thr Glu Val Asp Pro Thr His Phe Glu Lys Arg Phe Leu
    850                 855                 860

Lys Arg Ile Arg Asp Leu Gly Glu Gly His Phe Gly Lys Val Glu Leu
865                 870                 875                 880

Cys Arg Tyr Asp Pro Glu Asp Asn Thr Gly Glu Gln Val Ala Val Lys
                885                 890                 895

Ser Leu Lys Pro Glu Ser Gly Gly Asn His Ile Ala Asp Leu Lys Lys
            900                 905                 910

Glu Ile Glu Ile Leu Arg Asn Leu Tyr His Glu Asn Ile Val Lys Tyr
        915                 920                 925

Lys Gly Ile Cys Thr Glu Asp Gly Gly Asn Gly Ile Lys Leu Ile Met
930                 935                 940

Glu Phe Leu Pro Ser Gly Ser Leu Lys Glu Tyr Leu Pro Lys Asn Lys
945                 950                 955                 960

Asn Lys Ile Asn Leu Lys Gln Gln Leu Lys Tyr Ala Val Gln Ile Cys
                965                 970                 975

Lys Gly Met Asp Tyr Leu Gly Ser Arg Gln Tyr Val His Arg Asp Leu
            980                 985                 990

Ala Ala Arg Asn Val Leu Val Glu Ser Glu His Gln Val Lys Ile Gly
        995                 1000                1005

Asp Phe Gly Leu Thr Lys Ala Ile Glu Thr Asp Lys Glu Tyr Tyr Thr
    1010                1015                1020

Val Lys Asp Asp Arg Asp Ser Pro Val Phe Trp Tyr Ala Pro Glu Cys
1025                1030                1035                1040

Leu Met Gln Ser Lys Phe Tyr Ile Ala Ser Asp Val Trp Ser Phe Gly
                1045                1050                1055

Val Thr Leu His Glu Leu Leu Thr Tyr Cys Asp Ser Asp Ser Ser Pro
            1060                1065                1070

Met Ala Leu Phe Leu Lys Met Ile Gly Pro Thr His Gly Gln Met Thr
        1075                1080                1085

Val Thr Arg Leu Val Asn Thr Leu Lys Glu Gly Lys Arg Leu Pro Cys
    1090                1095                1100

Pro Pro Asn Cys Pro Asp Glu Val Tyr Gln Leu Met Arg Lys Cys Trp
1105                1110                1115                1120

Glu Phe Gln Pro Ser Asn Arg Thr Ser Phe Gln Asn Leu Ile Glu Gly
                1125                1130                1135

Phe Glu Ala Leu Leu Lys
            1140

<210> SEQ ID NO 36
<211> LENGTH: 1132
<212> TYPE: PRT
<213> ORGANISM: Homo sapiens

<400> SEQUENCE: 36

Met Gly Met Ala Cys Leu Thr Met Thr Glu Met Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
    50                  55                  60

Glu Glu Ile Cys Ile Ala Ala Ser Lys Ala Cys Gly Ile Thr Pro Val
65                  70                  75                  80
```

```
Tyr His Asn Met Phe Ala Leu Met Ser Glu Thr Glu Arg Ile Trp Tyr
                 85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
    290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
        355                 360                 365

Ile Asp Gly Tyr Tyr Arg Leu Thr Ala Asp Ala His His Tyr Leu Cys
370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
                405                 410                 415

Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
        435                 440                 445

Tyr Lys His Cys Leu Ile Thr Lys Asn Glu Asn Glu Glu Tyr Asn Leu
    450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
                485                 490                 495
```

-continued

```
Lys Cys Cys Pro Pro Lys Pro Lys Asp Lys Ser Asn Leu Leu Val Phe
            500             505             510

Arg Thr Asn Gly Val Ser Asp Val Pro Thr Ser Pro Thr Leu Gln Arg
        515             520             525

Pro Thr His Met Asn Gln Met Val Phe His Lys Ile Arg Asn Glu Asp
    530             535             540

Leu Ile Phe Asn Glu Ser Leu Gly Gln Gly Thr Phe Thr Lys Ile Phe
545             550             555             560

Lys Gly Val Arg Arg Glu Val Gly Asp Tyr Gly Gln Leu His Glu Thr
                565             570             575

Glu Val Leu Leu Lys Val Leu Asp Lys Ala His Arg Asn Tyr Ser Glu
            580             585             590

Ser Phe Phe Glu Ala Ala Ser Met Met Ser Lys Leu Ser His Lys His
        595             600             605

Leu Val Leu Asn Tyr Gly Val Cys Val Cys Gly Asp Glu Asn Ile Leu
    610             615             620

Val Gln Glu Phe Val Lys Phe Gly Ser Leu Asp Thr Tyr Leu Lys Lys
625             630             635             640

Asn Lys Asn Cys Ile Asn Ile Leu Trp Lys Leu Glu Val Ala Lys Gln
                645             650             655

Leu Ala Trp Ala Met His Phe Leu Glu Glu Asn Thr Leu Ile His Gly
            660             665             670

Asn Val Cys Ala Lys Asn Ile Leu Leu Ile Arg Glu Glu Asp Arg Lys
        675             680             685

Thr Gly Asn Pro Pro Phe Ile Lys Leu Ser Asp Pro Gly Ile Ser Ile
    690             695             700

Thr Val Leu Pro Lys Asp Ile Leu Gln Glu Arg Ile Pro Trp Val Pro
705             710             715             720

Pro Glu Cys Ile Glu Asn Pro Lys Asn Leu Asn Leu Ala Thr Asp Lys
                725             730             735

Trp Ser Phe Gly Thr Thr Leu Trp Glu Ile Cys Ser Gly Gly Asp Lys
            740             745             750

Pro Leu Ser Ala Leu Asp Ser Gln Arg Lys Leu Gln Phe Tyr Glu Asp
        755             760             765

Arg His Gln Leu Pro Ala Pro Lys Trp Ala Glu Leu Ala Asn Leu Ile
    770             775             780

Asn Asn Cys Met Asp Tyr Glu Pro Asp Phe Arg Pro Ser Phe Arg Ala
785             790             795             800

Ile Ile Arg Asp Leu Asn Ser Leu Phe Thr Pro Asp Tyr Glu Leu Leu
                805             810             815

Thr Glu Asn Asp Met Leu Pro Asn Met Arg Ile Gly Ala Leu Gly Phe
            820             825             830

Ser Gly Ala Phe Glu Asp Arg Asp Pro Thr Gln Phe Glu Glu Arg His
        835             840             845

Leu Lys Phe Leu Gln Gln Leu Gly Lys Gly Asn Phe Gly Ser Val Glu
    850             855             860

Met Cys Arg Tyr Asp Pro Leu Gln Asp Asn Thr Gly Glu Val Val Ala
865             870             875             880

Val Lys Lys Leu Gln His Ser Thr Glu Glu His Leu Arg Asp Phe Glu
                885             890             895

Arg Glu Ile Glu Ile Leu Lys Ser Leu Gln His Asp Asn Ile Val Lys
            900             905             910

Tyr Lys Gly Val Cys Tyr Ser Ala Gly Arg Arg Asn Leu Lys Leu Ile
```

```
                915                 920                 925

Met Glu Tyr Leu Pro Tyr Gly Ser Leu Arg Asp Tyr Leu Gln Lys His
    930                 935                 940

Lys Glu Arg Ile Asp His Ile Lys Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                1000                1005

Lys Val Lys Glu Pro Gly Glu Ser Pro Ile Phe Trp Tyr Ala Pro Glu
    1010                1015                1020

Ser Leu Thr Glu Ser Lys Phe Ser Val Ala Ser Asp Val Trp Ser Phe
1025                1030                1035                1040

Gly Val Val Leu Tyr Glu Leu Phe Thr Tyr Ile Glu Lys Ser Lys Ser
                1045                1050                1055

Pro Pro Ala Glu Phe Met Arg Met Ile Gly Asn Asp Lys Gln Gly Gln
            1060                1065                1070

Met Ile Val Phe His Leu Ile Glu Leu Leu Lys Asn Asn Gly Arg Leu
        1075                1080                1085

Pro Arg Pro Asp Gly Cys Pro Asp Glu Ile Tyr Met Ile Met Thr Glu
    1090                1095                1100

Cys Trp Asn Asn Asn Val Asn Gln Arg Pro Ser Phe Arg Asp Leu Ala
1105                1110                1115                1120

Leu Arg Val Asp Gln Ile Arg Asp Asn Met Ala Gly
                1125                1130

<210> SEQ ID NO 37
<211> LENGTH: 1124
<212> TYPE: PRT
<213> ORGANISM: Homo sapiens

<400> SEQUENCE: 37

Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
            20                  25                  30

Arg Ala Pro Gly Pro Pro Gln Arg Leu Ser Phe Ser Phe Gly Asp His
        35                  40                  45

Leu Ala Glu Asp Leu Cys Val Gln Ala Ala Lys Ala Ser Gly Ile Leu
    50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
            100                 105                 110

Glu Lys Cys His Arg Phe Gly Leu Arg Lys Asp Leu Ala Ser Ala Ile
        115                 120                 125

Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160
```

-continued

```
Glu Cys Leu Ser Leu Ala Val Leu Asp Leu Ala Arg Met Ala Arg Glu
            165                 170                 175
Gln Ala Gln Arg Pro Gly Glu Leu Leu Lys Thr Val Ser Tyr Lys Ala
        180                 185                 190
Cys Leu Pro Pro Ser Leu Arg Asp Leu Ile Gln Gly Leu Ser Phe Val
    195                 200                 205
Thr Arg Arg Ala Ile Arg Arg Thr Val Arg Arg Ala Leu Pro Arg Val
210                 215                 220
Ala Ala Cys Gln Ala Asp Arg His Ser Leu Met Ala Lys Tyr Ile Met
225                 230                 235                 240
Asp Leu Glu Arg Leu Asp Pro Ala Gly Ala Glu Thr Phe His Val
            245                 250                 255
Gly Leu Pro Gly Ala Leu Gly Gly His Asp Gly Leu Gly Leu Leu Arg
        260                 265                 270
Val Ala Gly Asp Gly Gly Ile Ala Trp Thr Gln Gly Glu Gln Glu Val
    275                 280                 285
Leu Gln Pro Phe Cys Asp Phe Pro Glu Ile Val Asp Ile Ser Ile Lys
    290                 295                 300
Gln Ala Pro Arg Val Gly Pro Ala Gly Glu His Arg Leu Val Thr Val
305                 310                 315                 320
Thr Arg Thr Asp Asn Gln Ile Leu Glu Ala Glu Phe Pro Gly Leu Pro
            325                 330                 335
Glu Ala Leu Ser Phe Val Ala Leu Val Asp Gly Tyr Phe Arg Leu Thr
        340                 345                 350
Thr Asp Ser Gln His Phe Phe Cys Lys Glu Val Ala Pro Pro Arg Leu
    355                 360                 365
Leu Glu Glu Val Ala Glu Gln Cys His Gly Pro Ile Thr Leu Asp Phe
370                 375                 380
Ala Ile Asn Lys Leu Lys Thr Gly Gly Ser Arg Pro Gly Ser Tyr Val
385                 390                 395                 400
Leu Arg Arg Ser Pro Gln Asp Phe Asp Ser Phe Leu Leu Thr Val Cys
            405                 410                 415
Val Gln Asn Pro Leu Gly Pro Asp Tyr Lys Gly Cys Leu Ile Arg Arg
        420                 425                 430
Ser Pro Thr Gly Thr Phe Leu Leu Val Gly Leu Ser Arg Pro His Ser
    435                 440                 445
Ser Leu Arg Glu Leu Leu Ala Thr Cys Trp Asp Gly Gly Leu His Val
    450                 455                 460
Asp Gly Val Ala Val Thr Leu Thr Ser Cys Cys Ile Pro Arg Pro Lys
465                 470                 475                 480
Glu Lys Ser Asn Leu Ile Val Val Gln Arg Gly His Ser Pro Pro Thr
            485                 490                 495
Ser Ser Leu Val Gln Pro Gln Ser Gln Tyr Gln Leu Ser Gln Met Thr
        500                 505                 510
Phe His Lys Ile Pro Ala Asp Ser Leu Glu Trp His Glu Asn Leu Gly
    515                 520                 525
His Gly Ser Phe Thr Lys Ile Tyr Arg Gly Cys Arg His Glu Val Val
    530                 535                 540
Asp Gly Glu Ala Arg Lys Thr Glu Val Leu Leu Lys Val Met Asp Ala
545                 550                 555                 560
Lys His Lys Asn Cys Met Glu Ser Phe Leu Glu Ala Ala Ser Leu Met
            565                 570                 575
Ser Gln Val Ser Tyr Arg His Leu Val Leu Leu His Gly Val Cys Met
```

-continued

```
                580                 585                 590
Ala Gly Asp Ser Thr Met Val Gln Glu Phe Val His Leu Gly Ala Ile
            595                 600                 605
Asp Met Tyr Leu Arg Lys Arg Gly His Leu Val Pro Ala Ser Trp Lys
610                 615                 620
Leu Gln Val Val Lys Gln Leu Ala Tyr Ala Leu Asn Tyr Leu Glu Asp
625                 630                 635                 640
Lys Gly Leu Pro His Gly Asn Val Ser Ala Arg Lys Val Leu Leu Ala
                    645                 650                 655
Arg Glu Gly Ala Asp Gly Ser Pro Pro Phe Ile Lys Leu Ser Asp Pro
            660                 665                 670
Gly Val Ser Pro Ala Val Leu Ser Leu Glu Met Leu Thr Asp Arg Ile
            675                 680                 685
Pro Trp Val Ala Pro Glu Cys Leu Arg Glu Ala Gln Thr Leu Ser Leu
            690                 695                 700
Glu Ala Asp Lys Trp Gly Phe Gly Ala Thr Val Trp Glu Val Phe Ser
705                 710                 715                 720
Gly Val Thr Met Pro Ile Ser Ala Leu Asp Pro Ala Lys Lys Leu Gln
                    725                 730                 735
Phe Tyr Glu Asp Arg Gln Gln Leu Pro Ala Pro Lys Trp Thr Glu Leu
            740                 745                 750
Ala Leu Leu Ile Gln Gln Cys Met Ala Tyr Glu Pro Val Gln Arg Pro
            755                 760                 765
Ser Phe Arg Ala Val Ile Arg Asp Leu Asn Ser Leu Ile Ser Ser Asp
        770                 775                 780
Tyr Glu Leu Leu Ser Asp Pro Thr Pro Gly Ala Leu Ala Pro Arg Asp
785                 790                 795                 800
Gly Leu Trp Asn Gly Ala Gln Leu Tyr Ala Cys Gln Asp Pro Thr Ile
                805                 810                 815
Phe Glu Glu Arg His Leu Lys Tyr Ile Ser Gln Leu Gly Lys Gly Asn
            820                 825                 830
Phe Gly Ser Val Glu Leu Cys Arg Tyr Asp Pro Leu Ala His Asn Thr
            835                 840                 845
Gly Ala Leu Val Ala Val Lys Gln Leu Gln His Ser Gly Pro Asp Gln
            850                 855                 860
Gln Arg Asp Phe Gln Arg Glu Ile Gln Ile Leu Lys Ala Leu His Ser
865                 870                 875                 880
Asp Phe Ile Val Lys Tyr Arg Gly Val Ser Tyr Gly Pro Gly Arg Pro
                885                 890                 895
Glu Leu Arg Leu Val Met Glu Tyr Leu Pro Ser Gly Cys Leu Arg Asp
            900                 905                 910
Phe Leu Gln Arg His Arg Ala Arg Leu Asp Ala Ser Arg Leu Leu Leu
            915                 920                 925
Tyr Ser Ser Gln Ile Cys Lys Gly Met Glu Tyr Leu Gly Ser Arg Arg
            930                 935                 940
Cys Val His Arg Asp Leu Ala Ala Arg Asn Ile Leu Val Glu Ser Glu
945                 950                 955                 960
Ala His Val Lys Ile Ala Asp Phe Gly Leu Ala Lys Leu Leu Pro Leu
                965                 970                 975
Asp Lys Asp Tyr Tyr Val Val Arg Glu Pro Gly Gln Ser Pro Ile Phe
            980                 985                 990
Trp Tyr Ala Pro Glu Ser Leu Ser Asp Asn Ile Phe Ser Arg Gln Ser
            995                 1000                1005
```

```
Asp Val Trp Ser Phe Gly Val Val Leu Tyr Glu Leu Phe Thr Tyr Cys
    1010                1015                1020

Asp Lys Ser Cys Ser Pro Ser Ala Glu Phe Leu Arg Met Met Gly Cys
1025                1030                1035                1040

Glu Arg Asp Val Pro Ala Leu Cys Arg Leu Leu Glu Leu Leu Glu Glu
                1045                1050                1055

Gly Gln Arg Leu Pro Ala Pro Pro Ala Cys Pro Ala Glu Val His Glu
                1060                1065                1070

Leu Met Lys Leu Cys Trp Ala Pro Ser Pro Gln Asp Arg Pro Ser Phe
                1075                1080                1085

Ser Ala Leu Gly Pro Gln Leu Asp Met Leu Trp Ser Gly Ser Arg Gly
                1090                1095                1100

Cys Glu Thr His Ala Phe Thr Ala His Pro Glu Gly Lys His His Ser
1105                1110                1115                1120

Leu Ser Phe Ser

<210> SEQ ID NO 38
<211> LENGTH: 427
<212> TYPE: PRT
<213> ORGANISM: Homo sapiens

<400> SEQUENCE: 38

Met Ser Arg Ser Lys Arg Asp Asn Asn Phe Tyr Ser Val Glu Ile Gly
  1               5                  10                  15

Asp Ser Thr Phe Thr Val Leu Lys Arg Tyr Gln Asn Leu Lys Pro Ile
                 20                  25                  30

Gly Ser Gly Ala Gln Gly Ile Val Cys Ala Ala Tyr Asp Ala Ile Leu
             35                  40                  45

Glu Arg Asn Val Ala Ile Lys Lys Leu Ser Arg Pro Phe Gln Asn Gln
 50                  55                  60

Thr His Ala Lys Arg Ala Tyr Arg Glu Leu Val Leu Met Lys Cys Val
 65                  70                  75                  80

Asn His Lys Asn Ile Ile Gly Leu Leu Asn Val Phe Thr Pro Gln Lys
                 85                  90                  95

Ser Leu Glu Glu Phe Gln Asp Val Tyr Ile Val Met Glu Leu Met Asp
                100                 105                 110

Ala Asn Leu Cys Gln Val Ile Gln Met Glu Leu Asp His Glu Arg Met
            115                 120                 125

Ser Tyr Leu Leu Tyr Gln Met Leu Cys Gly Ile Lys His Leu His Ser
        130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205

Trp Ser Val Gly Cys Ile Met Gly Glu Met Val Cys His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255
```

-continued

```
Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
            275                 280                 285

Leu Lys Ala Ser Gln Ala Arg Asp Leu Leu Ser Lys Met Leu Val Ile
            290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                    325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
            355                 360                 365

Asn Gly Val Ile Arg Gly Gln Pro Ser Pro Leu Gly Ala Ala Val Ile
            370                 375                 380

Asn Gly Ser Gln His Pro Ser Ser Ser Ser Val Asn Asp Val Ser
385                 390                 395                 400

Ser Met Ser Thr Asp Pro Thr Leu Ala Ser Asp Thr Asp Ser Ser Leu
                    405                 410                 415

Glu Ala Ala Gly Pro Leu Gly Cys Cys Arg
            420                 425

<210> SEQ ID NO 39
<211> LENGTH: 424
<212> TYPE: PRT
<213> ORGANISM: Homo sapiens

<400> SEQUENCE: 39

Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
            20                  25                  30

Gly Ser Gly Ala Gln Gly Ile Val Cys Ala Ala Phe Asp Thr Val Leu
        35                  40                  45

Gly Ile Ser Val Ala Val Lys Lys Leu Ser Arg Pro Phe Gln Asn Gln
    50                  55                  60

Thr His Ala Lys Arg Ala Tyr Arg Glu Leu Val Leu Leu Lys Cys Val
65                  70                  75                  80

Asn His Lys Asn Ile Ile Ser Leu Leu Asn Val Phe Thr Pro Gln Lys
                    85                  90                  95

Thr Leu Glu Glu Phe Gln Asp Val Tyr Leu Val Met Glu Leu Met Asp
            100                 105                 110

Ala Asn Leu Cys Gln Val Ile His Met Glu Leu Asp His Glu Arg Met
            115                 120                 125

Ser Tyr Leu Leu Tyr Gln Met Leu Cys Gly Ile Lys His Leu His Ser
        130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                    165                 170                 175

Cys Thr Asn Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Ile
```

```
                 195                 200                 205
Trp Ser Val Gly Cys Ile Met Gly Glu Leu Val Lys Gly Cys Val Ile
    210                 215                 220

Phe Gln Gly Thr Asp His Ile Asp Gln Trp Asn Lys Val Ile Glu Gln
225                 230                 235                 240

Leu Gly Thr Pro Ser Ala Glu Phe Met Lys Lys Leu Gln Pro Thr Val
                245                 250                 255

Arg Asn Tyr Val Glu Asn Arg Pro Lys Tyr Pro Gly Ile Lys Phe Glu
            260                 265                 270

Glu Leu Phe Pro Asp Trp Ile Phe Pro Ser Glu Ser Glu Arg Asp Lys
        275                 280                 285

Ile Lys Thr Ser Gln Ala Arg Asp Leu Leu Ser Lys Met Leu Val Ile
    290                 295                 300

Asp Pro Asp Lys Arg Ile Ser Val Asp Glu Ala Leu Arg His Pro Tyr
305                 310                 315                 320

Ile Thr Val Trp Tyr Asp Pro Ala Glu Ala Glu Ala Pro Pro Pro Gln
                325                 330                 335

Ile Tyr Asp Ala Gln Leu Glu Glu Arg Glu His Ala Ile Glu Glu Trp
            340                 345                 350

Lys Glu Leu Ile Tyr Lys Glu Val Met Asp Trp Glu Glu Arg Ser Lys
        355                 360                 365

Asn Gly Val Val Lys Asp Gln Pro Ser Asp Ala Ala Val Ser Ser Asn
    370                 375                 380

Ala Thr Pro Ser Gln Ser Ser Ile Asn Asp Ile Ser Ser Met Ser
385                 390                 395                 400

Thr Glu Gln Thr Leu Ala Ser Asp Thr Asp Ser Ser Leu Asp Ala Ser
                405                 410                 415

Thr Gly Pro Leu Glu Gly Cys Arg
            420

<210> SEQ ID NO 40
<211> LENGTH: 464
<212> TYPE: PRT
<213> ORGANISM: Homo sapiens

<400> SEQUENCE: 40

Met Ser Leu His Phe Leu Tyr Tyr Cys Ser Glu Pro Thr Leu Asp Val
1               5                   10                  15

Lys Ile Ala Phe Cys Gln Gly Phe Asp Lys Gln Val Asp Val Ser Tyr
            20                  25                  30

Ile Ala Lys His Tyr Asn Met Ser Lys Ser Lys Val Asp Asn Gln Phe
        35                  40                  45

Tyr Ser Val Glu Val Gly Asp Ser Thr Phe Thr Val Leu Lys Arg Tyr
    50                  55                  60

Gln Asn Leu Lys Pro Ile Gly Ser Gly Ala Gln Gly Ile Val Cys Ala
65                  70                  75                  80

Ala Tyr Asp Ala Val Leu Asp Arg Asn Val Ala Ile Lys Lys Leu Ser
                85                  90                  95

Arg Pro Phe Gln Asn Gln Thr His Ala Lys Arg Ala Tyr Arg Glu Leu
            100                 105                 110

Val Leu Met Lys Cys Val Asn His Lys Asn Ile Ile Ser Leu Leu Asn
        115                 120                 125

Val Phe Thr Pro Gln Lys Thr Leu Glu Glu Phe Gln Asp Val Tyr Leu
    130                 135                 140
```

-continued

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
            180                 185                 190

Ser Asn Ile Val Val Lys Ser Asp Cys Thr Leu Lys Ile Leu Asp Phe
        195                 200                 205

Gly Leu Ala Arg Thr Ala Gly Thr Ser Phe Met Met Thr Pro Tyr Val
    210                 215                 220

Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
                245                 250                 255

Val Arg His Lys Ile Leu Phe Pro Gly Arg Asp Tyr Ile Asp Gln Trp
            260                 265                 270

Asn Lys Val Ile Glu Gln Leu Gly Thr Pro Cys Pro Glu Phe Met Lys
        275                 280                 285

Lys Leu Gln Pro Thr Val Arg Asn Tyr Val Glu Asn Arg Pro Lys Tyr
    290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
            340                 345                 350

Ala Leu Gln His Pro Tyr Ile Asn Val Trp Tyr Asp Pro Ala Glu Val
        355                 360                 365

Glu Ala Pro Pro Pro Gln Ile Tyr Asp Lys Gln Leu Asp Glu Arg Glu
    370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
                405                 410                 415

Ser Gly Ala Ala Val Asn Ser Ser Glu Ser Leu Pro Pro Ser Ser Ser
            420                 425                 430

Val Asn Asp Ile Ser Ser Met Ser Thr Asp Gln Thr Leu Ala Ser Asp
        435                 440                 445

Thr Asp Ser Ser Leu Glu Ala Ser Ala Gly Pro Leu Gly Cys Cys Arg
    450                 455                 460

<210> SEQ ID NO 41
<211> LENGTH: 508
<212> TYPE: PRT
<213> ORGANISM: Homo sapiens

<400> SEQUENCE: 41

Gly Cys Gly Cys Ser Ser His Pro Glu Asp Trp Met Glu Asn Ile
1               5                   10                  15

Asp Val Cys Glu Asn Cys His Tyr Pro Ile Val Pro Leu Asp Gly Lys
                20                  25                  30

Gly Thr Leu Leu Ile Arg Asn Gly Ser Glu Val Arg Asp Pro Leu Val
            35                  40                  45

Thr Tyr Glu Gly Ser Asn Pro Pro Ala Ser Pro Leu Gln Asp Asn Leu
        50                  55                  60

```
Val Ile Ala Leu His Ser Tyr Glu Pro Ser His Asp Gly Asp Leu Gly
 65                  70                  75                  80

Phe Glu Lys Gly Glu Gln Leu Arg Ile Leu Glu Gln Ser Gly Glu Trp
                 85                  90                  95

Trp Lys Ala Gln Ser Leu Thr Thr Gly Gln Glu Gly Phe Ile Pro Phe
                100                 105                 110

Asn Phe Val Ala Lys Ala Asn Ser Leu Glu Pro Glu Pro Trp Phe Phe
                115                 120                 125

Lys Asn Leu Ser Arg Lys Asp Ala Glu Arg Gln Leu Leu Ala Pro Gly
                130                 135                 140

Asn Thr His Gly Ser Phe Leu Ile Arg Glu Ser Glu Ser Thr Ala Gly
145                 150                 155                 160

Ser Phe Ser Leu Ser Val Arg Asp Phe Asp Gln Asn Gln Gly Glu Val
                165                 170                 175

Val Lys His Tyr Lys Ile Arg Asn Leu Asp Asn Gly Gly Phe Tyr Ile
                180                 185                 190

Ser Pro Arg Ile Thr Phe Pro Gly Leu His Glu Leu Val Arg His Tyr
                195                 200                 205

Thr Asn Ala Ser Asp Gly Leu Cys Thr Arg Leu Ser Arg Pro Cys Gln
210                 215                 220

Thr Gln Lys Pro Gln Lys Pro Trp Trp Glu Asp Glu Trp Glu Val Pro
225                 230                 235                 240

Arg Glu Thr Leu Lys Leu Val Glu Arg Leu Gly Ala Gly Gln Phe Gly
                245                 250                 255

Glu Val Trp Met Gly Tyr Tyr Asn Gly His Thr Lys Val Ala Val Lys
                260                 265                 270

Ser Leu Lys Gln Gly Ser Met Ser Pro Asp Ala Phe Leu Ala Glu Ala
                275                 280                 285

Asn Leu Met Lys Gln Leu Gln His Gln Arg Leu Val Arg Leu Tyr Ala
                290                 295                 300

Val Val Thr Gln Glu Pro Ile Tyr Ile Ile Thr Glu Tyr Met Glu Asn
305                 310                 315                 320

Gly Ser Leu Val Asp Phe Leu Lys Thr Pro Ser Gly Ile Lys Leu Thr
                325                 330                 335

Ile Asn Lys Leu Leu Asp Met Ala Ala Gln Ile Ala Glu Gly Met Ala
                340                 345                 350

Phe Ile Glu Glu Arg Asn Tyr Ile His Arg Asp Leu Arg Ala Ala Asn
                355                 360                 365

Ile Leu Val Ser Asp Thr Leu Ser Cys Lys Ile Ala Asp Phe Gly Leu
                370                 375                 380

Ala Arg Leu Ile Glu Asp Asn Glu Tyr Thr Ala Arg Glu Gly Ala Lys
385                 390                 395                 400

Phe Pro Ile Lys Trp Thr Ala Pro Glu Ala Ile Asn Tyr Gly Thr Phe
                405                 410                 415

Thr Ile Lys Ser Asp Val Trp Ser Phe Gly Ile Leu Leu Thr Glu Ile
                420                 425                 430

Val Thr His Gly Arg Ile Pro Tyr Pro Gly Met Thr Asn Pro Glu Val
                435                 440                 445

Ile Gln Asn Leu Glu Arg Gly Tyr Arg Met Val Arg Pro Asp Asn Cys
                450                 455                 460

Pro Glu Glu Leu Tyr Gln Leu Met Arg Leu Cys Trp Lys Glu Arg Pro
465                 470                 475                 480
```

```
Glu Asp Arg Pro Thr Phe Asp Tyr Leu Arg Ser Val Leu Glu Asp Phe
                485                 490                 495
Phe Thr Ala Thr Glu Gly Gln Tyr Gln Pro Gln Pro
            500                 505

<210> SEQ ID NO 42
<211> LENGTH: 511
<212> TYPE: PRT
<213> ORGANISM: Homo sapiens

<400> SEQUENCE: 42

Gly Cys Ile Lys Ser Lys Gly Lys Asp Ser Leu Ser Asp Asp Gly Val
 1               5                  10                  15
Asp Leu Lys Thr Gln Pro Val Arg Asn Thr Glu Arg Thr Ile Tyr Val
             20                  25                  30
Arg Asp Pro Thr Ser Asn Lys Gln Gln Arg Pro Val Pro Glu Ser Gln
         35                  40                  45
Leu Leu Pro Gly Gln Arg Phe Gln Thr Lys Asp Pro Glu Glu Gln Gly
 50                  55                  60
Asp Ile Val Val Ala Leu Tyr Pro Tyr Asp Gly Ile His Pro Asp Asp
65                   70                  75                  80
Leu Ser Phe Lys Lys Gly Glu Lys Met Lys Val Leu Glu Glu His Gly
                 85                  90                  95
Glu Trp Trp Lys Ala Lys Ser Leu Leu Thr Lys Lys Glu Gly Phe Ile
            100                 105                 110
Pro Ser Asn Tyr Val Ala Lys Leu Asn Thr Leu Glu Thr Glu Glu Trp
        115                 120                 125
Phe Phe Lys Asp Ile Thr Arg Lys Asp Ala Glu Arg Gln Leu Leu Ala
130                 135                 140
Pro Gly Asn Ser Ala Gly Ala Phe Leu Ile Arg Glu Ser Glu Thr Leu
145                 150                 155                 160
Lys Gly Ser Phe Ser Leu Ser Val Arg Asp Phe Asp Pro Val His Gly
                165                 170                 175
Asp Val Ile Lys His Tyr Lys Ile Arg Ser Leu Asp Asn Gly Gly Tyr
            180                 185                 190
Tyr Ile Ser Pro Arg Ile Thr Phe Pro Cys Ile Ser Asp Met Ile Lys
        195                 200                 205
His Tyr Gln Lys Gln Ala Asp Gly Leu Cys Arg Arg Leu Glu Lys Ala
210                 215                 220
Cys Ile Ser Pro Lys Pro Gln Lys Pro Trp Asp Lys Asp Ala Trp Glu
225                 230                 235                 240
Ile Pro Arg Glu Ser Ile Lys Leu Val Lys Arg Leu Gly Ala Gly Gln
                245                 250                 255
Phe Gly Glu Val Trp Met Gly Tyr Tyr Asn Asn Ser Thr Lys Val Ala
            260                 265                 270
Val Lys Thr Leu Lys Pro Gly Thr Met Ser Val Gln Ala Phe Leu Glu
        275                 280                 285
Glu Ala Asn Leu Met Lys Thr Leu Gln His Asp Lys Leu Val Arg Leu
290                 295                 300
Tyr Ala Val Val Thr Arg Glu Glu Pro Ile Tyr Ile Ile Thr Glu Tyr
305                 310                 315                 320
Met Ala Lys Gly Ser Leu Leu Asp Phe Leu Lys Ser Asp Glu Gly Gly
                325                 330                 335
Lys Val Leu Leu Pro Lys Leu Ile Asp Phe Ser Ala Gln Ile Ala Glu
            340                 345                 350
```

```
Gly Met Ala Tyr Ile Glu Arg Lys Asn Tyr Ile His Arg Asp Leu Arg
            355                 360                 365

Ala Ala Asn Val Leu Val Ser Glu Ser Leu Met Cys Lys Ile Ala Asp
        370                 375                 380

Phe Gly Leu Ala Arg Val Ile Glu Asp Asn Glu Tyr Thr Ala Arg Glu
385                 390                 395                 400

Gly Ala Lys Phe Pro Ile Lys Trp Thr Ala Pro Glu Ala Ile Asn Phe
                405                 410                 415

Gly Cys Phe Thr Ile Lys Ser Asp Val Trp Ser Phe Gly Ile Leu Leu
            420                 425                 430

Tyr Glu Ile Val Thr Tyr Gly Lys Ile Pro Tyr Pro Gly Arg Thr Asn
        435                 440                 445

Ala Asp Val Met Thr Ala Leu Ser Gln Gly Tyr Arg Met Pro Arg Val
450                 455                 460

Glu Asn Cys Pro Asp Glu Leu Tyr Asp Ile Met Lys Met Cys Trp Lys
465                 470                 475                 480

Glu Lys Ala Glu Glu Arg Pro Thr Phe Asp Tyr Leu Gln Ser Val Leu
                485                 490                 495

Asp Asp Phe Tyr Thr Ala Thr Glu Gly Gln Tyr Gln Gln Pro
            500                 505                 510

<210> SEQ ID NO 43
<211> LENGTH: 360
<212> TYPE: PRT
<213> ORGANISM: Homo sapiens

<400> SEQUENCE: 43

Met Ser Gln Glu Arg Pro Thr Phe Tyr Arg Gln Glu Leu Asn Lys Thr
1               5                   10                  15

Ile Trp Glu Val Pro Glu Arg Tyr Gln Asn Leu Ser Pro Val Gly Ser
            20                  25                  30

Gly Ala Tyr Gly Ser Val Cys Ala Ala Phe Asp Thr Lys Thr Gly Leu
        35                  40                  45

Arg Val Ala Val Lys Lys Leu Ser Arg Pro Phe Gln Ser Ile Ile His
50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
        115                 120                 125

Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
```

-continued

```
            210                 215                 220
Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
                260                 265                 270

Val Phe Ile Gly Ala Asn Pro Leu Ala Val Asp Leu Leu Glu Lys Met
                275                 280                 285

Leu Val Leu Asp Ser Asp Lys Arg Ile Thr Ala Ala Gln Ala Leu Ala
290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
                340                 345                 350

Leu Asp Gln Glu Glu Met Glu Ser
                355                 360

<210> SEQ ID NO 44
<211> LENGTH: 947
<212> TYPE: PRT
<213> ORGANISM: Homo sapiens

<400> SEQUENCE: 44

Met Ala Val Met Glu Met Ala Cys Pro Gly Ala Pro Gly Ser Ala Val
1               5                   10                  15

Gly Gln Gln Lys Glu Leu Pro Lys Pro Lys Glu Lys Thr Pro Pro Leu
                20                  25                  30

Gly Lys Lys Gln Ser Ser Val Tyr Lys Leu Glu Ala Val Glu Lys Ser
                35                  40                  45

Pro Val Phe Cys Gly Lys Trp Glu Ile Leu Asn Asp Val Ile Thr Lys
                50                  55                  60

Gly Thr Ala Lys Glu Gly Ser Glu Ala Gly Pro Ala Ala Ile Ser Ile
65              70                  75                  80

Ile Ala Gln Ala Glu Cys Glu Asn Ser Gln Glu Phe Ser Pro Thr Phe
                85                  90                  95

Ser Glu Arg Ile Phe Ile Ala Gly Ser Lys Gln Tyr Ser Gln Ser Glu
                100                 105                 110

Ser Leu Asp Gln Ile Pro Asn Asn Val Ala His Ala Thr Glu Gly Lys
                115                 120                 125

Met Ala Arg Val Cys Trp Lys Gly Lys Arg Arg Ser Lys Ala Arg Lys
                130                 135                 140

Lys Arg Lys Lys Lys Ser Ser Lys Ser Leu Ala His Ala Gly Val Ala
145                 150                 155                 160

Leu Ala Lys Pro Leu Pro Arg Thr Pro Glu Gln Glu Ser Cys Thr Ile
                165                 170                 175

Pro Val Gln Glu Asp Glu Ser Pro Leu Gly Ala Pro Tyr Val Arg Asn
                180                 185                 190

Thr Pro Gln Phe Thr Lys Pro Leu Lys Glu Pro Gly Leu Gly Gln Leu
                195                 200                 205

Cys Phe Lys Gln Leu Gly Glu Gly Leu Arg Pro Ala Leu Pro Arg Ser
                210                 215                 220
```

```
Glu Leu His Lys Leu Ile Ser Pro Leu Gln Cys Leu Asn His Val Trp
225                 230                 235                 240

Lys Leu His His Pro Gln Asp Gly Gly Pro Leu Pro Leu Pro Thr His
            245                 250                 255

Pro Phe Pro Tyr Ser Arg Leu Pro His Pro Phe Pro Phe His Pro Leu
                260                 265                 270

Gln Pro Trp Lys Pro His Pro Leu Glu Ser Phe Leu Gly Lys Leu Ala
        275                 280                 285

Cys Val Asp Ser Gln Lys Pro Leu Pro Asp Pro His Leu Ser Lys Leu
290                 295                 300

Ala Cys Val Asp Ser Pro Lys Pro Leu Pro Gly Pro His Leu Glu Pro
305                 310                 315                 320

Ser Cys Leu Ser Arg Gly Ala His Glu Lys Phe Ser Val Glu Glu Tyr
                325                 330                 335

Leu Val His Ala Leu Gln Gly Ser Val Ser Ser Gln Ala His Ser
                340                 345                 350

Leu Thr Ser Leu Ala Lys Thr Trp Ala Ala Arg Gly Ser Arg Ser Arg
        355                 360                 365

Glu Pro Ser Pro Lys Thr Glu Asp Asn Glu Gly Val Leu Leu Thr Glu
370                 375                 380

Lys Leu Lys Pro Val Asp Tyr Glu Tyr Arg Glu Val His Trp Ala
385                 390                 395                 400

Thr His Gln Leu Arg Leu Gly Arg Gly Ser Phe Gly Glu Val His Arg
                405                 410                 415

Met Glu Asp Lys Gln Thr Gly Phe Gln Cys Ala Val Lys Lys Val Arg
                420                 425                 430

Leu Glu Val Phe Arg Ala Glu Glu Leu Met Ala Cys Ala Gly Leu Thr
                435                 440                 445

Ser Pro Arg Ile Val Pro Leu Tyr Gly Ala Val Arg Glu Gly Pro Trp
450                 455                 460

Val Asn Ile Phe Met Glu Leu Leu Glu Gly Gly Ser Leu Gly Gln Leu
465                 470                 475                 480

Val Lys Glu Gln Gly Cys Leu Pro Glu Asp Arg Ala Leu Tyr Tyr Leu
                485                 490                 495

Gly Gln Ala Leu Glu Gly Leu Glu Tyr Leu His Ser Arg Arg Ile Leu
                500                 505                 510

His Gly Asp Val Lys Ala Asp Asn Val Leu Leu Ser Ser Asp Gly Ser
            515                 520                 525

His Ala Ala Leu Cys Asp Phe Gly His Ala Val Cys Leu Gln Pro Asp
530                 535                 540

Gly Leu Gly Lys Ser Leu Leu Thr Gly Asp Tyr Ile Pro Gly Thr Glu
545                 550                 555                 560

Thr His Met Ala Pro Glu Val Val Leu Gly Arg Ser Cys Asp Ala Lys
                565                 570                 575

Val Asp Val Trp Ser Ser Cys Cys Met Met Leu His Met Leu Asn Gly
            580                 585                 590

Cys His Pro Trp Thr Gln Phe Phe Arg Gly Pro Leu Cys Leu Lys Ile
        595                 600                 605

Ala Ser Glu Pro Pro Pro Val Arg Glu Ile Pro Pro Ser Cys Ala Pro
610                 615                 620

Leu Thr Ala Gln Ala Ile Gln Glu Gly Leu Arg Lys Glu Pro Ile His
625                 630                 635                 640

Arg Val Ser Ala Ala Glu Leu Gly Gly Lys Val Asn Arg Ala Leu Gln
```

-continued

```
                645                 650                 655
Gln Val Gly Gly Leu Lys Ser Pro Trp Arg Gly Glu Tyr Lys Glu Pro
            660                 665                 670
Arg His Pro Pro Pro Asn Gln Ala Asn Tyr His Gln Thr Leu His Ala
        675                 680                 685
Gln Pro Arg Glu Leu Ser Pro Arg Ala Pro Gly Pro Arg Pro Ala Glu
    690                 695                 700
Glu Thr Thr Gly Arg Ala Pro Lys Leu Gln Pro Pro Leu Pro Pro Glu
705                 710                 715                 720
Pro Pro Glu Pro Asn Lys Ser Pro Pro Leu Thr Leu Ser Lys Glu Glu
                725                 730                 735
Ser Gly Met Trp Glu Pro Leu Pro Leu Ser Ser Leu Glu Pro Ala Pro
            740                 745                 750
Ala Arg Asn Pro Ser Ser Pro Glu Arg Lys Ala Thr Val Pro Glu Gln
        755                 760                 765
Glu Leu Gln Gln Leu Glu Ile Glu Leu Phe Leu Asn Ser Leu Ser Gln
    770                 775                 780
Pro Phe Ser Leu Glu Glu Gln Glu Gln Ile Leu Ser Cys Leu Ser Ile
785                 790                 795                 800
Asp Ser Leu Ser Leu Ser Asp Asp Ser Glu Lys Asn Pro Ser Lys Ala
                805                 810                 815
Ser Gln Ser Ser Arg Asp Thr Leu Ser Ser Gly Val His Ser Trp Ser
            820                 825                 830
Ser Gln Ala Glu Ala Arg Ser Ser Trp Asn Met Val Leu Ala Arg
        835                 840                 845
Gly Arg Pro Thr Asp Thr Pro Ser Tyr Phe Asn Gly Val Lys Val Gln
    850                 855                 860
Ile Gln Ser Leu Asn Gly Glu His Leu His Ile Arg Glu Phe His Arg
865                 870                 875                 880
Val Lys Val Gly Asp Ile Ala Thr Gly Ile Ser Ser Gln Ile Pro Ala
                885                 890                 895
Ala Ala Phe Ser Leu Val Thr Lys Asp Gly Gln Pro Val Arg Tyr Asp
            900                 905                 910
Met Glu Val Pro Asp Ser Gly Ile Asp Leu Gln Cys Thr Leu Ala Pro
        915                 920                 925
Asp Gly Ser Phe Ala Trp Ser Trp Arg Val Lys His Gly Gln Leu Glu
    930                 935                 940
Asn Arg Pro
945

<210> SEQ ID NO 45
<211> LENGTH: 545
<212> TYPE: PRT
<213> ORGANISM: Homo sapiens

<400> SEQUENCE: 45

Met Ser Asn Asn Gly Leu Asp Ile Gln Asp Lys Pro Pro Ala Pro Pro
1               5                   10                  15
Met Arg Asn Thr Ser Thr Met Ile Gly Val Gly Ser Lys Asp Ala Gly
            20                  25                  30
Thr Leu Asn His Gly Ser Lys Pro Leu Pro Pro Asn Pro Glu Glu Lys
        35                  40                  45
Lys Lys Lys Asp Arg Phe Tyr Arg Ser Ile Leu Pro Gly Asp Lys Thr
    50                  55                  60
```

-continued

```
Asn Lys Lys Lys Glu Lys Glu Arg Pro Glu Ile Ser Leu Pro Ser Asp
 65                  70                  75                  80

Phe Glu His Thr Ile His Val Gly Phe Asp Ala Val Thr Gly Glu Phe
                 85                  90                  95

Thr Gly Met Pro Glu Gln Trp Ala Arg Leu Leu Gln Thr Ser Asn Ile
            100                 105                 110

Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Val Ile Ala Pro
            180                 185                 190

Arg Pro Glu His Thr Lys Ser Val Tyr Thr Arg Ser Val Ile Glu Pro
        195                 200                 205

Leu Pro Val Thr Pro Thr Arg Asp Val Ala Thr Ser Pro Ile Ser Pro
    210                 215                 220

Thr Glu Asn Asn Thr Thr Pro Pro Asp Ala Leu Thr Arg Asn Thr Glu
225                 230                 235                 240

Lys Gln Lys Lys Pro Lys Met Ser Asp Glu Ile Leu Glu Lys
                245                 250                 255

Leu Arg Ser Ile Val Ser Val Gly Asp Pro Lys Lys Tyr Thr Arg
            260                 265                 270

Phe Glu Lys Ile Gly Gln Gly Ala Ser Gly Thr Val Tyr Thr Ala Met
        275                 280                 285

Asp Val Ala Thr Gly Gln Glu Val Ala Ile Lys Gln Met Asn Leu Gln
    290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
            340                 345                 350

Thr Asp Val Val Thr Glu Thr Cys Met Asp Glu Gly Gln Ile Ala Ala
        355                 360                 365

Val Cys Arg Glu Cys Leu Gln Ala Leu Glu Phe Leu His Ser Asn Gln
    370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
            420                 425                 430

Pro Glu Val Val Thr Arg Lys Ala Tyr Gly Pro Lys Val Asp Ile Trp
        435                 440                 445

Ser Leu Gly Ile Met Ala Ile Glu Met Ile Glu Gly Glu Pro Pro Tyr
    450                 455                 460

Leu Asn Glu Asn Pro Leu Arg Ala Leu Tyr Leu Ile Ala Thr Asn Gly
465                 470                 475                 480

Thr Pro Glu Leu Gln Asn Pro Glu Lys Leu Ser Ala Ile Phe Arg Asp
```

-continued

```
                485                 490                 495
Phe Leu Asn Arg Cys Leu Asp Met Asp Val Glu Lys Arg Gly Ser Ala
            500                 505                 510
Lys Glu Leu Leu Gln His Gln Phe Leu Lys Ile Ala Lys Pro Leu Ser
        515                 520                 525
Ser Leu Thr Pro Leu Ile Ala Ala Lys Glu Ala Thr Lys Asn Asn
    530                 535                 540
His
545

<210> SEQ ID NO 46
<211> LENGTH: 524
<212> TYPE: PRT
<213> ORGANISM: Homo sapiens

<400> SEQUENCE: 46

Met Ser Asp Asn Gly Glu Leu Glu Asp Lys Pro Pro Ala Pro Pro Val
  1               5                  10                  15
Arg Met Ser Ser Thr Ile Phe Ser Thr Gly Gly Lys Asp Pro Leu Ser
                 20                  25                  30
Ala Asn His Ser Leu Lys Pro Leu Pro Ser Val Pro Glu Glu Lys Lys
             35                  40                  45
Pro Arg His Lys Ile Ile Ser Ile Phe Ser Gly Thr Glu Lys Gly Ser
         50                  55                  60
Lys Lys Lys Glu Lys Glu Arg Pro Glu Ile Ser Pro Pro Ser Asp Phe
 65                  70                  75                  80
Glu His Thr Ile His Val Gly Phe Asp Ala Val Thr Gly Glu Phe Thr
                 85                  90                  95
Gly Met Pro Glu Gln Trp Ala Arg Leu Leu Gln Thr Ser Asn Ile Thr
                100                 105                 110
Lys Leu Glu Gln Lys Lys Asn Pro Gln Ala Val Leu Asp Val Leu Lys
            115                 120                 125
Phe Tyr Asp Ser Asn Thr Val Lys Gln Lys Tyr Leu Ser Phe Thr Pro
        130                 135                 140
Pro Glu Lys Asp Gly Leu Pro Ser Gly Thr Pro Ala Leu Asn Ala Lys
145                 150                 155                 160
Gly Thr Glu Ala Pro Ala Val Val Thr Glu Glu Asp Asp Asp Glu
                165                 170                 175
Glu Thr Ala Pro Pro Val Ile Ala Pro Arg Pro Asp His Thr Lys Ser
            180                 185                 190
Ile Tyr Thr Arg Ser Val Ile Asp Pro Val Pro Ala Pro Val Gly Asp
        195                 200                 205
Ser His Val Asp Gly Ala Ala Lys Ser Leu Asp Lys Gln Lys Lys Lys
    210                 215                 220
Pro Lys Met Thr Asp Glu Glu Ile Met Glu Lys Leu Arg Thr Ile Val
225                 230                 235                 240
Ser Ile Gly Asp Pro Lys Lys Lys Tyr Thr Arg Tyr Glu Lys Ile Gly
                245                 250                 255
Gln Gly Ala Ser Gly Thr Val Phe Thr Ala Thr Asp Val Ala Leu Gly
            260                 265                 270
Gln Glu Val Ala Ile Lys Gln Ile Asn Leu Gln Lys Gln Pro Lys Lys
        275                 280                 285
Glu Leu Ile Ile Asn Glu Ile Leu Val Met Lys Glu Leu Lys Asn Pro
    290                 295                 300
```

-continued

```
Asn Ile Val Asn Phe Leu Asp Ser Tyr Leu Val Gly Asp Glu Leu Phe
305                 310                 315                 320

Val Val Met Glu Tyr Leu Ala Gly Gly Ser Leu Thr Asp Val Val Thr
            325                 330                 335

Glu Thr Cys Met Asp Glu Ala Gln Ile Ala Ala Val Cys Arg Glu Cys
            340                 345                 350

Leu Gln Ala Leu Glu Phe Leu His Ala Asn Gln Val Ile His Arg Asp
        355                 360                 365

Ile Lys Ser Asp Asn Val Leu Leu Gly Met Glu Gly Ser Val Lys Leu
    370                 375                 380

Thr Asp Phe Gly Phe Cys Ala Gln Ile Thr Pro Glu Gln Ser Lys Arg
385                 390                 395                 400

Ser Thr Met Val Gly Thr Pro Tyr Trp Met Ala Pro Glu Val Val Thr
            405                 410                 415

Arg Lys Ala Tyr Gly Pro Lys Val Asp Ile Trp Ser Leu Gly Ile Met
            420                 425                 430

Ala Ile Glu Met Val Glu Gly Glu Pro Pro Tyr Leu Asn Glu Asn Pro
        435                 440                 445

Leu Arg Ala Leu Tyr Leu Ile Ala Thr Asn Gly Thr Pro Glu Leu Gln
    450                 455                 460

Asn Pro Glu Lys Leu Ser Pro Ile Phe Arg Asp Phe Leu Asn Arg Cys
465                 470                 475                 480

Leu Glu Met Asp Val Glu Lys Arg Gly Ser Ala Lys Glu Leu Leu Gln
            485                 490                 495

His Pro Phe Leu Lys Leu Ala Lys Pro Leu Ser Ser Leu Thr Pro Leu
            500                 505                 510

Ile Met Ala Ala Lys Glu Ala Met Lys Ser Asn Arg
            515                 520

<210> SEQ ID NO 47
<211> LENGTH: 544
<212> TYPE: PRT
<213> ORGANISM: Homo sapiens

<400> SEQUENCE: 47

Met Ser Asp Gly Leu Asp Asn Glu Glu Lys Pro Pro Ala Pro Pro Leu
1               5                   10                  15

Arg Met Asn Ser Asn Asn Arg Asp Ser Ser Ala Leu Asn His Ser Ser
            20                  25                  30

Lys Pro Leu Pro Met Ala Pro Glu Glu Lys Asn Lys Lys Ala Arg Leu
        35                  40                  45

Arg Ser Ile Phe Pro Gly Gly Gly Asp Lys Thr Asn Lys Lys Lys Glu
    50                  55                  60

Lys Glu Arg Pro Glu Ile Ser Leu Pro Ser Asp Phe Glu His Thr Ile
65                  70                  75                  80

His Val Gly Phe Asp Ala Val Thr Gly Glu Phe Thr Gly Ile Pro Glu
            85                  90                  95

Gln Trp Ala Arg Leu Leu Gln Thr Ser Asn Ile Thr Lys Leu Glu Gln
            100                 105                 110

Lys Lys Asn Pro Gln Ala Val Leu Asp Val Leu Lys Phe Tyr Asp Ser
        115                 120                 125

Lys Glu Thr Val Asn Asn Gln Lys Tyr Met Ser Phe Thr Ser Gly Asp
    130                 135                 140

Lys Ser Ala His Gly Tyr Ile Ala Ala His Pro Ser Ser Thr Lys Thr
145                 150                 155                 160
```

Ala Ser Glu Pro Pro Leu Ala Pro Pro Val Ser Glu Glu Asp Glu
            165                 170                 175

Glu Glu Glu Glu Glu Glu Asp Glu Asn Glu Pro Pro Val Ile Ala
            180                 185                 190

Pro Arg Pro Glu His Thr Lys Ser Ile Tyr Thr Arg Ser Val Val Glu
            195                 200                 205

Ser Ile Ala Ser Pro Ala Val Pro Asn Lys Glu Val Thr Pro Pro Ser
210                 215                 220

Ala Glu Asn Ala Asn Ser Ser Thr Leu Tyr Arg Asn Thr Asp Arg Gln
225                 230                 235                 240

Arg Lys Lys Ser Lys Met Thr Asp Glu Glu Ile Leu Glu Lys Leu Arg
            245                 250                 255

Ser Ile Val Ser Val Gly Asp Pro Lys Lys Tyr Thr Arg Phe Glu
            260                 265                 270

Lys Ile Gly Gln Gly Ala Ser Gly Thr Val Tyr Thr Ala Leu Asp Ile
            275                 280                 285

Ala Thr Gly Gln Glu Val Ala Ile Lys Gln Met Asn Leu Gln Gln Gln
290                 295                 300

Pro Lys Lys Glu Leu Ile Ile Asn Glu Ile Leu Val Met Arg Glu Asn
305                 310                 315                 320

Lys Asn Pro Asn Ile Val Asn Tyr Leu Asp Ser Tyr Leu Val Gly Asp
            325                 330                 335

Glu Leu Trp Val Val Met Glu Tyr Leu Ala Gly Gly Ser Leu Thr Asp
            340                 345                 350

Val Val Thr Glu Thr Cys Met Asp Glu Gly Gln Ile Ala Ala Val Cys
            355                 360                 365

Arg Glu Cys Leu Gln Ala Leu Asp Phe Leu His Ser Asn Gln Val Ile
            370                 375                 380

His Arg Asp Ile Lys Ser Asp Asn Ile Leu Leu Gly Met Asp Gly Ser
385                 390                 395                 400

Val Lys Leu Thr Asp Phe Gly Phe Cys Ala Gln Ile Thr Pro Glu Gln
            405                 410                 415

Ser Lys Arg Ser Thr Met Val Gly Thr Pro Tyr Trp Met Ala Pro Glu
            420                 425                 430

Val Val Thr Arg Lys Ala Tyr Gly Pro Lys Val Asp Ile Trp Ser Leu
            435                 440                 445

Gly Ile Met Ala Ile Glu Met Val Glu Gly Glu Pro Pro Tyr Leu Asn
450                 455                 460

Glu Asn Pro Leu Arg Ala Leu Tyr Leu Ile Ala Thr Asn Gly Thr Pro
465                 470                 475                 480

Glu Leu Gln Asn Pro Glu Arg Leu Ser Ala Val Phe Arg Asp Phe Leu
            485                 490                 495

Asn Arg Cys Leu Glu Met Asp Val Asp Arg Arg Gly Ser Ala Lys Glu
            500                 505                 510

Leu Leu Gln His Pro Phe Leu Lys Leu Ala Lys Pro Leu Ser Ser Leu
            515                 520                 525

Thr Pro Leu Ile Ile Ala Ala Lys Glu Ala Ile Lys Asn Ser Ser Arg
            530                 535                 540

<210> SEQ ID NO 48
<211> LENGTH: 591
<212> TYPE: PRT
<213> ORGANISM: Homo sapiens -continued

<400> SEQUENCE: 48

```
Met Phe Gly Lys Arg Lys Lys Arg Val Glu Ile Ser Ala Pro Ser Asn
 1               5                  10                  15

Phe Glu His Arg Val His Thr Gly Phe Asp Gln His Glu Gln Lys Phe
                20                  25                  30

Thr Gly Leu Pro Arg Gln Trp Gln Ser Leu Ile Glu Glu Ser Ala Arg
            35                  40                  45

Arg Pro Lys Pro Leu Val Asp Pro Ala Cys Ile Thr Ser Ile Gln Pro
        50                  55                  60

Gly Ala Pro Lys Thr Ile Val Arg Gly Ser Lys Gly Ala Lys Asp Gly
 65                 70                  75                  80

Ala Leu Thr Leu Leu Leu Asp Glu Phe Glu Asn Met Ser Val Thr Arg
                85                  90                  95

Ser Asn Ser Leu Arg Arg Asp Ser Pro Pro Pro Ala Arg Ala Arg
                100                 105                 110

Gln Glu Asn Gly Met Pro Glu Pro Ala Thr Thr Ala Arg Gly Gly
                115                 120                 125

Pro Gly Lys Ala Gly Ser Arg Gly Arg Phe Ala Gly His Ser Glu Ala
        130                 135                 140

Gly Gly Gly Ser Gly Asp Arg Arg Ala Gly Pro Glu Lys Arg Pro
145                 150                 155                 160

Lys Ser Ser Arg Glu Gly Ser Gly Gly Pro Gln Ser Ser Arg Asp
                165                 170                 175

Lys Arg Pro Leu Ser Gly Pro Asp Val Gly Thr Pro Gln Pro Ala Gly
            180                 185                 190

Leu Ala Ser Gly Ala Lys Leu Ala Ala Gly Arg Pro Phe Asn Thr Tyr
                195                 200                 205

Pro Arg Ala Asp Thr Asp His Pro Ser Arg Gly Ala Gln Gly Glu Pro
        210                 215                 220

His Asp Val Ala Pro Asn Gly Pro Ser Ala Gly Gly Leu Ala Ile Pro
225                 230                 235                 240

Gln Ser Ser Ser Ser Ser Arg Pro Pro Thr Arg Ala Arg Gly Ala
                245                 250                 255

Pro Ser Pro Gly Val Leu Gly Pro His Ala Ser Glu Pro Gln Leu Ala
            260                 265                 270

Pro Pro Ala Cys Thr Pro Ala Ala Pro Ala Val Pro Gly Pro Pro Gly
        275                 280                 285

Pro Arg Ser Pro Gln Arg Glu Pro Gln Arg Val Ser His Glu Gln Phe
    290                 295                 300

Arg Ala Ala Leu Gln Leu Val Val Asp Pro Gly Asp Pro Arg Ser Tyr
305                 310                 315                 320

Leu Asp Asn Phe Ile Lys Ile Gly Glu Gly Ser Thr Gly Ile Val Cys
                325                 330                 335

Ile Ala Thr Val Arg Ser Ser Gly Lys Leu Val Ala Val Lys Lys Met
                340                 345                 350

Asp Leu Arg Lys Gln Gln Arg Arg Glu Leu Leu Phe Asn Glu Val Val
            355                 360                 365

Ile Met Arg Asp Tyr Gln His Glu Asn Val Val Glu Met Tyr Asn Ser
        370                 375                 380

Tyr Leu Val Gly Asp Glu Leu Trp Val Val Met Glu Phe Leu Glu Gly
385                 390                 395                 400

Gly Ala Leu Thr Asp Ile Val Thr His Thr Arg Met Asn Glu Glu Gln
                405                 410                 415
```

```
Ile Ala Ala Val Cys Leu Ala Val Leu Gln Ala Leu Ser Val Leu His
            420                 425                 430

Ala Gln Gly Val Ile His Arg Asp Ile Lys Ser Asp Ser Ile Leu Leu
            435                 440                 445

Thr His Asp Gly Arg Val Lys Leu Ser Asp Phe Gly Phe Cys Ala Gln
            450                 455                 460

Val Ser Lys Glu Val Pro Arg Arg Lys Ser Leu Val Gly Thr Pro Tyr
465                 470                 475                 480

Trp Met Ala Pro Glu Leu Ile Ser Arg Leu Pro Tyr Gly Pro Glu Val
                485                 490                 495

Asp Ile Trp Ser Leu Gly Ile Met Val Ile Glu Met Val Asp Gly Glu
                500                 505                 510

Pro Pro Tyr Phe Asn Glu Pro Leu Lys Ala Met Lys Met Ile Arg
                515                 520                 525

Asp Asn Leu Pro Pro Arg Leu Lys Asn Leu His Lys Val Ser Pro Ser
530                 535                 540

Leu Lys Gly Phe Leu Asp Arg Leu Leu Val Arg Asp Pro Ala Gln Arg
545                 550                 555                 560

Ala Thr Ala Ala Glu Leu Leu Lys His Pro Phe Leu Ala Lys Ala Gly
                565                 570                 575

Pro Pro Ala Ser Ile Val Pro Leu Met Arg Gln Asn Arg Thr Arg
                580                 585                 590

<210> SEQ ID NO 49
<211> LENGTH: 719
<212> TYPE: PRT
<213> ORGANISM: Homo sapiens

<400> SEQUENCE: 49

Met Phe Gly Lys Lys Lys Lys Ile Glu Ile Ser Gly Pro Ser Asn
1               5                   10                  15

Phe Glu His Arg Val His Thr Gly Phe Asp Pro Gln Glu Gln Lys Phe
                20                  25                  30

Thr Gly Leu Pro Gln Gln Trp His Ser Leu Leu Ala Asp Thr Ala Asn
            35                  40                  45

Arg Pro Lys Pro Met Val Asp Pro Ser Cys Ile Thr Pro Ile Gln Leu
50                  55                  60

Ala Pro Met Lys Thr Ile Val Arg Gly Asn Lys Pro Cys Lys Glu Thr
65              70                  75                  80

Ser Ile Asn Gly Leu Leu Glu Asp Phe Asp Asn Ile Ser Val Thr Arg
                85                  90                  95

Ser Asn Ser Leu Arg Lys Glu Ser Pro Pro Thr Pro Asp Gln Gly Ala
                100                 105                 110

Ser Ser His Gly Pro Gly His Ala Glu Glu Asn Gly Phe Ile Thr Phe
            115                 120                 125

Ser Gln Tyr Ser Ser Glu Ser Asp Thr Thr Ala Asp Tyr Thr Thr Glu
130                 135                 140

Lys Tyr Arg Glu Lys Ser Leu Tyr Gly Asp Asp Leu Asp Pro Tyr Tyr
145                 150                 155                 160

Arg Gly Ser His Ala Ala Lys Gln Asn Gly His Val Met Lys Met Lys
                165                 170                 175

His Gly Glu Ala Tyr Tyr Ser Glu Val Lys Pro Leu Lys Ser Asp Phe
                180                 185                 190

Ala Arg Phe Ser Ala Asp Tyr His Ser His Leu Asp Ser Leu Ser Lys
```

-continued

```
            195                 200                 205
Pro Ser Glu Tyr Ser Asp Leu Lys Trp Glu Tyr Gln Arg Ala Ser Ser
    210                 215                 220

Ser Ser Pro Leu Asp Tyr Ser Phe Gln Phe Thr Pro Ser Arg Thr Ala
225                 230                 235                 240

Gly Thr Ser Gly Cys Ser Lys Glu Ser Leu Ala Tyr Ser Glu Ser Glu
                245                 250                 255

Trp Gly Pro Ser Leu Asp Asp Tyr Asp Arg Arg Pro Lys Ser Ser Tyr
            260                 265                 270

Leu Asn Gln Thr Ser Pro Gln Pro Thr Met Arg Gln Arg Ser Arg Ser
        275                 280                 285

Gly Ser Gly Leu Gln Glu Pro Met Met Pro Phe Gly Ser Ala Phe
    290                 295                 300

Lys Thr His Pro Gln Gly His Ser Tyr Asn Ser Tyr Thr Tyr Pro Arg
305                 310                 315                 320

Leu Ser Glu Pro Thr Met Cys Ile Pro Lys Val Asp Tyr Asp Arg Ala
                325                 330                 335

Gln Met Val Leu Ser Pro Pro Leu Ser Gly Ser Asp Thr Tyr Pro Arg
            340                 345                 350

Gly Pro Ala Lys Leu Pro Gln Ser Gln Ser Lys Ser Gly Tyr Ser Ser
        355                 360                 365

Ser Ser His Gln Tyr Pro Ser Gly Tyr His Lys Ala Thr Leu Tyr His
    370                 375                 380

His Pro Ser Leu Gln Ser Ser Gln Tyr Ile Ser Thr Ala Ser Tyr
385                 390                 395                 400

Leu Ser Ser Leu Ser Leu Ser Ser Thr Tyr Pro Pro Ser Trp
                405                 410                 415

Gly Ser Ser Asp Gln Gln Pro Ser Arg Val Ser His Glu Gln Phe
            420                 425                 430

Arg Ala Ala Leu Gln Leu Val Val Ser Pro Gly Asp Pro Arg Glu Tyr
        435                 440                 445

Leu Ala Asn Phe Ile Lys Ile Gly Glu Gly Ser Thr Gly Ile Val Cys
450                 455                 460

Ile Ala Thr Glu Lys His Thr Gly Lys Gln Val Ala Val Lys Lys Met
465                 470                 475                 480

Asp Leu Arg Lys Gln Gln Arg Arg Glu Leu Leu Phe Asn Glu Val Val
                485                 490                 495

Ile Met Arg Asp Tyr His His Asp Asn Val Val Asp Met Tyr Ser Ser
            500                 505                 510

Tyr Leu Val Gly Asp Glu Leu Trp Val Val Met Glu Phe Leu Glu Gly
        515                 520                 525

Gly Ala Leu Thr Asp Ile Val Thr His Thr Arg Met Asn Glu Glu Gln
    530                 535                 540

Ile Ala Thr Val Cys Leu Ser Val Leu Arg Ala Leu Ser Tyr Leu His
545                 550                 555                 560

Asn Gln Gly Val Ile His Arg Asp Ile Lys Ser Asp Ser Ile Leu Leu
                565                 570                 575

Thr Ser Asp Gly Arg Ile Lys Leu Ser Asp Phe Gly Phe Cys Ala Gln
            580                 585                 590

Val Ser Lys Glu Val Pro Lys Arg Lys Ser Leu Val Gly Thr Pro Tyr
        595                 600                 605

Trp Met Ala Pro Glu Val Ile Ser Arg Leu Pro Tyr Gly Thr Glu Val
    610                 615                 620
```

```
Asp Ile Trp Ser Leu Gly Ile Met Val Ile Glu Met Ile Asp Gly Glu
625                 630                 635                 640

Pro Pro Tyr Phe Asn Glu Pro Pro Leu Gln Ala Met Arg Arg Ile Arg
                645                 650                 655

Asp Ser Leu Pro Pro Arg Val Lys Asp Leu His Lys Val Ser Ser Val
            660                 665                 670

Leu Arg Gly Phe Leu Asp Leu Met Leu Val Arg Glu Pro Ser Gln Arg
        675                 680                 685

Ala Thr Ala Gln Glu Leu Leu Gly His Pro Phe Leu Lys Leu Ala Gly
690                 695                 700

Pro Pro Ser Cys Ile Val Pro Leu Met Arg Gln Tyr Arg His His
705                 710                 715

<210> SEQ ID NO 50
<211> LENGTH: 1089
<212> TYPE: PRT
<213> ORGANISM: Homo sapiens

<400> SEQUENCE: 50

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
```

-continued

```
                275                 280                 285
Glu Cys Ala Ala Arg Gln Ala Thr Arg Glu Val Lys Glu Met Lys Lys
    290                 295                 300
Val Thr Ile Ser Val His Glu Lys Gly Phe Ile Glu Ile Lys Pro Thr
305                 310                 315                 320
Phe Ser Gln Leu Glu Ala Val Asn Leu His Glu Val Lys His Phe Val
                325                 330                 335
Val Glu Val Arg Ala Tyr Pro Pro Arg Ile Ser Trp Leu Lys Asn
            340                 345                 350
Asn Leu Thr Leu Ile Glu Asn Leu Thr Glu Ile Thr Thr Asp Val Glu
        355                 360                 365
Lys Ile Gln Glu Ile Arg Tyr Arg Ser Lys Leu Lys Leu Ile Arg Ala
    370                 375                 380
Lys Glu Glu Asp Ser Gly His Tyr Thr Ile Val Ala Gln Asn Glu Asp
385                 390                 395                 400
Ala Val Lys Ser Tyr Thr Phe Glu Leu Leu Thr Gln Val Pro Ser Ser
                405                 410                 415
Ile Leu Asp Leu Val Asp Asp His His Gly Ser Thr Gly Gly Gln Thr
            420                 425                 430
Val Arg Cys Thr Ala Glu Gly Thr Pro Leu Pro Asp Ile Glu Trp Met
        435                 440                 445
Ile Cys Lys Asp Ile Lys Lys Cys Asn Asn Glu Thr Ser Trp Thr Ile
    450                 455                 460
Leu Ala Asn Asn Val Ser Asn Ile Ile Thr Glu Ile His Ser Arg Asp
465                 470                 475                 480
Arg Ser Thr Val Glu Gly Arg Val Thr Phe Ala Lys Val Glu Glu Thr
                485                 490                 495
Ile Ala Val Arg Cys Leu Ala Lys Asn Leu Leu Gly Ala Glu Asn Arg
            500                 505                 510
Glu Leu Lys Leu Val Ala Pro Thr Leu Arg Ser Glu Leu Thr Val Ala
        515                 520                 525
Ala Ala Val Leu Val Leu Leu Val Ile Val Ile Ser Leu Ile Val
    530                 535                 540
Leu Val Val Ile Trp Lys Gln Lys Pro Arg Tyr Glu Ile Arg Trp Arg
545                 550                 555                 560
Val Ile Glu Ser Ile Ser Pro Asp Gly His Glu Tyr Ile Tyr Val Asp
                565                 570                 575
Pro Met Gln Leu Pro Tyr Asp Ser Arg Trp Glu Phe Pro Arg Asp Gly
            580                 585                 590
Leu Val Leu Gly Arg Val Leu Gly Ser Gly Ala Phe Gly Lys Val Val
        595                 600                 605
Glu Gly Thr Ala Tyr Gly Leu Ser Arg Ser Gln Pro Val Met Lys Val
    610                 615                 620
Ala Val Lys Met Leu Lys Pro Thr Ala Arg Ser Ser Glu Lys Gln Ala
625                 630                 635                 640
Leu Met Ser Glu Leu Lys Ile Met Thr His Leu Gly Pro His Leu Asn
                645                 650                 655
Ile Val Asn Leu Leu Gly Ala Cys Thr Lys Ser Gly Pro Ile Tyr Ile
            660                 665                 670
Ile Thr Glu Tyr Cys Phe Tyr Gly Asp Leu Val Asn Tyr Leu His Lys
        675                 680                 685
Asn Arg Asp Ser Phe Leu Ser His His Pro Glu Lys Pro Lys Lys Glu
    690                 695                 700
```

```
Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
            725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
            755                 760                 765

Lys Lys Lys Ser Met Leu Asp Ser Glu Val Lys Asn Leu Leu Ser Asp
770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
            915                 920                 925

Met Val Lys Cys Trp Asn Ser Glu Pro Glu Lys Arg Pro Ser Phe Tyr
930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu Lys Asp Trp Glu Gly Gly Leu Asp
            995                 1000                1005

Glu Gln Arg Leu Ser Ala Asp Ser Gly Tyr Ile Ile Pro Leu Pro Asp
    1010                1015                1020

Ile Asp Pro Val Pro Glu Glu Glu Asp Leu Gly Lys Arg Asn Arg His
1025                1030                1035                1040

Ser Ser Gln Thr Ser Glu Glu Ser Ala Ile Glu Thr Gly Ser Ser Ser
                1045                1050                1055

Ser Thr Phe Ile Lys Arg Glu Asp Glu Thr Ile Glu Asp Ile Asp Met
            1060                1065                1070

Met Asp Asp Ile Gly Ile Asp Ser Ser Asp Leu Val Glu Asp Ser Phe
            1075                1080                1085

Leu

<210> SEQ ID NO 51
<211> LENGTH: 1106
<212> TYPE: PRT
```

-continued

<213> ORGANISM: Homo sapiens

<400> SEQUENCE: 51

```
Met Arg Leu Pro Gly Ala Met Pro Ala Leu Ala Leu Lys Gly Glu Leu
  1               5                  10                  15

Leu Leu Leu Ser Leu Leu Leu Leu Glu Pro Gln Ile Ser Gln Gly
             20                  25                  30

Leu Val Val Thr Pro Pro Gly Pro Glu Leu Val Leu Asn Val Ser Ser
             35                  40                  45

Thr Phe Val Leu Thr Cys Ser Gly Ser Ala Pro Val Val Trp Glu Arg
 50                  55                  60

Met Ser Gln Glu Pro Pro Gln Glu Met Ala Lys Ala Gln Asp Gly Thr
 65                  70                  75                  80

Phe Ser Ser Val Leu Thr Leu Thr Asn Leu Thr Gly Leu Asp Thr Gly
                 85                  90                  95

Glu Tyr Phe Cys Thr His Asn Asp Ser Arg Gly Leu Glu Thr Asp Glu
                100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
            130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
                180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
            210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
                260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
370                 375                 380

Arg Val Lys Val Ala Glu Ala Gly His Tyr Thr Met Arg Ala Phe His
385                 390                 395                 400
```

-continued

```
Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Pro His Ser Leu
        515                 520                 525

Pro Phe Lys Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
        675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
        755                 760                 765

Ser Asn Tyr Met Ala Pro Tyr Asp Asn Tyr Val Pro Ser Ala Pro Glu
    770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
```

-continued

```
                    820                 825                 830

Leu Ile Cys Glu Gly Lys Leu Val Lys Ile Cys Asp Phe Gly Leu Ala
            835                 840                 845

Arg Asp Ile Met Arg Asp Ser Asn Tyr Ile Ser Lys Gly Ser Thr Phe
        850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
        915                 920                 925

Ala Ser Asp Glu Ile Tyr Glu Ile Met Gln Lys Cys Trp Glu Glu Lys
    930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990

Pro Gly Phe His Gly Leu Arg Ser Pro Leu Asp Thr Ser Ser Val Leu
        995                1000                1005

Tyr Thr Ala Val Gln Pro Asn Glu Gly Asp Asn Asp Tyr Ile Ile Pro
   1010                1015                1020

Leu Pro Asp Pro Lys Pro Glu Val Ala Asp Glu Gly Pro Leu Glu Gly
1025                1030                1035                1040

Ser Pro Ser Leu Ala Ser Ser Thr Leu Asn Glu Val Asn Thr Ser Ser
                1045                1050                1055

Thr Ile Ser Cys Asp Ser Pro Leu Glu Pro Gln Asp Glu Pro Glu Pro
            1060                1065                1070

Glu Pro Gln Leu Glu Leu Gln Val Glu Pro Glu Pro Glu Leu Glu Gln
        1075                1080                1085

Leu Pro Asp Ser Gly Cys Pro Ala Pro Arg Ala Glu Ala Glu Asp Ser
   1090                1095                1100

Phe Leu
1105

<210> SEQ ID NO 52
<211> LENGTH: 313
<212> TYPE: PRT
<213> ORGANISM: Homo sapiens

<400> SEQUENCE: 52

Met Leu Leu Ser Lys Ile Asn Ser Leu Ala His Leu Arg Ala Ala Pro
  1               5                  10                  15

Cys Asn Asp Leu His Ala Thr Lys Leu Ala Pro Gly Lys Glu Lys Glu
             20                  25                  30

Pro Leu Glu Ser Gln Tyr Gln Val Gly Pro Leu Leu Gly Ser Gly Gly
         35                  40                  45

Phe Gly Ser Val Tyr Ser Gly Ile Arg Val Ser Asp Asn Leu Pro Val
     50                  55                  60

Ala Ile Lys His Val Glu Lys Asp Arg Ile Ser Asp Trp Gly Glu Leu
 65                  70                  75                  80
```

```
Pro Asn Gly Thr Arg Val Pro Met Glu Val Val Leu Lys Lys Val
                85                  90                  95

Ser Ser Gly Phe Ser Gly Val Ile Arg Leu Leu Asp Trp Phe Glu Arg
                100                 105                 110

Pro Asp Ser Phe Val Leu Ile Leu Glu Arg Pro Glu Pro Val Gln Asp
            115                 120                 125

Leu Phe Asp Phe Ile Thr Glu Arg Gly Ala Leu Gln Glu Glu Leu Ala
130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
    290                 295                 300

His Ser Leu Ser Pro Gly Pro Ser Lys
305                 310

<210> SEQ ID NO 53
<211> LENGTH: 606
<212> TYPE: PRT
<213> ORGANISM: Homo sapiens

<400> SEQUENCE: 53

Met Glu Pro Pro Arg Gly Pro Pro Ala Asn Gly Ala Glu Pro Ser Arg
1               5                   10                  15

Ala Val Gly Thr Val Lys Val Tyr Leu Pro Asn Lys Gln Arg Thr Val
                20                  25                  30

Val Thr Val Arg Asp Gly Met Ser Val Tyr Asp Ser Leu Asp Lys Ala
            35                  40                  45

Leu Lys Val Arg Gly Leu Asn Gln Asp Cys Cys Val Val Tyr Arg Leu
    50                  55                  60

Ile Lys Gly Arg Lys Thr Val Thr Ala Trp Asp Thr Ala Ile Ala Pro
65                  70                  75                  80

Leu Asp Gly Glu Glu Leu Ile Val Glu Val Leu Glu Asp Val Pro Leu
                85                  90                  95

Thr Met His Asn Phe Val Arg Lys Thr Phe Phe Ser Leu Ala Phe Cys
            100                 105                 110

Asp Phe Cys Leu Lys Phe Leu Phe His Gly Phe Arg Cys Gln Thr Cys
        115                 120                 125

Gly Tyr Lys Phe His Gln His Cys Ser Ser Lys Val Pro Thr Val Cys
    130                 135                 140
```

-continued

```
Val Asp Met Ser Thr Asn Arg Gln Gln Phe Tyr His Ser Val Gln Asp
145                 150                 155                 160

Leu Ser Gly Gly Ser Arg Gln His Glu Ala Pro Ser Asn Arg Pro Leu
            165                 170                 175

Asn Glu Leu Leu Thr Pro Gln Gly Pro Ser Pro Arg Thr Gln His Cys
            180                 185                 190

Asp Pro Glu His Phe Pro Phe Pro Ala Pro Ala Asn Ala Pro Leu Gln
            195                 200                 205

Arg Ile Arg Ser Thr Ser Thr Pro Asn Val His Met Val Ser Thr Thr
    210                 215                 220

Ala Pro Met Asp Ser Asn Leu Ile Gln Leu Thr Gly Gln Ser Phe Ser
225                 230                 235                 240

Thr Asp Ala Ala Gly Ser Arg Gly Gly Ser Asp Gly Thr Pro Arg Gly
                245                 250                 255

Ser Pro Ser Pro Ala Ser Val Ser Ser Gly Arg Lys Ser Pro His Ser
            260                 265                 270

Lys Ser Pro Ala Glu Gln Arg Glu Arg Lys Ser Leu Ala Asp Asp Lys
    275                 280                 285

Lys Lys Val Lys Asn Leu Gly Tyr Arg Asp Ser Gly Tyr Tyr Trp Glu
    290                 295                 300

Val Pro Pro Ser Glu Val Gln Leu Leu Lys Arg Ile Gly Thr Gly Ser
305                 310                 315                 320

Phe Gly Thr Val Phe Arg Gly Arg Trp His Gly Asp Val Ala Val Lys
                325                 330                 335

Val Leu Lys Val Ser Gln Pro Thr Ala Glu Gln Ala Gln Ala Phe Lys
            340                 345                 350

Asn Glu Met Gln Val Leu Arg Lys Thr Arg His Val Asn Ile Leu Leu
    355                 360                 365

Phe Met Gly Phe Met Thr Arg Pro Gly Phe Ala Ile Ile Thr Gln Trp
370                 375                 380

Cys Glu Gly Ser Ser Leu Tyr His His Leu His Val Ala Asp Thr Arg
385                 390                 395                 400

Phe Asp Met Val Gln Leu Ile Asp Val Ala Arg Gln Thr Ala Gln Gly
                405                 410                 415

Met Asp Tyr Leu His Ala Lys Asn Ile Ile His Arg Asp Leu Lys Ser
            420                 425                 430

Asn Asn Ile Phe Leu His Glu Gly Leu Thr Val Lys Ile Gly Asp Phe
    435                 440                 445

Gly Leu Ala Thr Val Lys Thr Arg Trp Ser Gly Ala Gln Pro Leu Glu
450                 455                 460

Gln Pro Ser Gly Ser Val Leu Trp Met Ala Ala Glu Val Ile Arg Met
465                 470                 475                 480

Gln Asp Pro Asn Pro Tyr Ser Phe Gln Ser Asp Val Tyr Ala Tyr Gly
                485                 490                 495

Val Val Leu Tyr Glu Leu Met Thr Gly Ser Leu Pro Tyr Ser His Ile
            500                 505                 510

Gly Cys Arg Asp Gln Ile Ile Phe Met Val Gly Arg Gly Tyr Leu Ser
    515                 520                 525

Pro Asp Leu Ser Lys Ile Ser Ser Asn Cys Pro Lys Ala Met Arg Arg
    530                 535                 540

Leu Leu Ser Asp Cys Leu Lys Phe Gln Arg Glu Glu Arg Pro Leu Phe
545                 550                 555                 560
```

-continued

```
Pro Gln Ile Leu Ala Thr Ile Glu Leu Leu Gln Arg Ser Leu Pro Lys
                565                 570                 575

Ile Glu Arg Ser Ala Ser Glu Pro Ser Leu His Arg Thr Gln Ala Asp
            580                 585                 590

Glu Leu Pro Ala Cys Leu Leu Ser Ala Ala Arg Leu Val Pro
595                 600                 605

<210> SEQ ID NO 54
<211> LENGTH: 765
<212> TYPE: PRT
<213> ORGANISM: Homo sapiens

<400> SEQUENCE: 54

Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Arg Pro
                20                  25                  30

Ala Ala Ser Ser Ala Ala Asp Pro Ala Ile Pro Glu Glu Val Trp Asn
            35                  40                  45

Ile Lys Gln Met Ile Lys Leu Thr Gln Glu His Ile Glu Ala Leu Leu
50              55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Met Asp Thr Val Thr Ser Ser Ser Ser Ser Ser Leu Ser
        115                 120                 125

Val Leu Pro Ser Ser Leu Ser Val Phe Gln Asn Pro Thr Asp Val Ala
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Ala Leu Thr Ser Gly Ser Ser Pro Ser Ala Pro
305                 310                 315                 320

Ala Ser Asp Ser Ile Gly Pro Gln Ile Leu Thr Ser Pro Ser Pro Ser
                325                 330                 335
```

-continued

```
Lys Ser Ile Pro Ile Pro Gln Pro Phe Arg Pro Ala Asp Glu Asp His
            340                 345                 350
Arg Asn Gln Phe Gly Gln Arg Asp Arg Ser Ser Ala Pro Asn Val
        355                 360                 365
His Ile Asn Thr Ile Glu Pro Val Asn Ile Asp Asp Leu Ile Arg Asp
        370                 375                 380
Gln Gly Phe Arg Gly Asp Gly Gly Ser Thr Thr Gly Leu Ser Ala Thr
385                 390                 395                 400
Pro Pro Ala Ser Leu Pro Gly Ser Leu Thr Asn Val Lys Ala Leu Gln
                405                 410                 415
Lys Ser Pro Gly Pro Gln Arg Glu Arg Lys Ser Ser Ser Ser Glu
            420                 425                 430
Asp Arg Asn Arg Met Lys Thr Leu Gly Arg Arg Asp Ser Ser Asp Asp
                435                 440                 445
Trp Glu Ile Pro Asp Gly Gln Ile Thr Val Gly Gln Arg Ile Gly Ser
    450                 455                 460
Gly Ser Phe Gly Thr Val Tyr Lys Gly Lys Trp His Gly Asp Val Ala
465                 470                 475                 480
Val Lys Met Leu Asn Val Thr Ala Pro Thr Pro Gln Gln Leu Gln Ala
                485                 490                 495
Phe Lys Asn Glu Val Gly Val Leu Arg Lys Thr Arg His Val Asn Ile
            500                 505                 510
Leu Leu Phe Met Gly Tyr Ser Thr Lys Pro Gln Leu Ala Ile Val Thr
            515                 520                 525
Gln Trp Cys Glu Gly Ser Ser Leu Tyr His His Leu His Ile Ile Glu
        530                 535                 540
Thr Lys Phe Glu Met Ile Lys Leu Ile Asp Ile Ala Arg Gln Thr Ala
545                 550                 555                 560
Gln Gly Met Asp Tyr Leu His Ala Lys Ser Ile Ile His Arg Asp Leu
                565                 570                 575
Lys Ser Asn Asn Ile Phe Leu His Glu Asp Leu Thr Val Lys Ile Gly
            580                 585                 590
Asp Phe Gly Leu Ala Thr Val Lys Ser Arg Trp Ser Gly Ser His Gln
        595                 600                 605
Phe Glu Gln Leu Ser Gly Ser Ile Leu Trp Met Ala Pro Glu Val Ile
    610                 615                 620
Arg Met Gln Asp Lys Asn Pro Tyr Ser Phe Gln Ser Asp Val Tyr Ala
625                 630                 635                 640
Phe Gly Ile Val Leu Tyr Glu Leu Met Thr Gly Gln Leu Pro Tyr Ser
                645                 650                 655
Asn Ile Asn Asn Arg Asp Gln Ile Ile Phe Met Val Gly Arg Gly Tyr
            660                 665                 670
Leu Ser Pro Asp Leu Ser Lys Val Arg Ser Asn Cys Pro Lys Ala Met
        675                 680                 685
Lys Arg Leu Met Ala Glu Cys Leu Lys Lys Arg Asp Glu Arg Pro
    690                 695                 700
Leu Phe Pro Gln Ile Leu Ala Ser Ile Glu Leu Leu Ala Arg Ser Leu
705                 710                 715                 720
Pro Lys Ile His Arg Ser Ala Ser Glu Pro Ser Leu Asn Arg Ala Gly
                725                 730                 735
Phe Gln Thr Glu Asp Phe Ser Leu Tyr Ala Cys Ala Ser Pro Lys Thr
        740                 745                 750
```

```
Pro Ile Gln Ala Gly Gly Tyr Gly Ala Phe Pro Val His
        755                 760                 765

<210> SEQ ID NO 55
<211> LENGTH: 648
<212> TYPE: PRT
<213> ORGANISM: Homo sapiens

<400> SEQUENCE: 55

Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
            20                  25                  30

Val Gln Gln Phe Gly Tyr Gln Arg Arg Ala Ser Asp Asp Gly Lys Leu
        35                  40                  45

Thr Asp Pro Ser Lys Thr Ser Asn Thr Ile Arg Val Phe Leu Pro Asn
50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125

Asp Phe Leu Asp His Val Pro Leu Thr Thr His Asn Phe Ala Arg Lys
130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
            260                 265                 270

Asp Ser Arg Met Ile Glu Asp Ala Ile Arg Ser His Ser Glu Ser Ala
        275                 280                 285

Ser Pro Ser Ala Leu Ser Ser Ser Pro Asn Asn Leu Ser Pro Thr Gly
290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
            340                 345                 350

Thr Arg Ile Gly Ser Gly Ser Phe Gly Thr Val Tyr Lys Gly Lys Trp
        355                 360                 365
```

His Gly Asp Val Ala Val Lys Ile Leu Lys Val Val Asp Pro Thr Pro
    370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
                420                 425                 430

Leu His Val Gln Glu Thr Lys Phe Gln Met Phe Gln Leu Ile Asp Ile
            435                 440                 445

Ala Arg Gln Thr Ala Gln Gly Met Asp Tyr Leu His Ala Lys Asn Ile
    450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
            500                 505                 510

Ala Pro Glu Val Ile Arg Met Gln Asp Asn Asn Pro Phe Ser Phe Gln
    515                 520                 525

Ser Asp Val Tyr Ser Tyr Gly Ile Val Leu Tyr Glu Leu Met Thr Gly
    530                 535                 540

Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
                565                 570                 575

Cys Pro Lys Ala Met Lys Arg Leu Val Ala Asp Cys Val Lys Lys Val
            580                 585                 590

Lys Glu Glu Arg Pro Leu Phe Pro Gln Ile Leu Ser Ser Ile Glu Leu
    595                 600                 605

Leu Gln His Ser Leu Pro Lys Ile Asn Arg Ser Ala Ser Glu Pro Ser
610                 615                 620

Leu His Arg Ala Ala His Thr Glu Asp Ile Asn Ala Cys Thr Leu Thr
625                 630                 635                 640

Thr Ser Pro Arg Leu Pro Val Phe
                645

<210> SEQ ID NO 56
<211> LENGTH: 535
<212> TYPE: PRT
<213> ORGANISM: Homo sapiens

<400> SEQUENCE: 56

Gly Ser Asn Lys Ser Lys Pro Lys Asp Ala Ser Gln Arg Arg Arg Ser
1               5                   10                  15

Leu Glu Pro Ala Glu Asn Val His Gly Ala Gly Gly Gly Ala Phe Pro
            20                  25                  30

Ala Ser Gln Thr Pro Ser Lys Pro Ala Ser Ala Asp Gly His Arg Gly
        35                  40                  45

Pro Ser Ala Ala Phe Ala Pro Ala Ala Ala Glu Pro Lys Leu Phe Gly
    50                  55                  60

Gly Phe Asn Ser Ser Asp Thr Val Thr Ser Pro Gln Arg Ala Gly Pro
65                  70                  75                  80

Leu Ala Gly Gly Val Thr Thr Phe Val Ala Leu Tyr Asp Tyr Glu Ser

-continued

```
                85                  90                  95
Arg Thr Glu Thr Asp Leu Ser Phe Lys Lys Gly Glu Arg Leu Gln Ile
            100                 105                 110
Val Asn Asn Thr Glu Gly Asp Trp Trp Leu Ala His Ser Leu Ser Thr
            115                 120                 125
Gly Gln Thr Gly Tyr Ile Pro Ser Asn Tyr Val Ala Pro Ser Asp Ser
            130                 135                 140
Ile Gln Ala Glu Glu Trp Tyr Phe Gly Lys Ile Thr Arg Arg Glu Ser
145                 150                 155                 160
Glu Arg Leu Leu Leu Asn Ala Glu Asn Pro Arg Gly Thr Phe Leu Val
                165                 170                 175
Arg Glu Ser Glu Thr Thr Lys Gly Ala Tyr Cys Leu Ser Val Ser Asp
                180                 185                 190
Phe Asp Asn Ala Lys Gly Leu Asn Val Lys His Tyr Lys Ile Arg Lys
            195                 200                 205
Leu Asp Ser Gly Gly Phe Tyr Ile Thr Ser Arg Thr Gln Phe Asn Ser
            210                 215                 220
Leu Gln Gln Leu Val Ala Tyr Tyr Ser Lys His Ala Asp Gly Leu Cys
225                 230                 235                 240
His Arg Leu Thr Thr Val Cys Pro Thr Ser Lys Pro Gln Thr Gln Gly
                245                 250                 255
Leu Ala Lys Asp Ala Trp Glu Ile Pro Arg Glu Ser Leu Arg Leu Glu
            260                 265                 270
Val Lys Leu Gly Gln Gly Cys Phe Gly Glu Val Trp Met Gly Thr Trp
            275                 280                 285
Asn Gly Thr Thr Arg Val Ala Ile Lys Thr Leu Lys Pro Gly Thr Met
            290                 295                 300
Ser Pro Glu Ala Phe Leu Gln Glu Ala Gln Val Met Lys Lys Leu Arg
305                 310                 315                 320
His Glu Lys Leu Val Gln Leu Tyr Ala Val Val Ser Glu Glu Pro Ile
                325                 330                 335
Tyr Ile Val Thr Glu Tyr Met Ser Lys Gly Ser Leu Leu Asp Phe Leu
                340                 345                 350
Lys Gly Glu Thr Gly Lys Tyr Leu Arg Leu Pro Gln Leu Val Asp Met
            355                 360                 365
Ala Ala Gln Ile Ala Ser Gly Met Ala Tyr Val Glu Arg Met Asn Tyr
            370                 375                 380
Val His Arg Asp Leu Arg Ala Ala Asn Ile Leu Val Gly Glu Asn Leu
385                 390                 395                 400
Val Cys Lys Val Ala Asp Phe Gly Leu Ala Arg Leu Ile Glu Asp Asn
                405                 410                 415
Glu Tyr Thr Ala Arg Gln Gly Ala Lys Phe Pro Ile Lys Trp Thr Ala
            420                 425                 430
Pro Glu Ala Ala Leu Tyr Gly Arg Phe Thr Ile Lys Ser Asp Val Trp
            435                 440                 445
Ser Phe Gly Ile Leu Leu Thr Glu Leu Thr Thr Lys Gly Arg Val Pro
            450                 455                 460
Tyr Pro Gly Met Val Asn Arg Glu Val Leu Asp Gln Val Glu Arg Gly
465                 470                 475                 480
Tyr Arg Met Pro Cys Pro Pro Glu Cys Pro Glu Ser Leu His Asp Leu
                485                 490                 495
Met Cys Gln Cys Trp Arg Lys Glu Pro Glu Glu Arg Pro Thr Phe Glu
            500                 505                 510
```

Tyr Leu Gln Ala Phe Leu Glu Asp Tyr Phe Thr Ser Thr Glu Pro Gln
        515                 520                 525

Tyr Gln Pro Gly Glu Asn Leu
        530             535

<210> SEQ ID NO 57
<211> LENGTH: 529
<212> TYPE: PRT
<213> ORGANISM: Homo sapiens

<400> SEQUENCE: 57

Met Gly Cys Val Phe Cys Lys Lys Leu Glu Pro Val Ala Thr Ala Lys
 1               5                   10                  15

Glu Asp Ala Gly Leu Glu Gly Asp Phe Arg Ser Tyr Gly Ala Ala Asp
            20                  25                  30

His Tyr Gly Pro Asp Pro Thr Lys Ala Arg Pro Ala Ser Ser Phe Ala
        35                  40                  45

His Ile Pro Asn Tyr Ser Asn Phe Ser Ser Gln Ala Ile Asn Pro Gly
    50                  55                  60

Phe Leu Asp Ser Gly Thr Ile Arg Gly Val Ser Gly Ile Gly Val Thr
65                  70                  75                  80

Leu Phe Ile Ala Leu Tyr Asp Tyr Glu Ala Arg Thr Glu Asp Asp Leu
                85                  90                  95

Thr Phe Thr Lys Gly Glu Lys Phe His Ile Leu Asn Asn Thr Glu Gly
            100                 105                 110

Asp Trp Trp Glu Ala Arg Ser Leu Ser Ser Gly Lys Thr Gly Cys Ile
        115                 120                 125

Pro Ser Asn Tyr Val Ala Pro Val Asp Ser Ile Gln Ala Glu Glu Trp
    130                 135                 140

Tyr Phe Gly Lys Ile Gly Arg Lys Asp Ala Glu Arg Gln Leu Leu Ser
145                 150                 155                 160

Pro Gly Asn Pro Gln Gly Ala Phe Leu Ile Arg Glu Ser Glu Thr Thr
                165                 170                 175

Lys Gly Ala Tyr Ser Leu Ser Ile Arg Asp Trp Asp Gln Thr Arg Gly
            180                 185                 190

Asp His Val Lys His Tyr Lys Ile Arg Lys Leu Asp Met Gly Gly Tyr
        195                 200                 205

Tyr Ile Thr Thr Arg Val Gln Phe Asn Ser Val Gln Glu Leu Val Gln
    210                 215                 220

His Tyr Met Glu Val Asn Asp Gly Leu Cys Asn Leu Leu Ile Ala Pro
225                 230                 235                 240

Cys Thr Ile Met Lys Pro Gln Thr Leu Gly Leu Ala Lys Asp Ala Trp
                245                 250                 255

Glu Ile Ser Arg Ser Ser Ile Thr Leu Glu Arg Arg Leu Gly Thr Gly
            260                 265                 270

Cys Phe Gly Asp Val Trp Leu Gly Thr Trp Asn Gly Ser Thr Lys Val
        275                 280                 285

Ala Val Lys Thr Leu Lys Pro Gly Thr Met Ser Pro Lys Ala Phe Leu
    290                 295                 300

Glu Glu Ala Gln Val Met Lys Leu Leu Arg His Asp Lys Leu Val Gln
305                 310                 315                 320

Leu Tyr Ala Val Val Ser Glu Glu Pro Ile Tyr Ile Val Thr Glu Phe
                325                 330                 335

Met Cys His Gly Ser Leu Leu Asp Phe Leu Lys Asn Pro Glu Gly Gln

-continued

```
                340                 345                 350
Asp Leu Arg Leu Pro Gln Leu Val Asp Met Ala Ala Gln Val Ala Glu
            355                 360                 365
Gly Met Ala Tyr Met Glu Arg Met Asn Tyr Ile His Arg Asp Leu Arg
        370                 375                 380
Ala Ala Asn Ile Leu Val Gly Glu Arg Leu Ala Cys Lys Ile Ala Asp
385                 390                 395                 400
Phe Gly Leu Ala Arg Leu Ile Lys Asp Asp Glu Tyr Asn Pro Cys Gln
                405                 410                 415
Gly Ser Lys Phe Pro Ile Lys Trp Thr Ala Pro Glu Ala Ala Leu Phe
            420                 425                 430
Gly Arg Phe Thr Ile Lys Ser Asp Val Trp Ser Phe Gly Ile Leu Leu
        435                 440                 445
Thr Glu Leu Ile Thr Lys Gly Arg Ile Pro Tyr Pro Gly Met Asn Lys
    450                 455                 460
Arg Glu Val Leu Glu Gln Val Glu Gln Gly Tyr His Met Pro Cys Pro
465                 470                 475                 480
Pro Gly Cys Pro Ala Ser Leu Tyr Glu Ala Met Glu Gln Thr Trp Arg
                485                 490                 495
Leu Asp Pro Glu Glu Arg Pro Thr Phe Glu Tyr Leu Gln Ser Phe Leu
            500                 505                 510
Glu Asp Tyr Phe Thr Ser Ala Glu Pro Gln Tyr Gln Pro Gly Asp Gln
        515                 520                 525
Thr

<210> SEQ ID NO 58
<211> LENGTH: 993
<212> TYPE: PRT
<213> ORGANISM: Homo sapiens

<400> SEQUENCE: 58

Met Pro Ala Leu Ala Arg Asp Ala Gly Thr Val Pro Leu Leu Val Val
 1               5                  10                  15
Phe Ser Ala Met Ile Phe Gly Thr Ile Thr Asn Gln Asp Leu Pro Val
                20                  25                  30
Ile Lys Cys Val Leu Ile Asn His Lys Asn Asn Asp Ser Ser Val Gly
            35                  40                  45
Lys Ser Ser Ser Tyr Pro Met Val Ser Glu Ser Pro Glu Asp Leu Gly
        50                  55                  60
Cys Ala Leu Arg Pro Gln Ser Ser Gly Thr Val Tyr Glu Ala Ala Ala
65                  70                  75                  80
Val Glu Val Asp Val Ser Ala Ser Ile Thr Leu Gln Val Leu Val Asp
                85                  90                  95
Ala Pro Gly Asn Ile Ser Cys Leu Trp Val Phe Lys His Ser Ser Leu
            100                 105                 110
Asn Cys Gln Pro His Phe Asp Leu Gln Asn Arg Gly Val Val Ser Met
        115                 120                 125
Val Ile Leu Lys Met Thr Glu Thr Gln Ala Gly Glu Tyr Leu Leu Phe
    130                 135                 140
Ile Gln Ser Glu Ala Thr Asn Tyr Thr Ile Leu Phe Thr Val Ser Ile
145                 150                 155                 160
Arg Asn Thr Leu Leu Tyr Thr Leu Arg Arg Pro Tyr Phe Arg Lys Met
                165                 170                 175
Glu Asn Gln Asp Ala Leu Val Cys Ile Ser Glu Ser Val Pro Glu Pro
```

-continued

```
                180                 185                 190
Ile Val Glu Trp Val Leu Cys Asp Ser Gln Gly Glu Ser Cys Lys Glu
            195                 200                 205
Glu Ser Pro Ala Val Val Lys Lys Glu Glu Lys Val Leu His Glu Leu
210                 215                 220
Phe Gly Thr Asp Ile Arg Cys Cys Ala Arg Asn Glu Leu Gly Arg Glu
225                 230                 235                 240
Cys Thr Arg Leu Phe Thr Ile Asp Leu Asn Gln Thr Pro Gln Thr Thr
                245                 250                 255
Leu Pro Gln Leu Phe Leu Lys Val Gly Glu Pro Leu Trp Ile Arg Cys
            260                 265                 270
Lys Ala Val His Val Asn His Gly Phe Gly Leu Thr Trp Glu Leu Glu
        275                 280                 285
Asn Lys Ala Leu Glu Glu Gly Asn Tyr Phe Glu Met Ser Thr Tyr Ser
    290                 295                 300
Thr Asn Arg Thr Met Ile Arg Ile Leu Phe Ala Phe Val Ser Ser Val
305                 310                 315                 320
Ala Arg Asn Asp Thr Gly Tyr Tyr Thr Cys Ser Ser Ser Lys His Pro
                325                 330                 335
Ser Gln Ser Ala Leu Val Thr Ile Val Gly Lys Gly Phe Ile Asn Ala
            340                 345                 350
Thr Asn Ser Ser Glu Asp Tyr Glu Ile Asp Gln Tyr Glu Glu Phe Cys
        355                 360                 365
Phe Ser Val Arg Phe Lys Ala Tyr Pro Gln Ile Arg Cys Thr Trp Thr
370                 375                 380
Phe Ser Arg Lys Ser Phe Pro Cys Glu Gln Lys Gly Leu Asp Asn Gly
385                 390                 395                 400
Tyr Ser Ile Ser Lys Phe Cys Asn His Lys His Gln Pro Gly Glu Tyr
                405                 410                 415
Ile Phe His Ala Glu Asn Asp Asp Ala Gln Phe Thr Lys Met Phe Thr
            420                 425                 430
Leu Asn Ile Arg Arg Lys Pro Gln Val Leu Ala Glu Ala Ser Ala Ser
        435                 440                 445
Gln Ala Ser Cys Phe Ser Asp Gly Tyr Pro Leu Pro Ser Trp Thr Trp
    450                 455                 460
Lys Lys Cys Ser Asp Lys Ser Pro Asn Cys Thr Glu Glu Ile Thr Glu
465                 470                 475                 480
Gly Val Trp Asn Arg Lys Ala Asn Arg Lys Val Phe Gly Gln Trp Val
                485                 490                 495
Ser Ser Ser Thr Leu Asn Met Ser Glu Ala Ile Lys Gly Phe Leu Val
            500                 505                 510
Lys Cys Cys Ala Tyr Asn Ser Leu Gly Thr Ser Cys Glu Thr Ile Leu
        515                 520                 525
Leu Asn Ser Pro Gly Pro Phe Pro Phe Ile Gln Asp Asn Ile Ser Phe
    530                 535                 540
Tyr Ala Thr Ile Gly Val Cys Leu Leu Phe Ile Val Val Leu Thr Leu
545                 550                 555                 560
Leu Ile Cys His Lys Tyr Lys Lys Gln Phe Arg Tyr Glu Ser Gln Leu
                565                 570                 575
Gln Met Val Gln Val Thr Gly Ser Ser Asp Asn Glu Tyr Phe Tyr Val
            580                 585                 590
Asp Phe Arg Glu Tyr Glu Tyr Asp Leu Lys Trp Glu Phe Pro Arg Glu
        595                 600                 605
```

```
Asn Leu Glu Phe Gly Lys Val Leu Gly Ser Gly Ala Phe Gly Lys Val
    610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
        675                 680                 685

Leu Ile Phe Glu Tyr Cys Cys Tyr Gly Asp Leu Leu Asn Tyr Leu Arg
    690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Asp Leu Asn Val Leu Thr
    770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
    930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 59
<211> LENGTH: 635
<212> TYPE: PRT
```

<213> ORGANISM: Homo sapiens

<400> SEQUENCE: 59

```
Met Ala Ser Ser Gly Met Ala Asp Ser Ala Asn His Leu Pro Phe Phe
1               5                   10                  15
Phe Gly Asn Ile Thr Arg Glu Glu Ala Glu Asp Tyr Leu Val Gln Gly
                20                  25                  30
Gly Met Ser Asp Gly Leu Tyr Leu Leu Arg Gln Ser Arg Asn Tyr Leu
            35                  40                  45
Gly Gly Phe Ala Leu Ser Val Ala His Gly Arg Lys Ala His His Tyr
    50                  55                  60
Thr Ile Glu Arg Glu Leu Asn Gly Thr Tyr Ala Ile Ala Gly Gly Arg
65                  70                  75                  80
Thr His Ala Ser Pro Ala Asp Leu Cys His Tyr His Ser Gln Glu Ser
                85                  90                  95
Asp Gly Leu Val Cys Leu Leu Lys Lys Pro Phe Asn Arg Pro Gln Gly
            100                 105                 110
Val Gln Pro Lys Thr Gly Pro Phe Glu Asp Leu Lys Glu Asn Leu Ile
        115                 120                 125
Arg Glu Tyr Val Lys Gln Thr Trp Asn Leu Gln Gly Gln Ala Leu Glu
    130                 135                 140
Gln Ala Ile Ile Ser Gln Lys Pro Gln Leu Glu Lys Leu Ile Ala Thr
145                 150                 155                 160
Thr Ala His Glu Lys Met Pro Trp Phe His Gly Lys Ile Ser Arg Glu
                165                 170                 175
Glu Ser Glu Gln Ile Val Leu Ile Gly Ser Lys Thr Asn Gly Lys Phe
            180                 185                 190
Leu Ile Arg Ala Arg Asp Asn Asn Gly Ser Tyr Ala Leu Cys Leu Leu
        195                 200                 205
His Glu Gly Lys Val Leu His Tyr Arg Ile Asp Lys Asp Lys Thr Gly
    210                 215                 220
Lys Leu Ser Ile Pro Glu Gly Lys Lys Phe Asp Thr Leu Trp Gln Leu
225                 230                 235                 240
Val Glu His Tyr Ser Tyr Lys Ala Asp Gly Leu Leu Arg Val Leu Thr
                245                 250                 255
Val Pro Cys Gln Lys Ile Gly Thr Gln Gly Asn Val Asn Phe Gly Gly
            260                 265                 270
Arg Pro Gln Leu Pro Gly Ser His Pro Ala Thr Trp Ser Ala Gly Gly
        275                 280                 285
Ile Ile Ser Arg Ile Lys Ser Tyr Ser Phe Pro Lys Pro Gly His Arg
    290                 295                 300
Lys Ser Ser Pro Ala Gln Gly Asn Arg Gln Glu Ser Thr Val Ser Phe
305                 310                 315                 320
Asn Pro Tyr Glu Pro Glu Leu Ala Pro Trp Ala Ala Asp Lys Gly Pro
                325                 330                 335
Gln Arg Glu Ala Leu Pro Met Asp Thr Glu Val Tyr Glu Ser Pro Tyr
            340                 345                 350
Ala Asp Pro Glu Glu Ile Arg Pro Lys Glu Val Tyr Leu Asp Arg Lys
        355                 360                 365
Leu Leu Thr Leu Glu Asp Lys Glu Leu Gly Ser Gly Asn Phe Gly Thr
    370                 375                 380
Val Lys Lys Gly Tyr Tyr Gln Met Lys Lys Val Val Lys Thr Val Ala
385                 390                 395                 400
```

-continued

```
Val Lys Ile Leu Lys Asn Glu Ala Asn Asp Pro Ala Leu Lys Asp Glu
                405                 410                 415

Leu Leu Ala Glu Ala Asn Val Met Gln Gln Leu Asp Asn Pro Tyr Ile
            420                 425                 430

Val Arg Met Ile Gly Ile Cys Glu Ala Glu Ser Trp Met Leu Val Met
        435                 440                 445

Glu Met Ala Glu Leu Gly Pro Leu Asn Lys Tyr Leu Gln Gln Asn Arg
450                 455                 460

His Val Lys Asp Lys Asn Ile Ile Glu Leu Val His Gln Val Ser Met
465                 470                 475                 480

Gly Met Lys Tyr Leu Glu Glu Ser Asn Phe Val His Arg Asp Leu Ala
                485                 490                 495

Ala Arg Asn Val Leu Leu Val Thr Gln His Tyr Ala Lys Ile Ser Asp
            500                 505                 510

Phe Gly Leu Ser Lys Ala Leu Arg Ala Asp Glu Asn Tyr Tyr Lys Ala
        515                 520                 525

Gln Thr His Gly Lys Trp Pro Val Lys Trp Tyr Ala Pro Glu Cys Ile
530                 535                 540

Asn Tyr Tyr Lys Phe Ser Ser Lys Ser Asp Val Trp Ser Phe Gly Val
545                 550                 555                 560

Leu Met Trp Glu Ala Phe Ser Tyr Gly Gln Lys Pro Tyr Arg Gly Met
                565                 570                 575

Lys Gly Ser Glu Val Thr Ala Met Leu Glu Lys Gly Glu Arg Met Gly
            580                 585                 590

Cys Pro Ala Gly Cys Pro Arg Glu Met Tyr Asp Leu Met Asn Leu Cys
        595                 600                 605

Trp Thr Tyr Asp Val Glu Asn Arg Pro Gly Phe Ala Ala Val Glu Leu
        610                 615                 620

Arg Leu Arg Asn Tyr Tyr Tyr Asp Val Val Asn
625                 630                 635

<210> SEQ ID NO 60
<211> LENGTH: 631
<212> TYPE: PRT
<213> ORGANISM: Homo sapeins

<400> SEQUENCE: 60

Met Asn Phe Asn Thr Ile Leu Glu Glu Ile Leu Ile Lys Arg Ser Gln
1               5                   10                  15

Gln Lys Lys Lys Thr Ser Pro Leu Asn Tyr Lys Glu Arg Leu Phe Val
            20                  25                  30

Leu Thr Lys Ser Met Leu Thr Tyr Tyr Glu Gly Arg Ala Glu Lys Lys
        35                  40                  45

Tyr Arg Lys Gly Phe Ile Asp Val Ser Lys Ile Lys Cys Val Glu Ile
    50                  55                  60

Val Lys Asn Asp Asp Gly Val Ile Pro Cys Gln Asn Lys Tyr Pro Phe
65                  70                  75                  80

Gln Val Val His Asp Ala Asn Thr Leu Tyr Ile Phe Ala Pro Ser Pro
                85                  90                  95

Gln Ser Arg Asp Leu Trp Val Lys Lys Leu Lys Glu Glu Ile Lys Asn
            100                 105                 110

Asn Asn Asn Ile Met Ile Lys Tyr His Pro Lys Phe Trp Thr Asp Gly
        115                 120                 125

Ser Tyr Gln Cys Cys Arg Gln Thr Glu Lys Leu Ala Pro Gly Cys Glu
    130                 135                 140
```

```
Lys Tyr Asn Leu Phe Glu Ser Ser Ile Arg Lys Ala Leu Pro Pro Ala
145                 150                 155                 160

Pro Glu Thr Lys Lys Arg Arg Pro Pro Pro Ile Pro Leu Glu Glu
            165                 170                 175

Glu Asp Asn Ser Glu Glu Ile Val Val Ala Met Tyr Asp Phe Gln Ala
            180                 185                 190

Ala Glu Gly His Asp Leu Arg Leu Glu Arg Gly Gln Glu Tyr Leu Ile
            195                 200                 205

Leu Glu Lys Asn Asp Val His Trp Trp Arg Ala Arg Asp Lys Tyr Gly
210                 215                 220

Asn Glu Gly Tyr Ile Pro Ser Asn Tyr Val Thr Gly Lys Lys Ser Asn
225                 230                 235                 240

Asn Leu Asp Gln Tyr Glu Trp Tyr Cys Arg Asn Met Asn Arg Ser Lys
                245                 250                 255

Ala Glu Gln Leu Leu Arg Ser Glu Asp Lys Glu Gly Gly Phe Met Val
            260                 265                 270

Arg Asp Ser Ser Gln Pro Gly Leu Tyr Thr Val Ser Leu Tyr Thr Lys
            275                 280                 285

Phe Gly Gly Glu Gly Ser Ser Gly Phe Arg His Tyr His Ile Lys Glu
290                 295                 300

Thr Thr Thr Ser Pro Lys Lys Tyr Tyr Leu Ala Glu Lys His Ala Phe
305                 310                 315                 320

Gly Ser Ile Pro Glu Ile Ile Glu Tyr His Lys His Asn Ala Ala Gly
                325                 330                 335

Leu Val Thr Arg Leu Arg Tyr Pro Val Ser Val Lys Gly Lys Asn Ala
            340                 345                 350

Pro Thr Thr Ala Gly Phe Ser Tyr Glu Lys Trp Glu Ile Asn Pro Ser
            355                 360                 365

Glu Leu Thr Phe Met Arg Glu Leu Gly Ser Gly Leu Phe Gly Val Val
            370                 375                 380

Arg Leu Gly Lys Trp Arg Ala Gln Tyr Lys Val Ala Ile Lys Ala Ile
385                 390                 395                 400

Arg Glu Gly Ala Met Cys Glu Glu Asp Phe Ile Glu Glu Ala Lys Val
                405                 410                 415

Met Met Lys Leu Thr His Pro Lys Leu Val Gln Leu Tyr Gly Val Cys
            420                 425                 430

Thr Gln Gln Lys Pro Ile Tyr Ile Val Thr Glu Phe Met Glu Arg Gly
            435                 440                 445

Cys Leu Leu Asn Phe Leu Arg Gln Arg Gln Gly His Phe Ser Arg Asp
450                 455                 460

Val Leu Leu Ser Met Cys Gln Asp Val Cys Glu Gly Met Glu Tyr Leu
465                 470                 475                 480

Glu Arg Asn Ser Phe Ile His Arg Asp Leu Ala Ala Arg Asn Cys Leu
                485                 490                 495

Val Ser Glu Ala Gly Val Val Lys Val Ser Asp Phe Gly Met Ala Arg
            500                 505                 510

Tyr Phe Leu Asp Asp Gln Tyr Thr Ser Ser Gly Ala Lys Phe Pro
            515                 520                 525

Val Lys Trp Cys Pro Pro Glu Val Phe Asn Tyr Ser Arg Phe Ser Ser
530                 535                 540

Lys Ser Asp Val Trp Ser Phe Gly Val Leu Met Trp Glu Val Phe Thr
545                 550                 555                 560
```

```
Glu Gly Arg Met Pro Phe Glu Lys Tyr Thr Asn Tyr Glu Val Val Thr
                565                 570                 575

Met Val Thr Arg Gly His Arg Leu Tyr Gln Pro Lys Leu Ala Ser Asn
            580                 585                 590

Tyr Val Tyr Glu Val Met Leu Arg Cys Trp Gln Glu Lys Pro Glu Gly
        595                 600                 605

Arg Pro Ser Phe Glu Asp Leu Leu Arg Thr Ile Asp Glu Leu Val Glu
    610                 615                 620

Cys Glu Glu Thr Phe Gly Arg
625             630

<210> SEQ ID NO 61
<211> LENGTH: 503
<212> TYPE: PRT
<213> ORGANISM: Homo sapiens

<400> SEQUENCE: 61

Met Glu Ala Ala Val Ala Ala Pro Arg Pro Arg Leu Leu Leu Leu Val
 1               5                  10                  15

Leu Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
    210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
    290                 295                 300
```

-continued

```
Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
            325                 330                 335

Lys Asn Ile Leu Val Lys Asn Gly Thr Cys Cys Ile Ala Asp Leu
        340                 345                 350

Gly Leu Ala Val Arg His Asp Ser Ala Thr Asp Thr Ile Asp Ile Ala
            355                 360                 365

Pro Asn His Arg Val Gly Thr Lys Arg Tyr Met Ala Pro Glu Val Leu
370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
435                 440                 445

Lys Leu Arg Pro Asn Ile Pro Asn Arg Trp Gln Ser Cys Glu Ala Leu
450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
            500

<210> SEQ ID NO 62
<211> LENGTH: 567
<212> TYPE: PRT
<213> ORGANISM: Homo sapiens

<400> SEQUENCE: 62

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
```

```
                    165                 170                 175
Gly Val Ala Ile Ser Val Ile Ile Phe Tyr Cys Tyr Arg Val Asn
            180                 185                 190
Arg Gln Gln Lys Leu Ser Ser Thr Trp Glu Thr Gly Lys Thr Arg Lys
        195                 200                 205
Leu Met Glu Phe Ser Glu His Cys Ala Ile Ile Leu Glu Asp Asp Arg
    210                 215                 220
Ser Asp Ile Ser Ser Thr Cys Ala Asn Asn Ile Asn His Asn Thr Glu
225                 230                 235                 240
Leu Leu Pro Ile Glu Leu Asp Thr Leu Val Gly Lys Gly Arg Phe Ala
            245                 250                 255
Glu Val Tyr Lys Ala Lys Leu Lys Gln Asn Thr Ser Glu Gln Phe Glu
        260                 265                 270
Thr Val Ala Val Lys Ile Phe Pro Tyr Glu Glu Tyr Ala Ser Trp Lys
    275                 280                 285
Thr Glu Lys Asp Ile Phe Ser Asp Ile Asn Leu Lys His Glu Asn Ile
290                 295                 300
Leu Gln Phe Leu Thr Ala Glu Glu Arg Lys Thr Glu Leu Gly Lys Gln
305                 310                 315                 320
Tyr Trp Leu Ile Thr Ala Phe His Ala Lys Gly Asn Leu Gln Glu Tyr
            325                 330                 335
Leu Thr Arg His Val Ile Ser Trp Glu Asp Leu Arg Lys Leu Gly Ser
        340                 345                 350
Ser Leu Ala Arg Gly Ile Ala His Leu His Ser Asp His Thr Pro Cys
    355                 360                 365
Gly Arg Pro Lys Met Pro Ile Val His Arg Asp Leu Lys Ser Ser Asn
370                 375                 380
Ile Leu Val Lys Asn Asp Leu Thr Cys Cys Leu Cys Asp Phe Gly Leu
385                 390                 395                 400
Ser Leu Arg Leu Asp Pro Thr Leu Ser Val Asp Asp Leu Ala Asn Ser
            405                 410                 415
Gly Gln Val Gly Thr Ala Arg Tyr Met Ala Pro Glu Val Leu Glu Ser
        420                 425                 430
Arg Met Asn Leu Glu Asn Ala Glu Ser Phe Lys Gln Thr Asp Val Tyr
    435                 440                 445
Ser Met Ala Leu Val Leu Trp Glu Met Thr Ser Arg Cys Asn Ala Val
450                 455                 460
Gly Glu Val Lys Asp Tyr Glu Pro Pro Phe Gly Ser Lys Val Arg Glu
465                 470                 475                 480
His Pro Cys Val Glu Ser Met Lys Asp Asn Val Leu Arg Asp Arg Gly
            485                 490                 495
Arg Pro Glu Ile Pro Ser Phe Trp Leu Asn His Gln Gly Ile Gln Met
        500                 505                 510
Val Cys Glu Thr Leu Thr Glu Cys Trp Asp His Asp Pro Glu Ala Arg
    515                 520                 525
Leu Thr Ala Gln Cys Val Ala Glu Arg Phe Ser Glu Leu Glu His Leu
530                 535                 540
Asp Arg Leu Ser Gly Arg Ser Cys Ser Glu Glu Lys Ile Pro Glu Asp
545                 550                 555                 560
Gly Ser Leu Asn Thr Thr Lys
            565

<210> SEQ ID NO 63
```

<211> LENGTH: 1138
<212> TYPE: PRT
<213> ORGANISM: Homo sapiens

<400> SEQUENCE: 63

```
Met Val Trp Arg Val Pro Pro Phe Leu Leu Pro Ile Leu Phe Leu Ala
1               5                   10                  15

Ser His Val Gly Ala Ala Val Asp Leu Thr Leu Leu Ala Asn Leu Arg
            20                  25                  30

Leu Thr Asp Pro Gln Arg Phe Phe Leu Thr Cys Val Ser Gly Glu Ala
        35                  40                  45

Gly Ala Gly Arg Gly Ser Asp Ala Trp Gly Pro Leu Leu Leu Glu
    50                  55                  60

Lys Asp Asp Arg Ile Val Arg Thr Pro Pro Gly Pro Pro Leu Arg Leu
65                  70                  75                  80

Ala Arg Asn Gly Ser His Gln Val Thr Leu Arg Gly Phe Ser Lys Pro
                85                  90                  95

Ser Asp Leu Val Gly Val Phe Ser Cys Val Gly Ala Gly Ala Arg
            100                 105                 110

Arg Thr Arg Val Ile Tyr Val His Asn Ser Pro Gly Ala His Leu Leu
        115                 120                 125

Pro Asp Lys Val Thr His Thr Val Asn Lys Gly Asp Thr Ala Val Leu
    130                 135                 140

Ser Ala Arg Val His Lys Glu Lys Gln Thr Asp Val Ile Trp Lys Ser
145                 150                 155                 160

Asn Gly Ser Tyr Phe Tyr Thr Leu Asp Trp His Glu Ala Gln Asp Gly
                165                 170                 175

Arg Phe Leu Leu Gln Leu Pro Asn Val Gln Pro Pro Ser Ser Gly Ile
            180                 185                 190

Tyr Ser Ala Thr Tyr Leu Glu Ala Ser Pro Leu Gly Ser Ala Phe Phe
        195                 200                 205

Arg Leu Ile Val Arg Gly Cys Gly Ala Gly Arg Trp Gly Pro Gly Cys
    210                 215                 220

Thr Lys Glu Cys Pro Gly Cys Leu His Gly Gly Val Cys His Asp His
225                 230                 235                 240

Asp Gly Glu Cys Val Cys Pro Pro Gly Phe Thr Gly Thr Arg Cys Glu
                245                 250                 255

Gln Ala Cys Arg Glu Gly Arg Phe Gly Gln Ser Cys Gln Glu Gln Cys
            260                 265                 270

Pro Gly Ile Ser Gly Cys Arg Gly Leu Thr Phe Cys Leu Pro Asp Pro
        275                 280                 285

Tyr Gly Cys Ser Cys Gly Ser Gly Trp Arg Gly Ser Gln Cys Gln Glu
    290                 295                 300

Ala Cys Ala Pro Gly His Phe Gly Ala Asp Cys Arg Leu Gln Cys Gln
305                 310                 315                 320

Cys Gln Asn Gly Gly Thr Cys Asp Arg Phe Ser Gly Cys Val Cys Pro
                325                 330                 335

Ser Gly Trp His Gly Val His Cys Glu Lys Ser Asp Arg Ile Pro Gln
            340                 345                 350

Ile Leu Asn Met Ala Ser Glu Leu Glu Phe Asn Leu Glu Thr Met Pro
        355                 360                 365

Arg Ile Asn Cys Ala Ala Ala Gly Asn Pro Phe Pro Val Arg Gly Ser
    370                 375                 380

Ile Glu Leu Arg Lys Pro Asp Gly Thr Val Leu Leu Ser Thr Lys Ala
```

-continued

```
            385                 390                 395                 400
Ile Val Glu Pro Glu Lys Thr Thr Ala Glu Phe Glu Val Pro Arg Leu
                405                 410                 415

Val Leu Ala Asp Ser Gly Phe Trp Glu Cys Arg Val Ser Thr Ser Gly
            420                 425                 430

Gly Gln Asp Ser Arg Arg Phe Lys Val Asn Val Lys Val Pro Pro Val
            435                 440                 445

Pro Leu Ala Ala Pro Arg Leu Leu Thr Lys Gln Ser Arg Gln Leu Val
        450                 455                 460

Val Ser Pro Leu Val Ser Phe Ser Gly Asp Gly Pro Ile Ser Thr Val
465                 470                 475                 480

Arg Leu His Tyr Arg Pro Gln Asp Ser Thr Met Asp Trp Ser Thr Ile
                485                 490                 495

Val Val Asp Pro Ser Glu Asn Val Thr Leu Met Asn Leu Arg Pro Lys
                500                 505                 510

Thr Gly Tyr Ser Val Arg Val Gln Leu Ser Arg Pro Gly Glu Gly Gly
            515                 520                 525

Glu Gly Ala Trp Gly Pro Pro Thr Leu Met Thr Thr Asp Cys Pro Glu
        530                 535                 540

Pro Leu Leu Gln Pro Trp Leu Glu Gly Trp His Val Glu Gly Thr Asp
545                 550                 555                 560

Arg Leu Arg Val Ser Trp Ser Leu Pro Leu Val Pro Gly Pro Leu Val
                565                 570                 575

Gly Asp Gly Phe Leu Leu Arg Leu Trp Asp Gly Thr Arg Gly Gln Glu
            580                 585                 590

Arg Arg Glu Asn Val Ser Ser Pro Gln Ala Arg Thr Ala Leu Leu Thr
        595                 600                 605

Gly Leu Thr Pro Gly Thr His Tyr Gln Leu Asp Val Gln Leu Tyr His
        610                 615                 620

Cys Thr Leu Leu Gly Pro Ala Ser Pro Pro Ala His Val Leu Leu Pro
625                 630                 635                 640

Pro Ser Gly Pro Pro Ala Pro Arg His Leu His Ala Gln Ala Leu Ser
                645                 650                 655

Asp Ser Glu Ile Gln Leu Thr Trp Lys His Pro Glu Ala Leu Pro Gly
            660                 665                 670

Pro Ile Ser Lys Tyr Val Val Glu Val Gln Val Ala Gly Gly Ala Gly
        675                 680                 685

Asp Pro Leu Trp Ile Asp Val Asp Arg Pro Glu Glu Thr Ser Thr Ile
        690                 695                 700

Ile Arg Gly Leu Asn Ala Ser Thr Arg Tyr Leu Phe Arg Met Arg Ala
705                 710                 715                 720

Ser Ile Gln Gly Leu Gly Asp Trp Ser Asn Thr Val Glu Glu Ser Thr
                725                 730                 735

Leu Gly Asn Gly Leu Gln Ala Glu Gly Pro Val Gln Glu Ser Arg Ala
            740                 745                 750

Ala Glu Glu Gly Leu Asp Gln Gln Leu Ile Leu Ala Val Val Gly Ser
        755                 760                 765

Val Ser Ala Thr Cys Leu Thr Ile Leu Ala Ala Leu Leu Thr Leu Val
770                 775                 780

Cys Ile Arg Arg Ser Cys Leu His Arg Arg Arg Thr Phe Thr Tyr Gln
785                 790                 795                 800

Ser Gly Ser Gly Glu Thr Ile Leu Gln Phe Ser Ser Gly Thr Leu
            805                 810                 815
```

```
Thr Leu Thr Arg Arg Pro Lys Leu Gln Pro Glu Pro Leu Ser Tyr Pro
            820                 825                 830

Val Leu Glu Trp Glu Asp Ile Thr Phe Glu Asp Leu Ile Gly Glu Gly
            835                 840                 845

Asn Phe Gly Gln Val Ile Arg Ala Met Ile Lys Lys Asp Gly Leu Lys
            850                 855                 860

Met Asn Ala Ala Ile Lys Met Leu Lys Glu Tyr Ala Ser Glu Asn Asp
865                 870                 875                 880

His Arg Asp Phe Ala Gly Glu Leu Glu Val Leu Cys Lys Leu Gly His
                885                 890                 895

His Pro Asn Ile Ile Asn Leu Leu Gly Ala Cys Lys Asn Arg Gly Tyr
                900                 905                 910

Leu Tyr Ile Ala Ile Glu Tyr Ala Pro Tyr Gly Asn Leu Leu Asp Phe
            915                 920                 925

Leu Arg Lys Ser Arg Val Leu Glu Thr Asp Pro Ala Phe Ala Arg Glu
            930                 935                 940

His Gly Thr Ala Ser Thr Leu Ser Ser Arg Gln Leu Leu Arg Phe Ala
945                 950                 955                 960

Ser Asp Ala Ala Asn Gly Met Gln Tyr Leu Ser Glu Lys Gln Phe Ile
                965                 970                 975

His Arg Asp Leu Ala Ala Arg Asn Val Leu Val Gly Glu Asn Leu Ala
                980                 985                 990

Ser Lys Ile Ala Asp Phe Gly Leu Ser Arg Gly Glu Glu Val Tyr Val
            995                 1000                1005

Lys Lys Thr Met Gly Arg Leu Pro Val Arg Trp Met Ala Ile Glu Ser
    1010                1015                1020

Leu Asn Tyr Ser Val Tyr Thr Thr Lys Ser Asp Val Trp Ser Phe Gly
1025                1030                1035                1040

Val Leu Leu Trp Glu Ile Val Ser Leu Gly Gly Thr Pro Tyr Cys Gly
                1045                1050                1055

Met Thr Cys Ala Glu Leu Tyr Glu Lys Leu Pro Gln Gly Tyr Arg Met
            1060                1065                1070

Glu Gln Pro Arg Asn Cys Asp Asp Glu Val Tyr Glu Leu Met Arg Gln
            1075                1080                1085

Cys Trp Arg Asp Arg Pro Tyr Glu Arg Pro Pro Phe Ala Gln Ile Ala
            1090                1095                1100

Leu Gln Leu Gly Arg Met Leu Glu Ala Arg Lys Ala Tyr Val Asn Met
1105                1110                1115                1120

Ser Leu Phe Glu Asn Phe Thr Tyr Ala Gly Ile Asp Ala Thr Ala Glu
                1125                1130                1135

Glu Ala

<210> SEQ ID NO 64
<211> LENGTH: 1124
<212> TYPE: PRT
<213> ORGANISM: Homo sapiens

<400> SEQUENCE: 64

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
            35                  40                  45
```

-continued

```
Trp Arg Pro His Glu Pro Ile Thr Ile Gly Arg Asp Phe Glu Ala Leu
 50                  55                  60

Met Asn Gln His Gln Asp Pro Leu Glu Val Thr Gln Asp Val Thr Arg
 65                  70                  75                  80

Glu Trp Ala Lys Lys Val Val Trp Lys Arg Glu Lys Ala Ser Lys Ile
                 85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
130                 135                 140

Lys Val Leu Ile Lys Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
450                 455                 460
```

```
Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
            515                 520                 525

His Pro Gly Pro Val Arg Arg Phe Thr Thr Ala Ser Ile Gly Leu Pro
            530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
            580                 585                 590

Val Pro Gly Asn Leu Thr Ser Val Leu Leu Asn Asn Leu His Pro Arg
            595                 600                 605

Glu Gln Tyr Val Val Arg Ala Arg Val Asn Thr Lys Ala Gln Gly Glu
            610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
            675                 680                 685

Ile Lys Asn Ala Thr Ile Ile Gln Tyr Gln Leu Lys Gly Leu Glu Pro
690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Met Leu Leu Ile Ala Ile Leu
            740                 745                 750

Gly Ser Ala Gly Met Thr Cys Leu Thr Val Leu Leu Ala Phe Leu Ile
            755                 760                 765

Ile Leu Gln Leu Lys Arg Ala Asn Val Gln Arg Arg Met Ala Gln Ala
770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
                805                 810                 815

Pro Val Leu Asp Trp Asn Asp Ile Lys Phe Gln Asp Val Ile Gly Glu
            820                 825                 830

Gly Asn Phe Gly Gln Val Leu Lys Ala Arg Ile Lys Lys Asp Gly Leu
            835                 840                 845

Arg Met Asp Ala Ala Ile Lys Arg Met Lys Glu Tyr Ala Ser Lys Asp
850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
```

```
                    885                 890                 895
Tyr Leu Tyr Leu Ala Ile Glu Tyr Ala Pro His Gly Asn Leu Leu Asp
                900                 905                 910
Phe Leu Arg Lys Ser Arg Val Leu Glu Thr Asp Pro Ala Phe Ala Ile
            915                 920                 925
Ala Asn Ser Thr Ala Ser Thr Leu Ser Ser Gln Gln Leu Leu His Phe
        930                 935                 940
Ala Ala Asp Val Ala Arg Gly Met Asp Tyr Leu Ser Gln Lys Gln Phe
945                 950                 955                 960
Ile His Arg Asp Leu Ala Ala Arg Asn Ile Leu Val Gly Glu Asn Tyr
                965                 970                 975
Val Ala Lys Ile Ala Asp Phe Gly Leu Ser Arg Gly Gln Glu Val Tyr
            980                 985                 990
Val Lys Lys Thr Met Gly Arg Leu Pro Val Arg Trp Met Ala Ile Glu
            995                1000                1005
Ser Leu Asn Tyr Ser Val Tyr Thr Thr Asn Ser Asp Val Trp Ser Tyr
        1010                1015                1020
Gly Val Leu Leu Trp Glu Ile Val Ser Leu Gly Gly Thr Pro Tyr Cys
1025                1030                1035                1040
Gly Met Thr Cys Ala Glu Leu Tyr Glu Lys Leu Pro Gln Gly Tyr Arg
                1045                1050                1055
Leu Glu Lys Pro Leu Asn Cys Asp Asp Glu Val Tyr Asp Leu Met Arg
            1060                1065                1070
Gln Cys Trp Arg Glu Lys Pro Tyr Glu Arg Pro Ser Phe Ala Gln Ile
            1075                1080                1085
Leu Val Ser Leu Asn Arg Met Leu Glu Arg Lys Thr Tyr Val Asn
        1090                1095                1100
Thr Thr Leu Tyr Glu Lys Phe Thr Tyr Ala Gly Ile Asp Cys Ser Ala
1105                1110                1115                1120
Glu Glu Ala Ala

<210> SEQ ID NO 65
<211> LENGTH: 1333
<212> TYPE: PRT
<213> ORGANISM: Rattus norvegicus

<400> SEQUENCE: 65

Met Val Ser Cys Trp Asp Thr Ala Val Leu Pro Tyr Ala Leu Leu Gly
 1               5                  10                  15
Cys Leu Leu Leu Thr Gly Tyr Gly Ser Gly Ser Lys Leu Lys Val Pro
                20                  25                  30
Glu Leu Ser Leu Lys Gly Thr Gln His Val Met Gln Ala Gly Gln Thr
            35                  40                  45
Leu Phe Leu Lys Cys Arg Gly Glu Ala Ala His Ser Trp Ser Leu Pro
        50                  55                  60
Thr Thr Val Ser Gln Glu Asp Lys Arg Leu Ser Ile Thr Pro Pro Ser
65                  70                  75                  80
Ala Cys Gly Arg Asp Asn Arg Gln Phe Cys Ser Thr Leu Thr Leu Asp
                85                  90                  95
Thr Ala Gln Ala Asn His Thr Gly Leu Tyr Thr Cys Arg Tyr Leu Pro
                100                 105                 110
Thr Ser Thr Ser Lys Lys Lys Lys Ala Glu Ser Ser Ile Tyr Ile Phe
            115                 120                 125
Val Ser Asp Ala Gly Ser Pro Phe Ile Glu Met His Thr Asp Ile Pro
```

-continued

```
            130                 135                 140
Lys Leu Val His Met Thr Glu Gly Arg Gln Leu Ile Ile Pro Cys Arg
145                 150                 155                 160

Val Thr Ser Pro Asn Val Thr Val Thr Leu Lys Lys Phe Pro Phe Asp
                165                 170                 175

Thr Leu Thr Pro Asp Gly Gln Arg Ile Thr Trp Asp Ser Arg Arg Gly
                180                 185                 190

Phe Ile Ile Ala Asn Ala Thr Tyr Lys Glu Ile Gly Leu Leu Asn Cys
                195                 200                 205

Glu Ala Thr Val Asn Gly His Leu Tyr Gln Thr Asn Tyr Leu Thr His
210                 215                 220

Arg Gln Thr Asn Thr Ile Leu Asp Val Gln Ile Arg Pro Pro Ser Pro
225                 230                 235                 240

Val Arg Leu Leu His Gly Gln Thr Leu Val Leu Asn Cys Thr Ala Thr
                245                 250                 255

Thr Glu Leu Asn Thr Arg Val Gln Met Ser Trp Asn Tyr Pro Gly Lys
                260                 265                 270

Ala Thr Lys Arg Ala Ser Ile Arg Gln Arg Ile Asp Arg Ser His Ser
                275                 280                 285

His Asn Asn Val Phe His Ser Val Leu Lys Ile Asn Asn Val Glu Ser
                290                 295                 300

Arg Asp Lys Gly Leu Tyr Thr Cys Arg Val Lys Ser Gly Ser Ser Phe
305                 310                 315                 320

Gln Ser Phe Asn Thr Ser Val His Val Tyr Glu Lys Gly Phe Ile Ser
                325                 330                 335

Val Lys His Arg Lys Gln Pro Val Gln Glu Thr Thr Ala Gly Arg Arg
                340                 345                 350

Ser Tyr Arg Leu Ser Met Lys Val Lys Ala Phe Pro Ser Pro Glu Ile
                355                 360                 365

Val Trp Leu Lys Asp Gly Ser Pro Ala Thr Leu Lys Ser Ala Arg Tyr
370                 375                 380

Leu Val His Gly Tyr Ser Leu Ile Ile Lys Asp Val Thr Thr Glu Asp
385                 390                 395                 400

Ala Gly Asp Tyr Thr Ile Leu Leu Gly Ile Lys Gln Ser Arg Leu Phe
                405                 410                 415

Lys Asn Leu Thr Ala Thr Leu Ile Val Asn Val Lys Pro Gln Ile Tyr
                420                 425                 430

Glu Lys Ser Val Ser Ser Leu Pro Ser Pro Leu Tyr Pro Leu Gly
                435                 440                 445

Ser Arg Gln Val Leu Thr Cys Thr Val Tyr Gly Ile Pro Arg Pro Thr
450                 455                 460

Ile Thr Trp Leu Trp His Pro Cys His His Asn His Ser Lys Glu Arg
465                 470                 475                 480

Tyr Asp Phe Cys Thr Glu Asn Glu Glu Ser Phe Ile Leu Asp Pro Ser
                485                 490                 495

Ser Asn Leu Gly Asn Arg Ile Glu Ser Ile Ser Gln Arg Met Thr Val
                500                 505                 510

Ile Glu Gly Thr Asn Lys Thr Val Ser Thr Leu Val Val Ala Asp Ser
                515                 520                 525

Gln Thr Pro Gly Ile Tyr Ser Cys Arg Ala Phe Asn Lys Ile Gly Thr
                530                 535                 540

Val Glu Arg Asn Ile Lys Phe Tyr Val Thr Asp Val Pro Asn Gly Phe
545                 550                 555                 560
```

-continued

```
His Val Ser Leu Glu Lys Met Pro Ala Glu Gly Asp Leu Lys Leu
            565                 570                 575

Ser Cys Val Val Asn Lys Phe Leu Tyr Arg Asp Ile Thr Trp Ile Leu
            580                 585                 590

Leu Arg Thr Val Asn Asn Arg Thr Met His His Ser Ile Ser Lys Gln
            595                 600                 605

Lys Met Ala Thr Thr Gln Asp Tyr Ser Ile Thr Leu Asn Leu Val Ile
            610                 615                 620

Lys Asn Val Ser Leu Glu Asp Ser Gly Thr Tyr Ala Cys Arg Ala Arg
625                 630                 635                 640

Asn Ile Tyr Thr Gly Glu Asp Ile Leu Arg Lys Thr Glu Val Leu Val
            645                 650                 655

Arg Asp Ser Glu Ala Pro His Leu Leu Gln Asn Leu Ser Asp Tyr Glu
            660                 665                 670

Val Ser Ile Ser Gly Ser Thr Thr Leu Asp Cys Gln Ala Arg Gly Val
            675                 680                 685

Pro Ala Pro Gln Ile Thr Trp Phe Lys Asn Asn His Lys Ile Gln Gln
            690                 695                 700

Glu Pro Gly Ile Ile Leu Gly Pro Gly Asn Ser Thr Leu Phe Ile Glu
705                 710                 715                 720

Arg Val Thr Glu Glu Asp Glu Gly Val Tyr Arg Cys Arg Ala Thr Asn
            725                 730                 735

Gln Lys Gly Ala Val Glu Ser Ala Ala Tyr Leu Thr Val Gln Gly Thr
            740                 745                 750

Ser Asp Lys Ser Asn Leu Glu Leu Ile Thr Leu Thr Cys Thr Cys Val
            755                 760                 765

Ala Ala Thr Leu Phe Trp Leu Leu Leu Thr Leu Phe Ile Arg Lys Leu
            770                 775                 780

Lys Arg Ser Ser Ser Glu Val Lys Thr Asp Tyr Leu Ser Ile Ile Met
785                 790                 795                 800

Asp Pro Asp Glu Val Pro Leu Asp Glu Gln Cys Glu Arg Leu Pro Tyr
            805                 810                 815

Asp Ala Ser Lys Trp Glu Phe Ala Arg Glu Arg Leu Lys Leu Gly Lys
            820                 825                 830

Ser Leu Gly Arg Gly Ala Phe Gly Lys Val Val Gln Ala Ser Ala Phe
            835                 840                 845

Gly Ile Lys Lys Ser Pro Thr Cys Arg Thr Val Ala Val Lys Met Leu
850                 855                 860

Lys Glu Gly Ala Thr Ala Ser Glu Tyr Lys Ala Leu Met Thr Glu Leu
865                 870                 875                 880

Lys Ile Leu Thr His Ile Gly His His Leu Asn Val Val Asn Leu Leu
            885                 890                 895

Gly Ala Cys Thr Lys Gln Gly Gly Pro Leu Met Val Ile Val Glu Tyr
            900                 905                 910

Cys Lys Tyr Gly Asn Leu Ser Asn Tyr Leu Lys Ser Lys Arg Asp Leu
            915                 920                 925

Phe Cys Leu Asn Lys Asp Ala Ala Leu His Met Glu Leu Lys Lys Glu
            930                 935                 940

Ser Leu Glu Pro Gly Leu Glu Gln Gly Gln Lys Pro Arg Leu Asp Ser
945                 950                 955                 960

Val Ser Ser Ser Ser Val Thr Ser Ser Ser Phe Pro Glu Asp Arg Ser
                    965                 970                 975
```

```
Val Ser Asp Val Glu Gly Asp Glu Asp Tyr Ser Glu Ile Ser Lys Gln
            980                 985                 990

Pro Leu Thr Met Glu Asp Leu Ile Ser Tyr Ser Phe Gln Val Ala Arg
        995                1000                1005

Gly Met Glu Phe Leu Ser Ser Arg Lys Cys Ile His Arg Asp Leu Ala
       1010                1015                1020

Ala Arg Asn Ile Leu Leu Ser Glu Asn Asn Val Val Lys Ile Cys Asp
1025                1030                1035                1040

Phe Gly Leu Ala Arg Asp Ile Tyr Lys Asn Pro Asp Tyr Val Arg Arg
               1045                1050                1055

Gly Asp Thr Arg Leu Pro Leu Lys Trp Met Ala Pro Glu Ser Ile Phe
       1060                1065                1070

Asp Lys Val Tyr Ser Thr Lys Ser Asp Val Trp Ser Tyr Gly Val Leu
           1075                1080                1085

Leu Trp Glu Ile Phe Ser Leu Gly Gly Ser Pro Tyr Pro Gly Val Gln
       1090                1095                1100

Met Asp Glu Asp Phe Cys Ser Arg Leu Lys Glu Gly Met Arg Met Arg
1105                1110                1115                1120

Thr Pro Glu Tyr Ala Thr Pro Glu Ile Tyr Gln Ile Met Leu Asp Cys
               1125                1130                1135

Trp His Lys Asp Pro Lys Glu Arg Pro Arg Phe Ala Glu Leu Val Glu
           1140                1145                1150

Lys Leu Gly Asp Leu Leu Gln Ala Asn Val Gln Gln Asp Gly Lys Asp
           1155                1160                1165

Tyr Ile Pro Leu Asn Ala Ile Leu Thr Arg Asn Ser Ser Phe Thr Tyr
       1170                1175                1180

Ser Thr Pro Thr Phe Ser Glu Asp Leu Phe Lys Asp Gly Phe Ala Asp
1185                1190                1195                1200

Pro His Phe His Ser Gly Ser Ser Asp Asp Val Arg Tyr Val Asn Ala
               1205                1210                1215

Phe Lys Phe Met Ser Leu Glu Arg Ile Lys Thr Phe Glu Glu Leu Ser
           1220                1225                1230

Pro Asn Ser Thr Ser Met Phe Glu Asp Tyr Gln Leu Asp Thr Ser Thr
           1235                1240                1245

Leu Leu Gly Ser Pro Leu Leu Lys Arg Phe Thr Trp Thr Glu Thr Lys
       1250                1255                1260

Pro Lys Ala Ser Met Lys Ile Asp Leu Arg Ile Ala Ser Lys Ser Lys
1265                1270                1275                1280

Glu Ala Gly Leu Ser Asp Leu Pro Arg Pro Ser Phe Cys Phe Ser Ser
               1285                1290                1295

Cys Gly His Ile Arg Pro Val Gln Asp Asp Glu Ser Glu Leu Gly Lys
           1300                1305                1310

Glu Ser Cys Cys Ser Pro Pro Pro Asp Tyr Asn Ser Val Val Leu Tyr
           1315                1320                1325

Ser Ser Pro Pro Ala
           1330

<210> SEQ ID NO 66
<211> LENGTH: 1356
<212> TYPE: PRT
<213> ORGANISM: Homo sapiens

<400> SEQUENCE: 66

Met Gln Ser Lys Val Leu Leu Ala Val Ala Leu Trp Leu Cys Val Glu
  1               5                  10                  15
```

-continued

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
                100                 105                 110

Val Ile Tyr Val Tyr Val Gln Asp Tyr Arg Ser Pro Phe Ile Ala Ser
            115                 120                 125

Val Ser Asp Gln His Gly Val Val Tyr Ile Thr Glu Asn Lys Asn Lys
        130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
            195                 200                 205

Tyr Gln Ser Ile Met Tyr Ile Val Val Val Gly Tyr Arg Ile Tyr
        210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

```
Asp Ser Tyr Gln Tyr Gly Thr Thr Gln Thr Leu Thr Cys Thr Val Tyr
        435                 440                 445

Ala Ile Pro Pro His His Ile His Trp Tyr Trp Gln Leu Glu Glu
450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
            485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
        755                 760                 765

Val Gly Thr Ala Val Ile Ala Met Phe Phe Trp Leu Leu Leu Val Ile
    770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
```

```
                    850                 855                 860
Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                    885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
            915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
            980                 985                 990

Glu Asp Leu Tyr Lys Asp Phe Leu Thr Leu Glu His Leu Ile Cys Tyr
            995                 1000                1005

Ser Phe Gln Val Ala Lys Gly Met Glu Phe Leu Ala Ser Arg Lys Cys
        1010                1015                1020

Ile His Arg Asp Leu Ala Ala Arg Asn Ile Leu Leu Ser Glu Lys Asn
1025                1030                1035                1040

Val Val Lys Ile Cys Asp Phe Gly Leu Ala Arg Asp Ile Tyr Lys Asp
                1045                1050                1055

Pro Asp Tyr Val Arg Lys Gly Asp Ala Arg Leu Pro Leu Lys Trp Met
                1060                1065                1070

Ala Pro Glu Thr Ile Phe Asp Arg Val Tyr Thr Ile Gln Ser Asp Val
            1075                1080                1085

Trp Ser Phe Gly Val Leu Leu Trp Glu Ile Phe Ser Leu Gly Ala Ser
            1090                1095                1100

Pro Tyr Pro Gly Val Lys Ile Asp Glu Glu Phe Cys Arg Arg Leu Lys
1105                1110                1115                1120

Glu Gly Thr Arg Met Arg Ala Pro Asp Tyr Thr Thr Pro Glu Met Tyr
                1125                1130                1135

Gln Thr Met Leu Asp Cys Trp His Gly Glu Pro Ser Gln Arg Pro Thr
                1140                1145                1150

Phe Ser Glu Leu Val Glu His Leu Gly Asn Leu Leu Gln Ala Asn Ala
            1155                1160                1165

Gln Gln Asp Gly Lys Asp Tyr Ile Val Leu Pro Ile Ser Glu Thr Leu
        1170                1175                1180

Ser Met Glu Glu Asp Ser Gly Leu Ser Leu Pro Thr Ser Pro Val Ser
1185                1190                1195                1200

Cys Met Glu Glu Glu Val Cys Asp Pro Lys Phe His Tyr Asp Asn
                1205                1210                1215

Thr Ala Gly Ile Ser Gln Tyr Leu Gln Asn Ser Lys Arg Lys Ser Arg
            1220                1225                1230

Pro Val Ser Val Lys Thr Phe Glu Asp Ile Pro Leu Glu Glu Pro Glu
        1235                1240                1245

Val Lys Val Ile Pro Asp Asp Asn Gln Thr Asp Ser Gly Met Val Leu
    1250                1255                1260

Ala Ser Glu Glu Leu Lys Thr Leu Glu Asp Arg Thr Lys Leu Ser Pro
1265                1270                1275                1280
```

-continued

Ser Phe Gly Gly Met Val Pro Ser Lys Ser Arg Glu Ser Val Ala Ser
                1285                1290                1295

Glu Gly Ser Asn Gln Thr Ser Gly Tyr Gln Ser Gly Tyr His Ser Asp
            1300                1305                1310

Asp Thr Asp Thr Thr Val Tyr Ser Ser Glu Glu Ala Glu Leu Leu Lys
        1315                1320                1325

Leu Ile Glu Ile Gly Val Gln Thr Gly Ser Thr Ala Gln Ile Leu Gln
    1330                1335                1340

Pro Asp Ser Gly Thr Thr Leu Ser Ser Pro Pro Val
1345                1350                1355

<210> SEQ ID NO 67
<211> LENGTH: 1298
<212> TYPE: PRT
<213> ORGANISM: Homo sapiens

<400> SEQUENCE: 67

Met Gln Arg Gly Ala Ala Leu Cys Leu Arg Leu Trp Leu Cys Leu Gly
 1               5                  10                  15

Leu Leu Asp Gly Leu Val Ser Gly Tyr Ser Met Thr Pro Pro Thr Leu
                20                  25                  30

Asn Ile Thr Glu Glu Ser His Val Ile Asp Thr Gly Asp Ser Leu Ser
            35                  40                  45

Ile Ser Cys Arg Gly Gln His Pro Leu Glu Trp Ala Trp Pro Gly Ala
        50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp

-continued

```
                290                 295                 300
Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
                340                 345                 350

Lys Leu Pro Val Lys Leu Ala Ala Tyr Pro Pro Glu Phe Gln Trp
                355                 360                 365

Tyr Lys Asp Gly Lys Ala Leu Ser Gly Arg His Ser Pro His Ala Leu
370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                405                 410                 415

Val Val Asn Val Pro Pro Gln Ile His Glu Lys Glu Ala Ser Ser Pro
                420                 425                 430

Ser Ile Tyr Ser Arg His Ser Arg Gln Ala Leu Thr Cys Thr Ala Tyr
                435                 440                 445

Gly Val Pro Leu Pro Leu Ser Ile Gln Trp His Trp Arg Pro Trp Thr
                450                 455                 460

Pro Cys Lys Met Phe Ala Gln Arg Ser Leu Arg Arg Gln Gln Gln
465                 470                 475                 480

Asp Leu Met Pro Gln Cys Arg Asp Trp Arg Ala Val Thr Thr Gln Asp
                485                 490                 495

Ala Val Asn Pro Ile Glu Ser Leu Asp Thr Trp Thr Glu Phe Val Glu
                500                 505                 510

Gly Lys Asn Lys Thr Val Ser Lys Leu Val Ile Gln Asn Ala Asn Val
                515                 520                 525

Ser Ala Met Tyr Lys Cys Val Val Ser Asn Lys Val Gly Gln Asp Glu
                530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
                565                 570                 575

Ser Cys Gln Ala Asp Ser Tyr Lys Tyr Glu His Leu Arg Trp Tyr Arg
                580                 585                 590

Leu Asn Leu Ser Thr Leu His Asp Ala His Gly Asn Pro Leu Leu Leu
                595                 600                 605

Asp Cys Lys Asn Val His Leu Phe Ala Thr Pro Leu Ala Ala Ser Leu
610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
                660                 665                 670

Gln Ala Leu Glu Ala Pro Arg Leu Thr Gln Asn Leu Thr Asp Leu Leu
                675                 680                 685

Val Asn Val Ser Asp Ser Leu Glu Met Gln Cys Leu Val Ala Gly Ala
                690                 695                 700

His Ala Pro Ser Ile Val Trp Tyr Lys Asp Glu Arg Leu Leu Glu Glu
705                 710                 715                 720
```

-continued

```
Lys Ser Gly Val Asp Leu Ala Asp Ser Asn Gln Lys Leu Ser Ile Gln
            725                 730                 735

Arg Val Arg Glu Glu Asp Ala Gly Arg Tyr Leu Cys Ser Val Cys Asn
            740                 745                 750

Ala Lys Gly Cys Val Asn Ser Ala Ser Val Ala Val Glu Gly Ser
            755                 760                 765

Glu Asp Lys Gly Ser Met Glu Ile Val Ile Leu Val Gly Thr Gly Val
            770                 775                 780

Ile Ala Val Phe Phe Trp Val Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Gln Cys Glu Tyr Leu Ser
            820                 825                 830

Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Val Glu Ala Ser Ala
            850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
            930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Arg Pro Gly Ser
            965                 970                 975

Ser Asp Arg Val Leu Phe Ala Arg Phe Ser Lys Thr Glu Gly Gly Ala
            980                 985                 990

Arg Arg Ala Ser Pro Asp Gln Glu Ala Glu Asp Leu Trp Leu Ser Pro
            995                 1000                1005

Leu Thr Met Glu Asp Leu Val Cys Tyr Ser Phe Gln Val Ala Arg Gly
            1010                1015                1020

Met Glu Phe Leu Ala Ser Arg Lys Cys Ile His Arg Asp Leu Ala Ala
1025                1030                1035                1040

Arg Asn Ile Leu Leu Ser Glu Ser Asp Val Val Lys Ile Cys Asp Phe
            1045                1050                1055

Gly Leu Ala Arg Asp Ile Tyr Lys Asp Pro Asp Tyr Val Arg Lys Gly
            1060                1065                1070

Ser Ala Arg Leu Pro Leu Lys Trp Met Ala Pro Glu Ser Ile Phe Asp
            1075                1080                1085

Lys Val Tyr Thr Thr Gln Ser Asp Val Trp Ser Phe Gly Val Leu Leu
            1090                1095                1100

Trp Glu Ile Phe Ser Leu Gly Ala Ser Pro Tyr Pro Gly Val Gln Ile
1105                1110                1115                1120

Asn Glu Glu Phe Cys Gln Arg Leu Arg Asp Gly Thr Arg Met Arg Ala
            1125                1130                1135
```

-continued

```
Pro Glu Leu Ala Thr Pro Ala Ile Arg Arg Ile Met Leu Asn Cys Trp
            1140                1145                1150

Ser Gly Asp Pro Lys Ala Arg Pro Ala Phe Ser Glu Leu Val Glu Ile
            1155                1160                1165

Leu Gly Asp Leu Leu Gln Gly Arg Gly Leu Gln Glu Glu Glu Glu Val
            1170                1175                1180

Cys Met Ala Pro Arg Ser Ser Gln Ser Ser Glu Glu Gly Ser Phe Ser
1185                1190                1195                1200

Gln Val Ser Thr Met Ala Leu His Ile Ala Gln Ala Asp Ala Glu Asp
                1205                1210                1215

Ser Pro Pro Ser Leu Gln Arg His Ser Leu Ala Ala Arg Tyr Tyr Asn
                1220                1225                1230

Trp Val Ser Phe Pro Gly Cys Leu Ala Arg Gly Ala Glu Thr Arg Gly
                1235                1240                1245

Ser Ser Arg Met Lys Thr Phe Glu Glu Phe Pro Met Thr Pro Thr Thr
            1250                1255                1260

Tyr Lys Gly Ser Val Asp Asn Gln Thr Asp Ser Gly Met Val Leu Ala
1265                1270                1275                1280

Ser Glu Glu Phe Glu Gln Ile Glu Ser Arg His Arg Gln Glu Ser Gly
                1285                1290                1295

Phe Arg

<210> SEQ ID NO 68
<211> LENGTH: 543
<212> TYPE: PRT
<213> ORGANISM: Homo sapiens

<400> SEQUENCE: 68

Met Gly Cys Ile Lys Ser Lys Glu Asn Lys Ser Pro Ala Ile Lys Tyr
1               5                   10                  15

Arg Pro Glu Asn Thr Pro Glu Pro Val Ser Thr Ser Val Ser His Tyr
            20                  25                  30

Gly Ala Glu Pro Thr Thr Val Ser Pro Cys Pro Ser Ser Ser Ala Lys
        35                  40                  45

Gly Thr Ala Val Asn Phe Ser Ser Leu Ser Met Thr Pro Phe Gly Gly
    50                  55                  60

Ser Ser Gly Val Thr Pro Phe Gly Gly Ala Ser Ser Phe Ser Val
65                  70                  75                  80

Val Pro Ser Ser Tyr Pro Ala Gly Leu Thr Gly Gly Val Thr Ile Phe
                85                  90                  95

Val Ala Leu Tyr Asp Tyr Glu Ala Arg Thr Thr Glu Asp Leu Ser Phe
            100                 105                 110

Lys Lys Gly Glu Arg Phe Gln Ile Ile Asn Asn Thr Glu Gly Asp Trp
        115                 120                 125

Trp Glu Ala Arg Ser Ile Ala Thr Gly Lys Asn Gly Tyr Ile Pro Ser
    130                 135                 140

Asn Tyr Val Ala Pro Ala Asp Ser Ile Gln Ala Glu Glu Trp Tyr Phe
145                 150                 155                 160

Gly Lys Met Gly Arg Lys Asp Ala Glu Arg Leu Leu Leu Asn Pro Gly
                165                 170                 175

Asn Gln Arg Gly Ile Phe Leu Val Arg Glu Ser Glu Thr Thr Lys Gly
            180                 185                 190

Ala Tyr Ser Leu Ser Ile Arg Asp Trp Asp Glu Ile Arg Gly Asp Asn
        195                 200                 205
```

```
Val Lys His Tyr Lys Ile Arg Lys Leu Asp Asn Gly Gly Tyr Tyr Ile
    210                 215                 220

Thr Thr Arg Ala Gln Phe Asp Thr Leu Gln Lys Leu Val Lys His Tyr
225                 230                 235                 240

Thr Glu His Ala Asp Gly Leu Cys His Lys Leu Thr Thr Val Cys Pro
                245                 250                 255

Thr Val Lys Pro Gln Thr Gln Gly Leu Ala Lys Asp Ala Trp Glu Ile
                260                 265                 270

Pro Arg Glu Ser Leu Arg Leu Glu Val Lys Leu Gly Gln Gly Cys Phe
                275                 280                 285

Gly Glu Val Trp Met Gly Thr Trp Asn Gly Thr Thr Lys Val Ala Ile
    290                 295                 300

Lys Thr Leu Lys Pro Gly Thr Met Met Pro Glu Ala Phe Leu Gln Glu
305                 310                 315                 320

Ala Gln Ile Met Lys Lys Leu Arg His Asp Lys Leu Val Pro Leu Tyr
                325                 330                 335

Ala Val Val Ser Glu Glu Pro Ile Tyr Ile Val Thr Glu Phe Met Ser
                340                 345                 350

Lys Gly Ser Leu Leu Asp Phe Leu Lys Glu Gly Asp Gly Lys Tyr Leu
            355                 360                 365

Lys Leu Pro Gln Leu Val Asp Met Ala Ala Gln Ile Ala Asp Gly Met
    370                 375                 380

Ala Tyr Ile Glu Arg Met Asn Tyr Ile His Arg Asp Leu Arg Ala Ala
385                 390                 395                 400

Asn Ile Leu Val Gly Glu Asn Leu Val Cys Lys Ile Ala Asp Phe Gly
                405                 410                 415

Leu Ala Arg Leu Ile Glu Asp Asn Glu Tyr Thr Ala Arg Gln Gly Ala
                420                 425                 430

Lys Phe Pro Ile Lys Trp Thr Ala Pro Glu Ala Ala Leu Tyr Gly Arg
            435                 440                 445

Phe Thr Ile Lys Ser Asp Val Trp Ser Phe Gly Ile Leu Gln Thr Glu
    450                 455                 460

Leu Val Thr Lys Gly Arg Val Pro Tyr Pro Gly Met Val Asn Arg Glu
465                 470                 475                 480

Val Leu Glu Gln Val Glu Arg Gly Tyr Arg Met Pro Cys Pro Gln Gly
                485                 490                 495

Cys Pro Glu Ser Leu His Glu Leu Met Asn Leu Cys Trp Lys Lys Asp
                500                 505                 510

Pro Asp Glu Arg Pro Thr Phe Glu Tyr Ile Gln Ser Phe Leu Glu Asp
            515                 520                 525

Tyr Phe Thr Ala Thr Glu Pro Gln Tyr Gln Pro Gly Glu Asn Leu
    530                 535                 540

<210> SEQ ID NO 69
<211> LENGTH: 619
<212> TYPE: PRT
<213> ORGANISM: Homo sapiens

<400> SEQUENCE: 69

Met Pro Asp Pro Ala His Leu Pro Phe Phe Tyr Gly Ser Ile Ser
1               5                   10                  15

Arg Ala Glu Ala Glu Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45
```

```
Ser Leu Val His Asp Val Arg Phe His His Phe Pro Ile Glu Arg Gln
     50                  55                  60

Leu Asn Gly Thr Tyr Ala Ile Ala Gly Gly Lys Ala His Cys Gly Pro
 65                  70                  75                  80

Ala Glu Leu Cys Glu Phe Tyr Ser Arg Asp Pro Asp Gly Leu Pro Cys
                 85                  90                  95

Asn Leu Arg Lys Pro Cys Asn Arg Pro Ser Gly Leu Glu Pro Gln Pro
             100                 105                 110

Gly Val Phe Asp Cys Leu Arg Asp Ala Met Val Arg Asp Tyr Val Arg
         115                 120                 125

Gln Thr Trp Lys Leu Glu Gly Glu Ala Leu Glu Gln Ala Ile Ile Ser
     130                 135                 140

Gln Ala Pro Gln Val Glu Lys Leu Ile Ala Thr Ala His Glu Arg
145                 150                 155                 160

Met Pro Trp Tyr His Ser Ser Leu Thr Arg Glu Glu Ala Glu Arg Lys
                 165                 170                 175

Leu Tyr Ser Gly Ala Gln Thr Asp Gly Lys Phe Leu Leu Arg Pro Arg
             180                 185                 190

Lys Glu Gln Gly Thr Tyr Ala Leu Ser Leu Ile Tyr Gly Lys Thr Val
         195                 200                 205

Tyr His Tyr Leu Ile Ser Gln Asp Lys Ala Gly Lys Tyr Cys Ile Pro
     210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                 245                 250                 255

Ser Ser Ala Ser Asn Ala Ser Gly Ala Ala Pro Thr Leu Pro Ala
             260                 265                 270

His Pro Ser Thr Leu Thr His Pro Gln Arg Arg Ile Asp Thr Leu Asn
         275                 280                 285

Ser Asp Gly Tyr Thr Pro Glu Pro Ala Arg Ile Thr Ser Pro Asp Lys
     290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                 325                 330                 335

Leu Leu Ile Ala Asp Ile Glu Leu Gly Cys Gly Asn Phe Gly Ser Val
             340                 345                 350

Arg Gln Gly Val Tyr Arg Met Arg Lys Lys Gln Ile Asp Val Ala Ile
         355                 360                 365

Lys Val Leu Lys Gln Gly Thr Glu Lys Ala Asp Thr Glu Glu Met Met
     370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                 405                 410                 415

Ala Gly Gly Gly Pro Leu His Lys Phe Leu Val Gly Lys Arg Glu Glu
             420                 425                 430

Ile Pro Val Ser Asn Val Ala Glu Leu Leu His Gln Val Ser Met Gly
         435                 440                 445

Met Lys Tyr Leu Glu Glu Lys Asn Phe Val His Arg Asp Leu Ala Ala
     450                 455                 460
```

```
Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
            485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
            565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
        610                 615

<210> SEQ ID NO 70
<211> LENGTH: 19
<212> TYPE: PRT
<213> ORGANISM: Homo sapiens

<400> SEQUENCE: 70

Lys Lys Lys Gly Pro Trp Leu Glu Glu Glu Glu Ala Tyr Gly Trp
1               5                   10                  15

Leu Asp Phe
```